United States Patent [19]

Los

[11] Patent Number: 4,608,079
[45] Date of Patent: Aug. 26, 1986

[54] IMIDAZOLIDINONES, AND IMIDAZOLIDIENTHIONES, PROCESS AND INTERMEDIATES FOR THE PREPARATION THEREOF, AND USE OF SAID COMPOUNDS AS HERBICIDAL AGENTS

[75] Inventor: Marinus Los, Pennington, N.J.

[73] Assignee: American Cyanamid Company, Stamford, Conn.

[21] Appl. No.: 616,741

[22] Filed: Jun. 4, 1984

Related U.S. Application Data

[63] Continuation-in-part of Ser. No. 519,613, Aug. 2, 1983, abandoned.

[51] Int. Cl.$^4$ .................. A01N 43/50; C07D 401/04; C07D 233/02
[52] U.S. Cl. ......................................... 71/92; 546/15; 546/170; 546/278; 548/301
[58] Field of Search .................. 548/301; 546/278, 15, 546/170

[56] References Cited

U.S. PATENT DOCUMENTS 4,170,462 10/1979 O'Neal ................................ 548/301
4,188,487 2/1980 Los .......................................... 71/92

OTHER PUBLICATIONS

Chemical Abstracts 96(9): 64202g (1982): "Herbicidal Composition for Selective Control of Undesired Plant Species": Lamb et al.

Primary Examiner—Paul R. Michl
Assistant Examiner—Alex H. Walker
Attorney, Agent, or Firm—H. G. Jackson

[57] ABSTRACT

This invention relates to novel imidazolidinone and imidazolidinethione compounds, a process and intermediates for the preparation of said compounds and a method for controlling undesirable plant species therewith.

31 Claims, No Drawings

IMIDAZOLIDINONES, AND IMIDAZOLIDIENTHIONES, PROCESS AND INTERMEDIATES FOR THE PREPARATION THEREOF, AND USE OF SAID COMPOUNDS AS HERBICIDAL AGENTS

This application is a continuation-in-part of pending application Ser. No. 519,613 filed Aug. 2, 1983, now abandoned.

This invention relates to novel imidazolidinone and imidazolidinethione compounds, a process and intermediates for the preparation of said compounds and a method for controlling undesirable plant species therewith.

More particularly, the present invention relates to novel, herbicidally effective, imidazolidinone and imidazolidinethione compounds of formula (I) having the structure:

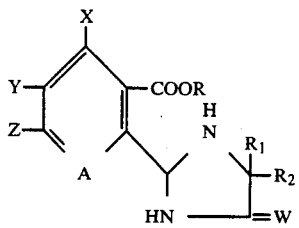

wherein
R is hydrogen;
$C_1$-$C_{12}$ alkyl optionally substituted with one of the following groups: $C_1$-$C_4$ alkoxy, halogen, hydroxyl, $C_3$-$C_6$ cycloalkyl, benzyloxy, furyl, phenyl, halophenyl, $C_1$-$C_4$ alkylphenyl, $C_1$-$C_4$ alkoxyphenyl nitrophenyl, carboxyl, $C_1$-$C_3$ alkoxycarbonyl, cyano or tri($C_1$-$C_3$)alkylammonium;
$C_3$-$C_{12}$ alkenyl optionally substituted with one of the following groups: $C_1$-$C_3$ alkoxy, phenyl, halogen, or $C_1$-$C_3$ alkoxycarbonyl or with two $C_1$-$C_4$ alkoxy groups or two halogen atoms;
$C_3$-$C_6$ cycloalkyl optionally substituted with one or two $C_1$-$C_3$ alkyl groups;
$C_3$-$C_{10}$ alkynyl; or,
a cation selected from alkali metals and organicammonium;
$R_1$ and $R_2$ each represent $C_1$-$C_3$ alkyl or cyclopropyl, with the proviso that the sum of the number of carbon atoms in $R_1$ and $R_2$ is 2 to 5; and when $R_1$ and $R_2$ are taken together with the carbon to which they are attached, they may form a $C_3$-$C_6$ cycloalkyl ring optionally substituted with methyl;
A is nitrogen or —$CR_3$;
W is oxygen or sulfur;
X is hydrogen, halogen or methyl;
Y and Z are each hydrogen, halogen, $C_1$-$C_6$ alkyl, $C_1$-$C_4$ hydroxyalkyl, $C_1$-$C_6$ alkoxy, $C_1$-$C_4$ alkylthio, phenoxy, $C_1$-$C_4$ haloalkyl, $OCF_2CHF_2$, $OCF_3$, $OCHF_2$, nitro, cyano, $NR_4R_5$, $C_3$-$C_8$ straight or branched alkenyloxy optionally substituted with one to three halogens, $C_3$-$C_8$ straight or branched alkynyloxy optionally substituted with one to three halogens, or phenyl optionally substituted with one $C_1$-$C_4$ alkyl, $C_1$-$C_4$ alkoxy or halogen;
$R_3$ is hydrogen, halogen, $C_1$-$C_4$ alkyl, $C_1$-$C_4$ alkoxy, $CF_3$, $NO_2$, $OCF_3$, $OCHF_2$ or $OCF_2CHF_2$;
$R_4$ is hydrogen or $C_1$-$C_4$ alkyl;
$R_5$ is $C_1$-$C_4$ alkyl;
And, when taken together, Y and Z may form a ring in which YZ is represented by
(1) the structure: —$(CH_2)_n$—, where n is an integer selected from 2, 3 and 4, provided that when A is —$CR_3$, then X is hydrogen; or
(2) by the structure:

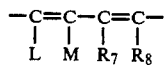

where, when A is $CR_3$, L, M, $R_7$ and $R_8$ each represent members selected from hydrogen, halogen, $C_1$-$C_4$ alkyl and $C_1$-$C_3$ alkoxy, and X is hydrogen; and when A is nitrogen, L, M, $R_7$ and $R_8$ each represent members selected from hydrogen, halogen, $C_1$-$C_4$ alkyl, $C_1$-$C_4$ alkoxy, $C_1$-$C_4$ alkylthio, $C_1$-$C_4$ alkylsulfonyl, $C_1$-$C_4$ haloalkyl, $NO_2$, CN, phenyl, phenoxy, amino, $OCF_3$, $OCHF_2$, $OCF_2CHF_2$, $C_1$-$C_4$ alkylamino, dialkyl($C_1$-$C_4$)amino, chlorophenyl, methylphenyl, $C_3$-$C_8$ straight or branched alkenyloxy optionally substituted with one to three halogens, $C_3$-$C_8$ straight or branched alkynyloxy optionally substituted with one to three halogens, or phenoxy substituted with one Cl, $CF_3$, $NO_2$ or $CH_3$ group, with the proviso that only one of L, M, $R_7$ or $R_8$, may represent a substituent other than hydrogen, halogen, $C_1$-$C_4$ alkyl or $C_1$-$C_4$ alkoxy; or
(3) by the structures:

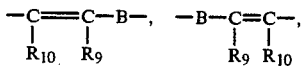

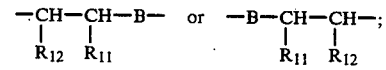

where B is oxygen or sulfur; $R_9$ and $R_{10}$ each represent a member selected from hydrogen, halogen, phenyl, or $C_1$-$C_4$ alkyl; $R_{11}$ and $R_{12}$ each represent a member selected from of hydrogen, $C_1$-$C_4$ alkyl and phenyl;
and when $R_1$ and $R_2$ are not the same, the optical and cis- and trans-isomers thereof and except when R is a salt-forming cation, the acid addition salts thereof.

As used in the present specification and claims, the term "halogen" means F, Cl, Br or I, unless otherwise specified.

Especially preferred compounds of the present invention are more precisely illustrated by formulas II, III, IV, V, VI, VII and VIII shown below.

The 2-(2-imidazolidinyl)benzoic acids, esters and salts of the present invention are depicted by formula II below:

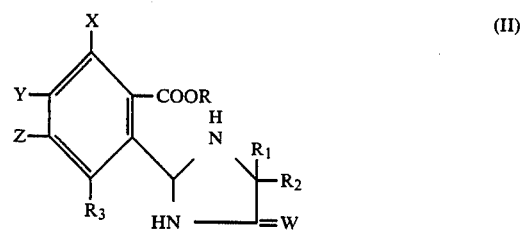

wherein R, $R_1$, $R_2$, $R_3$, X and W are as defined in reference to formula I above; Y and Z each, independently, represent members selected from hydrogen, halogen, $C_1$–$C_6$ alkyl, $C_1$–$C_6$ alkoxy, $C_1$–$C_4$ alkylthio, phenoxy, nitro, $C_1$–$C_4$ haloalkyl, $OCF_2CHF_2$, $OCF_3$, $OCHF_2$, CN, —$NR_4R_5$, $C_3$–$C_8$ straight or branched alkenyloxy optionally substituted with one to three halogens, $C_3$–$C_8$ straight or branched alkynyloxy optionally substituted with one to three halogens, or phenyl optionally substituted with one $C_1$–$C_4$ alkyl, $C_1$–$C_4$ alkoxy or halogen; $R_4$ is hydrogen or $C_1$–$C_4$ alkyl; $R_5$ is $C_1$–$C_4$ alkyl; and when taken together, Y and Z may form a ring in which YZ are represented by the structure: —$(CH_2)_n$—, where n is an integer selected from 2, 3 and 4 and X is hydrogen, or by the structure:

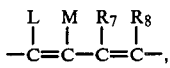

where L, M, $R_7$ and $R_8$ each represent members selected from hydrogen, halogen, $C_1$–$C_4$ alkyl and $C_1$–$C_3$ alkoxy; and when $R_1$ and $R_2$ are not the same, the optical and cis- and trans-isomers thereof and except when R is a salt-forming cation, the acid addition salts thereof.

Preferred 2-(2-imidazolidinyl)nicotinic acids, esters and salts of the present invention are depicted by formula III illustrated below:

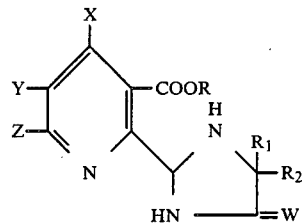

(III)

wherein R, $R_1$, $R_2$, W and X are as defined in reference to formula I above; Y and Z each, independently, represent members selected from hydrogen, halogen, $C_1$–$C_6$ alkyl, $C_1$–$C_6$ alkoxy, CN, $NO_2$, $OCF_3$, $OCHF_2$, $OCF_2CHF_2$, phenoxy, $C_1$–$C_4$ haloalkyl, $C_1$–$C_4$ alkylthio, $C_1$–$C_4$ hydroxyalkyl, $NR_4R_5$, $C_3$–$C_8$ straight or branched alkenyloxy optionally substituted with one to three halogens, $C_3$–$C_8$ straight or branched alkynyloxy optionally substituted with one to three halogens, or phenyl optionally substituted with one $C_1$–$C_4$ alkyl, $C_1$–$C_4$ alkoxy or halogen; $R_4$ is hydrogen or $C_1$–$C_4$ alkyl; $R_5$ is $C_1$–$C_4$ alkyl; and when taken together Y and Z may form a ring in which YZ are represented by the structure: —$(CH_2)_n$—, where n is an integer selected from 2, 3 and 4; and when $R_1$ and $R_2$ are not the same, the optical and cis- and trans-isomers thereof and except when R is a salt-forming cation, the acid addition salts thereof.

The 2-(2-imidazolidinyl)quinoline-3-carboxylic acids, esters and salts of the present invention are illustrated by formula IV below:

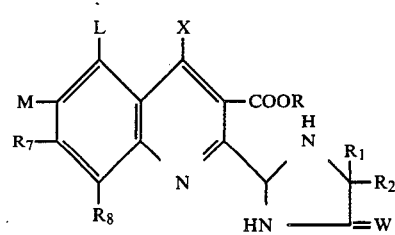

(IV)

wherein R, $R_1$, $R_2$, W and X, are as defined above in reference to formula I, and L, M, $R_7$ and $R_8$ represent a member selected from hydrogen, halogen, $C_1$–$C_4$ alkyl, $C_1$–$C_4$ alkoxy, $C_1$–$C_4$ alkylthio, $C_1$–$C_4$ alkylsulfonyl, $C_1$–$C_4$ haloalkyl, $NO_2$, CN, phenyl, phenoxy, amino, $CF_3$, $OCHF_2$, $OCF_2CHF_2$, $C_1$–$C_4$ alkylamino, dialkyl($C_1$–$C_4$)amino, chlorophenyl, methylphenyl, $C_3$–$C_8$ straight or branched alkenyloxy optionally substituted with one to three halogens, $C_3$–$C_8$ straight or branched alkynyloxy optionally substituted with one to three halogens, or phenoxy substituted with one Cl, $CF_3$, $NO_2$ or $CH_3$ group, with the proviso that only one of L, M, $R_7$ or $R_8$, may represent a substituent other than hydrogen, halogen, $C_1$–$C_4$ alkyl or $C_1$–$C_4$ alkoxy; and when $R_1$ and $R_2$ are not the same, the optical and cis- and trans-isomers thereof and except when R is a salt-forming cation, the acid addition salts thereof.

The 2-(2-imidazolidinyl)thieno- and furo[3,2-b]pyridine-6-carboxylic acids, esters and salts and the 2-(2-imidazolidinyl)-2,3-dihydrothieno- and furo[3,2-b]pyridine-6-carboxylic acids, esters and salts of the present invention are represented by formulas V and VI illustrated below:

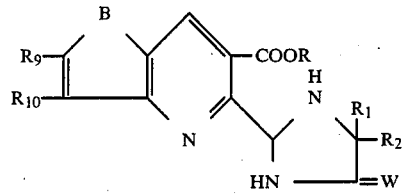

(V)

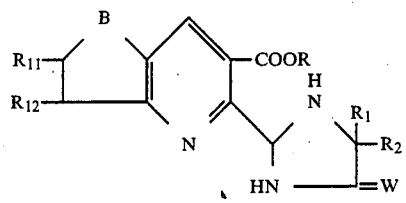

(VI)

wherein R, $R_1$, $R_2$, W and B, are as defined above in reference to formula I; $R_9$ and $R_{10}$ each represent a member selected from hydrogen, halogen, $C_1$–$C_4$ alkyl and phenyl; and $R_{11}$ and $R_{12}$ each represent hydrogen, $C_1$–$C_4$ alkyl or phenyl; and when $R_1$ and $R_2$ are not the same, the optical and cis- and trans-isomers thereof and except when R is a salt-forming cation, the acid addition salts thereof.

The 2-(2-imidazolidinyl)thieno- and furo[2,3-b]pyridine-5-carboxylic acids, esters and salts and the 2-(2-imidazolidinyl)-2,3-dihydrothieno- and furo[2,3-b]pyridine-5-carboxylic acids, esters and salts of the present invention are depicted by formulas VII and VIII illustrated below:

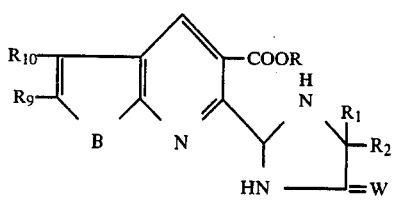

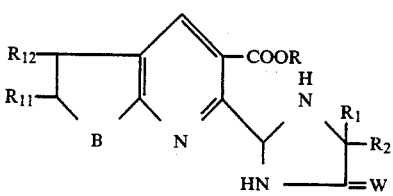

wherein R, $R_1$, $R_2$, W and B, are as defined above in reference to formula I, $R_9$ and $R_{10}$ each represent a member selected from hydrogen, halogen, $C_1$–$C_4$ alkyl and phenyl; $R_{11}$ and $R_{12}$ each represent a member selected from hydrogen, $C_1$–$C_4$ alkyl and phenyl; and when $R_1$ and $R_2$ are not the same, the optical isomers thereof and except when R is a salt-forming cation, the acid addition salts thereof.

In the present specification and claims, the alkali metals include: sodium, potassium and lithium, although sodium is generally preferred. Also, in the present specification and claims, unless otherwise specified, the term "organic ammonium" is defined as a group consisting of a positively charged nitrogen atom joined to form one to four aliphatic groups, each containing from one to 20 carbon atoms. Among the organic ammonium groups which are illustrative for the preparation of the aliphatic ammonium salts of the imidazolidinyl acids of formulas I through VIII are: monoalkylammonium, dialkylammonium, trialkylammonium, tetraalkylammonium, monoalkenylammonium, dialkenylammonium trialkenylammonium, monoalkynylammonium, dialkynylammonium, trialkynylammonium, monoalkanolammonium, dialkanolammonium, trialkanolammonium, $C_5$–$C_6$ cycloalkylammonium, piperidinium, morpholinium, pyrrolidinium, benzylammonium and equivalents thereof.

As indicated above, the present invention relates to imidazolidinone and imidazolidinethione compounds represented by formula I, a process and intermediates for preparation thereof and a method for controlling a wide variety of undesirable monocotyledonous and dicotyledonous plant species. These formula I compounds are unique in both their structure and their herbicidal activity. Although imidazolinyl benzoic acids, esters and salts are described as herbicidal agents in U.S. Pat. No. 4,188,487, issued Feb. 20, 1980, and imidazolinyl pyridines and quinolines are described as herbicidal agents in European Patent Application No. 81103638.3, said publications do not render the compounds of this invention obvious, since neither publication discloses compounds having an imidazolidinyl function, nor suggests a process by which the compounds of the present invention can be prepared. Moreover, it is surprising to find that the formula I compounds of this invention are frequently found to be highly selective and/or have a different pattern of activity relative to given crops than is found for said imidazolinyl counterparts.

Advantageously, many substituted and unsubstituted aromatic and heteroaromatic imidazolidinone and imidazolidinethione compounds represented by formula I can be prepared by reduction of the corresponding imidazolinone or imidazolinethione with, for example, at least about an equimolar amount of sodium cyanoborohydride in the presence of a solvent such as a $C_1$–$C_4$ aliphatic alcohol, aqueous alcoholic mixture or ether, followed by acidification to a pH between about 2.5 and 5 and preferably between 3 and 4, with a strong mineral acid such as hydrochloric acid, or an organic acid such as acetic or the like. This reduction is generally conducted at a temperature between 0° and 40° C. and is particularly effective for treatment of 2-(2-imidazolinyl)nicotinic acids and esters, but preferably the esters. It is likewise effective for reduction of the imidazolinyl function of many imidazolinyl benzoic acids and esters. The process is likewise effective for reducing the imidazolinyl function of the formula V and VI 2-(2-imidazolinyl)thieno and furo[3,2-b]pyridine-6-carboxylic acid esters and the formula VII and VIII 2-(2-imidazolinyl)thieno and furo[2,3-b]pyridine-5-carboxylic acid esters; but appears to be ineffective for reducing the imidazolinyl function of 2-(2-imidazolinyl)quinoline-3-carboxylic acid esters.

The above-described reduction may be graphically illustrated as follows:

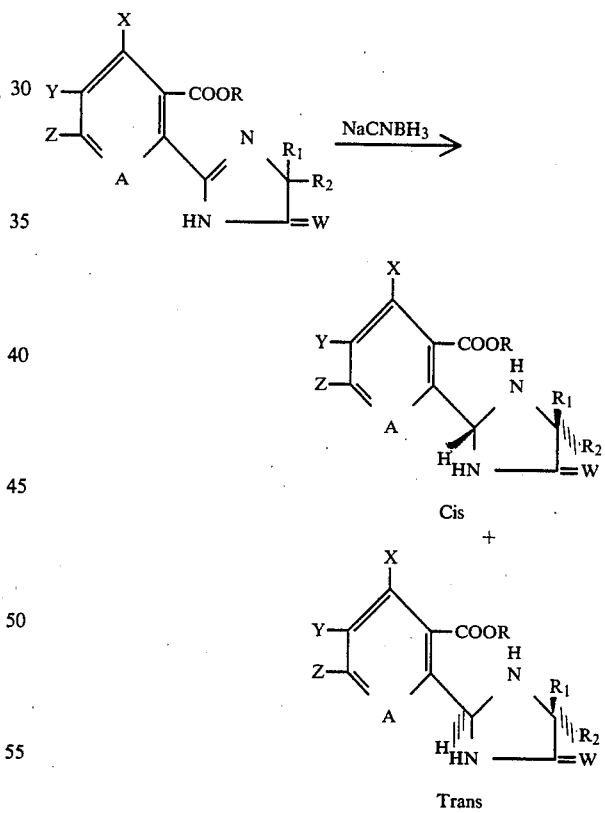

wherein R may be hydrogen, but preferably is a substituted or unsubstituted alkyl, alkenyl, alkynyl or cycloalkyl group as defined above in reference to formula I and $R_1$, $R_2$, W, X, Y. Z, and A are as defined in reference to said formula I, excepting that when A is —$CR_3$, $R_3$ cannot be fluorine.

As shown above, the imidazolidinones and imidazolidinethiones are obtained as a mixture of cis- and trans-isomers when $R_1$ and $R_2$ are not the same. These isomers are obtained in variable amounts. The mixtures are useful as such, but can frequently be separated chromatographically to give the pure cis- and trans-isomers, both of which are effective herbicidal agents.

Since the above-described reduction is not a universal method for the preparation of all substituted and unsubstituted aromatic and heteroaromatic imidazolidinones and imidazolidinethiones depicted by formula I, a variety of synthetic routes have been explored in order to provide effective procedures for the manufacture of the formula I imidazolidinones and imidazolidinethiones.

The reaction of an aldehyde of formula (X) with an amide of formula (IX) under acid catalysis is presumed to give the corresponding Schiff base as the initial product. Whether the Schiff base of general formula

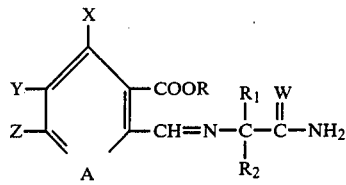

is isolated as such or cyclizes under the reaction conditions to the desired imidazolidinone depends on some unknown subtle factors. Nevertheless, if the Schiff base is isolated it can, in a separate reaction, by cyclized with trifluoroacetic acid to the imidazolidinone.

Accordingly, it has now been determined that the thioxo derivatives of the formula II 2-(2-imidazolidinyl)benzoates and both the oxo and thioxo derivatives of the formula III 2-(2-imidazolidinyl)nicotinates and the formula IV 2-(2-imidazolidinyl)quinoline-3-carboxylates can be synthesized by heating to refluxing temperature, a mixture of a formula IX aminoamide or aminothioamide with about an equimolar amount of an appropriate formula X substituted or unsubstituted alkyl, alkenyl, alkynyl or cycloalkyl 2-formylbenzoate, 2-formylpyridine-3-carboxylate or 2-formylquinoline-3-carboxylate, in the presence of an inert organic solvent such as benzene, toluene, or the like, and a strong organic acid, such as p-toluenesulfonic acid, under a blanket of nitrogen. These reactions may be graphically illustrated as follows:

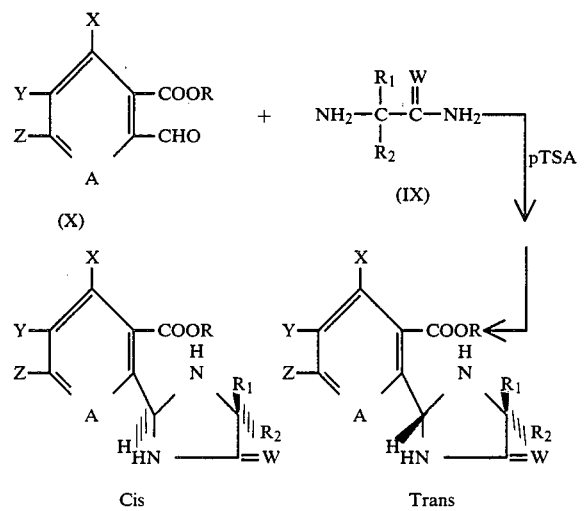

wherein R is a substituted or unsubstituted alkyl, alkenyl, alkynyl or cycloalkyl group as defined in reference to formula I and A, $R_1$, $R_2$, $R_3$, W, X, Y and Z are all as defined in reference to said formula I, with the proviso that (1) when A is $-CR_3$, W is S; and (2) when taken together, Y and Z may form a ring in which YZ are represented by (a) the structure: $-(CH_2)_n-$, where n is an integer selected from 2, 3 and 4, in which instance $R_3$ and X are each hydrogen; or (b)

where L, M, $R_7$ and $R_8$ each represent members from the group consisting of hydrogen, halogen, $C_1$–$C_4$ alkyl and $C_1$–$C_4$ alkoxy and $R_3$ and X are each hydrogen.

While the above procedure is effective for the synthesis of the thioxo derivatives of the formula II 2-(2-imidazolidinyl)benzoates and the oxo and thioxo derivatives of the 2-(2-imidazolidinyl)nicotinates and quinoline-3-carboxylates of formulas III and IV respectively, surprisingly, the reaction does not appear to lend itself to the preparation of the oxo derivatives of the formula II 2-(2-imidazolidinyl)benzoates without considerable modification.

To obtain the oxo derivatives of the formula II 2-(2-imidazolidinyl)benzoates, it has been found that approximately equimolar amounts of the formula XI substituted or unsubstituted alkyl, alkenyl, alkynyl or cycloalkyl 2-formylbenzoate and a formula XII aminoamide can be admixed and heated together in the presence of an organic acid such as p-toluenesulfonic acid and an aromatic solvent such as toluene, xylene or the like, to yield a Schiff base represented by formula XIII. This formula XIII Schiff base is then cyclized by treatment thereof with trifluoroacetic acid in the presence of a chlorinated hydrocarbon solvent such as methylene chloride. The reaction is preferably conducted under a blanket of nitrogen at a temperature between about $-5°$ and $+5°$ C. The reaction yields a mixture of cis- and trans-isomers of the formula XIV oxo-2-imidazolidinyl benzoate. The reaction may be illustrated as follows:

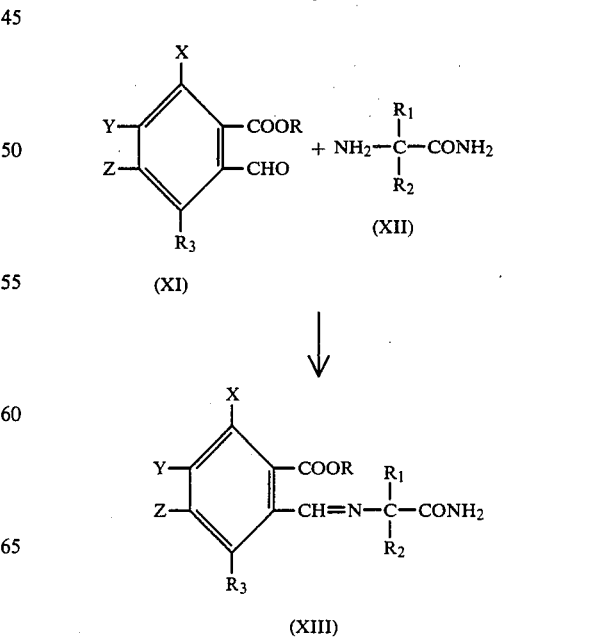

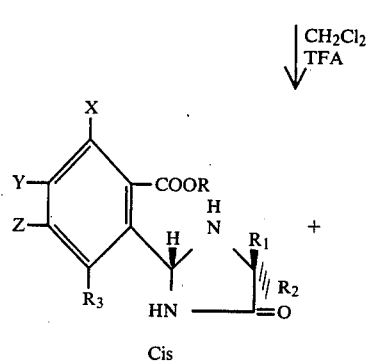

Cis

+

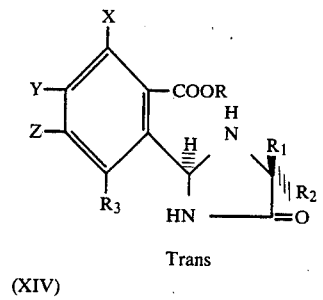

Trans (XIV)

Conversion of the esters of the formula I imidazolidinones and imidazolidinethiones to the corresponding acid addition salts thereof can be readily achieved by dispersing or dissolving said formula I imidazolidinone ester or imidazolidinethione ester in an organic solvent such as methylene chloride, chloroform, ether, or a $C_1$–$C_4$ aliphatic alcohol, and treating the thus-formed mixture with at least one equivalent and preferably an excess of a strong acid, particularly a strong mineral acid, such as hydrochloric acid, sulfuric acid, phosphoric acid, hydrobromic acid, or the like. The solvent may then be removed in vacuo and the residue crystallized from an organic solvent mixture such as ethyl acetate and ether to yield the corresponding formula I acid addition salt.

In a further embodiment of the invention, the formula I compounds, wherein R is hydrogen and $R_1$, $R_2$, $R_3$, W, X, Y, Z and A, are as defined therefore, can be prepared by dissolving or dispersing the formula I imidazolidinone ester or imidazolidinethione ester in a $C_1$–$C_4$ aliphatic alcohol, preferably absolute methanol, and admixing therewith at least one equivalent of strong base. In practice, the base is generally dissolved in water and the mixture heated to between about 20° and 50° C. The mixture is then cooled and adjusted to pH 6.5 to 7.5, and preferably about ph 7, with a strong mineral acid such as hydrochloric acid to yield the formula I imidazolidinone or imidazolidinethione wherein R is hydrogen and $R_1$, $R_2$, $R_3$, W, X, Y, Z and A are as defined for formula I compounds. The reaction can be illustrated as follows:

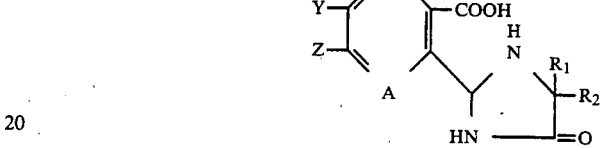

(I)

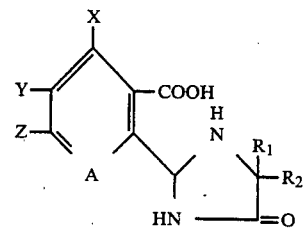

wherein R is other than hydrogen or a salt-forming cation, and $R_1$, $R_2$, W, X, Y, Z and A are as described with reference to formula I.

Formula I compounds, wherein R is a salt-forming cation, such as alkali metal or alkaline earth metal, and $R_1$, $R_2$, W, X, Y, Z and A are as defined for formula I, can be prepared by dissolving the salt-forming cation in a $C_1$–$C_4$ aliphatic alcohol, preferably absolute methanol, and admixing the formula I imidazolidinone acid or imidazolidinethione acid with the alcoholic solution of cation, preferably under a blanket of inert gas such as nitrogen, argon or the like, at a temperature between about 15° and 35° C. In this reaction, generally about one equivalent of salt-forming cation, such as sodium, potassium, calcium or barium, in the form of a hydroxide, carbonate, bicarbonate, or the like is used to convert one equivalent of the formula I acid to the corresponding alkali metal or alkaline earth metal salt.

To prepare the formula I compound in which R is ammonium or organic ammonium, the formula I acid is dissolved or dispersed in an organic solvent such as dioxane, tetrahydrofuran or the like, and the mixture treated with one equivalent of ammonia or the amine or the tetralkylammonium hydroxide. Among the amines which may be used in the above-said reaction are: methylamine, ethylamine, n-propylamine, isopropylamine, n-butylamine, isobutylamine, sec-butylamine, n-amylamine, iso-amylamine, hexylamine, heptylamine, octylamine, nonylamine, decylamine, undecylamine, dodecylamine, tridecylamine, tetradecylamine, pentadecylamine, hexadecylamine, heptadecylamine, octadecylamine, methylethylamine, methylisopropylamine, methylhexylamine, methylnonylamine, methylpentadecylamine, methyloctadecylamine, ethylbutylamine, ethylheptylamine, ethyloctylamine, hexylheptylamine, hexyloctylamine, dimethylamine, diethylamine, di-n-propylamine, diisopropylamine, di-n-amylamine, diisoamylamine, dihexylamine, diheptylamine, dioctylamine, trimethylamine, triethylamine, tri-n-propylamine, triisopropylamine, tri-n-butylamine, triisobutylamine, tri-sec-butylamine, tri-n-amylamine, ethanolamine, n-propanolamine, isopropanolamine, diethanolamine, N,N-diethylethanolamine, N-ethylpropanolamine, N-butylethanolamine, allylamine, n-butenyl-2-amine, n-pentenyl-2-amine, 2,3-dimethylbutenyl-2-amine, dibutenyl-2-amine, n-hexenyl-2-amine, propylenediamine, tallowamine, cyclopentylamine, cyclohexylamine, dicyclohexylamine, piperidine, morpholine, and pyrrolidine. Among tetralkylammonium hydroxides contemplated are: methyl, tetraethyl, trimethylbenzylammonium hydroxides. In practice, the ammonium or organic ammonium salt precipitates and can be separated from the solution by any convenient means, as by filtration or centrifugation, or the reaction mixture may be concentrated, and the remaining solvent removed with hexane, and the residue then dried to recover the ammonium or organic ammonium formula I salt. The reactions for the conversion of the formula I acids of the formula I salts described above may be graphically illustrated as follows:

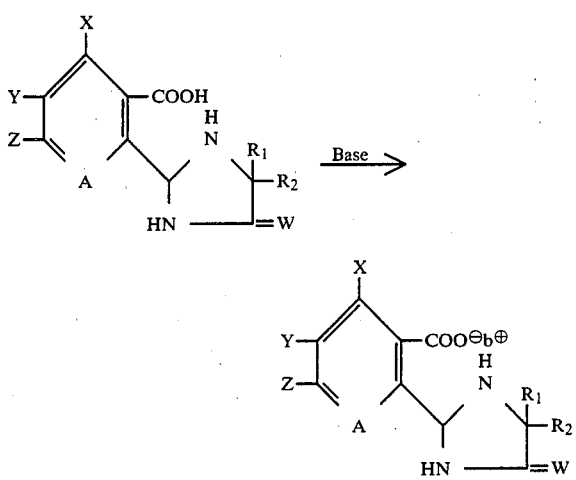

wherein $R_1$, $R_2$, W, X, Y, Z and A are as described in reference to formula I above and b is a salt-forming cation.

When $R_1$ and $R_2$ represent different substituents, the carbon to which $R_1$ and $R_2$ are attached is an asymmetric carbon, and the products (as well as their intermediates) exist in d- and l-forms as well as dl-forms.

As indicated above, the novel herbicidally effective formula I imidazolidinones and imidazolidinethiones of this invention, as illustrated by formula I, demonstrate significant chemical and biological similarities, provided that the integrity of the compound structure is maintained as expressed above.

Although the final products of the present invention, as depicted by formula I, are chemically and biologically similar, quite obviously, as the aromatic or heteroaromatic function is altered, so also are the intermediates, and the processes, for the preparation thereof altered. Therefore, the syntheses for the several preferred aromatic and heteroaromatic functions will be, hereinafter, discussed separately for the purpose of clarity.

The 5-oxo derivatives of imidazolinyl benzoic acids, esters and salts containing either no or one nitro, halogen, or $C_1$-$C_3$ alkyl group and a carboxylic acid function on the aromatic ring of the imidazolinyl benzoic acid, ester or salt are described in U.S. Pat. No. 4,188,487. The patented compounds are excellent herbicidal agents, but if the food requirements for the ever-expanding world population are to be met, still more effective and more selective herbicidal agents will be required to selectively protect crops from weed encroachment.

Although the present invention includes, as intermediates, certain of the patented oxo derivatives of 2-imidazolidinyl benzoic acids, esters and salts that contain a carboxylic acid function and either no or one substituent on the aromatic ring, the patentee does not teach or suggest the imidazolidinyl compounds of the present invention nor does it teach or suggest any method for obtaining the formula II 2-(2-imidazolidinyl)benzoic acids, esters or salts of the present invention from the patented compounds.

Accordingly, the intermediates necessary for the preparation of the formula II 2-(2-imidazolidinyl)benzoic acids, esters and salts of the present invention represented by the structure:

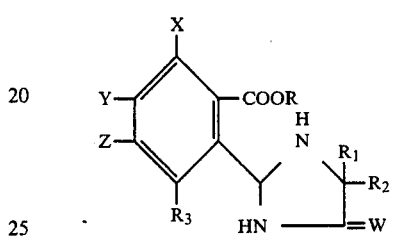

where R, $R_1$, $R_2$, $R_3$, W, X, Y and Z are as described above, can be prepared by reaction of an appropriately substituted formula XV benzoic acid with thionyl chloride and a catalytic amount of dimethylformamide. The mixture is admixed with an anhydrous aromatic solvent such as toluene, xylene or the like, and the solvent evaporated. The remaining residue is then diluted with an anhydrous non-protic solvent such as tetrahydrofuran and the resulting mixture admixed with a solution of a di($C_1$-$C_3$)alkylamine in anhydrous non-protic solvent. This reaction is preferably conducted under a blanket of inert gas at a temperature between about $-10°$ to $+10°$ C. and yields the formula XVI, substituted N,N-di($C_1$-$C_3$)alkylbenzamide. The formula XVI substituted benzamide is thereafter treated with sec-butyl lithium in an anhydrous non-protic solvent such as tetrahydrofuran (THF) in the presence of N,N,N',N'-tetramethylethylenediamine (TMEDA). The reaction mixture is preferably maintained under a blanket of inert gas, such as nitrogen, at a temperature between about $-75°$ and $-65°$ C. Thereafter, the reaction mixture is admixed with anhydrous THF saturated with carbon dioxide, then mixed with water. The aqueous phase is separated, cooled to between 0° and 10° C. and acidified to yield the formula XVII substituted phthalic acid. These reactions may be illustrated as follows:

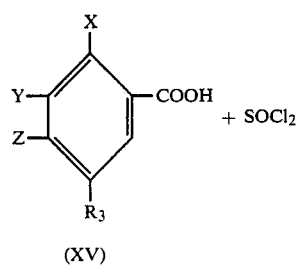

(XV)

1. Cat. DMF
2. HN(alkyl)$_2$

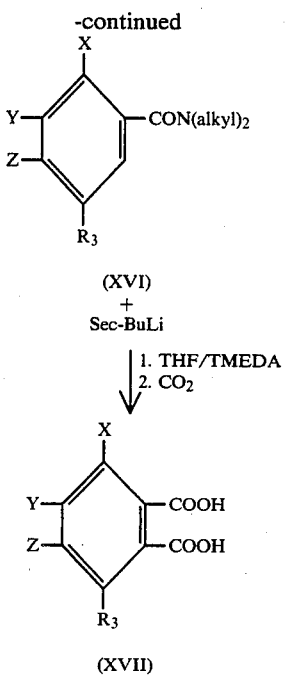

wherein X, Y, Z, and $R_3$ are as described in reference to formula III compounds excepting that $R_3$ cannot be fluorine.

The formula XVII substituted phthalic acid is treated with an excess of acetic anhydride, heated to refluxing temperature and concentrated in vacuo with anhydrous aromatic solvent such as toluene, xylene or the like, to obtain the substituted phthalic anhydride of formula XVIII. The substituted phthalic anhydride is then dissolved in anhydrous non-protic solvent such as THF and treated with an equimolar amount of a formula XIX α-aminocarbonitrile such as 2-amino-2,3-dimethylbutyronitrile and a trialkylamine such as triethylamine or trimethylamine at a temperature between about 20° and 30° C. Thereafter, the solvent is removed and the remaining residue heated to refluxing temperature in an excess of acetic anhydride to yield the substituted 1,3-dioxo-2-isoindoline alkylnitrile of formula XXI. It should be understood that when X, Y, Z or $R_3$ are hydroxyalkyl or $NHR_5$, these groups are protected as their acetyl derivative prior to treatment of the acids or diacids with thionyl chloride or acetic anhydride. The acetyl protecting group is then removed after or during the formation of the imidazolinone ring.

Alternatively, the formula XVIII substituted phthalic anhydride may be reacted with an equimolar amount of a formula XIX substituted α-aminocarbonitrile by heating the mixture to refluxing temperature in the presence of a chlorinated hydrocarbon solvent such as ethylene chloride, methylene chloride, dichloroethane or the like, to yield an isomeric mixture of the formula XXa and XXb monoamides of phthalic acid. The thus-formed acids may then be cyclized to the substituted 1,3-dioxo-2-isoindolinealkylnitrile depicted by formula XXI, by heating the reaction mixture to between about 20° and 100° C., with an excess of acetic anhydride, preferably in the presence of a catalytic amount of sodium acetate or potassium acetate. Hydration of the thus-formed substituted 1,3-dioxo-2-isoindolinealkylnitrile formula XXI is carried out by treating said formula XXI nitrile with a strong acid such as sulfuric acid containing a small amount of water. This reaction yields the formula XXII substituted 1,3-dioxo-2-isoindolinealkylamide and is generally conducted at a temperature between about 30° and 60° C. After heating, the mixture may be poured over ice and extracted with a chlorinated hydrocarbon such as chloroform, methylene chloride or the like. The solvent is then removed preferably by concentration in vacuo. Ring opening of the formula XXII substituted 1,3-dioxo-2-isooindolinealkylamide is achieved by treatment thereof with an equimolar amount of sodium methoxide in the presence of a lower alkyl alcohol, preferably at a temperature between about 20° and 30° C. The reaction mixture is thereafter neutralized to pH 7 with acetic acid to yield an isomeric mixture of the carbamoyl phthalamic acid esters illustrated by formulas XXIIIa and XXIIIb. Cyclization of the carbamoyl phthalamic acid esters can then be achieved by reaction thereof with approximately a 2-molar equivalent excess of phosphorous pentachloride in the presence of anhydrous toluene at a temperature between about 20° and 30° C. The reaction mixture is poured over ice to give the hydrochloride salt of the corresponding 2-(2-imidazolin-2-yl)benzoate depicted by formulas XXIVa and XXIVb. Treatment of the formulas XXIVa and XXIVb hydrochlorides with one equivalent of a base such as an alkali metal bicarbonate, carbonate hydroxide then gives the methyl benzoates as depicted in formulas XXIVa and XXIVb.

The above reactions are graphically illustrated in Flow Diagram I below.

FLOW DIAGRAM I

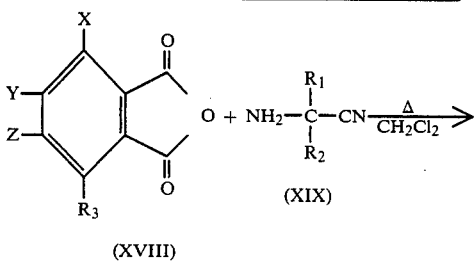

FLOW DIAGRAM I -continued

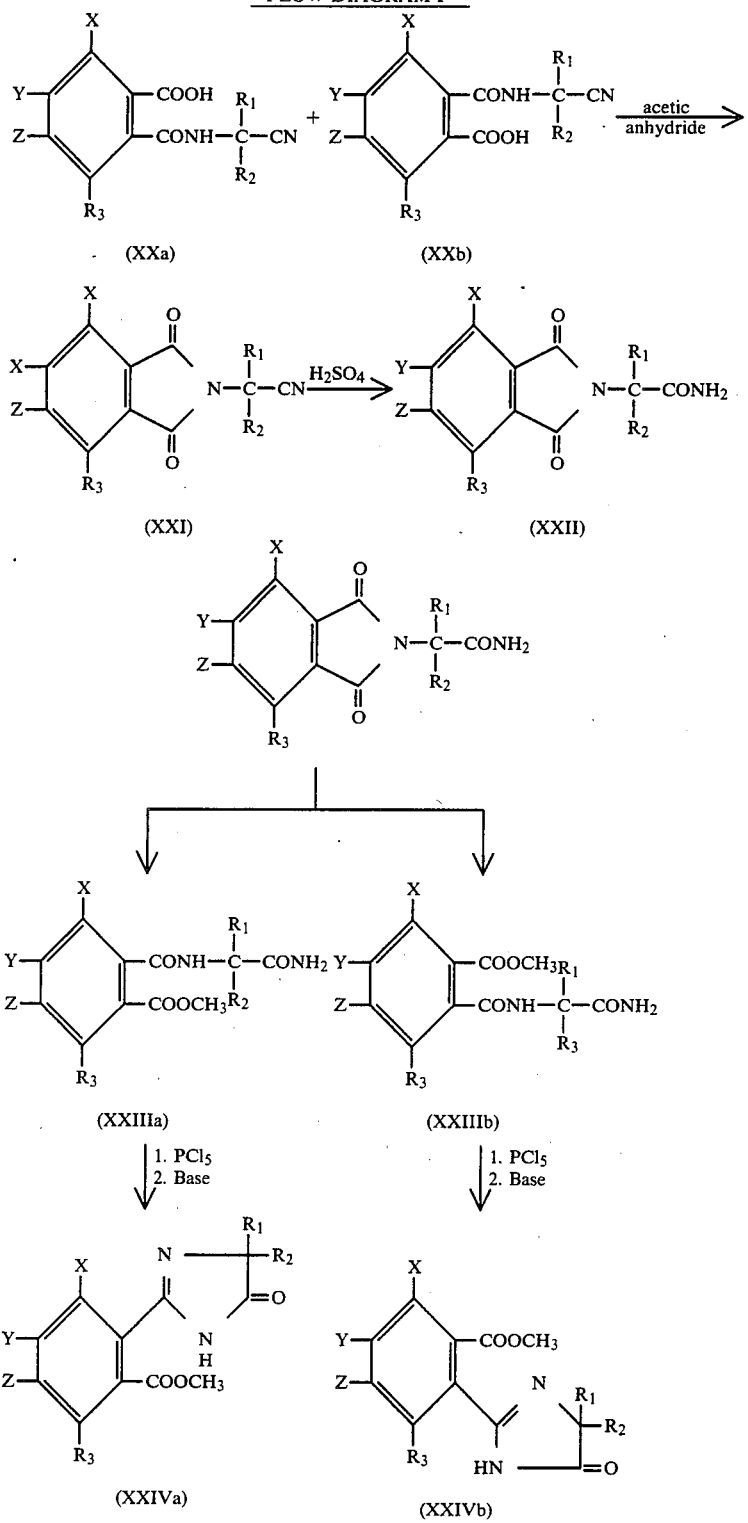

A preferred method for preparing the formula XXVIIIa and XXVIIIb substituted 5-oxo(and thioxo)-2-imidazolin-2-yl)benzoic acids, which are useful intermediates in the preparation of the formula II oxo and thioxo 2-(2-imidazolidinyl)benzoic acids, involves the preparation of the substituted or unsubstituted formula XVIII phthalic anhydride by reaction of a formula XVII substituted or unsubstituted phthalic acid with acetic anhydride, dimethoxyethane and pyridine. The thus-prepared phthalic anhydride of formula XVIII is then admixed with an equivalent amount of a formula XXVI carboxamide or thiocarboxamide, in the presence of an inert organic solvent such as a low-boiling ether (diethyl ether, tetrahydrofuran, dimethoxyethane)

acetonitrile, ethyl acetate or a halogenated hydrocarbon, at a temperature between 20° and 60° C. and preferably 25° to 30° C. under a blanket of inert gas such as nitrogen. When the reaction is essentially complete, the product is isolated by convenient means, e.g., filtration, distillation of the solvent or by extraction into aqueous base if the solvent is water immiscible. The reaction yields the isomeric phthalamic monoacid/monoamide products, formulas XXVIIa and XXVIIb.

The thus-formed mixture is then heated to about 25° to 100° C., with about 2 to 10 molar equivalents of aqueous alcoholic sodium or potassium hydroxide. The reaction is preferably conducted under a blanket of inert gas, such as nitrogen. If the product is insoluble in water, it will precipitate from the aqueous phase and be recovered by filtration or extraction. If the product is soluble in water, the mixture can be extracted with an organic solvent such as ether, methylene chloride or the like, and the extract concentrated to provide an isomeric mixture of the formula XXVIIIa and XXVIIIb substituted or unsutstituted 2-(5-oxo(or thioxo)-2-imidazolin-2-yl)benzoic acids. With compounds of formula XXVIIIa and XXVIIIb, where W is sulfur, conversion thereof to the corresponding formula II substituted or unsubstituted 2-(5-thioxo-2-imidazolidinyl)benzoic acid or benzoic acid isomeric mixture can be achieved by reduction with NaCNBH$_3$ as described above. It has also been found that certain of the formula XXVIIIa and XXVIIIb compounds, where W is oxygen, will undergo reduction with sodium cyanoborohydride to yield the corresponding formula II 5-oxo-2-(2-imidazolidinyl)benzoic acids. However, depending on the substitution on the aromatic ring of said compounds, some formula XXVIIIa and XXVIIIb compounds are found resistant or are not amenable to reduction with sodium cyanoborohydride. Thus, where it is found that the formula XXVIIIa and XXVIIIb oxo derivatives are not amenable to the above-said reduction, preparation of the formula II 5-oxo derivatives of the 2-(2-imidazolidinyl)benzoic acids and/or esters by the aldehyde route, as described above, is recommended. The above reactions are graphically illustrated in Flow Diagram II below.

FLOW DIAGRAM II

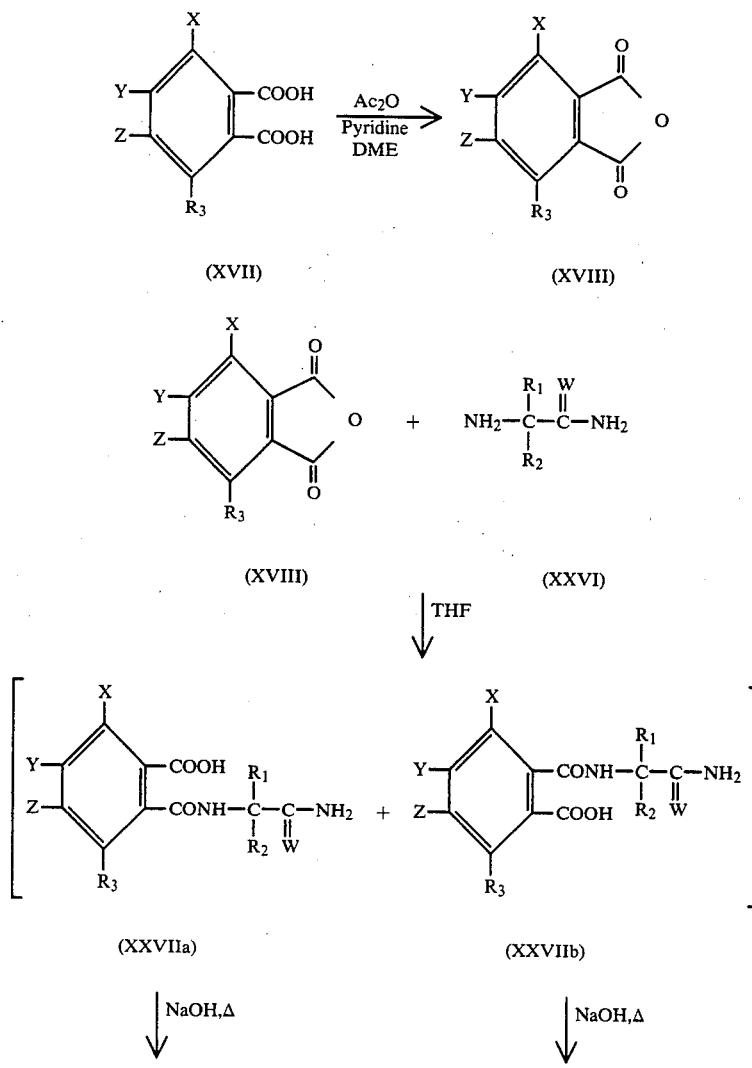

FLOW DIAGRAM II

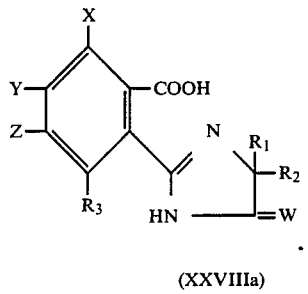
(XXVIIIa)

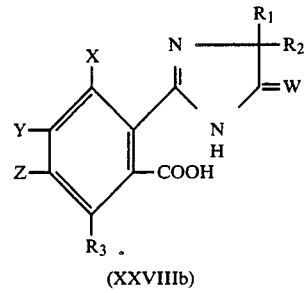
(XXVIIIb)

From the above discussions, it can be seen that many synthetic routes to the formula II 2-(2-imidazolidinyl)-benzoic acids and/or esters yield mixtures of the herbicidally effective acid or ester isomers. While these isomeric mixtures have been found to be very effective for the selective control of undesirable plant species, it has also been determined that, not infrequently, one of the isomers is somewhat more effective and/or selective than the other. Thus, it is sometimes desirable to direct a synthesis to a single isomer.

As an example of a synthetic route to a single isomer, formula XXIX, 3-nitrophthalic anhydride, may be dispersed or dissolved in an excess of $C_1$–$C_3$ alcohol and heated to refluxing temperature, generally between about 60° and 100° C. After refluxing, the alcohol is evaporated in vacuo and the residue recrystallized from ethyl acetate to yield the ring-opened formula XXX, 2-alkyl 3-nitrophthalate. The formula XXX compound is then dispersed in thionyl chloride and the resulting mixture maintained at a temperature between about 20° and 40° C. until the reaction is essentially complete. The mixture is concentrated and the residue taken up in an aromatic solvent such as toluene and concentrated again to yield the formula XXXI alkyl 2-(chlorocarbonyl)-6-nitrobenzoate. This formula XXXI nitrobenzoate is then admixed with about an equimolar amount of a formula XIX substituted α-aminocarboxamide and heated to refluxing temperature in the presence of a non-protic solvent such as tetrahydrofuran and a trialkylamine to yield the formula XXXII carbamoyl-6-nitrophthalamate. Cyclization of said formula XXXII carbamoyl-6-nitrophthalamate to the formula XXXIII 2-(2-imidazolin-2-yl)-6-nitrobenzoate can then be achieved with phosphorus pentachloride at an elevated temperature, generally between 60° and 100° C. The reaction is preferably conducted in the presence of an inert organic solvent, such as toluene or benzene. The above reactions are graphically illustrated in Flow Diagram III below.

FLOW DIAGRAM III

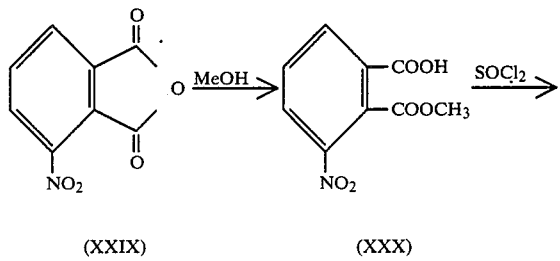
(XXIX)    (XXX)

-continued
FLOW DIAGRAM III

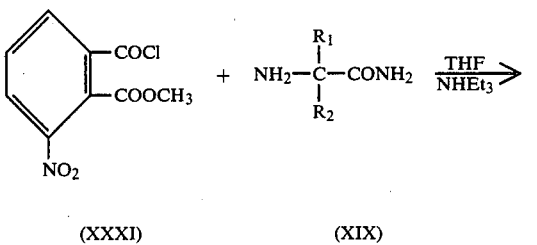
(XXXI)    (XIX)

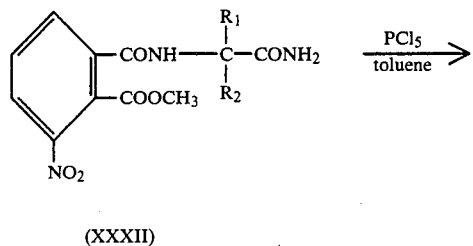
(XXXII)

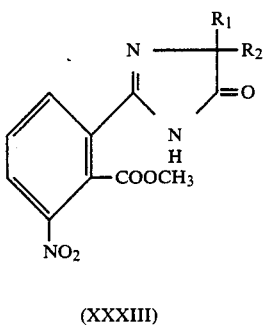
(XXXIII)

Another method for preparing mono-substituted and multi-substituted 2-(2-imidazolinyl)benozic acids and esters, many of which are useful intermediates in the preparation of the imidazolidinones and imidazolidinethiones of the present invention via reduction with sodium cyanoborohydride, involves the reaction of a formula XV, substituted benzoic acid with thionyl chloride and a catalytic amount of dimethylformamide to give the formula XXXIV substituted benzoylchloride. The reaction is preferably heated to between 25° and 40° C. and then evaporated in vacuo with an anhydrous aromatic solvent such as toluene, to give the substituted benzoyl chloride. The thus obtained substituted benzoyl chloride is then admixed with equimolar amounts of a formula XXVI carboxamide or thiocarboxamide and a trialkylamine, such as triethylamine, triisopropylamine of the like, in the presence of an non-protic solvent such as tetrahydrofuran. During addition of the reactants, the reaction mixture is generally maintained at a temperature between about 0° and 15° C. When addition is complete, the mixture is allowed to warm to ambient temperature, then treated with water and extracted with an organic solvent such as ethyl acetate to obtain the N-substituted benzamide of formula XXXV. The thus-formed N-substituted benzamide is then heated to a temperature of from 25° to 110° C. with about 2 to 10 molar equivalents of aqueous or aqueous alcoholic sodium or potassium hydroxide, preferably under a blanket of inert gas such as nitrogen. The reaction yields of the formula XXXVI substituted phenyl imidazolinone or imidazolinthione, which can be converted to the corresponding substituted (5-oxo(or 5-thioxo)-2-imidazolin-2-yl)benzoic acid depicted by formula XXXVII, using sec-butyl lithium and carbon dioxide. This reaction is preferably carried out by dissolving or dispersing the formula XXXVI substituted phenyl imidazolinone or imidazolinthione in tetrahydrofuran or other non-protic solvent and about three equivalents of tetramethylenediamine under a blanket of inert gas such as nitrogen. The reaction mixture is maintained at a temperature between about −70° and −50° C. and then treated with a solution of sec-butyl lithium in cyclohexane. Thereafter the reaction mixture is admixed with tetrahydrofuran saturated with carbon dioxide to yield the formula XXXVII substituted (5-oxo(or thioxo)-2-imidazolin-2-yl)benzoic acid. These reactions are illustrated graphically in Flow Diagram IV below.

FLOW DIAGRAM IV

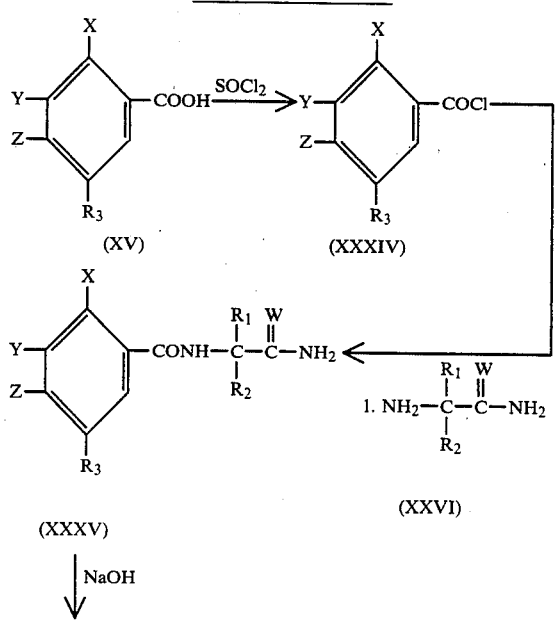

(XV)

(XXXIV)

(XXXV)

(XXVI)

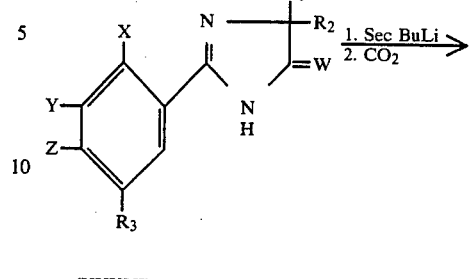

(XXXVI)

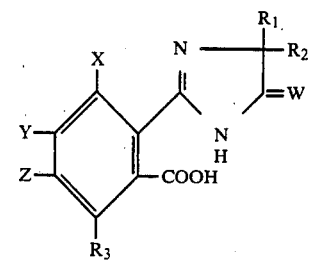

(XXXVII)

Alternatively, the formula XV substituted benzoic acid may be converted to the formula XXXIV benzoyl-chloride, as described above. Thereafter, the benzoyl-chloride is dispersed in tetrahydrofuran and admixed with a solution of 3 to 5 and preferably about 4 equivalents of diethylamine in tetrahydrofuran. Addition is generally conducted under a blanket of nitrogen while maintaining the temperature of the reaction mixture between about −10° and 0° C. The reaction yields the formula XXXVII substituted benzamide. The abovesaid substituted benzamide may then be dissolved in anhydrous tetrahydrofuran and treated with an equivalent amount of sec-butyl lithium dispersed in cyclohexane. This treatment is generally conducted under a blanket of nitrogen, while maintaining the temperature of the reaction mixture between about −70° and −50° C. Thereafter, the reaction mixture is admixed with anhydrous tetrahydrofuran saturated with carbon dioxide to yield the formula XXXIX substituted phthalamic acid. Treatment of a stirred solution of the substituted phthalamic acid in dry tetrahydrofuran with ethyl chloroformate followed by triethylamine and a solution of a formula XXVI carboxamide or thiocarboxamide in anhydrous tetrahydrofuran, yields the substituted N,N-diethylphthalamide of formula XL. Base cyclization of the formula XL substituted N,N-diethylphthalamide can be achieved by heating said formula XL compound with from 2 to 10 molar equivalents of aqueous or aqueous alcoholic sodium or potassium hydroxide to a temperature between about 25° and 110° C., preferably under a blanket of nitrogen. This reaction yields the formula XLI substituted N,N-diethyl(5-oxo(or thioxo)-2-imidazolin-2-yl)benzamide, which is readily converted to the corresponding acid of formula XLIII by heating with a concentrated mineral acid such as concentrated hydrochloric or hydrobromic acid. After acidification, the mixture is cooled, basified to a pH between 7 and 10, with alkali metal hydroxide, such as sodium hydroxide or potassium hydroxide and then carefully acidified to pH 3 with concentrated sulfuric acid. The formula XLI substituted N,N-diethyl(5-oxo(or thioxo)-2-imidazolin-2-yl)benzamide salt also undergoes transesterification with methanol and hydrogen chloride, yielding the corresponding formula XLII methyl ester of the said formula XLI N,N-diethylaminobenzamide. Treatment of the formula XLII substituted methyl(5-oxo(or thioxo)-2-imidazolin-2-yl)benzoate with aqueous or aqueous alcoholic alkali metal hydroxide at an elevated temperature between about 60° and 100° C., followed by acidification with hydrochloric acid then yields the formula XLIII substituted (5-oxo(or thioxo)-2-imidazolin-2-yl)benzoic acid. These reactions are illustrated in Flow Diagram IVa below. While such reactions are generically illustrated with regard to substituents for $R_1$, $R_2$, $R_3$, X, Y, Z and W, it should be noted that these reactions are especially applicable to compounds wherein W is oxygen, A is $CR_3$, $R_3$ is fluorine and R, $R_1$, $R_2$, X, Y and Z are as described with regard to the formula XLI, XLII and XLIII substituted (5-oxo-2-imidazolin-2-yl)benzoic acids, esters and salts.

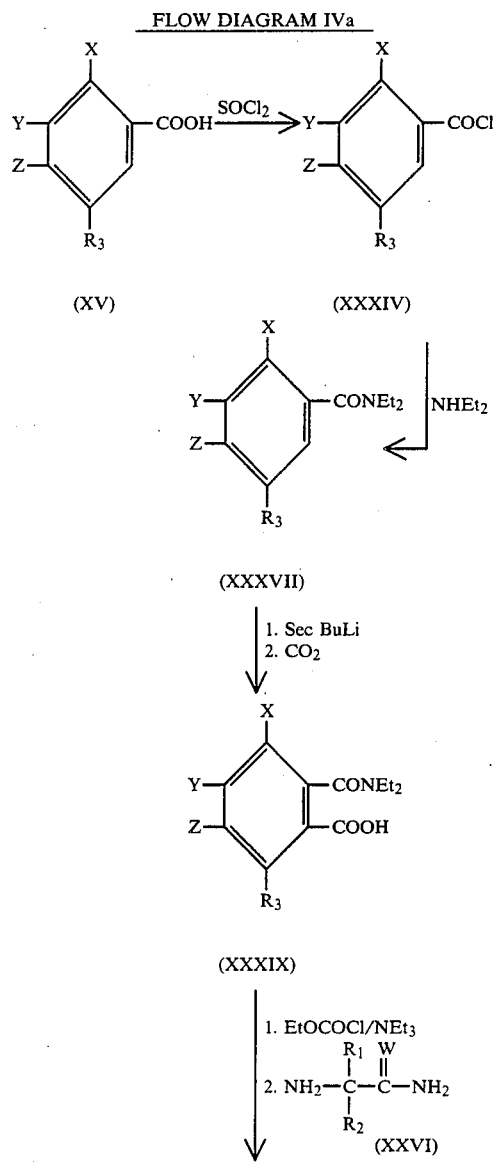

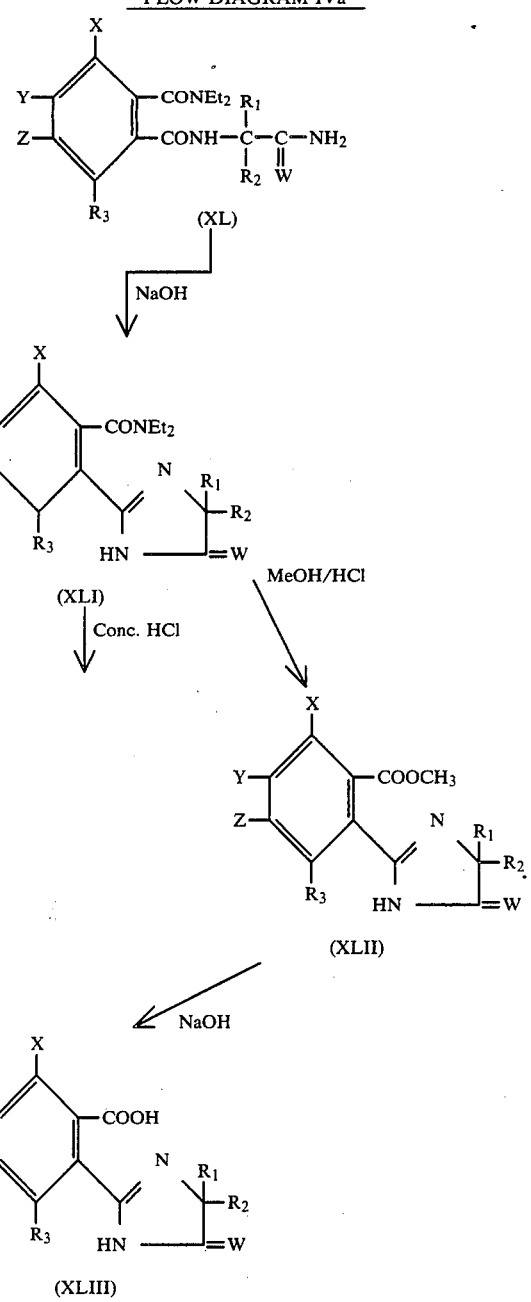

An alternative process for the preparation of substituted 2-(5-oxo(or thioxo)-2-imidazolin-2-yl)benzoic acids, involves the reaction of a substituted benzoyl chloride with a formula XXVI carboxamide or thiocarboxamide in the presence of a trialkylamine and a solvent such as tetrahydrofuran, to obtain an N-substituted benzamide. This N-substituted amide is then heated to 25° to 110° C. with an excess of aqueous or aqueous alcohol sodium or potassium hydroxide to yield a formula XLIV substituted phenyl imidazolinone or imidazolinethione. These reactions are similar to the initial reactions described above and illustrated in Flow Diagram IV. However, where it is desirable to provide an additional $C_1$-$C_3$ alkyl substituent on the substituted ring of the above-mentioned formula XLIV, imidazolinone or imidazolinethione, said imidazolinone or imidazolinethione may be dissolved in anhydrous tetrahydrofuran and treated with sec-butyl lithium, preferably dissolved in cyclohexane or other aromatic solvent. The addition of the sec-butyl lithium to the imidazolinone or imidazolinethione is preferably conducted over an extended period of time, up to several hours, while maintaining the reaction mixture at a temperature between about −50° and −75° C. When addition is complete, the reaction mixture is permitted to warm to between about −30° and −50° C. and then admixed with a $C_1-C_3$ alkyl iodide dispersed in tetrahydrofuran. After stirring the reaction mixture is allowed to warm to ambient temperature and then the solvent is evaporated in vacuo to obtain the formula XLV multi-substituted product. Reaction is graphically illustrated in Flow Diagram V, using methyl iodide and sec-butyl lithium for illustration.

Where it is desirable to provide a halogen substituent on the aromatic ring of the formula XLIV substituted imidazolinone or imidazolinethione, said substituted imidazolinone or imidazolinethione is dissolved in an anhydrous non-protic solvent such as tetrahydrofuran and treated with sec-butyl lithium dissolved in cyclohexane. The addition is made over a period of from about 0.5 to 2.0 hours while maintaining the reaction mixture at a temperature below about −50° C. The mixture is then warmed to a temperature between about −30° and −40° C. and halogenated with a halogenating agent such as hexachloroethane or the like, preferably dispersed in an anhydrous non-protic solvent such as tetrahydrofuran. the mixture is then permitted to warm to ambient temperature treated with iced saturated brine and then acidified to pH 3 with a strong mineral acid. Thereafter, the formula XLVI halogenated product is extracted from the reaction mixture with an organic solvent such as ether. This formula XLVI halogenated imidazolinone or imidazolinethione is then readily converted to the corresponding formula XLVII, substituted 2-(5-oxo(or thioxo)-2-imidazolin-2-yl)benzoic acid by reaction of said halogenated imidazolinone or imidazolinethione with sec-butyl lithium in the presence of tetrahydrofuran and tetramethylenediamine under a blanket of nitrogen, followed by admixture of the thus-prepared reaction mixture with anhydrous tetrahydrofuran, saturated with carbon dioxide. The formula XLVII product may be recovered from the reaction mixture by dispersing said mixture in water and acidifying the same with a strong mineral acid. The organic phase is then separated from the mixture and extracted with base. The aqueous phase is separated and acidified with mineral acid to yield the desired product. These reactions are illustrated in Flow Diagram V below.

FLOW DIAGRAM V

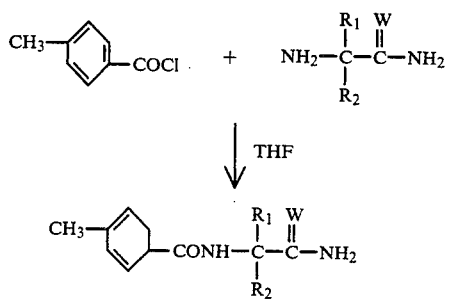

-continued
FLOW DIAGRAM V

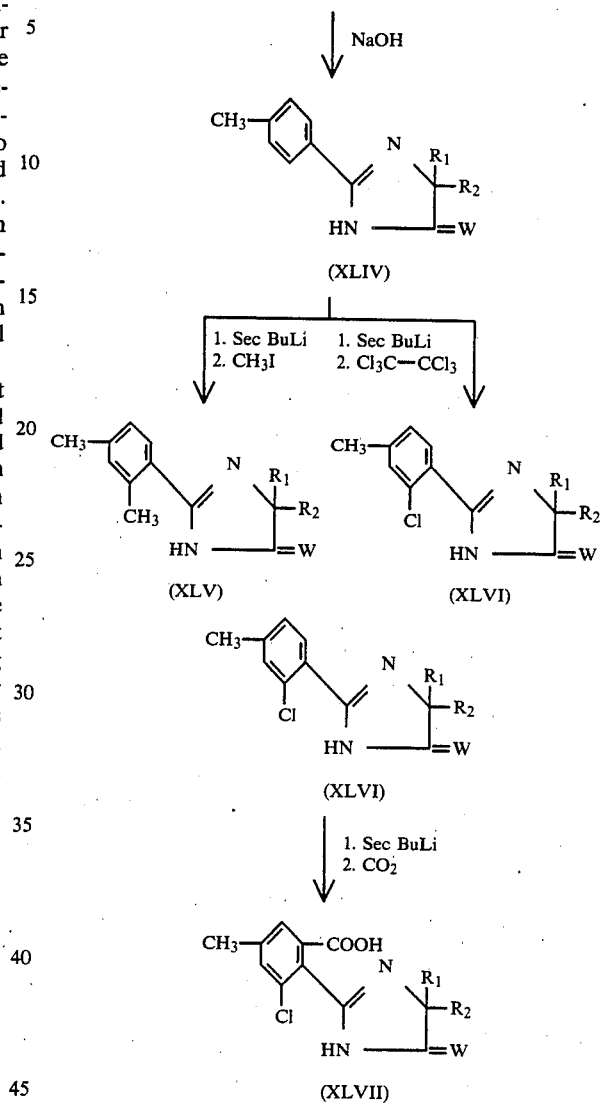

Another alternate route to the preparation of substituted (5-oxo(or thioxo)-2-imidazolin-2-yl)benzoic acids, esters and salts is graphically illustrated in Flow Diagram VI below. From this flow sheet, it can be seen that a substituted benzoyl chloride is treated with about 3 to 5 equivalents of a di-$C_1-C_3$ alkylamine, such as diethylamine in tetrahydrofuran to yield the corresponding substituted benzamide. This substituted benzamide may then be halogenated, if desired, after treatment thereof with sec-butyl lithium in the presence of tetrahydrofuran or other similar solvent. The sec-butyl lithium is generally dissolved in cyclohexane and added to the benzamide containing reaction mixture while maintaining the temperature thereof below −50° C., e.g. −50° to −75° C. When addition is complete, the mixture is warmed to −30° to −40° C. and a halogenating agent, such as hexachloroethane, dispersed in a non-protic solvent added thereto. This yields the halogenated derivative of the substituted benzamide which is readily converted to the corresponding substituted phthalamic acid by reaction with sec-butyl lithium in tetrahydrofuran and tetramethylenediamine under a blanket of nitrogen, followed by admixture of the thus-prepared composition with tetrahydrofuran saturated with carbon dioxide. Reaction of the thus-formed substituted phthalamic acid, with ethylchloroformate followed by triethylamine and a solution of a formula XXVI carboxamide or thiocarboxamide in anhydrous tetrahydrofuran, yields the substituted N,N-diethylphthalamides which undergoes base cyclization when heated to 25° to 110° C., with aqueous or aqueous alcoholic sodium or potassium hydroxide. The reaction provides a substituted benzamide which is readily converted to the corresponding acid by treatment with strong mineral acid or to the corresponding ester by transesterification with a $C_1$–$C_3$ alcohol, such as methanol and a strong mineral acid, as shown in Flow Diagram VI. The thus-prepared ester may then be heated with an alkali metal hydroxide and acidified with strong mineral acid to provide the substituted (5-oxo(or thioxo)-2-imidazolin-2-yl)benzoic acid. These reactions are illustrated in Flow Diagram VI below, where it can be seen that the final steps of this synthesis route are similar to the latter stages of the preparations illustrated in Flow Diagram IV, although the early stages of the systems differ. It should also be noted that this reaction sequence results in the formation of an isomer of the compound prepared by Flow Diagram V.

FLOW DIAGRAM VI

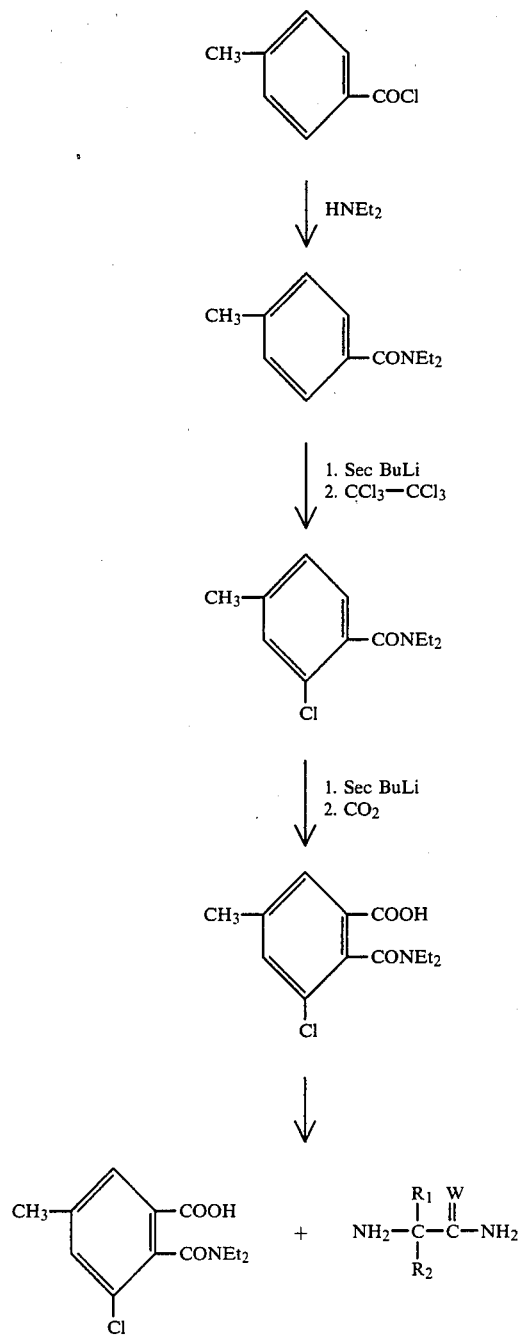

FLOW DIAGRAM VI

-continued

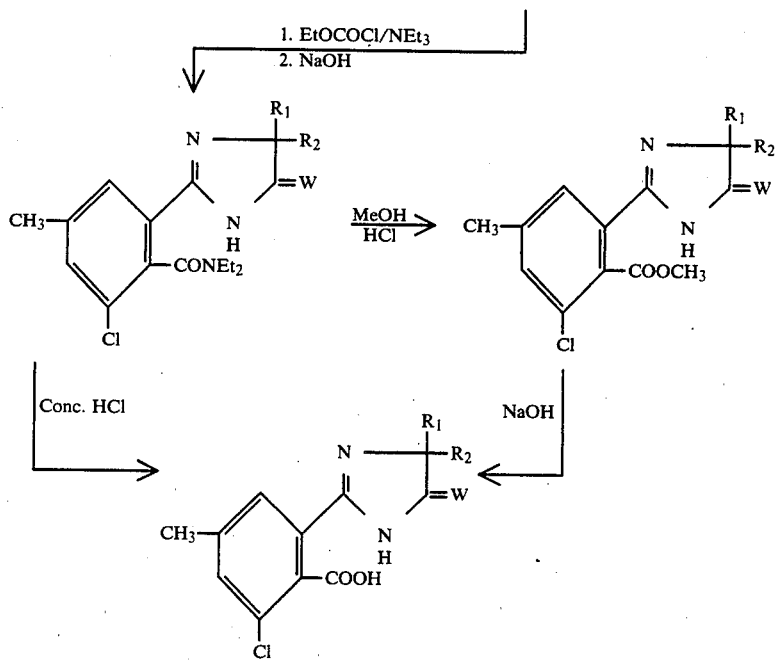

Preparation of formula II (5-oxo-2-imidazolidinyl)-benzoic acids, esters and salts, having a 3-fluoro substituent, with or without additional substituents in the 4, 5 and/or 6 positions of the aromatic ring, can be achieved starting with the appropriately substituted formula XlVIII fluoro-N,N-dialkylbenzamide, such as fluoro-N,N-diethylbenzamide. The synthesis involves reaction of the appropriately substituted fluoro-N,N-diethylbenzamide with sec-butyl lithium under a blanket of nitrogen, preferably in the presence of tetrahydrofuran and at a temperature between about −70° and −50° C. Thereafter, the reaction mixture is treated with anhydrous dimethylformamide while maintaining the temperature thereof between −50° and −70° C. After warming to ambient temperature, the mixture is treated with brine and extracted with an organic solvent such as ethyl acetate. The aqueous phase is separated and acidified with a strong mineral acid to pH 3–4 to yield the formula XLIX 4-fluoro-3-hydroxyphthalide or substituted 4-fluoro-3-hydroxyphthalide. The thus-obtained 4-fluoro-3-hydroxyphthalide is then mixed with an alkali metal carbonate such as sodium or potassium carbonate and at least an equimolar amount of a $C_1$–$C_3$ alkyl iodide such as methyl iodide and a loweralkyl ketone such as acetone. Heating the resulting mixture to refluxing temperature yields the formula L 3-fluoro-2-formylbenzoate or the substituted 3-fluoro-2-formylbenzoate.

The thus-formed 3-fluoro-2-formylbenzoate or substituted 3-fluoro-2-formylbenzoate is then admixed with approximately an equimolar amount of an appropriately substituted formula XII aminoamide and heated in the presence of an organic acid such as p-toluenesulfonic acid and an aromatic solvent such as toluene, xylene or the like, to give the formula LI 3-fluoro(carbamoyl)formimidoyl benzoate. This 3-fluoro(carbamoyl)formimidoyl benzoate is then cyclized by treatment with trifluoroacetic acid in the presence of a chlorinated hydrocarbon solvent such as methylene chloride, dichloroethane or chloroform. The reaction is preferably conducted under a blanket of inert gas such as nitrogen while maintaining the temperature of the reaction mixture between about −5° and +5° C. The reaction gives a mixture of the cis- and trans-isomers of the 3-fluoro-4-oxo-2-imidazolidinyl benzoate depicted by formulas LIIa and LIIb. The reactions are graphically illustrated in Flow Diagram VII below.

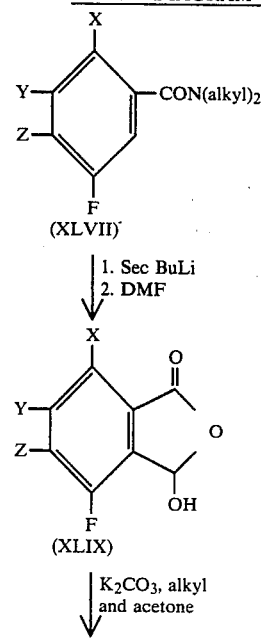

-continued
FLOW DIAGRAM VII

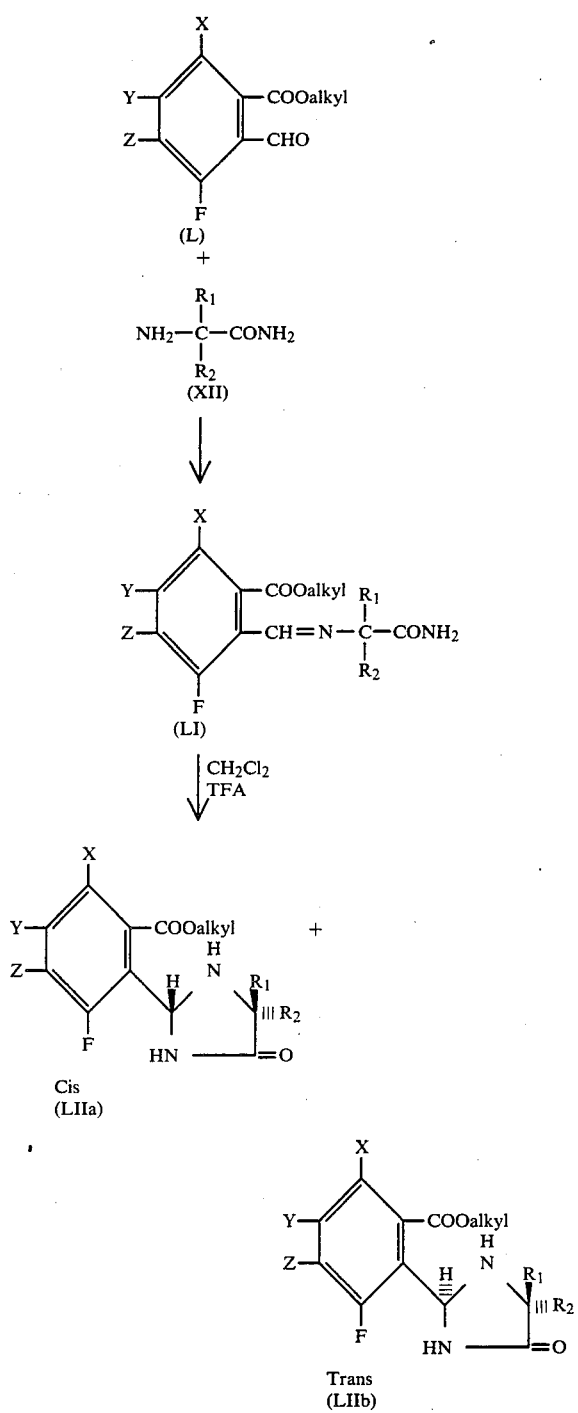

Cis
(LIIa)

Trans
(LIIb)

As mentioned above, it has been found that the aldehyde route described for the preparation of 3-fluoro-4-oxo-2-imidazolidinyl benzoates and illustrated in Flow Diagram VII above, is likewise applicable to the preparation of substituted and unsubstituted (4-oxo(and thioxo)-2-imidazolidinyl)nicotinates and the substituted and unsubstituted (4-oxo(and thioxo)-2-imidazolidinyl)-3-quinolinecarboxylates.

Substituted $C_1-C_{12}$ alkyl 2-formylnicotinates which are useful in the preparation of formula III 2-(2-imidazolidinyl)nicotinates, by the aldehyde route described above and illustrated in Flow Diagram VII, for synthesis of formula LIIa and LIIb substituted 3-fluoro-4-oxo-2-imidazolidinyl benzoates, can be prepared from substituted $C_1-C_{12}$ alkyl 2-methylnicotinates. For convenience and clarity, the following synthesis is described using substituted methyl 2-methylnicotinates as illustrative of this class of reactions.

In accordance with the process, equivalent amounts of a substituted methyl 2-methylnicotinate, represented by formula LIII and m-chloroperbenzoic acid are admixed in the presence of a chlorinated hydrocarbon such as methylene chloride, chloroform or the like. The reaction mixture is heated to refluxing temperature, then cooled to ambient temperature and excess peracid destroyed by addition of excess 1-hexene. Thereafter the solution is washed with sodium bicarbonate solution, dried and concentrated to give the corresponding substituted methyl methylnicotinate 1-oxide of formula LIV. The formula LIV 1-oxide is then heated to about 70° to 95° C. with an excess of acetic anhydride to yield the formula LV substituted methyl 2-acetoxymethylnicotinate. A cosolvent such as pyridine or pyridine/dimethoxyethane may also be used in the reaction, but is not essential. Oxidation of the formula LV acetoxymethylnicotinate with hydrogen peroxide in acetic acid yields the methyl 2-acetoxymethylnicotinate 1-oxide represented by formula LVI. This 1-oxide is then readily converted to the formula LVII methyl 2-diacetoxymethylnicotinate by reaction with an excess of acetic anhydride at a temperature between about 70° and 95° C., with or without a cosolvent such as pyridine or pyridine/dimethoxyethane. Treatment of the formula LVII methyl diacetoxymethylnicotinate with an alkali metal alkoxide such as sodium methoxide, sodium ethoxide, potassium butoxide, or the like, in the presence of a $C_1-C_4$ aliphatic alcohol then yields the substituted alkyl formylnicotinate such as methyl 2-formylnicotinate of formula LVIII.

Alternatively, it has also been found that the reaction of a substituted $C_1-C_{12}$ alkyl 2-methylnicotinate, depicted by formula LIII, with benzaldehyde at an elevated temperature, yields the formula LIX methyl 2-styrylnicotinate which, when ozonized gives the formula LVIII substituted alkyl formylnicotinate.

Additionally, it has been found that treatment of the formula LV substituted methyl 2-acetoxymethylnicotinate with an alkali metal alkoxide such as sodium methoxide, in the presence of a lower aliphatic alcohol at an elevated temperature, yields the corresponding substituted methyl 2-hydroxymethylnicotinate of formula LX. The substituted methyl 2-hydroxymethylnicotinate is then converted to the formula LVIII substituted methyl formylnicotinate by oxidation with selenium dioxide or lead tetraacetate.

The above reactions are graphically illustrated in Flow Diagram VIII.

FLOW DIAGRAM VIII
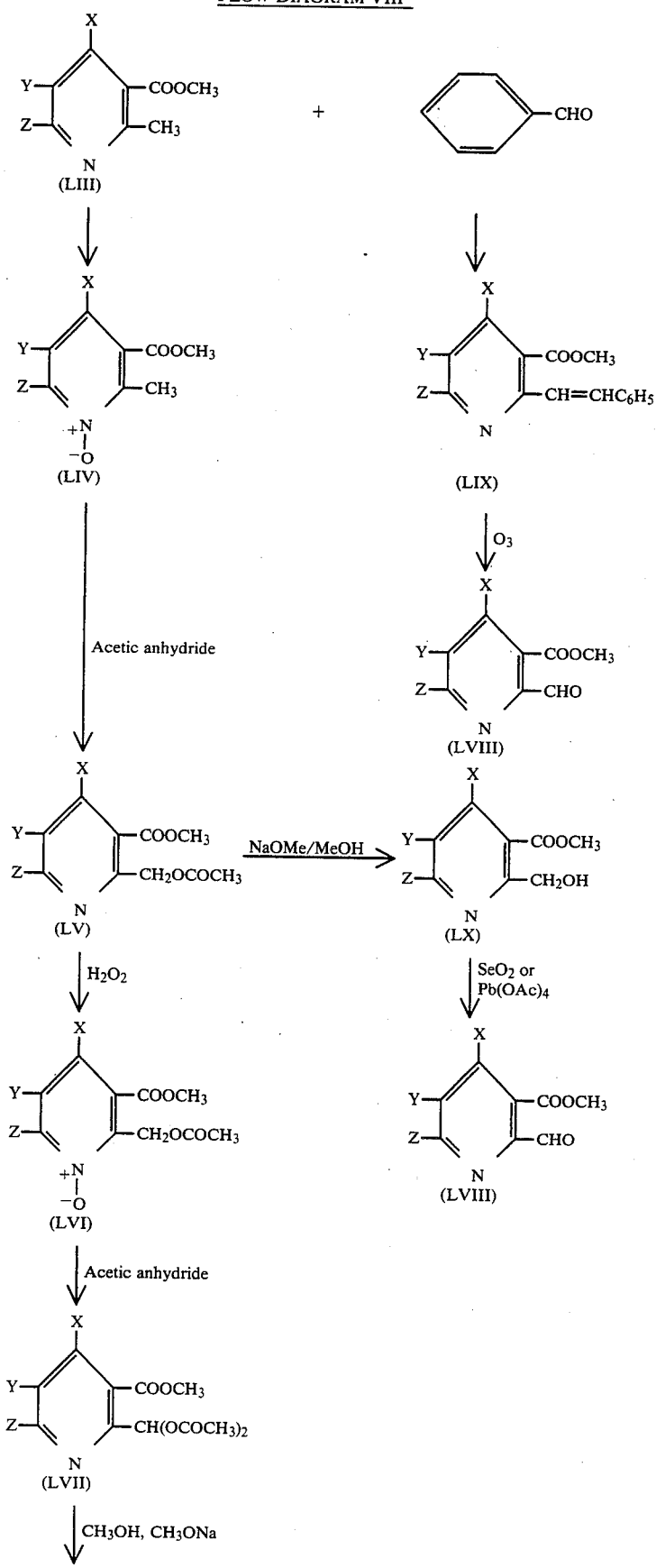

FLOW DIAGRAM VIII
-continued

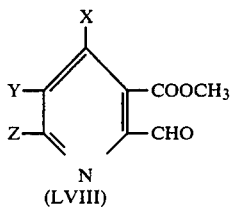
(LVIII)

The reduction of quinolinic acid diesters with diisobutylaluminum hydride is also an effective route to alkyl 3-formylnicotinates. The synthesis of these quinolinic acid diesters is described in European Patent Application 81103638.3, Publication No. 0 041 623.

The aldehyde route to the preparation of the formula LVIIa and LVIIb substituted (4-oxo(and thioxo)-2-imidazolidinyl)benzoates is likewise effective for the preparation of the substituted and unsubstituted (4-oxo-2-imidazolidinyl)quinoline-3-carboxylates from the substituted 2-formylquinoline-3-carboxylates.

The process for the preparation of these substituted 2-formylquinoline-3-carboxylate intermediates involves the reaction of an appropriately substituted aniline, depicted by formula LXI:

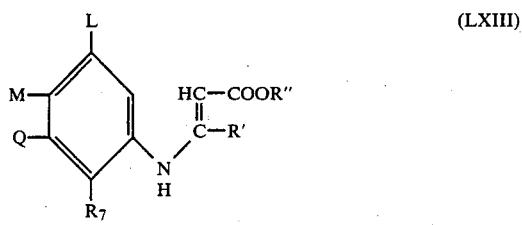

wherein L, M, $R_7$ and $R_8$ are as defined in reference to formula IV 2-(2-imidazolidinyl)quinoline-5-carboxylic acids, esters and salts; with approximately an equimolar amount of a keto-ester depicted by formula LXII and having the structure:

$$R'-CO-CH_2COOR'' \qquad \text{(LXII)}$$

wherein R' is $CH_3$ or COOR" and R" is $C_1$–$C_4$ alkyl. This reaction is optionally conducted in the presence of an organic sulfonic acid such as p-toluenesulfonic acid hydrate, camphorsulfonic acid, or aniline hydrochloride, in the presence of an organic solvent such as cyclohexane, toluene, benzene, xylene, monochlorobenzene, orthodichlorobenzene and mixtures thereof, or the like at a temperature from about 20° to 110° C. It is preferred to continuously remove the water which is formed during the reaction by distillation either at atmospheric or under reduced pressures of as low as 50 mm of Hg while maintaining the reaction temperature in a range of 75° to 80° C. The reaction yields the β-anilino-α,β-unsaturated ester of formula LXIII i.e.,

(LXIII)

wherein L, M, Q, $R_7$, R', and R" are as described above.

The thus-formed β-anilino-α,β-unsaturated ester of formula LXIII is then reacted with an approximately equimolar amount of an immonium salt hving the structure:

(LXIV)

wherein R'" is $C_1$–$C_6$ alkyl or

(LXIVa)

wherein n is 4 or 5, and referred to respectively as formula LXIV or LXIIa. The reaction is conducted in the presence of a hydrocarbon solvent such as toluene or a chlorinated hydrocarbon solvent such as methylene chloride, dichloroethane, orthodichlorobenzene, chlorobenzene, or mixtures thereof, at a temperature between about 40° and 110° C., for a period of time sufficient to essentially complete the reaction and yield the formula LXV alkyl ester of 2-methyl-3-quinolinecarboxylic acid, if R' is $CH_3$ in the formula LXVII β-anilino-α,β-unsaturated ester of the quinoline-2,3-dicarboxylate if R' is COOR" in the formula LXVIII β-anilino-α,β-unsaturated ester.

Alternatively, the formula LXI substituted aniline, wherein L, M, $R_7$ and $R_8$ are as described above, can be reached with about an equimolar amount of a formula LXVI acetylene dicarboxylate having the structure:

where R" is $C_1$–$C_4$ alkyl. This reaction is generally carried out in the presence of a solvent such as dichloroethane or a $C_1$–$C_4$ alcohol such as methanol, at a temperature between 0° and 100° C. to yield a β-anilino-α,β-unsaturated ester as formula LXIII. The β-anilino-α,β-unsaturated ester of formula LXIII is then reacted with an immonium salt depicted by formula LXIV having the structure:

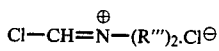

wherein R''' is $C_1$-$C_6$ alkyl or LXIVa having the structure:

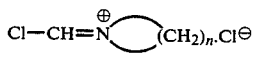

where n is 4 or 5. While the anion in formulas LXIV or LXIVa is shown as $Cl^\ominus$, it should be recognized that when $POCl_3$ is used to prepare the Vilsmeier reagent, the anion is $PO_2Cl_2^\ominus$. This reaction is generally conducted in the presence of a solvent such as methylene chloride, dichloroethane, monochlorobenzene, orthodichlorobenzene, or toluene at a temperature between 40° and 110° C. for a period of time sufficient to complete the reaction and yield the quinoline-2,3-dicarboxylate shown as formula LXVa having the structure:

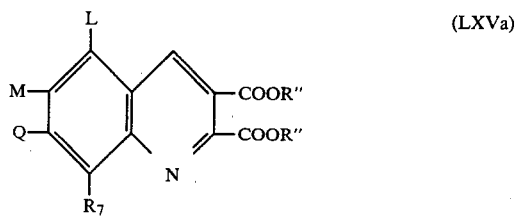
(LXVa)

wherein L, M, Q, $R_7$ and R'' are as described above.

The immonium salt formula LXIV or LXIVa utilized in the above cyclization reactions may, hereafter, be referred to as the Vilsmeier reagent. This reagent may be generated from a (N,N-dialkyl or N-alkyl,—N-phenyl)formamide reaction with $POCl_3$, $COCl_2$, $ClCO$—$COCl$ or $SOCl_2$ in a hydrocarbon or chlorinated hydrocarbon solvent.

Conversion of the 2-methyl-3-quinoline-carboxylate shown as formula LXV in which $R'$=$CH_3$ to the corresponding aldehyde of formula LXVII can be achieved in a manner similar to that described above for the conversion of the substituted 2-methylnicotinate of formula LIII to the corresponding 2-formylnicotinate of LVIII.

Conversion of the quinoline-2,3-dicarboxylate, shown as formulas LXV and LXVa, to the corresponding aldehyde shown as formula LXVII having the structure:

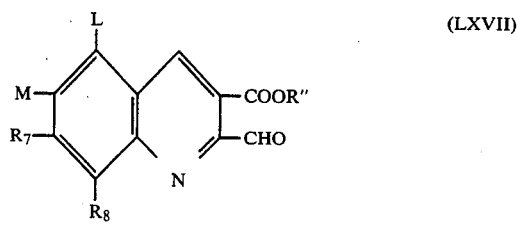
(LXVII)

where L, M, $R_7$, $R_8$ and R'' are as defined above, can be achieved by reaction of the formula LXV quinoline-2,3-dicarboxylate with diisobutylaluminum hydride. The reaction is preferably conducted in the presence of a non-protic solvent such as tetrahydrofuran under a blanket of inert gas.

These reactions are graphically illustrated in Flow Diagram IX below.

FLOW DIAGRAM IX

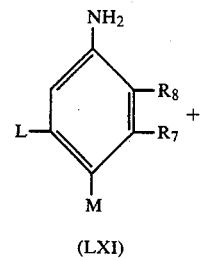
(LXI)

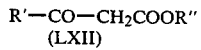
(LXII)

or

(LXVI)

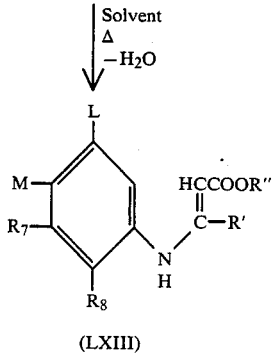
(LXIII)

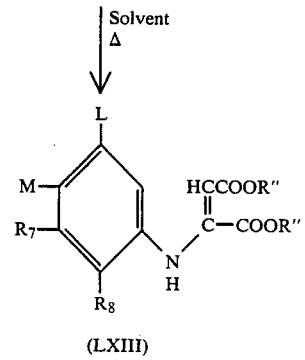
(LXIII)

-continued
FLOW DIAGRAM IX

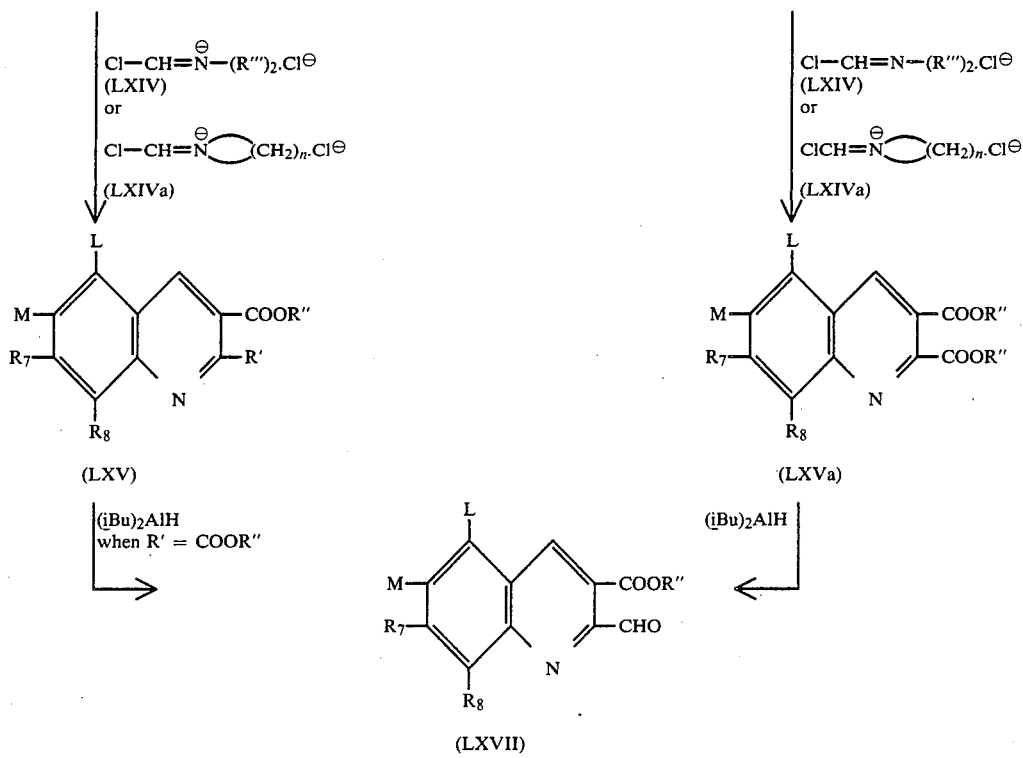

As indicated above, formula V 2-(2-imidazolidinyl)-thieno- and furo[3,2-b]pyridine-6-carboxylates, formula VI 2-(2-imidazolidinyl)-2,3-dihydrothieno- and furo[3,2-b]pyridine-6-carboxylates, formula VII 2-(2-imidazolidinyl)thieno- and furo[2,3-b]pyridine-5-carboxylates and formula VIII 2-(2-imidazolidinyl)-2,3-dihydrothieno- and furo[2,3-b]pyridine-5-carboxylates, can be obtained, in accordance with the present invention, by reduction of the corresponding (2-imidazolin-2-yl)thieno- and furo[2,3-b] and [3,2-b]pyridines with sodium cyanoborohydride. These 2-(2-imidazolin-2-yl)thieno- and furo[2,3-b] and [3,2-b]pyridine intermediates, necessary for the preparation of the formula V, VI, VII and VIII, 2-(2-imidazolidinyl)thieno- and furo[2,3-b] and [3,2-b]pyridines, of the present invention are described in the copending application for U.S. Letters Patent of Marinus Los, David William Ladner and Barrington Cross, Ser. No. 500,219, filed June 2, 1983, and incorporated herein by reference thereto.

The 2-(2-imidazolin-2-yl)thieno and furo[2,3-b] and [3,2-b]pyridine intermediates, useful in the preparation of the formula V, VI, VII and VIII 2-(2-imidazolidinyl)-thieno- and furo[3,2-b] and [3,2-b]pyridines of the present invention are depicted by formulas Va, VIa, VIIa and VIIIa, illustrated below.

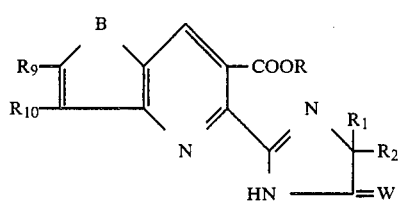
(Va)

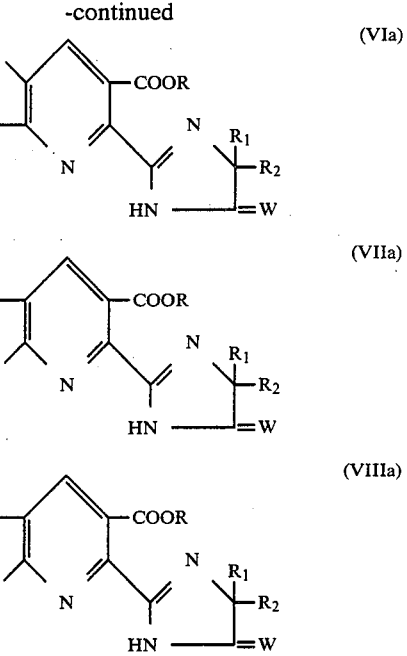

wherein R, $R_1$, $R_2$, $R_9$, $R_{10}$, $R_{11}$, $R_{12}$, B and W are as described above in reference to compounds of formula V, VI, VII and VIII.

While for convenience, the imidazolinone and imidazolinethione imidazolinyl intermediates referred to throughout are illustrated by single structures, it should be recognized that the imidazolinyl function in these compounds may exist in either tautomeric form, i.e.:

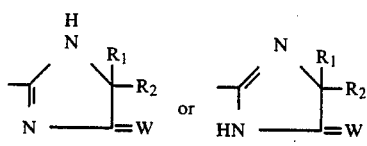

The formula Va, VIa, VIIa and VIIIa, intermediates for the compounds of the present invention may be prepared from the appropriately substituted thieno- and furo[2,3-b] and [3,2-b]pyridinedicarboxylic acids and esters of formulas LXXI and LXXIa illustrated below.

Since $R_9$ and $R_{10}$ represent substituents selected from hydrogen, halogen, $C_1$-$C_4$ alkyl and phenyl, and $R_{11}$ and $R_{12}$ represent hydrogen, $C_1$-$C_4$ alkyl and phenyl; for the purposes of the following discussion, which relates to the preparation of the formula Va, VIa, VIIa and VIIIa, 2-(2-imidazolin-2-yl)thieno and furo[2,3-b] and [3,2-b]pyridines, compound structures involved in the synthesis under discussion will be illustrated with $R_9$ and $R_{10}$.

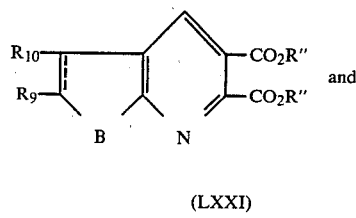

(LXXI)

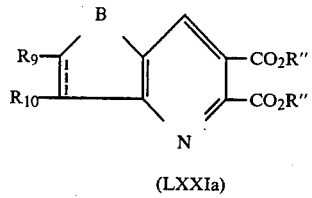

(LXXIa)

wherein $R_9$, $R_{10}$ and B are as previously described and R" is methyl or ethyl.

Methods suitable for preparing formula Va, VIa, VIIa and VIIIa unsaturated compounds wherein ═ is a double bond from the formula (LXXI) and (LXXIa) pyridinedicarboxylic acid esters are illustrated in Flow Diagram X below.

Thus formula (LXXI) and (LXXIa) diesters may be hydrolyzed to the corresponding thieno- and furo-2,3-pyridinedicarboxylic acids of formula (LXXII) and (LXXIIa) by reaction thereof with a strong base such as potassium hydroxide or sodium hydroxide. Acid anhydrides of formula (LXXIII) and (LXXIIIa) may then be prepared by treatment of the formula (LXXII) and (LXXIIa) pyridinedicarboxylic acids with, for example, acetic anhydride. Reaction of formula (LXXIII) and (LXXXIIIa) anhydrides with an appropriately substituted aminocarboxamide or aminothiocarboxamide depicted by formula (IX) yields carbamoyl nicotinic acids of formula (LXXIV) and (LXXIVa). Treatment of the thus-formed formula (LXXIV) and (LXXIVa) carbamoyl nicotonic acids with about 2 to 10 molar equivalents of aqueous or aqueous alcoholic sodium or potassium hydroxide, preferably under a blanket of inert gas such as nitrogen, cooling and acidifying to pH 2 to 4 with a strong mineral acid such as hydrochloric acid or sulfuric acid gives herbicidally effective 6-(4,4-disubstituted-5-oxo-(or thiono)-2-imidazolin-2-yl)thieno- and furo[2,3-b]pyridine-5-carboxylic acids, and 5-(4,4-disubstituted-5-oxo-(or thiono)-2-imidazolin-2-yl)thieno- and furo[3,2-b]pyridine-6-carboxylic acids encompassed by formulas (Va) and (VIIa).

Formula (Va) and (VIIa) 5-(2-imidazolin-2-yl)thieno- and furopyridine esters, wherein R represents a substituent other than hydrogen or a salt-forming cation, and $R_1$, $R_2$, $R_9$, $R_{10}$ and B are as described above can be prepared by reacting a novel thieno- or furoimidazopyrrolopyridinedione, represented by formulas (LXXV) and (LXXVa), hereinbelow, in Flow Diagram (XI), with an appropriate alcohol and corresponding alkali metal alkoxide at a temperature ranging between about 20° and about 50° C.

Formula (LXXV) and (LXXVa) thieno- and furoimidazopyrrolopyridinediones may conveniently be prepared from formula (VIIa) and (Va) acids, where B is H by treatment with one equivalent of dicyclohexylcarbodiimide in an inert solvent such as methylene chloride as illustrated in Flow Diagram (XI) below.

FLOW DIAGRAM (X)

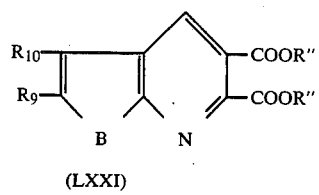

(LXXI)

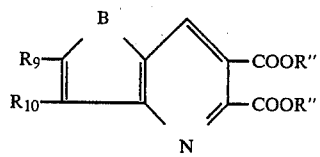

(LXXIa)

1. Aqueous ethanolic NaOH Δ
2. HCl

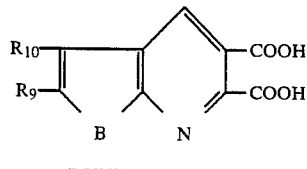

(LXXII)

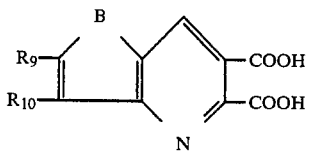

(LXXIIa)

-continued
FLOW DIAGRAM (X)
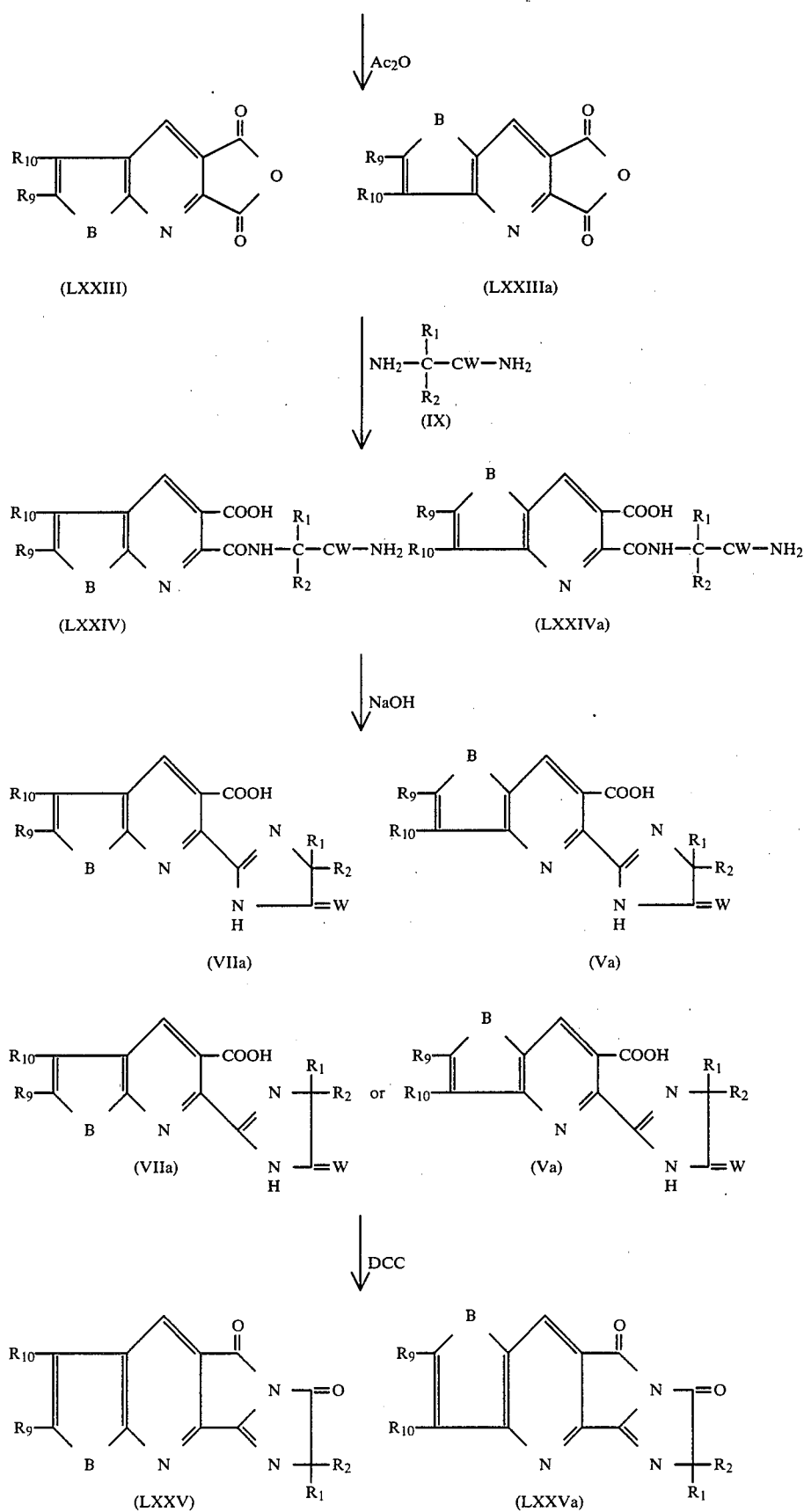

g (0.11 mol) 2-amino-2,3-dimethylbutyronitrile, 13.9 mL (0.10 mol) of triethylamine and 150 mL anhydrous tetrahydrofuran at room temperature. After 72 hours, the solvent is removed in vacuo to give a dark oily residue. This oil is dispersed in 200 mL of acetic anhydride and heated to reflux for two hours, allowed to cool to room temperature over a 48 hour period and concentrated in vacuo to give a heavy black oil. After chromatography on silica gel twice using methylene chloride and mixtures of methylene chloride in hexanes respectively, 14.6 g of pale yellow solid is obtained, mp 104°–108° C. This solid, 4-chloro-α-isopropyl-α,5-dimethyl-1,3-dioxo-2-isoindolineacetonitrile, is analytically pure, and infrared and proton nmr spectra are consistent with desired structure.

EXAMPLE 5

Preparation of 4-chloro-α-isopropyl-α,5-dimethyl-1,3-dioxo-2-isoindoleacetamide

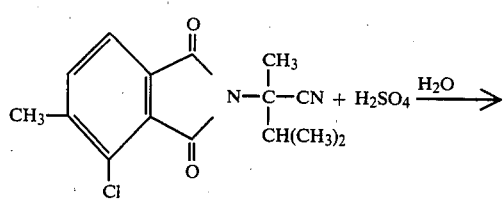

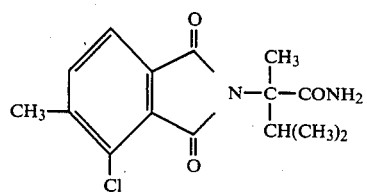

A solution of 9.5 g (0.033 mol) of 4-chloro-α-isopropyl-2,5-dimethyl-1,3-dioxo-2-isoindolineacetonitrile in 30 mL methylene chloride is added dropwise to a mixture of 15 mL 95% sulfuric acid plus 2 mL water at 5° C. Rapid stirring is continued for a total of 24 hours at ambient temperatures. The reaction mixture is heated at 40° C. for three hours and then poured over 250 mL ice. The cold aqueous mixture is extracted with a total volume of 350 mL chloroform. The organic phases are combined, washed with 200 mL water, dried over magnesium sulfate and concentrated in vacuo to give 8.8 g of a light beige solid residue, mp 198°–203° C. This solid can be recrystallized from ethyl acetate/ether to give a analytically pure 4-chloro-α-isopropyl-α,5-dimethyl-1,3-dioxo-2-isoindolineacetamide as a white solid, mp 215°–218° C. The infrared and proton nmr spectra are consistent with the desired structure.

EXAMPLE 6

Preparation of 3-chloro-4-methyl-N-(1-carbamoyl-1,2-dimethylpropyl)-phthalamic acid, methyl ester

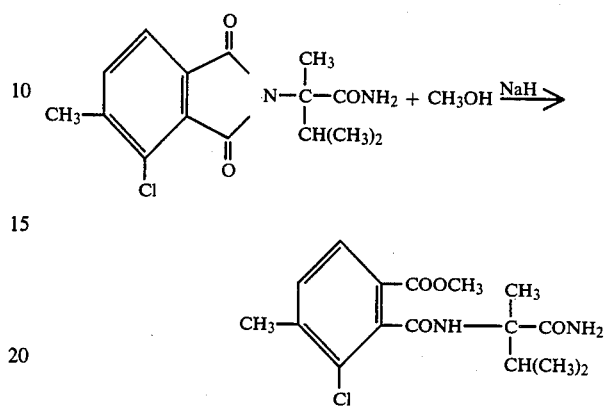

A stirred solution of 6.0 g (0.019 mol) of 4-chloro-2-isopropyl-2,5-dimethyl-1,3-dioxo-2-isoindolinacetamide in 200 mL methanol is treated portion-wise with 0.93 g (0.019 mol) of 50% mineral oil dispersion of sodium hydride. After 16 hours at ambient temperatures, 1.1 mL (0.021 mol) of acetic acid is added dropwise (final pH=7) and the solvents are removed in vacuo. The residue is dispersed in 75 mL water and extracted with a total of 300 mL of ethyl acetate. The organic phases are combined, dried over magnesium sulfate and evaporated in vacuo to give a pale orange gum. After trituration with 50 mL ether and filtration, 4.0 g of a pale orange solid is obtained. The infrared and proton nmr is consistent with the desired structure. This solid is used as is without further purification.

EXAMPLE 7

Preparation of methyl 3-chloro-2-(4-isopropyl-4-methyl-5-oxo-2-imidazolin-2-yl)-p-toluate hydrochloride

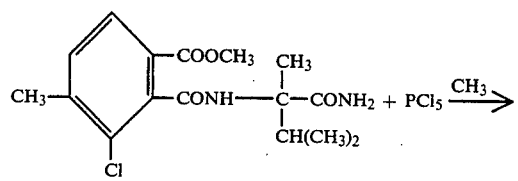

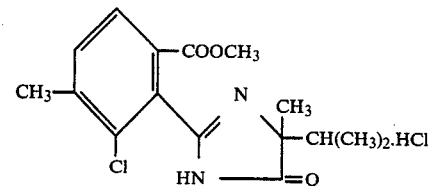

A stirred mixture of 6.1 g (0.029 mol) of phosphorous pentachloride in 100 mL anhydrous toluene is treated portion wise with 4.0 g (0.012 mol) of methyl 3-chloro-4-methyl-N-(1-carbamoyl-1,2-dimethylpropyl)phthalamate. After 72 hours at room temperature, the reaction mixture is poured over 350 mL ice and stirred at ambient temperatures until the ice melts. The resulting three phases are filtered, the off-white solid is dried in vacuo at 53° C. for two hours to give 3.5 g methyl 3-chloro-2-(4-isopropyl-4-methyl-5-oxo-2-(imidazolin-2-yl)-p-toluate hydrochloride, mp 233°–235° C.

EXAMPLE 8

Preparation of methyl 3-chloro-2-(4-isopropyl-4-methyl-5-oxo-2-imidazolin-2-yl)-p-toluate

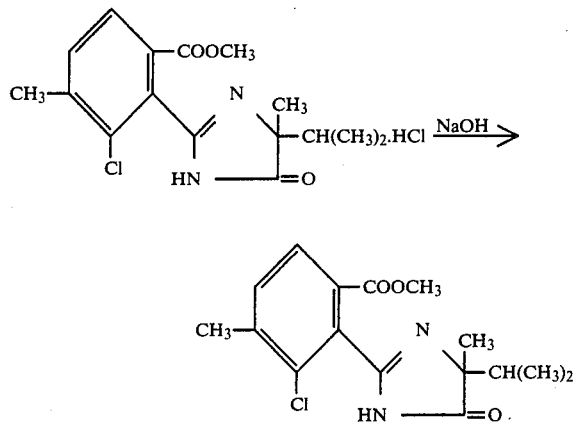

To a dispersion of 1.8 g (5.0 mmol) of the hydrochloride salt prepared in Example 7 in 20 mL water is added 2.5 mL of a 2N sodium hydroxide solution (5.0 mmol) and 50 mL ethyl acetate. With vigorous stirring, the mixture is carefully acidified to pH 3 with concentrated sulfuric acid. The phases are separated and the aqueous phase is extracted with 50 mL ethyl acetate. All organic phases are combined, dried over magnesium sulfate and concentrated in vacuo to give 1.4 g white crystalline residue, mp 178°–180° C. A sample recrystallized from ethyl acetate gave analytically pure methyl 3-chloro-2-(4-isopropyl-4-methyl-5-oxo-2-imidazolin-2-yl)-p-toluate, mp 181°–183° C.

EXAMPLE 9

Preparation of 2-methyl 3-nitrophthalate

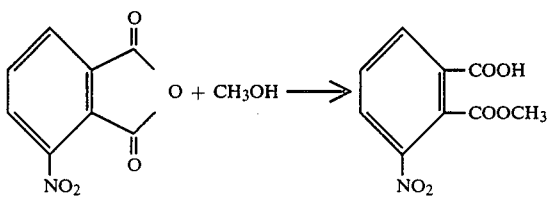

A solution containing 10 g 3-nitrophthalic anhydride in 125 mL absolute ethanol is heated under reflux for 16 hours. Concentration of the solution gives a gray solid residue which is recrystallized from ethyl acetate to give 2-methyl 3-nitrophthalate, mp 154°–156° C.

EXAMPLE 10

Methyl N-(1-carbamoyl-1,2-dimethylpropyl)-6-nitrophthalamate

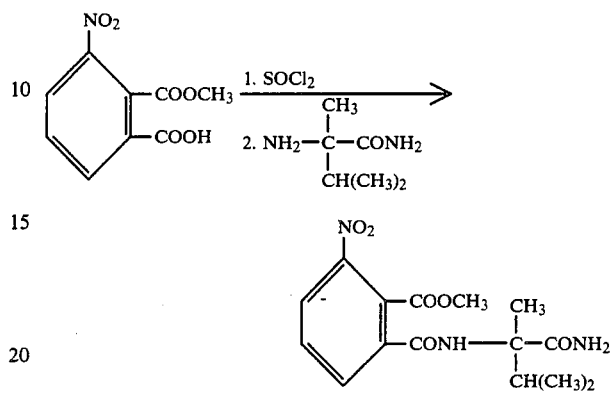

A suspension of 4.94 g 2-methyl 3-nitrophthalate in 20 mL thionyl chloride is stirred at room temperature for 72 hours. The mixture is concentrated and the residue dissolved in toluene and again concentrated. This process is repeated.

The residue (crude acid chloride) in 30 mL dry THF is added dropwise at room temperature with stirring under nitrogen to a solution containing 3.84 g 2-amino-2,3-dimethylbutyramide and 4.4 mL triethylamine in 50 mL dry THF. After stirring at room temperature for 24 hours, 50 mL water and 50 mL CH$_2$Cl$_2$ is added, the phases separated and the aqueous phase reextracted with 50 mL ethyl acetate. The combined organic extract is dried and concentrated. The residue is triturated with ether to give the product which is recrystallized from ethyl acetate to give the desired product with mp 100°–107° C.

EXAMPLE 11

Preparation of methyl 2-(4-isopropyl-4-methyl-5-oxo-2-imidazolin-2-yl)-6-nitrobenzoate

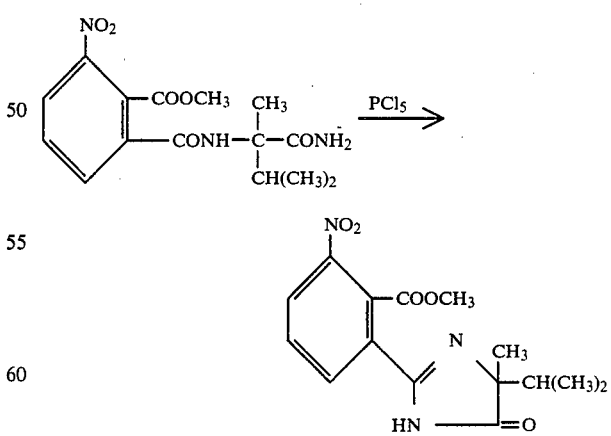

A mixture containing 3.4 g amide and 5.2 g PCl$_5$ in 100 mL dry toluene is heated on a steam bath for one hour. The mixture is cooled to 5° C. and filtered to give 2.6 g hydrochloride salt of the desired imidazolinone, mp 194°–197° C.

herbicidal 2,3-dihydro furo[2,3-b] and [3,2-b]pyridines may be prepared by catalytic reduction of the formula (Va) or (VIIa) (2-imidazolin-2-yl) product, or (LXXI) and (LXXIa) furo[2,3-b] and [3,2-b]pyridine-5,6-diesters as for example with hydrogen and palladium on carbon, provided that $R_9$ and $R_{10}$ are substituents which are not reduced by such a procedure. This then provides novel 2,3-dihydro herbicidal compounds illustrated below.

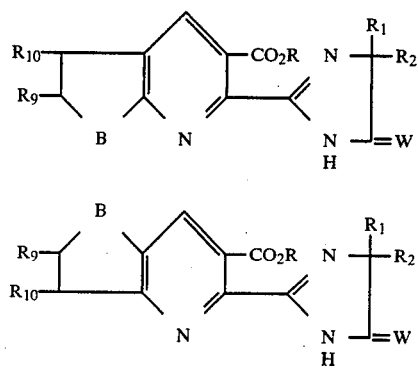

wherein $R_9$, $R_{10}$, B, W, $R_1$, $R_2$ and $R_B$ are as described for (Va) and (VIIA).

The formula I imidazolidinone and imidazolidinethione compounds of the present invention are highly effective preemergence and postemergence herbicidal agents, useful for the control of a wide variety of undesirable monocotyledonous and dicotyledonous plant species. Surprisingly, it has also been found that these formula I imidazolidinone and imidazolidinethione compounds are well tolerated by a variety of crops including: sunflowers; graminaceous crops such as corn, rice, turf, barley and wheat; and leguminous crops such as soybeans. While herbicidal selectivity of the formula I imidazolidinones and imidazolidinethiones of this invention may vary with compound structure from crop to crop, the presence of the dihydroimidazolinyl function, which is unique to all of the formula I imidazolidines and imidazolidinethiones of this invention, appears to impart herbicidal selectivity to said compounds. This selectivity thus permits application of the active compounds to newly planted fields or to maturing crops for control of undesirable grasses and broadleaf weeds in the presence of said crops.

It is also surprising to find that the compounds of this invention, frequently exhibit plant growth regulating activity when employed at nonherbicidal rates of application. When applied to cereal crops such as wheat and barley, it is not uncommon to find that the treated plants are shorter, less suseptible to lodging due to adverse whether conditions, show increased tillering and frequently demonstrate increased crop yield. It has likewise been found that yield increases can also be obtained from corn, soybeans and sunflowers, treated with the formula I imidazolidinones or imidazolidinethiones of this invention.

In practice, the formula I imidazolidinones and imidazolidinethiones may be applied to the foliage of undesirable monocotyledonous or dicotyledonous plants or to soil containing seeds or other propagating organs of said plants such as tubers, rhizomes or stolons, at rages generally between about 0.032 and 4.0 kg/ha, and preferably between about 0.063 and 2.0 kg/ha, although rates as high as 8.0 kg/ha may be used if desired.

Effective plant growth regulating activity is generally obtained when the above-said formula I compounds are applied to crops at rates below herbicidal rates. Obviously, this rate will vary from compound to compound.

The formula I imidazolidinones and imidazolidinethiones of the present invention may be applied to the foliage of plants or to soil containing seeds or other propagating organs thereof, in the form of a liquid spray, as a ULV concentrate or as a solid formulation.

When the formula I compounds are prepared as alkali metal or organoammonium salts, said salts are frequently found to be water soluble and can simply be dispersed in water, with or without the addition of a surfactant, and applied as an aqueous spray. Said formula I compounds may also be prepared as wettable powders, flowable concentrates, emulsifiable concentrates, granular formulations or the like.

A typical emulsifiable concentrate can be prepared by dissolving about 5 to 25% by weight of the active ingredient in about 65 to 90% by weight of N-methylpyrrolidone, isophorone, butyl cellosolve, methylacetate or the like and dispersing therein about 5 to 10% by weight of a nonionic surfactant such as an alkylphenoxy polyethoxy alcohol. This concentrate is dispersed in water for application as a liquid spray or it may be applied directly as an ultra low volume concentrate in the form of discrete droplets having a mass median diameter between about 17 and 150 microns particle size.

Wettable powders can be prepared by grinding together about 20 to 45% by weight of a finely divided carrier such as kaolin, bentonite, diatomaceous earth, attapulgite, or the like, 45 to 80% by weight of the active compound, 2 to 5% by weight of a dispersing agent such as sodium lignosulfonate, and 2 to 5% by weight of a nonionic surfactant, such as octylphenoxy polyethoxy ethanol, nonylphenoxy polyethoxy ethanol or the like.

A typical flowable liquid can be prepared by admixing about 40% by weight of the active ingredient with about 2% by weight of a gelling agent such as bentonite, 3% by weight of a dispersing agent such as sodium lignosulfonate, 1% by weight of polyethylene glycol and 54% by weight of water.

When the compounds of the invention are to be used as herbicides where soil treatments are involved, the compounds may be prepared and applied as granular products. Preparation of the granular product can be achieved by dissolving the active compound in a solvent such as methylene chloride, N-methylpyrrolidone or the like and spraying the thus-prepared solution on a granular carrier such as corncob grits, sand, attapulgite, kaolin or the like.

The granular product thus-prepared generally comprises about 3 to 20% by weight of the active ingredient and about 97 to 80% by weight of the granular carrier.

In order to facilitate a further understanding of the invention, the following examples are presented primarily for the purpose of illustrating certain more specific details thereof. The invention is not to be deemed limited thereby except as defined in the claims. Unless otherwise noted, all parts are by weight.

EXAMPLE 1

Preparation of 3-chloro-N,N-diethyl-p-toluamide

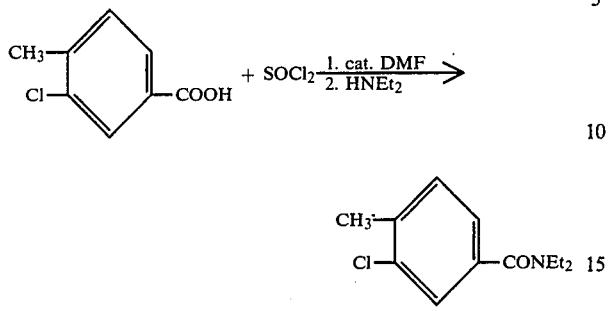

A mixture of 32.2 g (0.19 mol) of 3-chloro-4-methyl-benzoic acid in 100 mL of thionyl chloride is treated with 2 drops of dimethylformamide and heated on a steam bath for one hour. The clear amber solution is evaporated in vacuo several times with anhydrous toluene to give a clear amber oily residue. After dilution to a volume of 125 mL with anhydrous tetrahydrofuran, the 3-chloro-4-methyl-benzoyl chloride is added dropwise to a stirred solution of 43.3 mL (0.418 mol) of diethylamine in 300 mL anhydrous tetrahydrofuran under $N_2$ at $-5°$ C. The reaction mixture is allowed to come to room temperature over a 72 hour period then is treated with 300 mL water. The phases are separated; the aqueous phase is extracted with a total of 300 mL ethyl acetate. All organic phases are combined, washed with 300 mL of a saturated sodium chloride solution, dried over magnesium sulfate and concentrated in vacuo to give 40.0 g of a clear dark red oil. The infrared and proton nmr spectra are consistent with the desired structure. Gas-liquid chromatography analysis gives a purity of 96%.

EXAMPLE 2

Preparation of 3-chloro-4-methylphthalic acid

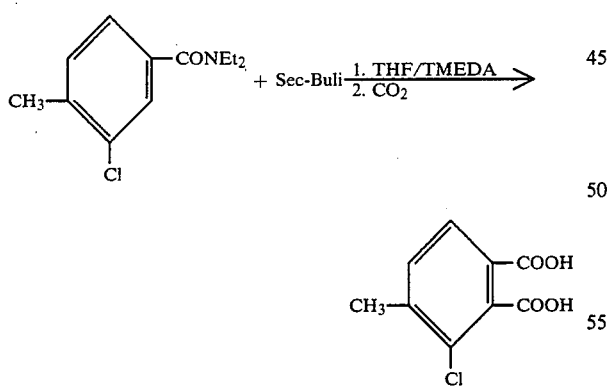

A stirred solution of 16.6 mL (0.11 mol) of N,N,N',N'-tetramethylethylenediamine in 300 mL of anhydrous tetrahydrofuran is treated dropwise with 100 mL of a 1.1M solution of sec-butyl lithium (0.11 mol) in cyclohexane at $-70°$ to $-68°$ C. under nitrogen. After stirring at $-68°$ C. for 15 minutes, the reaction solution is treated dropwise with a solution of 22.6 g (0.10 mol) of 3-chloro-N,N-diethyl-p-toluamide in 50 mL of anhydrous tetrahydrofuran at $-65°$ to $-60°$ C. The reaction mixture is stirred at $-65°$ C. for 30 minutes, then poured over 350 mL anhydrous THF, saturated with carbon dioxide and allowed to stir at ambient temperatures for four days. The reaction mixture is treated with 300 mL water, the phases are separated, and the aqueous phase is washed with a total volume of 300 mL ethyl acetate. The aqueous phase is cooled to 5° C. and carefully acidified with concentrated sulfuric acid to pH 3. The heavy oil precipitate is extracted into a total of 900 mL of ethyl acetate. These organic phases are combined, washed with 300 mL saturated sodium chloride solution, dried over magnesium sulfate and concentrated to give an orange oily residue (25.1 g) which crystallized on long standing. The infrared and mass spectra are consistent with the desired structure.

EXAMPLE 3

Preparation of 3-chloro-4-methylphthalic anhydride

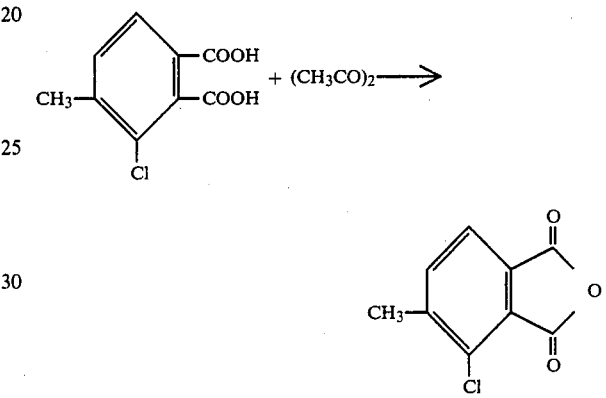

A stirred solution of 21.5 g (0.10 mol) of 3-chloro-4-methylphthalic acid in 300 mL acetic anhydride is heated under reflux for six hours, allowed to cool to room temperature and concentrated in vacuo several times with anhydrous toluene. A viscous, dark, amber syrup is obtained, characterized by an infrared spectrum and used without further purification.

EXAMPLE 4

Preparation of 4-chloro-α-isopropyl-α,5-dimethyl-1,3-dioxo-2-isiondolineacetonitrile

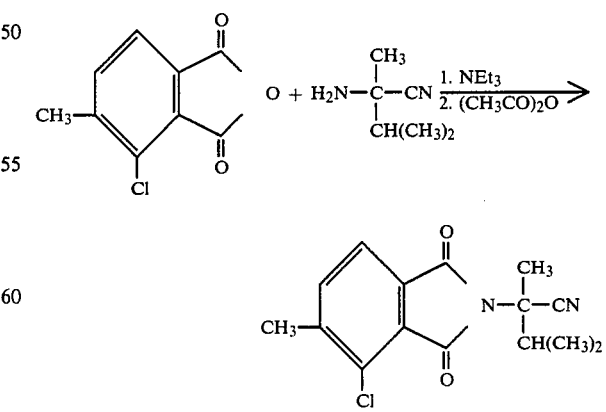

A stirred solution of 19.7 g (0.10 mol) of 3-chloro-4-methylphthalic anhydride in 200 mL anhydrous tetrahydrofuran is treated all at once with a mixture of 12.3

This salt is dispersed in a mixture of 20 mL water containing 1.0 g sodium bicarbonate and 75 mL ethyl acetate and the mixture stirred at room temperature for 16 hours. The organic phase is separated, dried and concentrated to give analytically pure methyl 2-(4-isopropyl-4-methyl-5-oxo-2-imidazolin-2-yl)-6-nitrobenzoate, mp 159°–162° C.

EXAMPLE 12

Preparation of
6-fluoro-N,N-diisopropyl-5-methylphthalamic acid

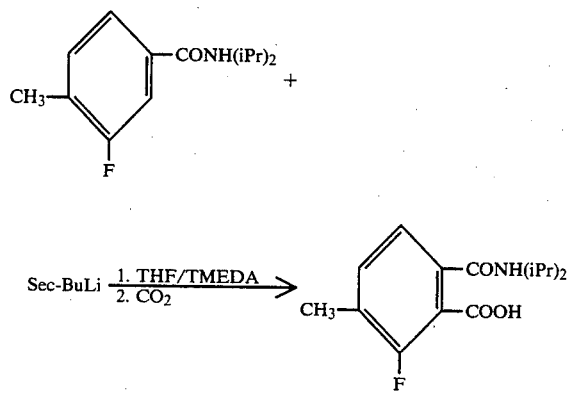

A stirred solution of 7.0 mL (0.046 mol) of N,N,N',N'-tetramethylethylenediamine in 75 mL dry THF under nitrogen is treated dropwise with 42 mL of a 1.1M solution of sec-BuLi in cyclohexane (0.046 mol) at −75° to −65° C. After addition is complete, a solution of 10.0 g (0.042 mol) of 3-fluoro-N,N-diisopropyl-p-toluamide in 125 mL dry THF is added dropwise at −65° to −60° C. At completion of addition, the reaction mixture is poured over 300 mL of a saturated solution of CO₂ in THF and allowed to warm to room temperature. A 125 mL portion of ice water is added (caution, foaming) and the mixture is cautiously acidified to pH 2–3 with concentrated sulfuric acid. The phases are separated, the organic phase is washed with 100 mL of a saturated NaCl solution. The aqueous phases are combined and extracted with a total of 300 mL ethyl acetate. The organic phases are combined, dried over MgSO₄ and concentrated in vacuo to give 13.0 g of a yellow glass residue which crystallizes in 200 mL ether to give 8.2 g of 6-fluoro-N,N-diisopropyl-5-methylphthalamic and as an analytically pure white solid, mp 147°–149° C.

EXAMPLE 13

Preparation of
N²-(1-carbamoyl-1,2-dimethylpropyl)-3-fluoro-N',N'-diisopropyl-4-methylphthalamide

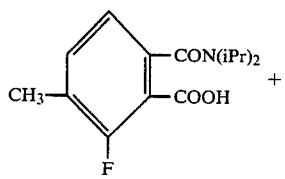

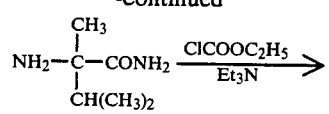

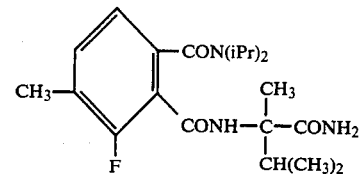

To a stirred solution of 8.18 g 6-fluoro-N,N-diisopropyl-5-methylphthalamic acid in 100 mL dry THF at −2° C. and under nitrogen is added dropwise 2.78 mL ethylchloroformate followed by 4.5 mL triethylamine. After one-half hour, there is added dropwise a solution of 3.77 g 2-amino-2,3-dimethylbutyramide in 125 mL dry THF at −2° to +2° C. After the addition, the mixture is allowed to warm to room temperature and stirred for three hours. To the mixture is added 100 mL water. The organic phase is separated, washed with brine and the combined aqueous phases extracted with 100 mL ethyl acetate. The combined organic phases are dried (MgSO₄) and concentrated to give a foam which is used directly in the next step.

EXAMPLE 14

Preparation of
3-fluoro-N,N-diisopropyl-2-(4-isopropyl-4-methyl-5-oxo-2-imidazolin-2-yl)-p-toluamide

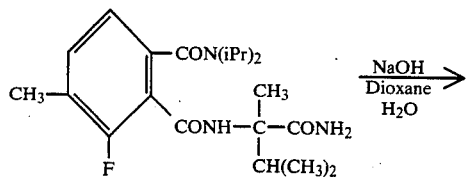

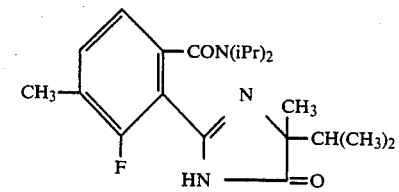

The crude product of Example 13 is dissolved in 75 ml 1.93N NaOH solution, 25 mL dioxane added and the mixture heated at 80° C. for 16 hours. After cooling, the mixture is acidified with concentrated H₂SO₄ to pH 3 and extracted several times with ethyl acetate. The extract is washed with brine, dried and concentrated to give a foam which was crystallized from ether to give the product, 3-fluoro-N,N-diisopropyl-2-(4-isopropyl-4-methyl-5-oxo-2-imidazolin-2-yl)-p-toluamide as a white crystalline solid, mp 205°–210° C. which is analytically pure.

EXAMPLE 15

Preparation of 3-fluoro-2-(4-isopropyl-4-methyl-5-oxo-2-imidazolin-2-yl)-p-toluic acid

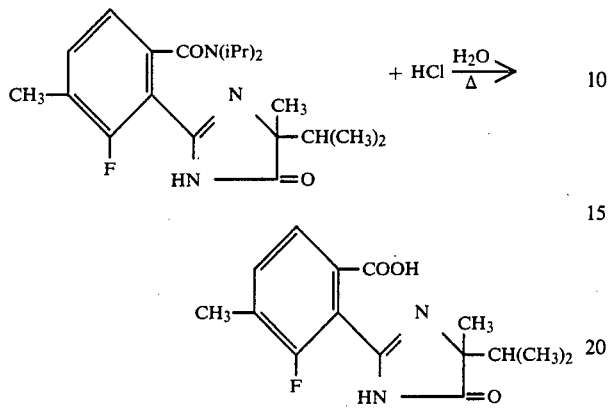

A solution of 1.0 g (2.7 mmols) of 3-fluoro-N,N-diisopropyl-2-(4-isopropyl-4-methyl-5-oxo-2-imidazolin-2-yl)-p-toluamide in 20 mL of concentrated hydrochloric acid is heated to reflux (a copious white solid precipitates). Another 15 mL of concentrated hydrochloric acid is added and the solution is heated under reflux for seven hours. After cooling to room temperature, the mixture is basified to pH 7 to 10 with a 6N NaOH solution, then carefully adjusted to pH 3 with concentrated sulfuric acid. The mixture is filtered, the clear filtrate is treated with 250 mL ethyl acetate and stirred vigorously for 24 hours. The organic phase is separated, dried over MgSO₄ and concentrated in vacuo to give 0.44 g of a white foam which is crystallized ether to give 3-fluoro-2-(4-isopropyl-4-methyl-5-oxo-2-imidazolin-2-yl)-p-toluic acid as a white solid, mp 164°–170° C.

EXAMPLE 16

Preparation of N-(1-carbamoyl-1,2-dimethylpropyl)-p-toluamide

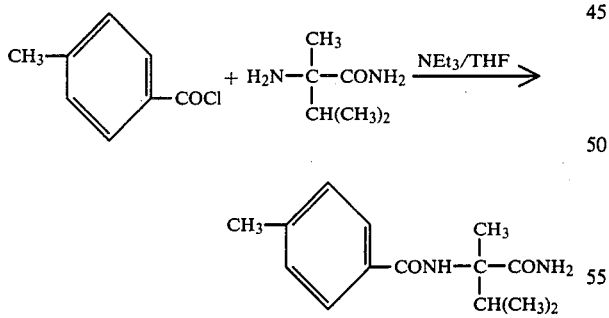

A stirred mixture containing 13.0 g (0.10 mol) of 2-amino-2,3-dimethylbutyramide and 15.3 mL (0.11 mol) of triethylamine in 150 mL of dry THF is treated dropwise at 5° to 10° C. with a solution of 15.5 g (0.10 mol) of p-toluoyl chloride in 25 mL dry THF. After being allowed to warm to ambient temperatures over a 16 hour period, the reaction mixture is treated with 50 mL water and stirred for one hour. The resulting three phases are filtered; the filtrate is separated and the aqueous phase is extracted with 150 mL ethyl acetate. All organic phases are combined, washed with 100 mL of a saturated NaCl solution, dried over magnesium sulfate and concentrated in vacuo. A white solid residue is obtained which weighs 17.3 g, mp 145°–152° C. The nmr spectrum is consistent with the desired structure.

EXAMPLE 17

Preparation of 4-isopropyl-4-methyl-2-p-tolyl-2-imidazolin-5-one

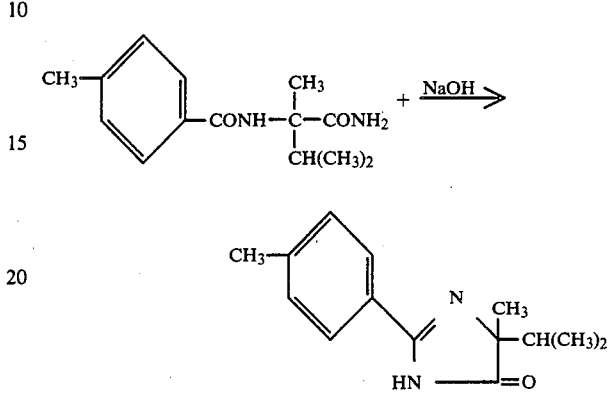

A mixture of 24.8 g (0.10 mol) of N-(1-carbamoyl-1,2-dimethylpropyl)-p-toluamide in 263 mL of a 2N sodium hydroxide solution (0.50 mol NaOH) is heated with 100 mL p-dioxane and heated on a steam bath for 72 hours. The p-dioxane is removed in vacuo and the remaining aqueous solution is cooled to 5°–10° C. After carefully acidifying to pH 3–4 with concentrated sulfuric acid, the reaction mixture is extracted with a total of 750 mL methylene chloride. The organic phase is washed with 200 mL of a saturated sodium chloride solution, dried over magnesium sulfate and evaporated to dryness in vacuo to give a yellow solid residue, weighing 22.1 g. The nmr spectrum is consistent with the desired structure. This compound can be recrystallized from acetonitrile to give analytically pure 4-isopropyl-4-methyl-2-p-tolyl-2-imidazolin-5-one mp 151°–154° C.

EXAMPLE 18

Preparation of 2-(2-chloro-p-tolyl)-4-isopropyl-4-methyl-2-imidazolin-5-one

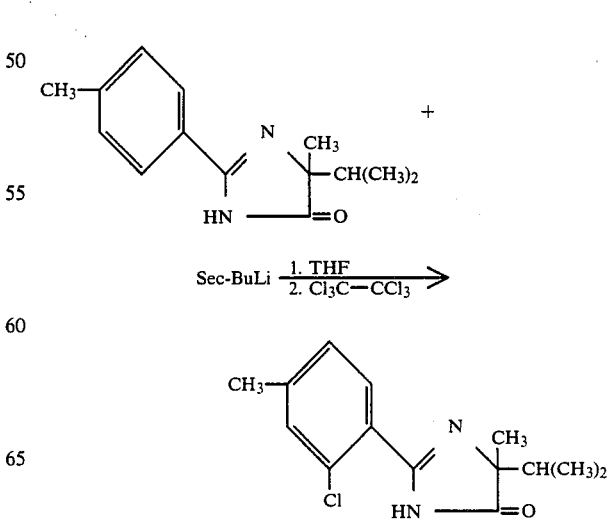

A mechanically stirred solution of 20.0 g (0.087 mol) of 4-isopropyl-4-methyl-2-p-tolyl-2-imidazolin-5-one in 200 mL of dry tetrahydrofuran is treated dropwise with 160 mL of a 1.2M solution of sec-butyl lithium (0.191 mol) in cyclohexane over a 40 minute period at $-72°$ to $-65°$ C. After stirring the resulting bright red solution at $-40°$ to $-35°$ for one and one-half hours, a solution of 21.4 g (0.090 mol) of hexachloroethane in 125 mL of dry tetrahydrofuran is added dropwise. Addition temperature is allowed to reach $-20°$ C.

After warming to room temperature over a 16 hour period, the reaction is treated with 200 mL of ice water plus 200 mL of a saturated sodium chloride solution. The mixture is carefully acidified to pH 3 with concentrated sulfuric acid. The phases are separated and the aqueous phase is extracted with 200 mL ether. The organic phases are combined, dried over magnesium sulfate and concentrated to give a dark brown oily residue. After chromatography on silica gel using mixtures of ether in methylene chloride as eluent, the product (6.7 g) is obtained as a light beige solid, mp 156°–160° C. The infrared and proton nmr spectra are consistent with the desired structure. A sample recrystallized from ether had mp 152°–165° C. and was analytically pure.

EXAMPLE 19

Preparation of 5-chloro-6-(4-isopropyl-4-methyl-5-oxo-2-imidazolin-2-yl)-m-toluic acid

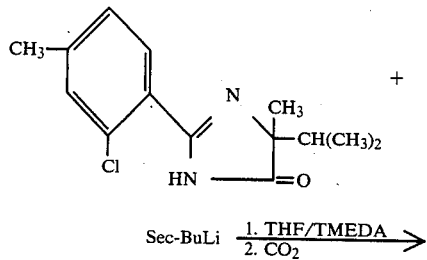

Sec-BuLi $\xrightarrow{\text{1. THF/TMEDA} \atop \text{2. CO}_2}$ +

-continued

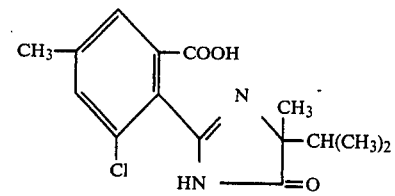

A stirred solution of 3.7 g (0.014 mol) of 2-(2-chloro-p-tolyl)-4-isopropyl-4-methyl-2-imidazolin-5-one in 70 mL anhydrous tetrahydrofuran and 4.7 mL (0.031 mol) of N,N,N',N'-tetramethylethylenediamine under $N_2$ is treated at $-70°$ to $-63°$ C. dropwise with 26 mL of a 1.2M solution of sec-butyl lithium (0.031 mol) in cyclohexane. After stirring for two hours at $-55°$ to $-45°$ C., the reaction is poured over 300 mL anhydrous THF saturated with carbon dioxide. The mixture is allowed to come to room temperature over a 16 hour period and then treated with 250 mL water and carefully acidified with ice cooling, to pH 3 with concentrated sulfuric acid. The phases are separated; the aqueous phase is extracted with 150 mL of ethyl acetate. The organic phases are combined and extracted with 50 mL of an 0.5N solution of sodium hydroxide. The basic aqueous phase is cooled to 5°–10° C. and carefully acidified to pH 3 with concentrated sulfuric acid to give a fine white solid precipitate. After filtration, the solid is dried in vacuo at 54° C. for 16 hours to give 3.5 g product, mp 240°–245° C. An analytically pure sample of 5-chloro-6-(4-isopropyl-4-methyl-5-oxo-2-imidazolin-2-yl)-m-toluic acid, mp 245°–248° C., is obtained by recrystallization of the product from ethanol.

EXAMPLE 20

Preparation of 2-(5-imidazolidinyl)benzoic acids and esters

The procedures described in Examples 9–11, 12–15 and 16–19 are effective for preparing a wide variety of substituted and unsubstituted 2-(2-imidazolin-2-yl)benzoic acids and esters which can be reduced to the formula II 2-(2-imidazolidinyl)benzoic acids and esters using sodium cyanoborohydride. Among the 2-(2-imidazolin-2-yl)benzoic acids and esters prepared by these procedures are those described below in Table I.

TABLE I

Compounds prepared by the procedures described in Examples 1–19 having the structure:

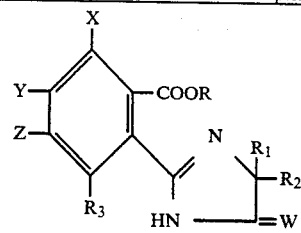

| R | $R_1$ | $R_2$ | W | X | Y | Z | $R_3$ | mp °C. |
|---|---|---|---|---|---|---|---|---|
| $CH_3$ | $CH_3$ | $CH(CH_3)_2$ | O | $NO_2$ | H | H | $(NO_2)$ | 172–178 IM |
| H | $CH_3$ | $CH(CH_3)_2$ | O | H | H | $NO_2$ | H | 224–238 |
| $CH_3$ | $CH_3$ | $CH(CH_3)_2$ | O | $NO_2$ | H | H | H | 159–162 |
| $CH_3$ | $CH_3$ | $CH(CH_3)_2$ | O | H | H | $NO_2$ | H | 140–145 |
| H | $CH_3$ | $CH(CH_3)_2$ | O | H | F | H | H | 213–215 |
| $CH_3$ | $CH_3$ | $CH(CH_3)_2$ | O | H | F | H | H | 114–121 |
| H | $CH_3$ | $CH(CH_3)_2$ | O | H | H | H | $NO_2$ | 153–160 |
| H | $CH_3$ | $CH(CH_3)_2$ | O | H | $C_2H_5$ | H | H | 182–184 |
| $CH_3$ | $CH_3$ | $CH(CH_3)_2$ | O | H | $C_2H_5$ | H | H | 105–107 |

TABLE I-continued

Compounds prepared by the procedures described in Examples 1-19 having the structure:

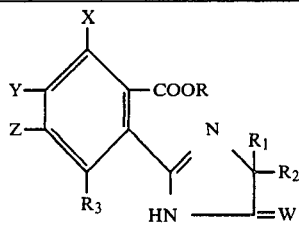

| R | $R_1$ | $R_2$ | W | X | Y | Z | $R_3$ | mp °C. |
|---|---|---|---|---|---|---|---|---|
| $C_2H_5$ | $CH_3$ | $CH(CH_3)_2$ | O | H | $C_2H_5$ | H | H | 133–135 |
| $CH_2C_6H_5$ | $CH_3$ | $CH(CH_3)_2$ | O | H | $C_2H_5$ | H | H | 115–118 |
| $CH_2C\equiv CH$ | $CH_3$ | $CH(CH_3)_2$ | O | H | $C_2H_5$ | H | H | 128–131 |
| $CH_2$-furanyl | $CH_3$ | $CH(CH_3O_2$ | O | H | $C_2H_5$ | H | H | 102–105 |
| H | $CH_3$ | $CH(CH_3)_2$ | O | F | H | H | H | 224–225 |
| H | $CH_3$ | $CH(CH_3)_2$ | O | $NO_2$ | H | H | H | 215–216 |
| $CH_3$ | $CH_3$ | $CH(CH_3)_2$ | O | F | H | H | H | 150–157 |
| $CH_3$ | $CH_3$ | $CH(CH_3)_2$ | O | H | H | $C_2H_5$ | H | 162–163 |
| H | $CH_3$ | $CH(CH_3)_2$ | O | H | H | $C_2H_5$ | H | 268–(dec) (HCl salt) |
| $CH_3$ | $CH_3$ | $CH(CH_3)_2$ | O | H | H | H | $CH_3$ | 159–161 |
| H | $CH_3$ | $CH(CH_3)_2$ | O | H | H | $C_2H_5$ | H | 101–108 |
| $CH_3$ | $CH_3$ | $CH(CH_3)_2$ | O | H | H | H | Cl | 147–150 |
| H | $CH_3$ | $CH(CH_3)_2$ | O | H | H | H | Cl | 210–214 |
| $CH_3$ | $CH_3$ | $CH(CH_3)_2$ | O | H | H | F | H | 156–162 |
| $CH_3$ | $CH_3$ | $CH(CH_3)_2$ | O | H | $CF_3$ | $(CF_3)$ | H | 109–121 |
| H | $CH_3$ | $CH(CH_3)_2$ | O | H | $CF_3$ | H | H | 214.5–216 |
| $CH_3$ | $CH_3$ | $CH(CH_3)_2$ | O | H | OH | (OH) | H | 119–129 |
| $CH_3$ | $CH_3$ | $CH(CH_3)_2$ | O | H | H | H | $NH_2$ | 142–150 |
| H | $CH_3$ | $CH(CH_3)_2$ | O | H | H | H | $N(CH_3)_2$ | 210–217 |
| $CH_3$ | $CH_3$ | $CH(CH_3)_2$ | O | H | H | H | $N(CH_3)_2$ | 125–133 |
| $CH_3$ | $CH_3$ | $CH(CH_3)_2$ | O | H | $OCH_3$ | H | H | 54–60 |
| H | $CH_3$ | $CH(CH_3)_2$ | O | H | $OCH_3$ | H | H | 188.5–190 |
| $CH_3$ | $CH_3$ | $CH(CH_3)_2$ | O | $OCH_3$ | H | H | H | 145–148 |
| H | $CH_3$ | $CH(CH_3)_2$ | O | $OCH_3$ | H | H | H | 188–190 |
| $CH_3$ | $CH_3$ | $CH(CH_3)_2$ | O | H | H | H | $OCH_3$ | 158–163 |
| H | $CH_3$ | $CH(CH_3)_2$ | O | H | H | H | $CF_3$ | 213–215 |
| H | $CH_3$ | $CH(CH_3)_2$ | O | H | H | H | $OCH_3$ | 196–200 ½ $H_2SO_4$ salt |
| $CH_3$ | $CH_3$ | $CH(CH_3)_2$ | O | H | H | H | $CF_3$ | 161–165 |
| $CH_2C_6H_5$ | $CH_3$ | $CH(CH_3)_2$ | O | H | $CH_3$ | $CH_3$ | H | 149–152 |
| $CH_2$-furanyl | $CH_3$ | $CH(CH_3)_2$ | O | H | $CH_3$ | $CH_3$ | H | 129–137 |
| $\overset{+}{NH_3}$—$CH(CH_3)_2$ | $CH_3$ | $CH(CH_3)_2$ | O | H | $CH_3$ | $CH_3$ | H | glass |
| $CH_3$ | $CH_3$ | $CH(CH_3)_2$ | O | H | $CH_3$ | $CH_3$ | H | 140–141 |
| $CH_2C\equiv CH$ | $CH_3$ | $CH(CH_3)_2$ | O | H | $CH_3$ | $CH_3$ | H | 165–167 |
| H | $CH_3$ | $CH(CH_3)_2$ | O | H | $CH_3$ | $CH_3$ | H | 188–189 |
| H | $CH_3$ | $CH(CH_3)_2$ | O | H | $CH_3$ | $CH_3$ | H | 259–263 (dec) (HCl salt) |
| $CH_3$ | $CH_3$ | $CH(CH_3)_2$ | O | H | $CH_3$ | H | $CH_3$ | 167–169.5 |
| H | $CH_3$ | $CH(CH_3)_2$ | O | H | $CH_3$ | H | $CH_3$ | 206–208.5 |
| $CH_3$ | $CH_3$ | $CH(CH_3)_2$ | O | H | H | $CH_3$ | $CH_3$ | 173.5–177 |
| H | $CH_3$ | $CH(CH_3)_2$ | O | H | H | $CH_3$ | $CH_3$ | 177–198 |
| H | $CH_3$ | $CH(CH_3)_2$ | O | H | Cl | $CH_3$ | H | 188–191 |
| $CH_3$ | $CH_3$ | $CH(CH_3)_2$ | O | H | Cl | $CH_3$ | H | 118–132 |
| H | $CH_3$ | $CH(CH_3)_2$ | O | Cl | $CH_3$ | H | H | 213–222 |
| $CH_3$ | $CH_3$ | $CH(CH_3)_2$ | O | F | $CH_3$ | H | H | 129–132 |
| $CH_3$ | $CH_3$ | $CH(CH_3)_2$ | O | H | —$(CH_2)_4$— | | H | 145–152 |
| H | $CH_3$ | $CH(CH_3)_2$ | O | H | —$(CH_2)_4$— | | H | 200–203 |
| H | $CH_3$ | $CH(CH_3)_2$ | O | H | $CH_3$ | H | Cl | 245–248 |
| $CH_3$ | $CH_3$ | $CH(CH_3)_2$ | O | H | $CH_3$ | H | Cl | 184–189 |
| H | $CH_3$ | $CH(CH_3)_2$ | O | $CH_3$ | H | $CH_3$ | H | 200–207 |
| $CH_2C\equiv CH$ | $CH_3$ | $CH(CH_3)_2$ | O | $CH_3$ | H | $CH_3$ | H | 121–125 |
| $CH_3$ | $CH_3$ | $CH(CH_3)_2$ | O | $CH_3$ | H | $CH_3$ | H | 145–148 |
| $CH_3$ | $CH_3$ | $CH(CH_3)_2$ | O | H | Cl | Cl | H | 170–173 |
| H | $CH_3$ | $CH(CH_3)_2$ | O | H | Cl | Cl | H | 223–224 |
| $CH_3$ | $CH_3$ | $CH(CH_3)_2$ | O | H | H | $CH_3$ | Cl | 181–183 |
| $CH_3$ | $CH_3$ | $CH(CH_3)_2$ | O | $CH_3$ | H | H | $CH_3$ | 124–146 |

TABLE I-continued

Compounds prepared by the procedures described in Examples 1-19 having the structure:

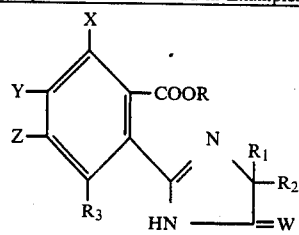

| R | R₁ | R₂ | W | X | Y | Z | R₃ | mp °C. |
|---|---|---|---|---|---|---|---|---|
| H | CH₃ | CH(CH₃)₂ | O | CH₃ | H | H | H | >250 HCl salt |
| H | CH₃ | CH(CH₃)₂ | O | CH₃ | —CH=CH₂—CH=CH₂— | | H | 196–204 |
| H | CH₃ | CH(CH₃)₂ | S | H | H | CH₃ | Cl | 204–206 |
| H | CH₃ | CH(CH₃)₂ | S | H | H | H | H | 134–138 |
| CH₃ | CH₃ | CH(CH₃)₂ | S | H | H | H | H | 172–175 (R) |
| H | CH₃ | CH(CH₃)₂ | S | H | H | H | H | 161–163 (R) |
| CH₃ | CH₃ | CH(CH₃)₂ | S | H | H | H | H | 142–144 |
| CH₂C₆H₅ | CH₃ | CH(CH₃)₂ | S | H | H | H | H | — |
| ⁺NH₃—CH(CH₃)₂ | CH₃ | CH(CH₃)₂ | S | H | H | H | H | — |
| (CH₃)₃N⁺—C₆H₅ | CH₃ | CH(CH₃)₂ | S | H | H | H | H | 148–150 |
| OCH₂C≡CH | CH₃ | CH(CH₃)₂ | S | H | H | H | H | 132.5–134 |
| C₂H₅ | CH₃ | CH(CH₃)₂ | S | H | H | H | H | 150–152 |
| —CH₂-furanyl | CH₃ | CH(CH₃)₂ | S | H | H | H | H | 195–198 (dec) HCl salt |
| CH₃ | CH₃ | CH(CH₃)₂ | S | H | H | H | H | 127–129 |
| CH(CH₃)₂ | CH₃ | CH(CH₃)₂ | S | H | H | H | H | 175–200 (dec) |
| Na⁺ | CH₃ | CH(CH₃)₂ | S | H | H | H | H | >285 |
| Ca⁺⁺/2 | CH₃ | CH(CH₃)₂ | O | CH₃ | H | H | CH₃ | 225.5–229 |
| H | CH₃ | CH(CH₃)₂ | O | H | H | CH₃ | F | 164–170 |
| H | CH₃ | CH(CH₃)₂ | S | H | CH₃ | (CH₃) | H | 149–160 M |
| H | CH₃ | CH(CH₃)₂ | S | H | CH₃ | (CH₃) | H | 105–123 M |
| H | CH₃ | CH(CH₃)₂ | S | H | CH₃ | H | H | 133–141 |
| CH₃ | CH₃ | CH(CH₃)₂ | S | H | CH₃ | H | H | 188–191 |
| CH₃ | CH₃ | CH(CH₃)₂ | O | H | H | CH₂OH | H | 195–199 |
| CH₃ | CH₃ | CH(CH₃)₂ | O | —(CH₂)₃— | | H | H | 142–144 |
| CH₃ | CH₃ | CH(CH₃)₂ | O | H | —(CH₂)₃— | | H | 139–142 |
| H | CH₃ | CH(CH₃)₂ | O | H | —(CH₂)₃— | | H | 186–189 |
| H | CH₃ | CH(CH₃)₂ | O | | | | H | 157–161 |
| CH₃ | CH₃ | CH(CH₃)₂ | S | SCH₃ | H | H | H | 100–104 |
| H | —CH(CH₂)₄— CH₃ | | O | H | H | CH₂OH | H | 214–218 |
| CH₃ | CH₃ | CH(CH₃)₂ | O | H | H | H | H | 113–114 |
| CH₃ | CH₃ | CH(CH₃)₂ | O | H | CH₂OH | H | H | 229–231 |
| H | —CH(CH₂)₄— CH₃ | | O | H | CH₂OH | H | H | 207–210 |
| H | CH₃ | CH(CH₃)₂ | O | H | H | H | H | 136–140 |
| H | CH₃ | CH(CH₃)₂ | O | H | —(CH₂)₂— | | H | 201–203 |
| CH₃ | CH₃ | CH(CH₃)₂ | O | H | —(CH₂)₂— | | H | 130–135 |
| CH₃ | CH₃ | CH(CH₃)₂ | O | H | H | H | SCH₃ | 113–115 |
| CH₃ | CH₃ | CH(CH₃)₂ | O | H | CH₂F | H | H | 113–118 |
| H | CH₃ | CH(CH₃)₂ | O | H | H | H | SCH₃ | 201–205 |
| CH₃ | CH₃ | CH(CH₃)₂ | O | H | SCH₃ | H | H | 130–131 |
| H | CH₃ | CH(CH₃)₂ | O | H | SCH₃ | H | H | 105–116 |
| H | CH₃ | CH(CH₃)₂ | S | CH₃ | H | CH₃ | H | 191–193 |
| H | CH₃ | CH(CH₃)₂ | O | H | CH₂F | H | H | 205–210 |
| CH₃ | CH₃ | CH(CH₃)₂ | O | H | OCHF₂ | (OCHF₂) | H | 155–157 M |
| CH₃ | CH₃ | CH(CH₃)₂ | O | OCHF₂ | H | (OCHF₂) | H | 119–129 M |
| H | CH₃ | CH(CH₃)₂ | O | H | OCHF₂ | (OCHF₂) | H | 146–148 M |
| CH₃ | CH₃ | CH(CH₃)₂ | O | H | H | CH₂F | H | 117–119 |
| H | CH₃ | CH(CH₃)₂ | S | H | —(CH₂)₂— | | H | 187–192 |
| CH₃ | CH₃ | CH(CH₃)₂ | O | H | OCF₃ | H | H | 99–102 |
| CH₃ | CH₃ | CH(CH₃)₂ | S | CH₃ | H | CH₃ | H | 128–130 |
| CH₃ | CH₃ | CH(CH₃)₂ | S | H | OCH₃ | H | H | 170–171 |
| CH₃ | CH₃ | CH(CH₃)₂ | S | H | —(CH₂)₂— | | H | 199–201 |

TABLE I-continued

Compounds prepared by the procedures described in Examples 1-19 having the structure:

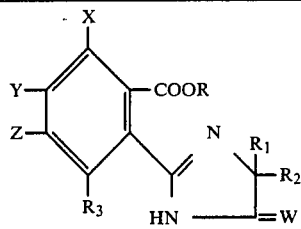

| R | R₁ | R₂ | W | X | Y | Z | R₃ | mp °C. |
|---|---|---|---|---|---|---|---|---|
| CH₃ | CH₃ | CH(CH₃)₂ | S | H | OCHF₂ | (OCHF₂) | H | 153–155 M |
| H | CH₃ | CH(CH₃)₂ | O | H | OCF₃ | H | H | 250–251 |
| H | CH₃ | CH(CH₃)₂ | S | H | OCH₃ | H | H | 124–126 |

IM = isomeric mixture where second on the ring is shown in ( ).

EXAMPLE 21

Preparation of trans-methyl o-(4-isopropyl-4-methyl-5-oxo-2-imidazolidinyl)benzoate

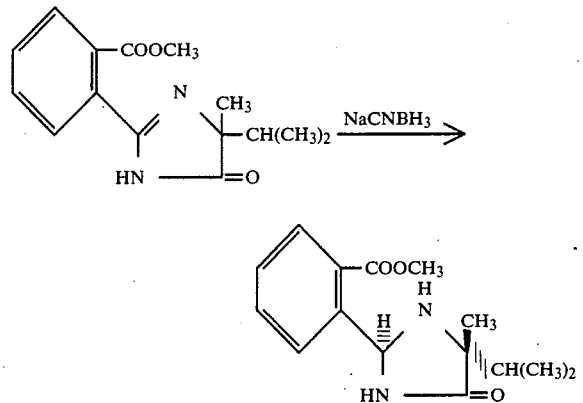

To a stirred solution containing 27.4 g methyl o-(4-isopropyl-4-methyl-5-oxo-2-imidazolin-2-yl)benzoate in 200 mL methanol is added one equivalent of 2N methanolic HCl. Then 6.3 g sodium cyanoborohydride is added and enough methanolic HCl to maintain a pH of 2-3. Two further aliquots of the hydride (4 g and 2 g) are added with continual adjustment of the pH of the solution to 2-3.

After stirring overnight, the pH of the solution is first adjusted to one with concentrated HCl followed by adjustment to pH 5 with 2N NaOH. The mixture is filtered, the filtrate concentrated in vacuo and the residue distributed between ethyl acetate and water, the organic extract dried and concentrated. Trituration of this residue gives a crystalline solid, 15 g, mp 111°-122° C. Purification of 7 g of this material by chromatography on a silica gel using 20 to 40% ethyl acetate in hexane gives 6.7 g crystalline product which is crystallized from ether-hexane to give 5.5 g trans-methyl o-(4-isopropyl-4-methyl-5-oxo-2-imidazolidinyl)benzoate, mp 124°-126° C.

Other compounds that can be prepared by the above procedure are illustrated in Table II below.

TABLE II

| R | R₁ | R₂ | W | X | Y | Z | R₃ | mp °C. | |
|---|---|---|---|---|---|---|---|---|---|
| n-C₃H₇ | CH₃ | CH(CH₃)₂ | O | H | H | H | H | 107–110.5 | trans |
| CH₂C≡CH | CH₃ | CH(CH₃)₂ | O | H | H | H | H | 118–120 | trans |
| CH₃ | CH₃ | CH(CH₃)₂ | O | H | H | H | H | 121–122 | trans |
| H | CH₃ | CH(CH₃)₂ | O | H | H | H | H | 250 | (dec) |
| CH₃ | CH₃ | CH(CH₃)₂ | O | H | CH₃ | (CH₃) | H | 123–130 | mixture |
| CH₃ | CH₃ | CH(CH₃)₂ | O | H | H | CH₂F | H | 121–127 | mixture |
| CH₃ | CH₃ | CH(CH₃)₂ | O | H | OCF₃ | H | H | 108–111 | trans or cis |
| CH₃ | CH₃ | CH(CH₃)₂ | O | H | SCH₃ | H | H | 40–54 | mixture |

EXAMPLE 24

Preparation of methyl 3-fluoro-2-formylbenzoate

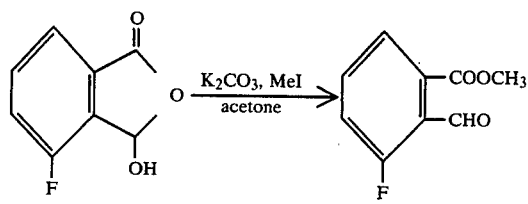

A stirred mixture containing 7.36 g 4-fluoro-3-hydroxyphthalide, 18.15 g potassium carbonate and 11 mL methyl iodide in 125 mL acetone is heated at reflux for two hours. After stirring overnight at room temperature, the mixture is filtered and concentrated. The residue is dispersed in 200 mL ether, filtered and the filtrate concentrated to give 7.6 g residue which is used directly without further purification. The nmr spectrum of this material is consistent with that expected for the desired product.

EXAMPLE 23

Preparation of 4-fluoro-3-hydroxyphthalide

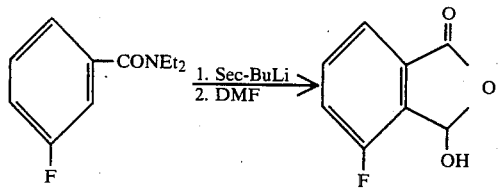

To a stirred solution of 10 g m-fluoro-N,N-diethylbenzamide in 250 mL THF under nitrogen at −70° C. is added dropwise 52 mL of a 1M solution of sec-butyl lithium in cyclohexane. After the addition, 5.0 mL dry dimethylformamide is added dropwise at −60° to −65° C. The mixture is stirred a further one hour at this temperature and 50 mL ice added. The mixture is allowed to reach room temperature and stirred for a further two hours. After the addition of 100 mL of brine, the phases are separated and the aqueous phase extracted with 150 mL ethyl acetate. The combined organic phases are dried and concentrated to give 3.5 g of a mixture of two compounds, one being 3-fluoro-2-formyl-N,N-diethylbenzamide.

The aqueous phase above, after standing at room temperature overnight is acidified to pH 3-4 with concentrated $H_2SO_4$. The precipitate is extracted into ethyl acetate, the organic phase dried and concentrated to give 8.5 g crystalline residue. This material is recrystallized from methylene chloride to give analytically pure 4-fluoro-3-hydroxyphthalide, mp 113°–120° C.

EXAMPLE 22

Preparation of methyl o-(4-isopropyl-4-methyl-5-thioxo-2-imidazolidinyl)benzoate

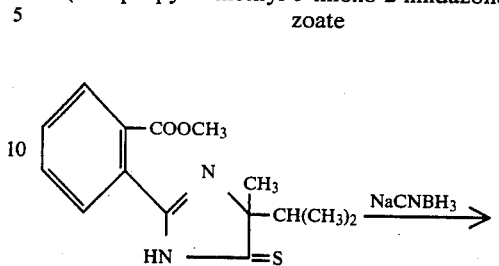

A stirred solution containing 5.0 g methyl o-(4-isopropyl-4-methyl-5-thioxo-2-imidazolin-2-yl)benzoate in 50 mL absolute methanol is cooled to 0° C. and 1.4 mL concentrated HCl added. The mixture is allowed to come to room temperature and 1.07 g sodium cyanoborohydride added. The pH of the mixture is maintained at ~3 by the addition of 2N methanolic HCl. After two hours, a further 1.07 g sodium cyanoborohydride is added and the pH of the solution kept at ~3. After stirring overnight, the mixture is cooled to 5° C., concentrated HCl added to give a solution pH of 0–1. The pH is then adjusted to 5–6 with 5N NaOH and the methanol removed in vacuo. The residue is distributed between water and $CH_2Cl_2$. The organic phase is separated, dried and concentrated. The residue is chromatographed on silica gel using 4:1, hexane:ethyl acetate to give the product as the fastest moving component. The methyl o-(4-isopropyl-4-methyl-5-thioxo-2-imidazolidinyl)benzoate was obtained as a crystalline solid, mp 115°–121° C. Analysis by nmr indicates this to be predominantly the cis-isomer contaminated with some of the trans-isomer.

Other compounds can be prepared by this procedure using the appropriately substituted thioxo-2-(imidazolin-2-yl)benzoate starting material.

EXAMPLE 25

Preparation of methyl o-[N-(1-carbamoyl-1,2-dimethylpropyl)formimidoyl]benzoate

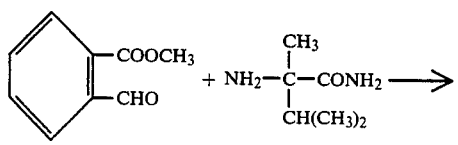

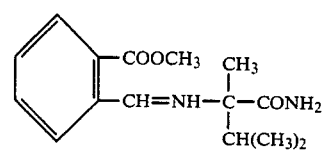

A mixture containing 5.0 g methyl 2-formylbenzoate [C. Brown and M. V. Sargent, J. Chem. Soc. (C), 1818 (1969)] and 4.0 g 2-amino-2,3-dimethylbutyramide and 50 mg p-toluenesulfonic acid in 100 mL toluene is heated under reflux under a Dean-Stark water separator for three hours. The mixture is filtered and concentrated in vacuo. The residue crystallizes on standing and is recrystallized from etherhexane to give analytically pure methyl o-[N-(1-carbamoyl-1,2-dimethylpropyl)-formimidoyl]benzoate, mp 79°-80.5° C.

Using essentially the same procedure but substituting methyl 3-fluoro-2-formylbenzoate for methyl 2-formylbenzoate gives the corresponding product, methyl 3-fluoro-2-[N-(1-carbamoyl-1,2-dimethylpropyl)formimidoyl]benzoate, mp 125°-131° C.

EXAMPLE 26

Preparation of cis- and trans-methyl 2-(4-isopropyl-4-methyl-5-oxo-2-imidazolidinyl)benzoate

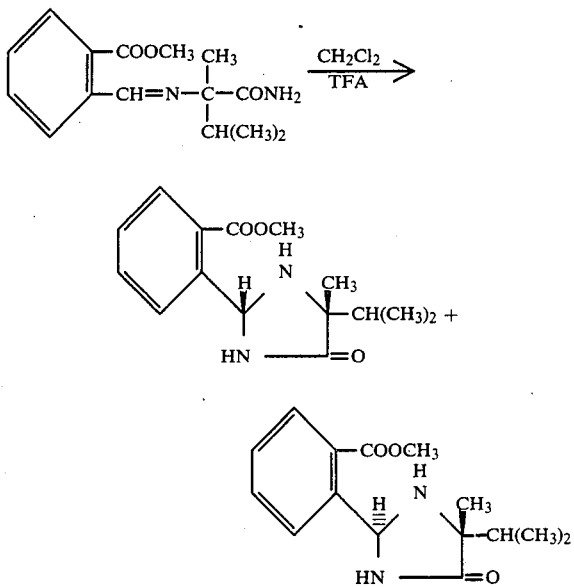

To a stirred suspension of 4.14 g of methyl o-[N-(1-carbamoyl-1,2-dimethylpropyl)formimidoyl]benzoate in 50 mL methylene chloride under nitrogen and at 0° C. is added 1.25 mL trifluoroacetic acid. The mixture is allowed to warm to room temperature and stirred overnight. After cooling to 0° C., saturated aqueous sodium bicarbonate solution is added to give a pH of 7-8. The organic phase is separated, dried and concentrated to give an oil which slowly crystallized. The nmr spectrum of a sample recrystallized from acetonitrile, mp 143°-153° C. showed the product to be a mixture of cis- and trans-methyl 2-(5-isopropyl-5-methyl-4-oxo-2-imidazolidinyl)benzoate.

Other compounds can be prepared by the above procedure using an appropriately substituted 2-formylbenzoate in the procedure of Example 25 and employing the resulting carbamoyl formimidoyl benzoate in the above procedure. For example, trans-methyl 3-fluoro-2-(4-isopropyl-4-methyl-5-oxo-2-imidazolidinyl)benzoate, mp 98°-104° C. can be prepared this way.

EXAMPLE 27

Preparation of cis- and trans-methyl o-(4-isopropyl-4-methyl-5-thioxo-2-imidazolidinyl)benzoate

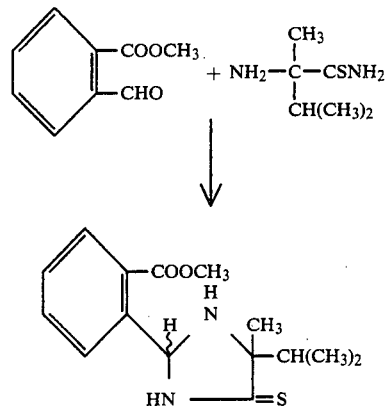

A mixture containing 4.5 g methyl 2-formylbenzoate, 4.0 g 2-amino-2,3-dimethylthiobutyramide and 20 mg p-toluenesulfonic acid in 100 mL toluene is heated under reflux under a Dean-Stark water separator for four hours. The mixture is cooled, filtered and concentrated to give a crystalline solid which is crystallized from CH₂Cl₂-hexanes to give 6 g of analytically pure cis- and trans-methyl o-(4-isopropyl-4-methyl-5-thioxo-2-imidazolidinyl)benzoate, mp 140°-142.5° C. This is predominantly the trans-isomer.

Other compounds can be prepared by this procedure using the appropriately substituted 2-formylbenzoate. For example, using essentially the same procedure but using methyl 3-fluoro-2-formylbenzoate as starting material, there is obtained cis- and transmethyl 3-fluoro-2-(4-isopropyl-4-methyl-5-thioxo-2-imidazolidinyl)benzoate, mp 115°-123° C. Similarly prepared are

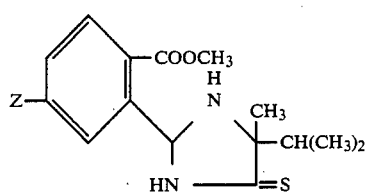

where Z=OCH₃, mp 112-114 (mixture) and Z=SCH₃, 124-138 (mixture).

EXAMPLE 27-A

Preparation of trans-3-fluoro-2-(4-isopropyl-4-methyl-5-oxo-2-imidazolidinyl)benzoic acid

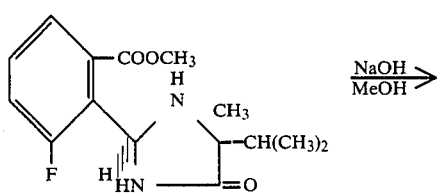

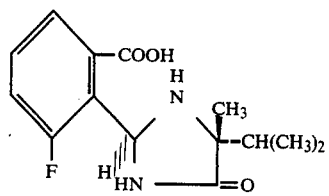

To a warm solution containing 1.3 ester in 5 mL methanol is added 2.5 mL NaOH and the mixture stirred overnight at room temperature. The solution is acidified to pH 3 with conc. $H_2SO_4$. The mixture is diluted with 6 mL water and ethyl acetate, filtered and the aqueous phase separated. The aqueous toluene on cooling deposited the product as a fine white crystalline solid mp 183°–184° C.

By using similar conditions and the appropriate starting ester, the following acids can be prepared.

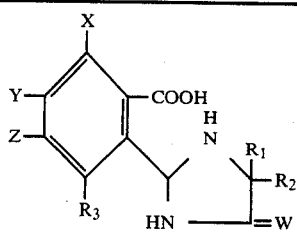

| $R_1$ | $R_2$ | W | X | Y | Z | $R_3$ | mp °C. |
|---|---|---|---|---|---|---|---|
| $CH_3$ | $CH(CH_3)_2$ | S | H | H | H | H | 190–192 trans |
| $CH_3$ | $CH(CH_3)_2$ | S | H | H | H | F | 145–146 resolidifies and melts at 235° C. cis and trans |
| $CH_3$ | $CH(CH_3)_2$ | O | H | H | $CH_2F$ | H | |
| $CH_3$ | $CH(CH_3)_2$ | O | H | $OCF_3$ | H | H | 179–183 cis or trans |
| $CH_3$ | $CH(CH_3)_2$ | S | H | H | $-SCH_3$ | H | 196–199 cis and trans |
| $CH_3$ | $CH(CH_3)_2$ | S | H | H | $OCH_3$ | H | 175–177 cis and trans |
| $CH_3$ | $CH(CH_3)_2$ | O | H | $SCH_3$ | H | H | |

EXAMPLE 28

Preparation of methyl 2-(4-isopropyl-4-methyl-5-oxo-2-imidazolin-yl)nicotinate

This method involves the formation of trycyclic compounds, without isolation, directly forming the nicotinic acid esters:

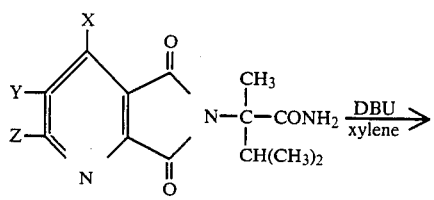

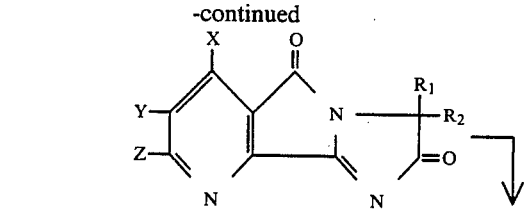

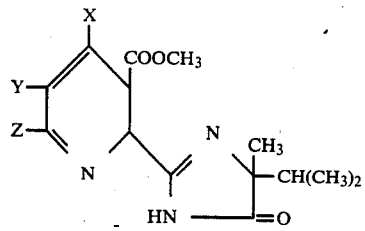

+

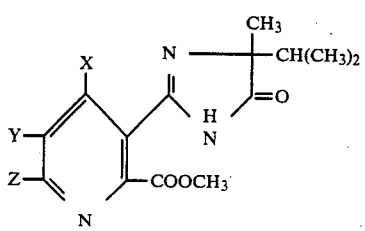

A mixture of 25 g amide and 1 mL 1,5-diazabicyclo-[5.4.0]undec-5-ene(DBU) in 500 ml xylene is heated under reflux for one hour under a Dean-Stark water separator. The mixture is cooled somewhat, the water separator removed, 100 mL anhydrous methanol added and the mixture heated under reflux for one hour. The solvents are then removed in vacuo and the product isolated by chromatography as to give 13.65 g product mp 120°–122° C. Other esters as described in Example 28 in the same manner using the appropriately substituted amide starting material. This procedure is also described in European Patent Application 81103638.3, publication No. 0.041,623.

EXAMPLE 29

Preparation of methyl 2-(4-isopropyl-4-methyl-5-oxo-2-imidazolin-2-yl)nicotinate A mixture of 13.65 g of the nicotinate and 9.69 g phosphorus pentachloride in 110 mL dry toluene is heated with stirring to 80° C. After one and one-half hours, the thick mixture is cooled, filtered and the solid washed with ether and dried. This is the hydrochloride salt of the desired product.

This salt is dissolved in 60 mL water; neutralized with sodium bicarbonate, the resulting precipitate removed by filtration, washed with water and air-dried to give the product:

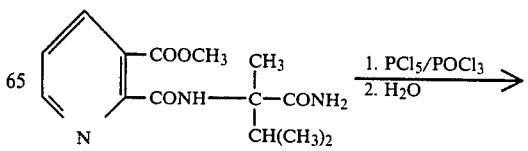

-continued

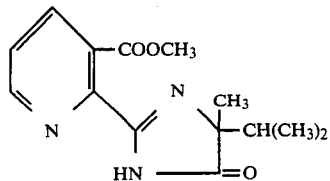

A mixture of 5.0 g nicotinate and 7.1 g phosphorus pentachloride in 40 mL phosphorus oxychloride is stirred at room temperature overnight. The phosphorous oxychloride is removed in vacuo, the residue suspended in 40 mL toluene and again concentrated. This is repeated. Water (40 mL) is added to the residue and the mixture heated to reflux and held there for one hour. After cooling, the mixture is extracted with methylene chloride, the extract dried and concentrated to give 1.05 g of the desired product. The pH of the aqueous phase from the methylene chloride extraction is adjusted to 5–6 with sodium bicarbonate solution and the mixture extracted again with methylene chloride. The dried extract was concentrated and the residue crystallized to give a further 2.65 g of the desired product.

The following nicotinic acid esters are prepared by one or more of the methods described above:

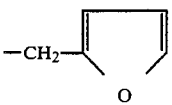

| R | $R_1$ | $R_2$ | X | Y | Z | mp °C. |
|---|---|---|---|---|---|---|
| $CH_3$ | $CH_3$ | $C_2H_5$ | H | H | H | 126.5–128.5 |
| $CH_2=CH$ | $CH_3$ | $CH(CH_3)_2$ | H | H | H | 104.0–106.0 |
| $CH_3$ | \-CH-(CH$_2$)$_4$- \| CH$_3$ | | H | H | H | 151.0–155.3 |
| $CH_2C\equiv CH$ | \-CH-(CH$_2$)$_4$- \| CH$_3$ | | H | H | H | 117.0–120.0 |
| $CH_2C_6H_5$ | \-CH-(CH$_2$)$_4$- \| CH$_3$ | | H | H | H | 148.5–151.3 |
| $CH_2C\equiv CH$ | $CH_3$ | $CH_3$ | H | H | H | 171.0–173.0 |
| $CH_3$ | $CH_3$ | $CH_3$ | H | H | H | 148.0–150.0 |
| $CH_2C_6H_5$ | $CH_3$ | $CH_3$ | H | H | H | 142.0–144.0 |
| $CH_2C_6H_5$ | $CH_3$ | $C_2H_5$ | H | H | H | 118.0–120.0 |
| $CH_2C\equiv CH$ | $CH_3$ | $C_2H_5$ | H | H | H | 138.0–140.0 |
| —$C_{12}H_{25}$—n | $CH_3$ | $CH(CH_3)_2$ | H | H | H | 55.0–57.0 |
| —$C_2H_5$ | $CH_3$ | $CH(CH_3)_2$ | H | H | H | 72.0–75.0 |
| $CH_2CH_2OCH_2C_6H_5$ | $CH_3$ | $CH(CH_3)_2$ | H | H | H | 90.0–92.5 |
| —CH$_2$-(furyl) | $CH_3$ | $CH(CH_3)_2$ | H | H | H | 120.5–122.0 |
| —$CH(CH_3)_2$ | $CH_3$ | $CH(CH_3)_2$ | H | H | H | 94.0–97.5 |
| —$CH_2C_6H_5$ | $CH_3$ | $CH(CH_3)_2$ | H | H | H | 122.0–125.0 |
| —$CH_2$—$C\equiv C$—$C_7H_{15}$—n | $CH_3$ | $CH(CH_3)_2$ | H | H | H | oil |
| $CH_2CH_2OCH_3$ | $CH_3$ | $CH(CH_3)_2$ | H | H | H | 60.0–63.0 |
| $CH_2CH=CH_2$ | $CH_3$ | $CH(CH_3)_2$ | H | H | H | 81.0–84.0 |
| —CH—CH=CH$_2$ \| CH$_3$ | $CH_3$ | $CH(CH_3)_2$ | H | H | H | oil |
| CH$_2$—C=CH$_2$ \| CH$_3$ | $CH_3$ | $CH(CH_3)_2$ | H | H | H | 98.0–100.0 |
| CH—C≡CH \| CH$_3$ | $CH_3$ | $CH(CH_3)_2$ | H | H | H | oil |
| $CH_2$—CH=CHCH$_3$ | $CH_3$ | $CH(CH_3)_2$ | H | H | H | 87.0–89.0 |
| —$C(CH_3)_3$ | $CH_3$ | $CH(CH_3)_2$ | H | H | H | 124.0–126.0 |

-continued

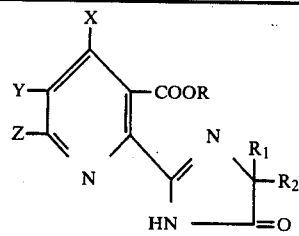

| R | R₁ | R₂ | X | Y | Z | mp °C. |
|---|---|---|---|---|---|---|
| cyclohexyl | CH₃ | CH(CH₃)₂ | H | H | H | 95.0–98.0 |
| $C_{18}H_{37}$—n | CH₃ | CH(CH₃)₂ | H | H | H | 77.3–79.2 |
| CH₂C₆H₅ | CH₃ | CH(CH₃)₂ | H | H | H | 116.5–119.0 |
| —CH₂C₆H₅ | CH₃ | CH₂CH(CH₃)₂ | H | H | H | 76.0–78.5 |
| CH₃ | CH₃ | CH₂CH(CH₃)₂ | H | H | H | 92.0–94.0 |
| —C₄H₉—n | CH₃ | CH₂(CH₃)₂ | H | H | H | 54.0–57.0 |
| CH₂C≡CH | CH₃ | CHCH(CH₃)₂ | H | H | H | 128.5–131.0 |
| CH₃ | CH₃ | cyclopropyl | H | H | H | 128.0–131.0 |
| CH₂C₆H₅ | CH₃ | cyclopropyl | H | H | H | 111.0–113.0 |
| CH₃ | CH₃ | CH(CH₃)₂ | H | H | OCH₃ | 154.0–155.0 |
| CH₂—CH=CH—C₇H₁₅—n | CH₃ | CH(CH₃)₂ | H | H | H | oil |
| CH₂—C(Cl)=CH₂ | CH₃ | CH(CH₃)₂ | H | H | H | 73.0–77.0 |
| C₆H₁₃—n | CH₃ | CH(CH₃)₂ | H | H | H | oil |
| CH(CH₃)CH=CH—CH₃ | CH₃ | CH(CH₃)₂ | H | H | H | oil |
| CH₃ | —(CH₂)₅— | | H | H | H | 146.0–148.0 |
| CH₂CH=(CH₃)₂ | CH₃ | CH(CH₃)₂ | H | H | H | 77.5–79.0 |
| CH₂C₆H₅ | —(CH₂)₅— | | H | H | H | 117.0–122.0 |
| CH₂≡CCH₂OH | CH₃ | CH(CH₃)₂ | H | H | H | gum |
| CH₂C₆H₅ | C₂H₅ | C₂H₅ | H | H | H | 114.5–118.0 |
| C(CH₃)C≡CH | CH₃ | CH(CH₃)₂ | H | H | H | 128.0–132.0 |
| CH₂CH₂N⊕(CH₃)₃I⊖ | CH₃ | CH(CH₃)₂ | H | H | H | 165.0–175.0 |
| CH₃ | C₂H₅ | C₂H₅ | H | H | H | 132.5–135.5 |
| C(CH₃)₂C≡CH | CH₃ | CH(CH₃)₂ | H | H | H | 104.0–106.0 |
| CH₂C≡CH | CH₃ | Δ | H | H | H | 122.0–124.0 |
| CH₂C≡CH | —(CH₂)— | | H | H | H | 164.5–166.5 |
| CH₃ | CH₃ | CH(CH₃)₂ | CH₃ | H | H | 114.0–115.5 |
| CH₂C≡CH | C₂H₅ | C₂H₅ | H | H | H | 135.5–137.0 |
| CH₂—C₆H₄—OCH₃ | CH₃ | CH(CH₃)₂ | H | H | H | 111.0–113.0 |
| CH₂—C₆H₄—Cl | CH₃ | CH(CH₃)₂ | H | H | H | 136.0–138.0 |
| CH₂—C₆H₄—NO₂ | CH₃ | CH(CH₃)₂ | H | H | H | 131.5–133.0 |
| CH₂COOCH₃ | CH₃ | CH(CH₃)₂ | H | H | H | 104.0–108.0 |
| CH₂—CH(OC(CH₃)₂CH₃)(OCHO) | CH₃ | CH(CH₃)₂ | H | H | H | oil |

-continued

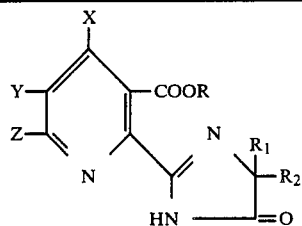

| R | R₁ | R₂ | X | Y | Z | mp °C. |
|---|---|---|---|---|---|---|
| CH₂CH₂CH₂COOC₂H₅ | CH₃ | CH(CH₃)₂ | H | H | H | 133.0–135.0 |
| CH₃ | CH₃ | CH(CH₃)₂ | Br | H | H | 122.5–126.0 |
| CH₂CH=CH—COOC₂H₅ | CH₃ | CH(CH₃)₂ | H | H | H | oil |
| (CH₂)₄COOCH₃ | CH₃ | CH(CH₃)₂ | H | H | H | oil |
| CH₂—C₆H₄—C(CH₃) | CH₃ | CH(CH₃)₂ | H | H | H | 108.0–111.0 |
| CH₂CH₂—C₆H₅ | CH₃ | CH(CH₃)₂ | H | H | H | 107.0–109.0 |
| CH₂—C₆H₅ | CH₃ | CH(CH₃)₂ | CH₃ | H | H | 130.0–132.0 |
| CH₂CH=CH—C₆H₅ | CH₃ | CH(CH₃)₂ | H | H | H | 113.0–115.0 |
| CH₂CH=C(CH₃)—CH₂CH₂CH=C(CH₃)₂ | CH₃ | CH(CH₃)₂ | H | H | H | oil |
| CH₂CH(OH)CH₂OH | CH₃ | CH(CH₃)₂ | H | H | H | oil |
| (CH₂)₃C≡CH | CH₃ | CH(CH₃)₂ | H | H | H | 73.0–75.0 |
| CH₂CH₂-pinanyl(CH₃,CH₃) | CH₃ | CH(CH₃)₂ | H | H | H | oil |
| CH(C₆H₅)COOCH₃ | CH₃ | CH(CH₃)₂ | H | H | H | oil |
| CH₂CH₂—C(CH₃)=CH₂ | CH₃ | CH(CH₃)₂ | H | H | H | oil |
| (CH₂)₉CH=CH₂ | CH₃ | CH(CH₃)₂ | H | H | H | oil |
| CH(CH₃)C₆H₅ | CH₃ | CH(CH₃)₂ | H | H | H | oil |
| CH₃ | —[CH(CH₂)₄\|CH₃]— | | H | H | H | 122.0–124.0 |
| CH₂—C₆H₅ | —[CH(CH₂)₄\|CH₃]— | | H | H | H | 123.0–125.0 |
| CH₂C≡CH | —[CH(CH₂)₄\|CH₃]— | | H | H | H | 132.0–134.5 |
| CH₃ | CH₃ | CH(CH₃)₂ | H | H | Cl | 102.5–104.5 |
| CH₂COOCH₂CH₃ | CH₃ | CH(CH₃)₂ | H | H | H | 86.0–90.0 |
| CH₂COOH | CH₃ | CH(CH₃)₂ | H | H | H | 187.0–189.0 |
| CH₂COOCH₂C₆H₅ | CH₃ | CH(CH₃)₂ | H | H | H | 121.5–123.0 |
| CH₂COOH | CH₃ | CH(CH₃)₂ | H | H | H | 106.0–110.0 |

-continued

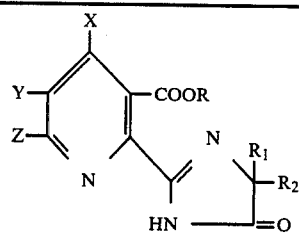

| R | R₁ | R₂ | X | Y | Z | mp °C. |
|---|---|---|---|---|---|---|
| CH₃ | CH₃ | CH(CH₃)₂ | H | H | H | 110.5–114.0 [α]$_D$ = +27.28 |
| CH₂C₆H₅ | CH₃ | CH(CH₃)₂ | H | H | H | 102.0–105.0 [α]$_D$ = +13.08 |
| CH₂C₆H₅ | CH₃ | CH(CH₃)₂ | H | H | H | 104.0–107.0 [α]$_D$ = −12.76 |
| CH₃ | CH₃ | CH(CH₃)₂ | H | H | N(CH₃)₂ | 184.5–185.5 |
| N=C(CH₃)₂ | CH₃ | CH(CH₃)₂ | H | H | H | 117.0–119.5 |
| CH₂CCl₃ | CH₃ | CH(CH₃)₂ | H | H | H | 114.0–116.0 |
| CH₃ | CH₃ | CH(CH₃)₂ | H | H | OC₆H₅ | 128.0–131.0 |
| CH₃ | CH₃ | CH(CH₃)₂ | H | C₄H₉—n | H | 69.0–71.5 |
| CH₃ | CH₃ | CH(CH₃)₂ | Cl | H | H | 110.0–113.0 |
| CH₃ | CH₃ | CH(CH₃)₂ | H | H | CF₃ | 96.5–100.0 |
| CH₃ | CH₃ | CH(CH₃)₂ | H | H | ⟨C₆H₄-Cl⟩ | |
| CH₃ | CH₃ | CH(CH₃)₂ | H | H | ⟨C₆H₄-CH₃⟩ | 190.0–191.0 |
| C₂H₅ | CH₃ | CH(CH₃)₂ | H | H | n-C₃H₇ | 85.0–87.0 |
| CH₃ | CH₃ | CH(CH₃)₂ | H | H | n-C₃H₇ | 124.0–126.0 |
| CH(CH₃)₂ | CH₃ | CH(CH₃)₂ | H | H | n-C₃H₇ | 115.0–122.0 |
| CH₃ | CH₃ | CH(CH₃)₂ | H | H | i-C₃H₇ | 122.0–124.5 |
| C₂H₅ | CH₃ | CH(CH₃)₂ | H | H | i-C₃H₇ | — |
| CH(CH₃)₂ | CH₃ | CH(CH₃)₂ | H | H | i-C₃H₇ | 106.5–110.5 |
| CH₃ | CH₃ | CH(CH₃)₂ | H | —(CH₂)₅— | | 170.0–174.0 |
| CH₃ | CH₃ | CH(CH₃)₂ | H | CH₃ | H | 129.0–130.5 |
| CH₃ | CH₃ | CH(CH₃)₂ | H | H | C₆H₅ | 162.0–164.0 |
| CH₃ | CH₃ | CH(CH₃)₂ | H | H | CH₃ | 95.5–97.5 |
| C₂H₅ | CH₃ | CH(CH₃)₂ | H | H | C₂H₅ | 110.0–113.0 |
| CH(CH₃)₂ | CH₃ | CH(CH₃)₂ | H | H | C₂H₅ | 111.0–123.0 |
| CH₃ | CH₃ | CH(CH₃)₂ | H | H | C₂H₅ | 139.0–140.0 |

EXAMPLE 29-A

Preparation of ethyl 2-[2-(dimethylamino)vinyl]-5-nitronicotinate

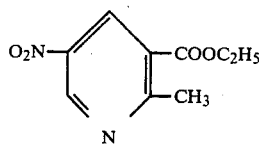

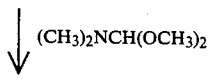

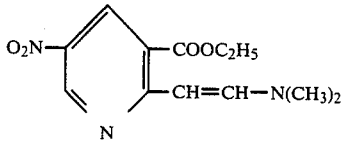

A solution containing 20.88 g of ethyl 2-methyl-5-nitronicotinate in 100 mL 1,1-dimethoxytrimethylamine is heated at reflux for three hours and 15 minutes. The mixture is cooled and the solid collected by filtration, washed with methanol and air dried to give 26 g of the desired enamine as a dark red solid mp 176°–179° C.

EXAMPLE 29-B

Preparation of Ethyl [N-(1-carbamoyl-1,2-dimethylpropyl)formimidoyl]-5-nitronicotinate

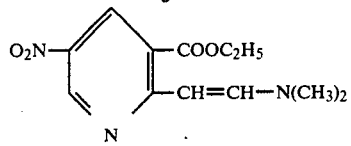

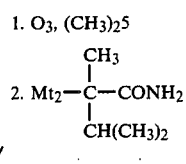

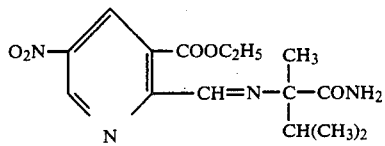

To a solution containing 18.9 g of the enamine in 200 mL $CH_2Cl_2$ and 10 mL methanol cooled in an ice bath is added ozone from a Welsback Ozone Generator operated at 120 v and air at 8 psi. This is continued until the red color of the enamine is discharged. The ozone is replaced by nitrogen and then 10 mL dimethylsulfide added. After 15 minutes, 9.8 g 2-amino-2,3-dimethylbutyramide is added, the reaction mixture transferred to a 500 mL flask and concentrated. The residue is dissolved in 300 mL toluene and heated at reflux under a nitrogen atmosphere under a Dean-Stark water trap. After one hour, the solvent is removed and the residue, which is mainly the Schiff base is a black gum, used without further purification.

EXAMPLE 29-C

Preparation of cis- and trans-ethyl 2-(4-isopropyl-4-methyl-5-oxo-2-imidazolidinyl)-5-nitronicotinate

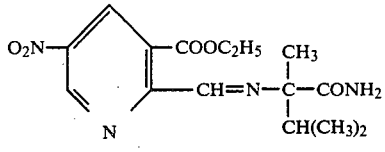

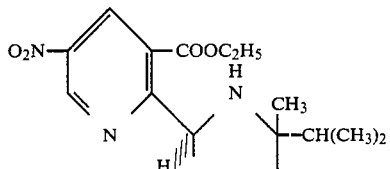

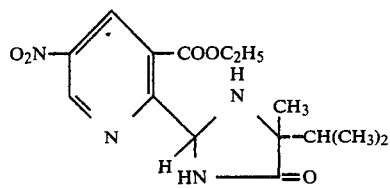

The crude Schiff base as described above is dissolved in 50 mL $CH_2Cl_2$ and treated with 4.6 mL trifluoroacetic acid at room temperature. After one hour an additional 1 mL acid is added and stirring continued for one hour. The mixture is cooled, 5.5 g sodium bicarbonate added. After the slow and careful addition of water, stirring is continued until $CO_2$ evolution ceases. The pH is adjusted to 7 with saturated sodium bicarbonate solution and the $CH_2Cl_2$ layer removed. The aqueous phase was reextracted three times with $CH_2Cl_2$. The combined extracts are dried and concentrated to give the crude product as a dark semi-solid. This material is chromatographed on silica gel, using ether and hexane-ethyl acetate mixtures to develop and elute the products. The trans-ethyl 2-(4-isopropyl-4-methyl-5-oxo-2-imidazolidinyl)-5-nicotinate is eluted first and recyrstallized from $CH_2Cl_2$-hexane to give the pure trans-isomer mp 116°–120° C.

The cis-isomer is eluted later and is recrystallized from $CH_2Cl_2$-hexane to give pure cis-ethyl 2-(4-isopropyl-4-methyl-5-oxo-2-imidazolidinyl)-5-nitronicotinate mp 149°–150° C.

EXAMPLE 29-D

Preparation of methyl 2-(4-isopropyl-4-methyl-5-oxo-2-imidazolin-2-yl)-5-(methylthio)nicotinate

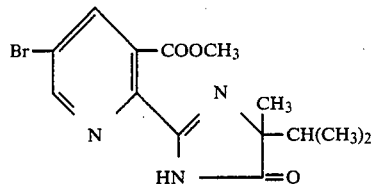

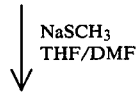

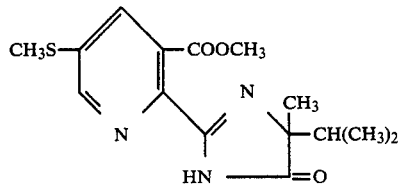

To a stirred solution containing 1.0 g bromo compound in 5 mL THF and 2 mL DMF is added 210 mg sodium methyl mercaptide under nitrogen. After two hours at 60° C., the mixture is cooled to room temperature, the pH adjusted to 4 with acetic acid, poured over ice and extracted with 2×50 mL ether. The extract is dried and concentrated to give a yellow oil which slowly solidifies. Recrystallization of this solid from ether/hexane gives the pure methyl 2-(4-isopropyl-4-methyl-5-oxo-2-imidazolin-2-yl)-5-(methylthio)-nicotinate, mp 107°–108° C.

EXAMPLE 30

Preparation of cis- and trans-methyl 6-(allyloxy)-2-(4-isopropyl-4-methyl-5-oxo-2-imidazolidinyl)nicotinate

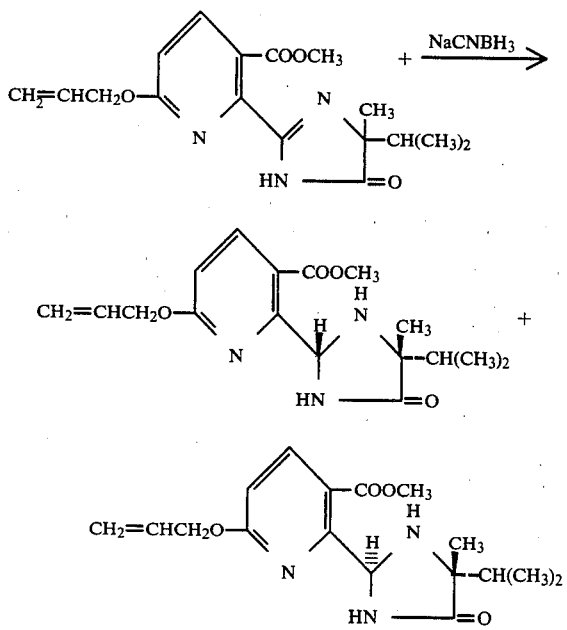

A solution containing 7.0 g (22.1 mmol) methyl 6-(allyloxy)-2-(4-isopropyl-4-methyl-5-oxo-2-imidazolin-2-yl)nicotinate in 70 mL absolute methanol is cooled to 0° C. and a few drops of methyl orange indicator added. To the stirred solution is added 1.8 mL (22.1 mmol) concentrated HCl. The red solution is warmed to room temperature and 1.4 g (22.1 mol) sodium cyanoborohydride is added. Slowly, the solution turns to an orange color (pH~4) and 2N methanolic HCl is added to the mixture until a red tint is observed (pH~3). This procedure of pH adjustment is repeated until there is no longer a change. After stirring overnight at room temperature, the solution is cooled to 0° C., the pH adjusted to ~0 with concentrated HCl to decompose residual NaCNBH$_3$. The pH is then adjusted to 5–6 with 5N NaOH. The methanol is removed in vacuo and enough water added to the residue to dissolve inorganic salts. This mixture is thoroughly extracted with CH$_2$Cl$_2$, the extracts dried and concentrated. The residue (~7.8 g) is a thick oil which is chromatographed on 350 g silica gel. Using 1:1 CH$_2$Cl$_2$-hexane followed by ether as eluants results in the separation of 0.35 g starting material. Further elution with ether results in the isolation of 1.87 g of the trans-isomer, and further elution with 10% methanol in ether gives 5.2 g of the cis-isomer.

The trans-isomer is recrystallized from CH$_2$Cl$_2$-hexanes to give 1.16 g of analytically pure trans-methyl 6-(allyloxy)-2-(4-isopropyl-4-methyl-5-oxo-2-imidazolidinyl)nicotinate, mp 144°–142° C.

Similarly the cis-isomer is recrystallized from CH$_2$Cl$_2$-hexane to give 4.6 g analytically pure cis-methyl 6-(alloxy)-2-(4-isopropyl-4-methyl-5-oxo-2-imidazolidinyl)nicotinate, mp 120°–122° C.

Using essentially the same procedure but substituting the appropriate 5-oxo- or 5-thioxo-imidazolinyl nicotinate for methyl 6-(allyloxy)-2-(4-isopropyl-4-methyl-5-oxo-2-imidazolin-2-yl)nicotinate, gives the following 5-oxo- and 5-thioxoimidazolidinyl nicotinates.

Other compounds that can be prepared by the above procedure are described in Table III below.

TABLE III

Preparation of formula 2-(2-imidazolidinyl)nicotinates

| R | R$_1$ | R$_2$ | W | X | Y | Z | Imidazolinyl nicotinate mp °C. | Imidazolidinyl nicotinate mp °C. cis | trans |
|---|---|---|---|---|---|---|---|---|---|
| CH$_3$ | CH$_3$ | C$_2$H$_5$ | O | H | H | H | 126.5–128.5 | | |
| CH$_2$≡CH | CH$_3$ | CH(CH$_3$)$_2$ | O | H | H | H | 104.0–106.0 | 109–114 | 120–121 |
| CH$_3$ | —CH—(CH$_2$)$_4$— CH$_3$ | | O | H | H | H | 151.0–155.3 | | |
| CH$_2$C≡CH | —CH—(CH$_2$)$_4$— CH$_3$ | | O | H | H | H | 117.0–120.0 | | |
| CH$_2$C$_6$H$_5$ | —CH—(CH$_2$)$_4$— CH$_3$ | | O | H | H | H | 148.5–151.3 | | |
| CH$_2$C≡CH | CH$_3$ | CH$_3$ | O | H | H | H | 171.0–173.0 | | |

TABLE III-continued

Preparation of formula 2-(2-imidazolidinyl)nicotinates $$\text{(pyridine with X, Y, Z, COOR, imidazoline)} \xrightarrow{NaCNBH_3} \text{(reduced imidazolidinyl product)}$$

| R | R₁ | R₂ | W | X | Y | Z | Imidazolinyl nicotinate mp °C | Imidazolidinyl nicotinate mp °C cis | trans |
|---|---|---|---|---|---|---|---|---|---|
| CH₃ | CH₃ | CH₃ | O | H | H | H | 148.0–150.0 | | |
| CH₂C₆H₅ | CH₃ | CH₃ | O | H | H | H | 142.0–144.0 | | |
| CH₂C₆H₅ | CH₃ | C₂H₅ | O | H | H | H | 118.0–120.0 | 147–151 | (mixture) |
| CH₂C≡CH | CH₃ | C₂H₅ | O | H | H | H | 138.0–140.0 | | |
| CH₃ | CH₃ | CH(CH₃)₂ | O | H | H | CF₃ | 96.5–100.0 | | |
| CH₃ | CH₃ | CH(CH₃)₂ | O | H | H | –C₆H₄–Cl (p) | — | | |
| CH₃ | CH₃ | CH(CH₃)₂ | O | H | H | –C₆H₄–CH₃ (p) | 190.0–191.0 | 184.0–185.0 | 189.0–190.0 |
| C₂H₅ | CH₃ | CH(CH₃)₂ | O | H | H | n-C₃H₇ | 85.0–87.0 | | |
| CH₃ | CH₃ | CH(CH₃)₂ | O | H | H | n-C₃H₇ | 124.0–126.0 | | |
| CH(CH₃)₂ | CH₃ | CH(CH₃)₂ | O | H | H | n-C₃H₇ | 115.0–122.0 | | |
| CH₃ | CH₃ | CH(CH₃)₂ | O | H | H | i-C₃H₇ | 122.0–124.5 | | |
| C₂H₅ | CH₃ | CH(CH₃)₂ | O | H | H | i-C₃H₇ | — | | |
| CH(CH₃)₂ | CH₃ | CH(CH₃)₂ | O | H | H | i-C₃H₇ | 106.5–110.5 | | |
| CH₃ | CH₃ | CH(CH₃)₂ | O | H | –(CH₂)₅– | | 170.0–174.0 | | |
| CH₃ | CH₃ | CH(CH₃)₂ | O | H | CH₃ | H | 129.0–130.5 | 133–134 | 116.5–118.0 |
| CH₃ | CH₃ | CH(CH₃)₂ | O | H | H | C₆H₅ | 162.0–164.0 | | |
| CH₃ | CH₃ | CH(CH₃)₂ | O | H | H | CH₃ | 95.5–97.5 | 145.0–147.5 | 120.0–123.5 |
| C₂H₅ | CH₃ | CH(CH₃)₂ | O | H | H | C₂H₅ | 110.0–113.0 | | |
| CH(CH₃)₂ | CH₃ | CH(CH₃)₂ | O | H | H | C₂H₅ | 111.0–123.0 | | |
| CH₃ | CH₃ | CH(CH₃)₂ | O | H | H | C₂H₅ | 139.0–140.0 | | |
| CH₃ | CH₃ | CH(CH₃)₂ | O | H | C₂H₅ | H | 96.0–99.0 | 119.0–123.0 | 106.0–111.0 |
| CH₂C₆H₅ | CH₃ | CH(CH₃)₂ | O | H | C₂H₅ | H | 121.0–123.5 | gum | 92.0–100.0 |
| CH₃ | CH₃ | CH(CH₃)₂ | O | H | H | OCH₂–CH=CH₂ | 117.0–119.0 | 120.0–122.0 | 141.0–142.0 |
| CH₃ | CH₃ | CH(CH₃)₂ | O | H | H | H | 110.5–114.0 [α]_D = +27.28 | 95.5–102.0 | 89.0–94.0 |
| CH₂C₆H₅ | CH₃ | CH(CH₃)₂ | O | H | H | H | 102.0–105.0 [α]_D = +13.08 | | |
| CH₂C₆H₅ | CH₃ | CH(CH₃)₂ | O | H | H | H | 104.0–107.0 [α]_D = −12.76 | | |
| CH₃ | CH₃ | CH(CH₃)₂ | O | H | H | N(CH₃)₂ | 184.5–185.5 | 162.0–164.0 | 136.0–139.0 |
| N=C(CH₃)₂ | CH₃ | CH(CH₃)₂ | O | H | H | H | 117.0–119.5 | | |
| CH₂CCl₃ | CH₃ | CH(CH₃)₂ | O | H | H | H | 114.0–116.0 | | |
| CH₃ | CH₃ | CH(CH₃)₂ | O | H | H | OC₆H₅ | 128.0–131.0 | | |
| CH₃ | CH₃ | CH(CH₃)₂ | O | H | C₄H₉–n | H | 69.0–71.5 | | |
| CH₃ | CH₃ | CH(CH₃)₂ | O | Cl | H | H | 110.0–113.0 | | |
| CH₃ | CH₃ | CH(CH₃)₂ | O | H | SCH₃ | H | 107.0–108.0 | 141.0–142.0 | 158.0–159.0 |
| CH₃ | –[CH(CH₂)₄ / CH₃]– | | O | H | H | H | 122.0–124.0 | | |

TABLE III-continued
Preparation of formula 2-(2-imidazolidinyl)nicotinates

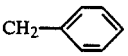

| R | R₁ | R₂ | W | X | Y | Z | Imidazolinyl nicotinate mp °C. | Imidazolidinyl nicotinate mp °C. cis | trans |
|---|---|---|---|---|---|---|---|---|---|
| CH₂—C₆H₅ | —[CH(CH₂)₄ / CH₃]— | | O | H | H | H | 123.0–125.0 | | |
| CH₂C≡CH | —[CH(CH₂)₄ / CH₃]— | | O | H | H | H | 132.0–134.5 | | |
| CH₃ | CH₃ | CH(CH₃)₂ | O | H | H | Cl | 102.5–104.5 | 146.0–148.0 | 118.0–120.0 |
| CH₂COOCH₂CH₃ | CH₃ | CH(CH₃)₂ | O | H | H | H | 86.0–90.0 | | |
| CH₂COOH | CH₃ | CH(CH₃)₂ | O | H | H | H | 187.0–189.0 | | |
| CH₂COOCH₂C₆H₅ | CH₃ | CH(CH₃)₂ | O | H | H | H | 121.5–123.0 | | |
| CH₂COOH | CH₃ | CH(CH₃)₂ | O | H | H | H | 106.0–110.0 | | |
| CH₃ | CH₃ | CH(CH₃)₂ | O | H | H | H | 110.0–112.0 [α]$_D$ = +27.41 | | |
| CH₃ | CH₃ | CH(CH₃)₂ | S | H | H | H | 105.0–109.0 | 142.0–143.5 | 127.0–129.0 |
| CH₃ | CH₃ | CH(CH₃)₂ | S | H | CH₃ | H | 135.0–137.5 | 155.0–157.0 | 149.0–151.5 |
| CH₂CH₂—C₆H₅ | CH₃ | CH(CH₃)₂ | O | H | H | H | 107.0–109.0 | | |
| CH₂—C₆H₅ | CH₃ | CH(CH₃)₂ | O | CH₃ | H | H | 130.0–132.0 | | |
| CH₂CH=CH—C₆H₅ | CH₃ | CH(CH₃)₂ | O | H | H | H | 113.0–115.0 | | |
| CH₂CH=C(CH₃)—CH₂CH₂CH=C(CH₃)₂ | CH₃ | CH(CH₃)₂ | O | H | H | H | oil | | |
| CH₂CH(OH)CH₂OH | CH₃ | CH(CH₃)₂ | O | H | H | H | oil | | |
| (CH₂)₃C≡CH | CH₃ | CH(CH₃)₂ | O | H | H | H | 73.0–75.0 | | |
| CH₂CH₂—[pinanyl CH₃,CH₃] | CH₃ | CH(CH₃)₂ | O | H | H | H | oil | | |
| CH(C₆H₅)COOCH₃ | CH₃ | CH(CH₃)₂ | O | H | H | H | oil | | |
| CH₂CH₂—C(CH₃)=CH₂ | CH₃ | CH(CH₃)₂ | O | H | H | H | oil | | |
| (CH₂)₉CH=CH₂ | CH₃ | CH(CH₃)₂ | O | H | H | H | oil | | |
| CH(CH₃)C₆H₅ | CH₃ | CH(CH₃)₂ | O | H | H | H | oil | | |
| CH₂—C₆H₄—OCH₃ | CH₃ | CH(CH₃)₂ | O | H | H | H | 111.0–113.0 | | |
| CH₂—C₆H₄—Cl | CH₃ | CH(CH₃)₂ | O | H | H | H | 136.0–138.0 | | |
| CH₂—C₆H₄—NO₂ | CH₃ | CH(CH₃)₂ | O | H | H | H | 131.5–133.0 | | |

TABLE III-continued

Preparation of formula 2-(2-imidazolidinyl)nicotinates

| R | $R_1$ | $R_2$ | W | X | Y | Z | Imidazolinyl nicotinate mp °C. | Imidazolidinyl nicotinate mp °C. cis | trans |
|---|---|---|---|---|---|---|---|---|---|
| $CH_2COOCH_3$ | $CH_3$ | $CH(CH_3)_2$ | O | H | H | H | 104.0–108.0 | | |
| $CH_2$—CH—O  $CH_3$ / HCO—O  $CH_3$ | $CH_3$ | $CH(CH_3)_2$ | O | H | H | H | 95.0–97.0 | | |
| $CH_2CH_2CH_2COOC_2H_5$ | $CH_3$ | $CH(CH_3)_2$ | O | H | H | H | oil | | |
| $CH(CH_3)COOCH_3$ | $CH_3$ | $CH(CH_3)_2$ | O | H | H | H | 133.0–135.0 | | |
| $CH_3$ | $CH_3$ | $CH(CH_3)_2$ | O | H | Br | H | 122.5–126.0 | | |
| $CH_2CH=CH$—$COOC_2H_5$ | $CH_3$ | $CH(CH_3)_2$ | O | H | H | H | oil | | |
| $(CH_2)_4COOCH_3$ | $CH_3$ | $CH(CH_3)_2$ | O | H | H | H | oil | | |
| $CH_2$—C$_6$H$_4$—$C(CH_3)_3$ | $CH_3$ | $CH(CH_3)_2$ | O | H | H | H | 108.0–111.0 | | |
| $CH_2$—C(Cl)=$CH_2$ | $CH_3$ | $CH(CH_3)_2$ | O | H | H | H | 73.0–77.0 | | |
| $C_6H_{13}$—n | $CH_3$ | $CH(CH_3)_2$ | O | H | H | H | oil | | |
| $CH(CH_3)CH=CH$—$CH_3$ | $CH_3$ | $CH(CH_3)_2$ | O | H | H | H | oil | | |
| $CH_3$ | —$(CH_2)_5$— | | O | H | H | H | 146.0–148.0 | | |
| $CH_2CH=(CH_3)_2$ | $CH_3$ | $CH(CH_3)_2$ | O | H | H | H | 77.5–79.0 | | |
| $CH_2C_6H_5$ | —$(CH_2)_5$— | | O | H | H | H | 117.0–122.0 | | |
| $CH_3$ | $CH_3$ | $CH(CH_3)_2$ | O | H | $OCH_3$ | H | 101.0–102.5 | 93.0–94.0 | 113.0–114.0 |
| $CH_2\equiv CCH_2OH$ | $CH_3$ | $CH(CH_3)_2$ | O | H | H | H | gum | | |
| $CH_2C_6H_5$ | $C_2H_5$ | $C_2H_5$ | O | H | H | H | 114.5–118.0 | | |
| $C(CH_3)C\equiv CH$ | $CH_3$ | $CH(CH_3)_2$ | O | H | H | H | 128.0–132.0 | | |
| $CH_2CH_2N^\oplus(CH_3)_3I^\ominus$ | $CH_3$ | $CH(CH_3)_2$ | O | H | H | H | 165.0–175.0 | | |
| $CH_3$ | $C_2H_5$ | $C_2H_5$ | O | H | H | H | 132.5–135.5 | | |
| $C(CH_3)_2C\equiv CH$ | $CH_3$ | $CH(CH_3)_2$ | O | H | H | H | 104.0–106.0 | | |
| $CH_2C\equiv CH$ | $CH_3$ | Δ | O | H | H | H | 122.0–124.0 | | |
| $CH_2C\equiv CH$ | —$(CH_2)$— | | O | H | H | H | 164.5–166.5 | | |
| $CH_3$ | $CH_3$ | $CH(CH_3)_2$ | O | $CH_3$ | H | H | 114.0–115.5 | | |
| $CH_2C\equiv CH$ | $C_2H_5$ | $C_2H_5$ | O | H | H | H | 135.0–137.0 | | |
| —$C(CH_3)_3$ | $CH_3$ | $CH(CH_3)_2$ | O | H | H | H | 124.0–126.0 | | |
| $CH_3$ | $CH_3$ | $CH(CH_3)_2$ | O | H | H | —$(CH_2)_3$— | 160.0–162.0 | 146.0–147.0 | 119.0–120.0 |
| cyclohexyl-CH$_2$ | $CH_3$ | $CH(CH_3)_2$ | O | H | H | H | 95.0–98.0 | | |
| $C_{18}H_{37}$—n | $CH_3$ | $CH(CH_3)_2$ | O | H | H | H | 77.3–79.2 | | |
| $CH_2C_6H_5$ | $CH_3$ | $CH(CH_3)_2$ | O | H | H | H | 116.5–119.0 | | |
| n-$C_3H_7$ | $CH_3$ | $CH_2CH(CH_3)_2$ | O | H | H | H | 76.0–78.5 | | |
| $CH_3$ | $CH_3$ | $CH(CH_3)_2$ | O | H | H | H | 92.0–94.0 | | |
| —$C_4H_9$—n | $CH_3$ | $CH(CH_3)_2$ | O | H | H | H | 54.0–57.0 | | |
| $CH_2C\equiv CH$ | $CH_3$ | $CHCH(CH_3)_2$ | O | H | H | H | 128.5–131.0 | | |
| $CH_3$ | $CH_3$ | cyclopropyl | O | H | H | H | 128.0–131.0 | | |
| $CH_2C_6H_5$ | $CH_3$ | cyclopropyl | O | H | H | H | 111.0–113.0 | | |
| $CH_3$ | $CH_3$ | $CH(CH_3)_2$ | O | H | H | $OCH_3$ | 154.0–155.0 | 158.0–160.0 | 128.5–130.5 |
| $CH_2$—CH=CH—$C_7H_{15}$—n | $CH_3$ | $CH(CH_3)_2$ | O | H | H | H | oil | | |
| —$C_{12}H_{25}$—n | $CH_3$ | $CH(CH_3)_2$ | O | H | H | H | 55.0–57.0 | | |
| —$C_2H_5$ | $CH_3$ | $CH(CH_3)_2$ | O | H | H | H | 72.0–75.0 | | |
| $CH_2CH_2OCH_2C_6H_5$ | $CH_3$ | $CH(CH_3)_2$ | O | H | H | H | 90.0–92.5 | | |

TABLE III-continued
Preparation of formula 2-(2-imidazolidinyl)nicotinates

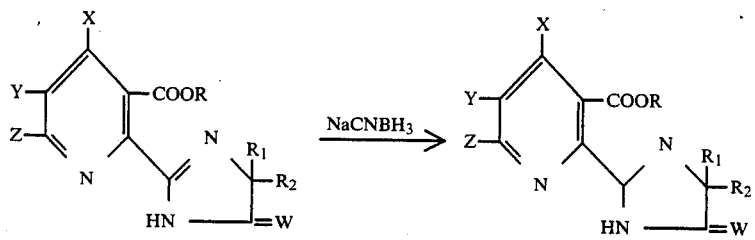

| R | R₁ | R₂ | W | X | Y | Z | Imidazolinyl nicotinate mp °C | Imidazolidinyl nicotinate mp °C cis | trans |
|---|---|---|---|---|---|---|---|---|---|
| —CH₂-furyl | CH₃ | CH(CH₃)₂ | O | H | H | H | 120.5–122.0 | | |
| —CH(CH₃)₂ | CH₃ | CH(CH₃)₂ | O | H | H | H | 94.0–97.5 | | |
| —CH₂C₆H₅ | CH₃ | CH(CH₃)₂ | O | H | H | H | 122.0–125.0 | 111.0–113.5 | 95.0–97.5 |
| —CH₂—C≡C—C₇H₁₅—n | CH₃ | CH(CH₃)₂ | O | H | H | H | oil | | |
| CH₂CH₂OCH₃ | CH₃ | CH(CH₃)₂ | O | H | H | H | 60.0–63.0 | | |
| CH₂CH=CH₂ | CH₃ | CH(CH₃)₂ | O | H | H | H | 81.0–84.0 | 116.0–117.0 | 109.0–111.0 |
| —CH(CH₃)—CH=CH₂ | CH₃ | CH(CH₃)₂ | O | H | H | H | oil | | |
| CH₂—C(CH₃)=CH₂ | CH₃ | CH(CH₃)₂ | O | H | H | H | 98.0–100.0 | | |
| CH₃ | CH₃ | CH(CH₃)₂ | O | H | Cl | H | 109.0–111.0 | 129.0–131.0 | 114.0–116.0 |
| CH₃ | CH₃ | CH(CH₃)₂ | O | H | —OCH₂CH=CH₂ | H | 103.0–105.0 | 88.0–90.0 | 119.0–120.0 |
| CH₂C₆H₅ | CH₃ | CH(CH₃)₂ | O | H | CH₃ | H | 135.0–137.0 | — | 90.0–97.0 |
| CH₃ | CH₃ | CH(CH₃)₂ | O | H | —OCH₂C≡CH | H | 83.0–84.0 | 103.0–105.0 | 116.0–117.0 |
| CH₃ | CH₃ | CH(CH₃)₂ | O | H | —OCHF₂ | H | 105.0–107.0 | 99.0–100.5 | 137.0–138.0 |
| CH₃ | CH₃ | CH(CH₃)₂ | O | H | CF₃ | H | 167.0–170.0 | | |

EXAMPLE 31

Preparation of cis- and trans-5-ethyl-2-(4-isopropyl-4-methyl-5-oxo-2-imidazolidinyl)nicotinic acid

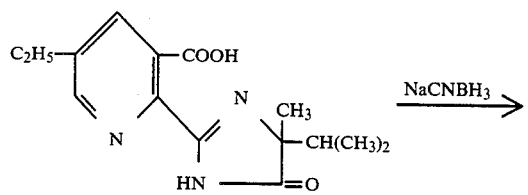 NaCNBH₃ → 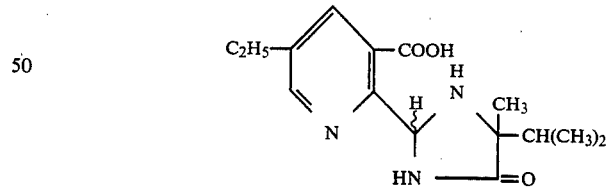

To a stirred slurry of 2.89 g 5-ethyl-2-(4-isopropyl-4-methyl-5-oxo-2-imidazolin-2-yl)nicotinic acid in 20 mL methanol and one equivalent of 2N methanolic HCl is added under nitrogen 0.6 g sodium cyanoborohydride. Methanolic HCl is added to maintain a pH of 2–3. After stirring the pH of the mixture is adjusted to 1 with concentrated HCl and after 15 minutes, again adjusted to 3 with saturated NaHCO₃ solution. After filtration, the solution is extracted with ethyl acetate. The pH of the aqueous phase is again adjusted to 3 and again extracted with ethyl acetate. A crystalline precipitate of cis- and trans-5-ethyl-2-(4-isopropyl-4-methyl-5-oxo-2-imidazolidinyl)nicotinate is formed which can be recrystallized from ethanol to give the product as a white crystalline solid mp 208°–210° C. This contains about 66% of the cis- and 34% of the trans-isomer.

EXAMPLE 32

Preparation of cis-6-(allyloxy)-2-(4-isopropyl-4-methyl-5-oxo-2-imidazolidynyl)nicotinic acid

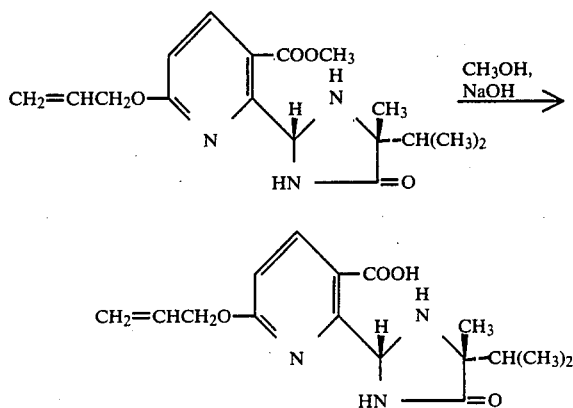

To a solution containing 3.9 g (12.2 mmol) cis-methyl 6-(allyloxy)-2-(4-isopropyl-4-methyl-5-oxo-2-imidazolidinyl)nicotinate in a minimum absolute methanol (~15 mL) is added 12.2 mL 2N NaOH solution. A precipitate results and the mixture is heated with stirring to 45° C. and maintained at that temperature for one hour. The solution becomes clear. It is cooled to 0° C. and 12.2 mL 2N HCl added. A solid precipitates which is collected, washed with ether and air dried. This material (3.2 g) is recrystallized from methylene chloride-hexane to give 2.3 g analytically pure cis-6-(allyloxy)-2-(4-isopropyl-4-methyl-5-oxo-2-imidazolidinyl)nicotinic acid, mp 193°–194° C.

By using essentially the same procedure, but substituting the appropriate methyl 5-oxo or thioxoimidazolinyl nicotinate or quinoline-3-carboxylate for cis-methyl 6-(allyloxy)-2-(4-isopropyl-4-methyl-5-oxo-2-imidazolinyl)nicotinate, the following 5-oxo or 5-thioxoimidazolidinyl nicotinic, or quinoline-3-carboxylic acids are prepared. The reaction can be illustrated as follows using nicotinates as representative of the reaction.

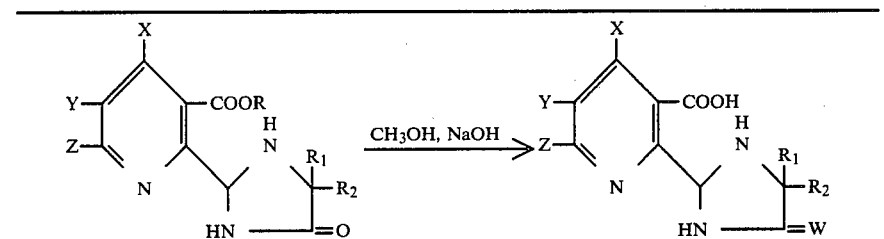

| $R_1$ | $R_2$ | W | X | Y | Z | acid mp °C. |
|---|---|---|---|---|---|---|
| $CH_3$ | $CH(CH_3)_2$ | O | H | $C_2H_5$ | H | 208.0–210.0 mixture |
| $CH_3$ | $CH(CH_3)_2$ | O | H | $CH_3$ | H | 206.0–207.0 cis |
| $CH_3$ | $CH(CH_3)_2$ | O | H | H | $CH_3$ | 183.5–185.0 cis |
| $CH_3$ | $CH(CH_3)_2$ | O | H | H | H | 172.0–174.0 cis |
| $CH_3$ | $CH(CH_3)_2$ | O | H | H | H | 190.0–191.5 trans |
| $CH_3$ | $CH(CH_3)_2$ | O | H | H | H | 182.0–184.0 (R) cis |
| $CH_3$ | $CH(CH_3)_2$ | O | H | H | $CH_3O$ | 203.0–205.0 cis |
| $CH_3$ | $CH(CH_3)_2$ | O | H | H | Cl | 177.0–180.0 cis |
| $CH_3$ | $CH(CH_3)_2$ | S | H | H | H | 186.0–188.0 cis |
| $CH_3$ | $CH(CH_3)_2$ | O | H | —CH=CH—CH=CH— | | 202.0–204.0 cis |
| $CH_3$ | $CH(CH_3)_2$ | O | H | CH=CH—CH=CH— | | 220.0–221.0 trans |
| $CH_3$ | $CH(CH_3)_2$ | O | H | $OCH_3$ | H | 197.0–199.0 cis |
| $CH_3$ | $CH(CH_3)_2$ | O | H | —$(CH_2)_3$— | | 220.0–222.0 cis |
| $CH_3$ | $CH(CH_3)_2$ | O | H | $(CH_2)_3$— | | 221.0–224.0 trans |
| $CH_3$ | $CH(CH_3)_2$ | O | H | $C_2H_5$ | H | 205.0–206.0 cis |
| $CH_3$ | $CH(CH_3)_2$ | O | H | $C_2H_5$ | H | 209.0–211.0 trans |
| $CH_3$ | $C_2H_5$ | O | H | H | H | 156.0–162.0 mixture |
| $CH_3$ | $CH(CH_3)_2$ | O | H | $CH_3$ | H | 207.0–208.0 trans |
| $CH_3$ | $CH(CH_3)_2$ | S | H | $CH_3$ | H | amorphous mixture |
| $CH_3$ | $CH(CH_3)_2$ | O | H | Cl | H | 208.0–211.0 cis |
| $CH_3$ | $CH(CH_3)_2$ | O | H | Cl | H | 183.0–223.0 mixture |
| $CH_3$ | $CH(CH_3)_2$ | O | H | $OCH_2CH=CH_2$ | H | 168.0–170.0 trans |
| $CH_3$ | $CH(CH_3)_2$ | O | H | $OCH_2CH=CH_2$ | H | 183.0–184.0 cis |
| $CH_3$ | $CH(CH_3)_2$ | O | H | $OCH_2C≡CH$ | H | 192.0–193.0 cis |
| $CH_3$ | $CH(CH_3)_2$ | O | H | $OCH_2C≡CH$ | H | 163.0–165.0 trans |
| $CH_3$ | $CH(CH_3)_2$ | O | H | $CH_3$ | H | 203.0–205.0 cis (2R, 4R) |
| $CH_3$ | $CH(CH_3)_2$ | O | H | $CH_3$ | H | 222.0–223.0 trans (2S, 4R) |
| $CH_3$ | $CH(CH_3)_2$ | O | H | H |  | 254.0–255.0 trans |
| $CH_3$ | $CH(CH_3)_2$ | O | H | $OCHF_2$ | H | 204.0–205.0 trans |
| $CH_3$ | $CH(CH_3)_2$ | O | H | $OCHF_2$ | H | 211.0–212.0 cis |

-continued

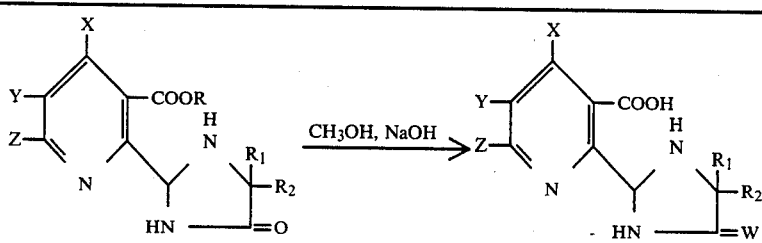

| $R_1$ | $R_2$ | W | X | Y | Z | acid mp °C. |
|---|---|---|---|---|---|---|
| $CH_3$ | $CH(CH_3)_2$ | O | H | H | $N(CH_3)_2$ | 243.5–245.0 cis |
| $CH_3$ | $CH(CH_3)_2$ | O | H | $SCH_3$ | H | 198.0–200.0 cis |
| $CH_3$ | $CH(CH_3)_2$ | O | H | $CF_3$ | H | cis |

EXAMPLE 33

Preparation of cis-methyl 2-(4-isopropyl-4-methyl-5-oxo-2-imidazolidinyl)nicotinate hydrochloride

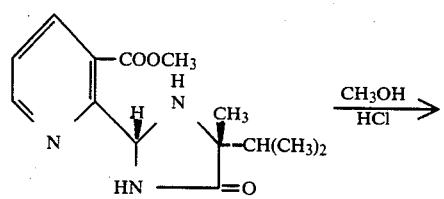

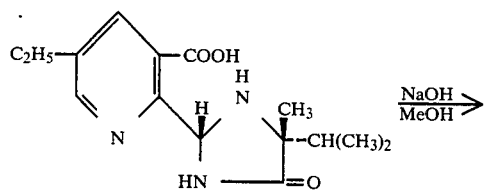

To 2.0 g cis-methyl 2-(4-isopropyl-4-methyl-5-oxo-2-imidazolidinyl)nicotinate is added 25 mL of 2N methanolic HCl. The solvent is removed in vacuo and the residue is crystallized from ethyl acetate-ether to give the hydrochloride salt, mp 189°–192° C. Other acid addition salts may be prepared by the above procedure using the appropriately substituted formula III 2-(2-imidazolidinyl)nicotinate.

EXAMPLE 34

Preparation of sodium 5-ethyl-2-(4-isopropyl-4-methyl-5-oxo-2-imidazolidinyl)nicotinate

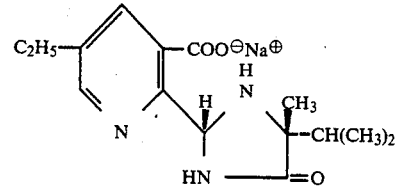

-continued

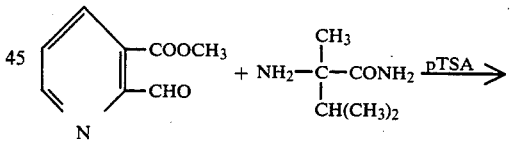

To 1.0 g 5-ethyl-2-(4-isopropyl-4-methyl-5-oxo-2-imidazolidinyl)nicotinic acid is added a solution of 0.1498 g sodium hydroxide in 20 mL absolute methanol. The mixture is stirred under nitrogen at room temperature overnight. The solvent is removed to give a solid which is dried in a vacuum oven at 60° C. for two days. The thus-formed sodium 5-ethyl-2-(4-isopropyl-4-methyl-5-oxo-2-imidazolidinyl)nicotinate darkens at 230° C. and decomposes at 247°–250° C.

EXAMPLE 35

Preparation of cis-methyl 2-(4-isopropyl-4-methyl-5-oxo-2-imidazolidinyl)nicotinate

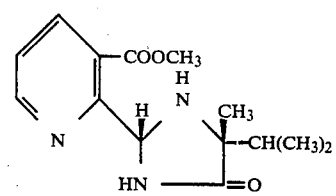

A solution containing 1.24 g methyl 2-formylpyridine-3-carboxylate [Bull. Soc. Chem. France, 36, 78–83 (1969)], 1.0 g 2-amino-2,3-dimethylbutyramide and 20 g p-toluene sulfonic acid is heated under reflux under nitrogen with a Dean-Stark water separator for six hours. The solution is filtered while hot and the filtrate concentrated in vacuo to leave a dark oil. The oil is extracted into ether, the ether concentrated to give a yellow solid. This solid is recrystallized from a mixture of hexane-ether and methylene chloride to give cis-methyl 2-(4-isopropyl-4-methyl-5-oxo-2- imidazolidinyl)nicotinate, mp 118.5°–120° C., identical to one of the products obtained from the sodium cyanoborohydride reduction of methyl 2-(4-isopropyl-4-methyl-5-oxo-imidazolin-2-yl)nicotinate. The presence of the corresponding trans-isomer is indicated by nmr spectroscopy. Following the above procedure and using the appropriately substituted 2-formylpyridine-3-carboxylate yields the formula III 2-(2-imidazolidinyl)-nicotinic acids and esters reported in Table IV below.

TABLE IV

Preparation of formula III 2-(2-imidazolidinyl)nicotinic acids and esters

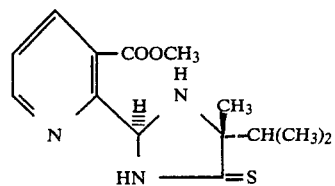

| R | $R_1$ | $R_2$ | X | Y | Z | mp °C. |
|---|---|---|---|---|---|---|
| $CH_3$ | $CH_3$ | $CH(CH_3)_2$ | H | H | H | 118.5–120.0 cis |
| $CH_2C_6H_5$ | $CH_3$ | $CH(CH_3)_2$ | H | H | H | 107.0–109.0 cis |
| $CH_2$-furyl | $CH_3$ | $CH(CH_3)_2$ | H | H | H | 111.0–113.5 cis |
| $CH_2C\equiv CH$ | $CH_3$ | $CH(CH_3)_2$ | H | H | H | 109.0–114.0 cis |
| $CH_2CH=CH$ | $CH_3$ | $CH(CH_3)_2$ | H | H | H | 116.0–117.0 cis |
| $CH_3$ | $CH_3$ | $CH(CH_3)_2$ | H | H | H | 99.6–102.0 (R isomer) cis |
| $CH_3$ | $CH_3$ | $CH(CH_3)_2$ | H | $C_2H_5$ | H | 119.0–123.0 cis |
| $CH_2C_6H_5$ | $CH_3$ | $CH(CH_3)_2$ | H | $C_2H_5$ | H | gum |
| $CH_3$ | $CH_3$ | $CH(CH_3)_2$ | H | $CH_3$ | H | 133.0–134.0 cis |
| $CH_3$ | $CH_3$ | $CH(CH_3)_2$ | H | H | $CH_3$ | 145.0–147.5 cis |
| $CH_3$ | $CH_3$ | $CH(CH_3)_2$ | H | $OCH_3$ | H | 158.0–160.0 cis |
| $CH_3$ | $CH_3$ | $CH(CH_3)_2$ | H | H | $OCH_2CH=CH_2$ | 120.0–122.0 cis |
| $CH_3$ | $CH_3$ | $CH(CH_3)_2$ | H | H | Cl | 146.0–148.0 cis |
| $CH_3$ | $CH_3$ | $CH(CH_3)_2$ | H | $CH_3$ | $CH_3$ | 123.0–130.0 |
| $C_2H_5$ | $CH_3$ | $CH(CH_3)_2$ | H | —CH=CH—CH=CH— | | 156.0–164.0 cis |

EXAMPLE 36

Preparation of cis- and trans-methyl 2-(4-isopropyl-4-methyl-5-thioxo-2-imidazolidinyl)-nicotinate

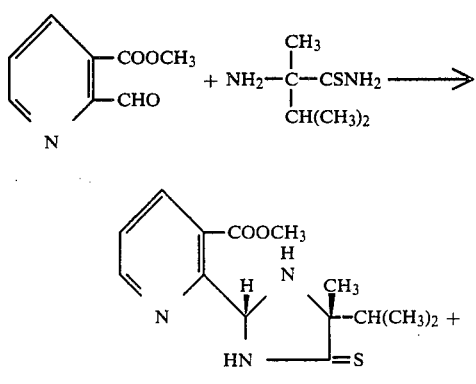

Using essentially the same conditions as described in Example 35, but substituting 2-amino-2,3-dimethylthiobutyramide for 2-amino-2,3-dimethylbutyramide gives a mixture of cis- and trans-methyl 2-(4-isopropyl-4-methyl-5-thioxo-2-imidazolidinyl)nicotinate from which essentially pure trans-isomer, mp 127°–129° C. can be isolated by chromatography of the crude product on silica gel. The melting point of the cis-isomer is 142°–143.5° C.

EXAMPLE 37

Preparation of cis- and trans-ethyl 2-(4-isopropyl-4-methyl-5-oxo-2-imidazolidinyl-2-yl)quinoline-3-carboxylate

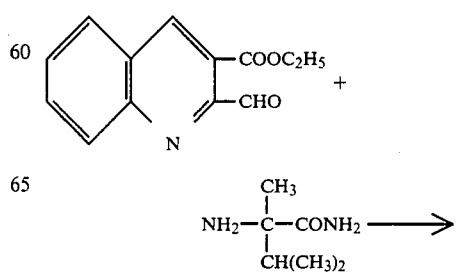

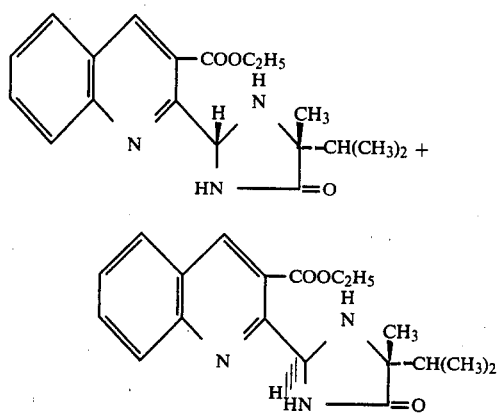

Using essentially the same procedure as described in Example 35, but substituting ethyl 2-formylquinoline-3-carboxylate, [Godard etal., Bull. Chem. Soc. France, 906 (1971)] for the methyl 2-formylnicotinate, there is formed the cis-ethyl 2-(4-isopropyl-4-methyl-5-oxo-2-imidazolin-2-yl)quinoline-3-carboxylate, mp 156°–164° C. and trans-methyl 2-(4-isopropyl-4-methyl-5-oxo-2-imidazolin-2-yl)quinoline-3-carboxylate, mp 163°–164° C. Following the procedure of Example 33 but substituting a substituted 2-formylcarboxylate and using an appropriately substituted aminoamide in place of 2-amino-2,3-dimethylbutyramide will give the substituted formula IV 2-(2-imidazolidinyl)quinoline-3-carboxylate.

EXAMPLE 38

Preparation of dimethyl thieno[3,2-b]pyridine-5,6-dicarboxylate

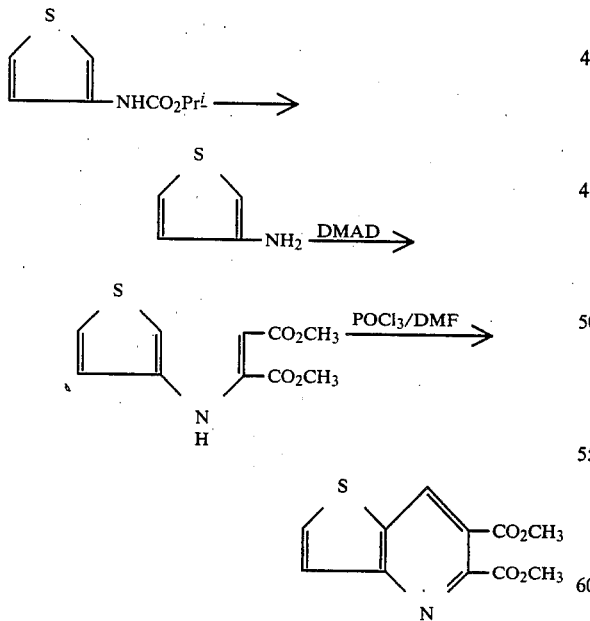

A mixture of isopropyl-3-thiophenecarbamate (177 g; 0.975 mol) in methanol (1.2 l) and water (2.8 l) containing sodium hydroxide (200 g) is heated at reflux for four hours. Methanol is removed under reduced pressure and the cooled reaction extracted with ether (5 l), and these extracts are washed with water, aqueous sodium chloride and dried. Evaporation under reduced pressure affords 3-aminothiophene as an oil in 57% crude yield.

3-Aminothiophene is redissolved in methanol (500 mL) cooled in an ice bath and dimethylacetylenedicarboxylate (80 g; 0.50 mol) is added dropwise. The mixture is stirred at room temperature for 15 hours and 30 minutes, the methanol removed under reduced pressure and 1,2-dichloroethane is added. This solvent is also evaporated off to give dimethyl 3-thienylaminobutenedioate as an oil.

A Vilsmeier reagent is prepared by adding dropwise, with stirring phosphorus oxychloride (86 g, 0.56 mol) to a cooled (5° C.) solution of DMF (41 g, 0.56 mol) in 1,2-dichloroethane (200 mL). This reagent is stirred at room temperature for one hour and 40 minutes, diluted with 1,2-dichloroethane (100 mL), cooled to 5° C. and then the above dimethyl ester dissolved in 1,2-dichloroethane (400 mL) is added to the Vilsmeier reagent at 5° C. dropwise over a 25 minute period. The reaction temperature is raised to room temperature for 15 minutes, then to reflux for a further two hours and 25 minutes. The cooled reaction mixture is chromatographed directly on a silica gel column affording 35.7 g (15%) of dimethyl thieno[3,2-b]pyridine-5,6-dicarboxylate mp 124°–125.5° C. after crystallization from hexane-ethyl acetate. A second crop (10.3 g) with mp 121°–124° C. is obtained giving an overall yield from isopropyl 3-thiophenecarbamate of 19%.

Utilizing the above procedure and substituting the appropriate substituted aminothiophene for isopropyl 3-aminothiophenecarbamate yields the compounds illustrated below.

| $R_9$ | $R_{10}$ | R″ | mp °C. |
|---|---|---|---|
| H | H | $CH_3$ | 126–127 |
| $CH_3$ | H | $CH_3$ | — |
| Cl | H | $CH_3$ | — |

EXAMPLE 39

Preparation of dimethyl thieno[3,2-b]pyridine-5,6-dicarboxylate

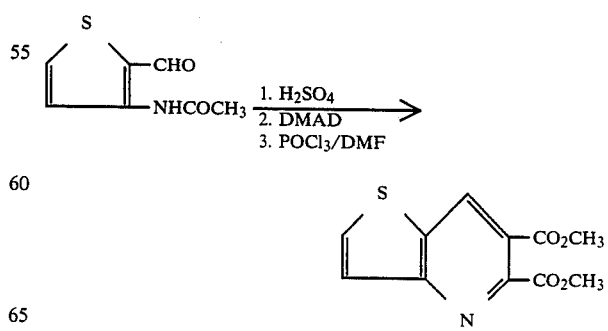

To concentrated sulfuric acid (170 mL), stirred at room temperature is added in portions 3-acetylamino-2- formylthiophene (17.5 g, 0.103 mol). The mixture is heated at 50° C. for 30 minutes, cooled and poured into an ice-water mixture. After neutralizing with an excess of sodium acetate, the mixture is ether (1×2 l) extracted. The organic layer was dried over anhydrous Na$_2$SO$_4$ and stripped to a dark red gum consisting of 3-amino-2-formylthiophene. Dimethylacetylenedicarboxylate (DMAD) (13 mL) in acetic acid (5 mL), piperidine (5 mL), methylene chloride (100 mL) and toluene (100 mL) is added to the 3-amino-2-formylthiophene and the mixture stirred overnight. Methylene chloride is removed by distillation and then the mixture heated at reflux for 24 hours. After cooling an additional 13 mL of DMAD is added and the reaction heated to reflux again for seven and one-half hours. After standing for 60 hours at room temperature, the solvents are removed and the dimethyl thieno[3,2-b]pyridine-5,6-dicarboxylate product is obtained by chromatography, after eluting with hexane-ethyl acetate, mp 124°–125° C.

EXAMPLE 40

Preparation of dimethyl 3-chloro[3,2-b]pyridine-5,6-dicarboxylate and dimethyl 2,3-dichlorothieno[3,2-b]pyridine-5,6-dicarboxylate

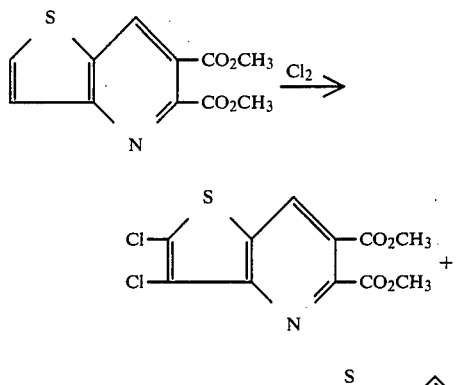

A solution of dimethyl thieno[3,2-b]pyridine-5,6-dicarboxylate (15 g 0.0525 mol) in acetic acid (680 mL) and sodium acetate (86 g, 0.093 mol) is maintained at 58° C. while chlorine is slowly introduced during five hours and 45 minutes. After reaction is complete, the mixture is flushed with nitrogen, ethyl acetate (200 mL) is added and solid sodium chloride filtered off and washed with ethyl acetate. The mother liquors and washes are combined and the solvents removed under reduced pressure. The residue is dissolved in methylene chloride and the solution washed with water, back extracted with methylene chloride and the combined methylene chloride layers washed with aqueous sodium bicarbonate, dried and stripped to give 18 g of solid. Chromatography on silica gel with 15% ethyl acetate-hexane, then 20% ethyl acetate-hexane gives the 2,3-dichloro compound, mp 173°–178° C., 1.3 g, followed by the 3-chlorothieno compound mp 166°–173° C. after crystallization from ethyl acetate-hexane.

EXAMPLE 11

Preparation of dimethyl 3-bromothieno[3,2-b]pyridine-5,6-dicarboxylate

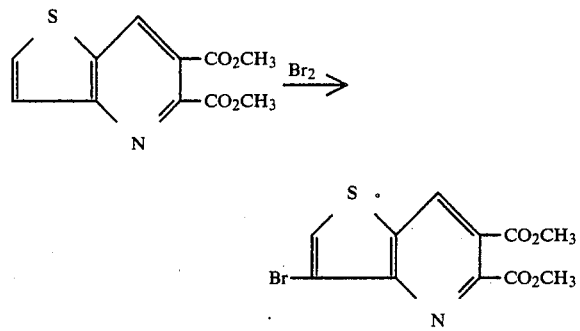

A solution of bromine (20 g, 0.125 mol) in acetic acid (50 mL) is added dropwise over three hours to a solution of dimethyl thieno[3,2-b]pyridine-5,6-dicarboxylate, (26.3 g, 0.104 mol), containing sodium acetate (17.2 g, 0.2 mol) in acetic acid (300 mL) at 85° C. Additional sodium acetate (18 g) and bromine (20 g) in acetic acid (50 mL) is added over an hour and the mixture stirred at 85° C. overnight. Bromine (10 g) is added in one portion then left at 85° C. for four hours. The mixture is cooled and treated with aqueous sodium bisulfite, diluted with ethyl acetate and concentrated. The reaction product is partitioned between water and methylene chloride and the organic layer washed with aqueous sodium chloride and the solvent removed. The residue is washed with ether to give 25 g of crude product, mp 165°–168° C. Recrystallization from methanol gave needles of dimethyl 3-bromothieno[3,2-b]pyridine-5,6-dicarboxylate, mp 168°–169° C.

EXAMPLE 42

Preparation of thieno[3,2-b]pyridine-5,6-dicarboxylic acid

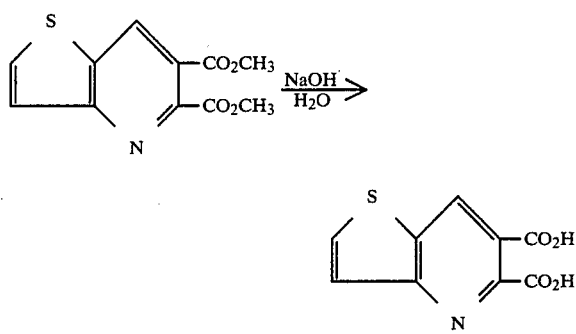

Dimethyl thieno[3,2-b]pyridine-5,6-dicarboxylate (3.75 g, 0.0149 mol) is added to a solution of sodium hydroxide (1.8 g, 0.045 mol) in water (20 mL) and the mixture is warmed at 60° C. for 20 hours. The reaction mixture is diluted with water, cooled in an ice bath, and acidified by the addition of concentrated hydrochloric acid. A precipitate of thieno[3,2-b]pyridine-5,6-dicarboxylic acid is filtered off and dried overnight to give 3.1 g (93%) mp>380° C.

Utilizing the above procedure and substituting the appropriate substituted thieno[3,2-b]pyridine-5,6-dicarboxylic acid diester yields the compounds illustrated below.

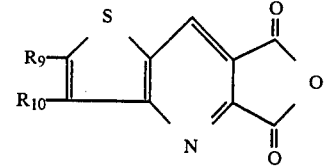

| R9 | R10 | mp °C. |
|---|---|---|
| H | H | >380 |
| H | Cl | None taken |
| H | Br | >380 |
| H | I | |
| H | F | |
| H | CN | |
| H | OCH3 | |
| H | OH | |
| H | NO2 | |
| H | N(CH3)2 | |
| CH3 | H | |
| H | CH3 | |
| CH3 | CH3 | |
| H | OCHF2 | |
| H | SCH3 | |
| H | SO2N(CH3)2 | |
| C6H5 | H | |
| —(CH2)3— | | |
| —(CH2)4— | | |
| —(CH)4— | | |
| Cl | Cl | |
| H | C6H5 | |
| C6H5 | H | |
| H | OC6H5 | |
| CF3 | H | |

EXAMPLE 43

Preparation of 3-chlorothieno[3,2-b]pyridine 5,6-dicarboxylic acid anhydride

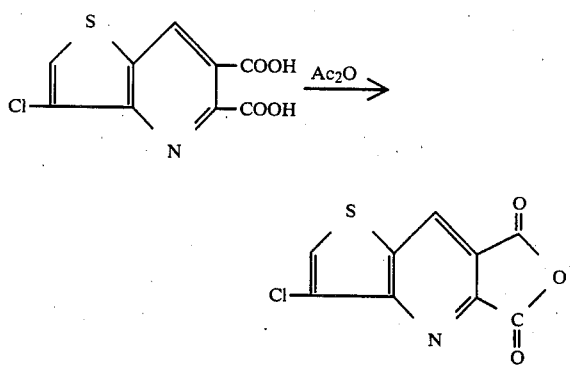

3-Chlorothieno[3,2-b]pyridine-5,6-dicarboxylic acid (1.45 g) is heated at 85° to 90° C. for 30 minutes then 90° to 102° C. for 30 minutes in acetic anhydride (7 mL). The reaction is cooled, the solids filtered off and washed with ether to give 1.2 g of 3-chlorothieno[3,2-b]pyridine-5,6-dicarboxylic acid anhydride.

Utilizing the above procedure and substituting the appropriate pyridine-5,6-dicarboxylic acid for 3-chlorothieno[3,2-b]pyridine-5,6-dicarboxylic acid yields the compounds illustrated below.

| R9 | R10 | mp °C. |
|---|---|---|
| H | H | 266-267 |
| H | Cl | Solid no mp obtained |
| H | Br | >380 |
| Cl | H | |
| Cl | Cl | |
| H | NO2 | |
| CH3 | H | |
| H | N(CH3)2 | |
| H | SCH3 | |
| H | OCH3 | |
| H | CH3 | |
| H | F | |
| H | I | |
| CH3 | CH3 | |
| H | CN | |
| H | OCHF2 | |
| C6H5 | H | |
| H | SO2N(CH3)2 | |
| —(CH2)3— | | |
| —(CH2)4— | | |
| —(CH)4— | | |
| Cl | Cl | |
| H | C6H5 | |
| C6H5 | H | |
| H | OC6H5 | |
| CF3 | H | |

EXAMPLE 44

Preparation of 5-[(1-carbamoyl-1,2-dimethylpropyl)]-3-chlorothieno[3,2-b]pyridine-6-carboxylic acid

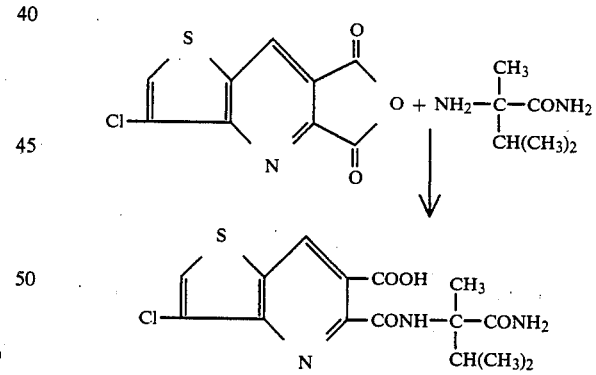

2-Amino-2,3-dimethylbutyramide (0.71 g) all in one portion is added to a stirred solution of 3-chlorothieno[3,2-b]pyridine-5,6-dicarboxylic acid anhydride, (1.2 g) in THF (1.0 mL). After standing for five minutes, the ice bath is removed and the reaction stirred at room temperature for 28 hours. THF (5 mL) is added and the mixture heated at reflux for two hours and then set aside overnight. The cooled mixture is filtered and the collected solid washed with ether to give 1.4 g of the desired 5-[(1-carbamoyl-1,2-dimethylpropyl)carbamoyl]3-chlorothieno[3,2-b]pyridine-6-carboxylic acid.

Utilizing the above procedure and substituting the appropriate pyridine-5,6-dicarboxylic acid anhydride for 3-chlorothieno[3,2-b]pyridine-5,6-dicarboxylic acid anhydride and the appropriate aminoamide yields the compounds illustrated below.

| R9 | R10 | R1 | R2 | mp °C. |
|---|---|---|---|---|
| H | H | $CH_3$ | $i\text{-}C_3H_7$ | |
| H | Cl | $CH_3$ | $i\text{-}C_3H_7$ | not pure |
| Cl | H | $CH_3$ | $i\text{-}C_3H_7$ | |
| Cl | Cl | $CH_3$ | $i\text{-}C_3H_7$ | |
| H | Br | $CH_3$ | $i\text{-}C_3H_7$ | |
| H | Me | $CH_3$ | $i\text{-}C_3H_7$ | |
| H | $NO_2$ | $CH_3$ | $i\text{-}C_3H_7$ | |
| H | $N(CH_3)_2$ | $CH_3$ | $i\text{-}C_3H_7$ | |
| H | $SCH_3$ | $CH_3$ | $i\text{-}C_3H_7$ | |
| H | $OCH_3$ | $CH_3$ | $i\text{-}C_3H_7$ | |
| $CH_3$ | H | $CH_3$ | $i\text{-}C_3H_7$ | |
| H | $SCH_3$ | $CH_3$ | $i\text{-}C_3H_7$ | |
| H | H | $CH_3$ | $C_3H_7$ | |
| H | H | $CH_3$ | $C_2H_5$ | |
| H | $OCHF_2$ | $CH_3$ | $i\text{-}C_3H_7$ | |
| $CH_3$ | $CH_3$ | $CH_3$ | $i\text{-}C_3H_7$ | |
| H | CN | $CH_3$ | $i\text{-}C_3H_7$ | |
| H | F | $CH_3$ | $i\text{-}C_3H_7$ | |
| H | I | $CH_3$ | $i\text{-}C_3H_7$ | |
| H | $SO_2N(CH_3)_2$ | $CH_3$ | $i\text{-}C_3H_7$ | |
| $C_6H_5$ | H | $CH_3$ | $i\text{-}C_3H_7$ | |
| —$(CH_2)_3$— | | $CH_3$ | $i\text{-}C_3H_7$ | |
| —$(CH_2)_4$— | | $CH_3$ | $i\text{-}C_3H_7$ | |
| —$(CH)_4$— | | $CH_3$ | $i\text{-}C_3H_7$ | |
| H | $C_6H_5$ | $CH_3$ | $i\text{-}C_3H_7$ | |
| $C_6H_5$ | H | $CH_3$ | $i\text{-}C_3H_7$ | |
| H | $OC_6H_5$ | $CH_3$ | $i\text{-}C_3H_7$ | |
| $CF_3$ | H | $CH_3$ | $i\text{-}C_3H_7$ | |

EXAMPLE 45

Preparation of 5-(4-isopropyl-4-methyl-5-oxo-2-imidazolin-2-yl)thieno[3,2-b]pyridine-6-carboxylic acid

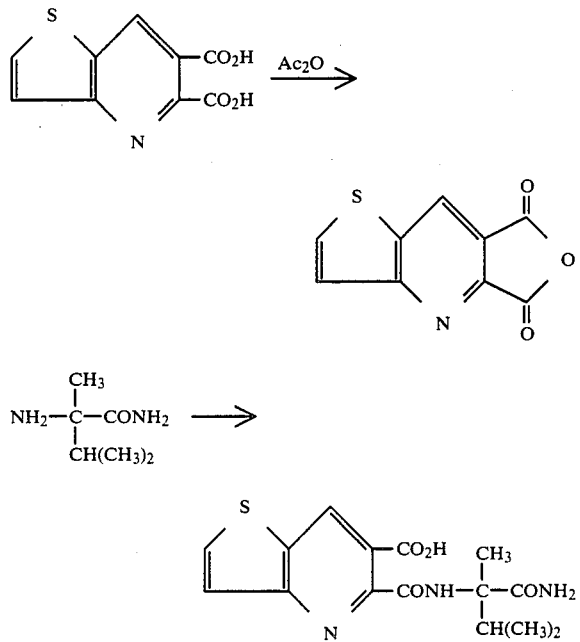

Thieno[3,2-b]pyridine-5,6-dicarboxylic acid (2.5 g, 0.011 mol) is heated slowly to 85° C. for one hour with acetic anhydride (25 mL), then cooled, filtered and washed with diethyl ether to give the anhydride as a solid, mp 266°–267° C. A mixture of the anhydride and 2-amino-2,3-dimethylbutyramide (2.6 g, 0.02 mol) in THF (70 mL) is stirred at room temperature for 15 hours. After heating at reflux for two hours, the mixture is cooled and diluted with THF (50 mL). Solid 5-[(1-carbamoyl-1,2-dimethylpropyl)carbamoyl]thieno[3,2-b]pyridine-6-carboxylic acid is filtered off, washed with ether and dried. The above solid is mixed with an aqueous 60 mL) solution of sodium hydroxide (6 g 0.05 mol) and heated at 85° C. for two hours and 30 minutes, then set aside at room temperature overnight. After cooling in an ice bath, the mixture is acidified to pH 3 with concentrated hydrochloric acid. A solid (3 g) is filtered off and dried. Crystallization from ethyl acetate affords (5-(4-isopropyl-4-methyl-5-oxo-2-imidazolin-2-yl)thieno[3,2-b]pyridine-6-carboxylic acid, mp 242°–244° C. in 46% yield.

Utilizing the above procedure and substituting the appropriate pyridine-5,6-dicarboxylic acid for thieno[3,2-b]pyridine-5,6-dicarboxylic acid yields the compounds illustrated below.

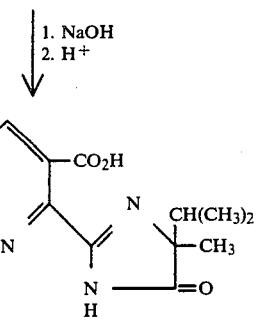

| R9 | R10 | mp °C. |
|---|---|---|
| H | H | 242–244 |
| H | Cl | 238–239 |
| H | Br | 226–227 |
| Cl | H | 226–267 |

EXAMPLE 46

Preparation of diethyl furo[3,2-b]pyridine-5,6-dicarboxylate

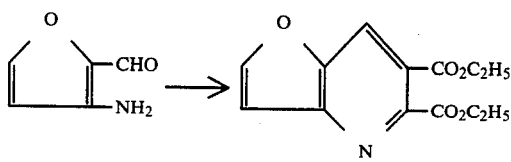

3-Amino-2-formylfuran, prepared from 3-azido-2-formylfuran (8.9 g 0.065 mol) is dissolved in ethanol and to this solution diethyl oxalacetate (12.23 g, 0.065 mol) and ten drops of piperidine are added. In addition pulverized 3 Å molecular sieve is added and the reaction stirred at 65°-60° C. for three hours, then additional diethyl oxalacetate (2.2 g) is added. The reaction is essentially complete after 12 hours at 55°-60° C. On cooling the reaction is filtered, and the filtrate concentrated and then dissolved in ethyl acetate, water washed, then brine washed, dried over anhydrous magnesium sulfate and stripped to dryness. The residue is dissolved in 3:1 hexane:ethyl acetate and passed through a flash chromatographic column in two stages. First it is filtered by vacuum through a four to five inch pad of silica from which the last three fractions containing the required product are collected and combined. These combined fractions are then passed through a six inch column eluting under pressure with ethyl acetate:hexane 3:1 and 2:1. Diethyl furo[3,2-b]pyridine-5,6-dicarboxylate 4.15 g (24%) is obtained after crystallization from hexane-ether, of mp 60°-64° C., and with a mass spectrum m/e of 264.

Utilizing the above procedure and substituting the appropriate furan for 3-amino-2-formylfuran yields the compounds illustrated below.

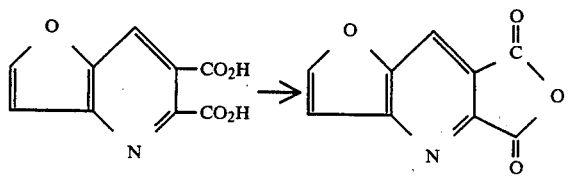

| $R_9$ | $R_{10}$ | R″ | mp °C. |
|-------|----------|-----|--------|
| H | H | $C_2H_5$ | 60-64 |
| H | Cl | $C_2H_5$ | |
| $CH_3$ | H | $C_2H_5$ | |
| H | $CH_3$ | $C_2H_5$ | |
| $C_2H_5$ | H | $C_2H_5$ | |
| H | $C_2H_5$ | $C_2H_5$ | |
| $CH_3$ | $CH_3$ | $C_2H_5$ | |

EXAMPLE 47

Preparation of furo[3,2-b]pyridine-5,6-dicarboxylic acid

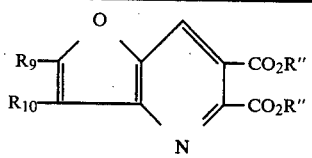

Furo[3,2-b]pyridine-5,6-dicarboxylic acid, diethyl ester (1.1 g, 0.0042 mol) is dissolved in 95% ethanol (20 mL) containing 10% aqueous sodium hydroxide (20 mL) and set aside at 0° C. for two days. The mixture is cooled, acidified and the solvent removed under reduced pressure. Water 5 mL is added and the hydrated product diacid obtained as a brown solid by filtration, 3.31 g (99%), mp 183° C. (dec). Anal calcd. as $C_9H_5NO_5.2\frac{1}{2}H_2O$ C, 42.86; H, 3.99; N, 5.55 found: C, 42.63; H, 2.63; N, 5.46.

EXAMPLE 48

Preparation of furo[3,2-b]pyridine-5,6-dicarboxylic acid anhydride

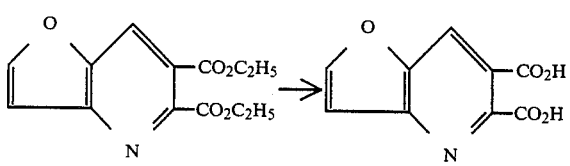

Furo[3,2-b]pyridine-5,6-dicarboxylic acid (3.3 g, 0.0159 mol) in acetic anhydride (100 mL) is heated to 70°-80° C. for six hours. The reaction mixture is cooled, filtered and the solid is washed with ether to give 3.01 (100%) of crude furo[3,2-b]pyridine-5,6-dicarboxylic acid anhydride.

EXAMPLE 49

Preparation of 5-[(1-carbamoyl-1,2-dimethylpropyl)carbamoyl]-furo[3,2-b]pyridine-6-carboxylic acid and 5-(4-isopropyl-4-methyl-5-oxo-2-imidazolin-2-yl)furo[3,2-b]pyridine-6-carboxylic acid

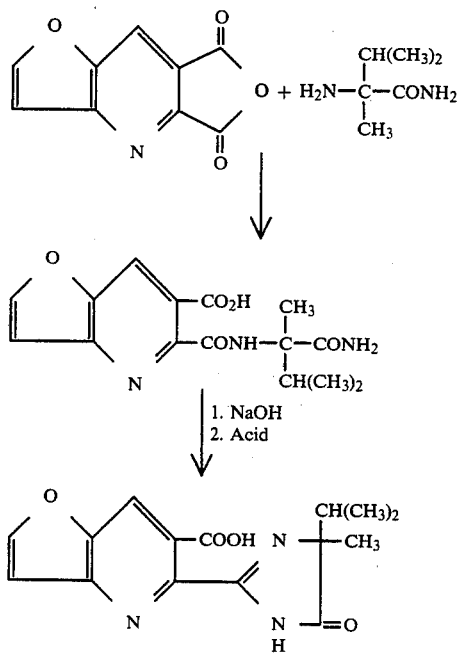

Furo[3,2-b]pyridine-5,6-dicarboxylic acid anhydride (3.01 g, 0.015 mol) is suspended in THF (100 mL) to which 2-amino-2,3-dimethylbutyramide (2.3 g, 0.018 mol) is added. After stirring for 20 hours, the solution is stripped to an oily solid which dissolves in a water/dilute sodium hydroxide solution. The alkaline solution is extracted with methylene chloride, and then acidified and reextracted with methylene chloride but on stirring only minute traces of material is isolated. The water layer is concentrated to an oily solid which is dissolved in ethanol, filtered and concentrated to a purple gum which is predominantly the crude product, 5-[(1-carbamoyl-1,2-dimethylpropyl)carbamoyl]furo[3,2-b]pyridine-6-carboxylic acid and is used without further purification to prepare the final 2-imidazolin-2-yl product by dissolving it in 10% sodium hydroxide solution (40 mL) and warming at 80° C. for three hours. On cooling the reaction is acidified and a small amount of solid precipitated out and was filtered off. Concentration of mother liquors gives a second crop, which is collected and combined with the first crop. Purification is effected by taking half of the material and separating on silica gel preparative glass plates as bands. The slower running band using methylene chloride:ethyl acetate:-chloroform:methanol 1:1:1:1 as eluant, affords the desired 2-imidazolin-2-yl product, mp 214°–223° C. (dec), Esters may then be prepared by the procedures described in Example 20.

Utilizing the above procedure and substituting the appropriate furo[3,2-b]pyridine-5,6-dicarboxylic anhydride yields the compounds illustrated below.

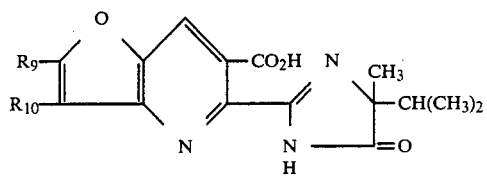

| $R_9$ | $R_{10}$ | mp °C. |
|---|---|---|
| H | H | 214–223 (dec) |
| H | Cl | |
| $CH_3$ | H | |
| H | $CH_3$ | |
| $C_2H_5$ | H | |
| H | $C_2H_5$ | |
| $CH_3$ | $CH_3$ | |

EXAMPLE 50

Preparation of dimethyl thieno[2,3-b]pyridine-5,6-dicarboxylate

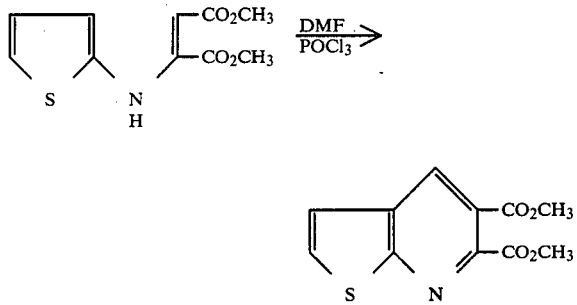

A Vilsmeier reagent is prepared by adding dropwise, with stirring, phosphorus oxychloride (40.29 g, 0.26 mol) to a cooled (10° C.) solution of DMF (19.0 g, 0.26 mol) in 1,2-dichloroethane (40 mL) in an $N_2$ atmosphere. This reagent is stirred at room temperature for one hour and 45 minutes. Dimethyl-2-thienylaminobutenedioate (63.4 g, 0.26 mol) dissolved in 1,2-dichloroethane (300 mL) is added dropwise to the Vilsmeier reagent at 7°–10° C. The reaction temperature is raised to room temperature for 15 minutes, then to reflux for 12 hours. The cooled reaction mixture is concentrated and the residue chromatographed on a silica gel column with ethyl acetate-hexane, affording dimethylthieno[2,3-b]pyridine-5,6-dicarboxylate (29 g, 45%) as a solid.

Utilizing the above procedure and substituting the appropriate dimethyl-2-thienylaminobutenedioate yields the compounds illustrated below.

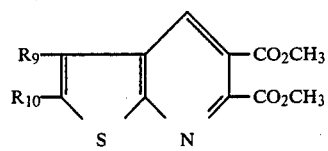

| $R_9$ | $R_{10}$ | mp °C. |
|---|---|---|
| $CH_3$ | H | 80–82 |
| H | H | solid |
| H | $CH_3$ | |
| $CH_3$ | $CH_3$ | |
| H | $C_6H_5$ | |
| $C_6H_5$ | H | |
| $CF_3$ | H | |

EXAMPLE 51

Preparation of dimethyl 3-bromothieno[2,3-b]pyridine-5,6-dicarboxylate

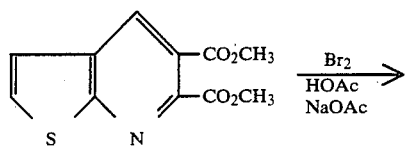

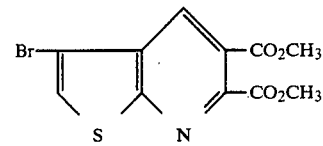

Bromine (0.33, 0.00206 mol) in acetic acid (8 mL) is added to a stirred solution of dimethylthieno[2,3-b]pyridine-5,6-dicarboxylate (0.5 g, 0.00187 mol) in acetic acid containing sodium acetate (0.31 g, 0.00377 mol) at 40° C. The reaction mixture is heated at 75° C. for 18 hours. Evaluation of the mixture by tlc (silica gel) indicated incomplete reaction. Additional bromine (0.33 g) in acetic acid and sodium acetate (0.31 g) is added and heating at 75° C. continued for six hours. The reaction mixture is diluted with water and extracted into ethyl acetate. The separated organic layer is dried over anhydrous $MgSO_4$, filtered, and the filtrate concentrated to an oil which solidifies on standing. Crystallization of the crude product from ethyl acetate-hexanes yields the dimethyl 3-bromothieno[2,3-b]pyridine-5,6-dicarboxylate as white needles mp 86°–87.5° C.

This compound may readily be converted to a variety of substituted-thieno[2,3-b]pyridine compounds as illustrated below, while electrophilic substitution such as nitration or halogenation yields the additional compounds also listed below.

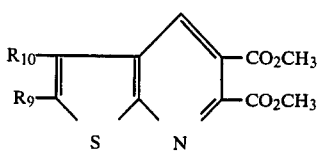

| $R_9$ | $R_{10}$ | mp °C. |
|---|---|---|
| H | H | |
| H | Cl | 104–110 |
| H | Br | 86–87.5 |
| H | I | |
| H | F | |
| H | CN | |
| H | SCH$_3$ | |
| H | OCH$_3$ | |
| H | N(CH$_3$)$_2$ | |
| H | OCHF$_2$ | |
| H | NO$_2$ | |
| H | CHO | |
| H | CH$_2$Cl | |
| CH$_3$ | H | 80–82 |
| H | CH$_3$ | |
| Cl | H | |
| Cl | Cl | 84–89 |
| CH$_3$ | CH$_3$ | |
| H | SO$_2$N(CH$_3$)$_2$ | |
| —(CH$_2$)$_4$— | | |
| —(CH)$_4$— | | |
| —(CH$_2$)$_3$— | | |
| C$_6$H$_5$ | H | |
| H | OC$_6$H$_5$ | |
| CF$_3$ | H | |

EXAMPLE 52

Preparation of thieno[2,3-b]pyridine-5,6-dicarboxylic acid

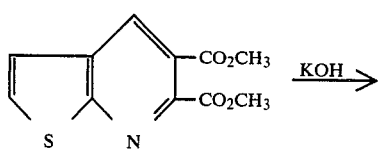

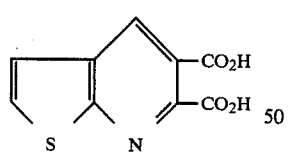

A solution containing dimethyl thieno[2,3-b]pyridine-5,6-dicarboxylate (27.75 g, 0.11 mol) and potassium hydroxide (30.98 g, 0.55 mol) in methanol (200 mL) under a N$_2$ atmosphere is heated at reflux for two hours. The reaction mixture is cooled and sufficient water added to dissolve any solids present before evaporating the mixture to dryness. The resulting solid is dissolved in a minimum volume of water, cooled in an ice bath and acidified with concentrated H$_2$SO$_4$ to pH ~1. Thieno[2,3-b]pyridine-5,6-dicarboxylic acid is filtered off and dried overnight to give 23.36 g mp 272°–275° C.

Utilizing the above procedure and substituting the appropriate substituted dialkylthieno[2,3-b]pyridine-5,6-dicarboxylate yields the compounds illustrated below.

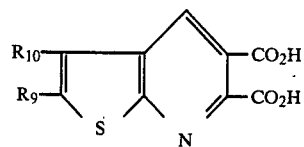

| $R_9$ | $R_{10}$ | mp °C. |
|---|---|---|
| H | H | 272–275 |
| H | Cl | >300 |
| H | Br | >315 |
| H | I | |
| H | F | |
| H | CN | |
| H | SCH$_3$ | |
| H | OCH$_3$ | |
| H | N(CH$_3$)$_2$ | |
| H | OCHF$_2$ | |
| H | NO$_2$ | |
| H | CHO | |
| H | CH$_2$Cl | |
| H | CH$_3$ | 180–183 (dec) |
| CH$_3$ | H | |
| Cl | H | |
| Cl | Cl | |
| CH$_3$ | CH$_3$ | |
| C$_6$H$_5$ | H | |
| H | SO$_2$N(CH$_3$)$_2$ | |
| —(CH$_2$)$_3$— | | |
| —(CH$_2$)$_4$— | | |
| —(CH)$_4$— | | |
| H | OC$_6$H$_5$ | |
| H | C$_6$H$_5$ | |
| CF$_3$ | H | |

EXAMPLE 53

Preparation of thieno[2,3-b]pyridine-5,6-dicarboxylic anhydride

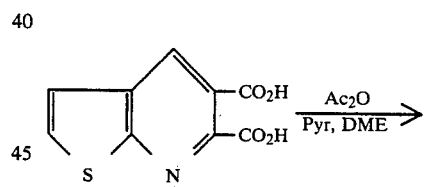

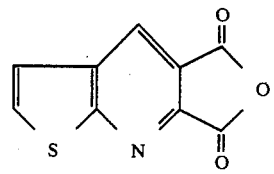

Acetic anhydride (37.4 g, 0.366 mol) is added to a stirred suspension of thieno[2,3-b]pyridine-5,6-dicarboxylic acid (21.52 g, 0.096 mol) in dimethoxyethane (175 mL) in an inert N$_2$ atmosphere. Upon addition of pyridine (16.78 g, 0.21 mol) at room temperature an exotherm to 45° C. is observed and a homogeneous solution results. The reaction mixture is then stirred at room temperature and the resulting solid filtered off, washed with ether and air dried to give 14.8 g (75%) of thieno[2,3-b]pyridine-5,6-dicarboxylic acid anhydride.

Utilizing the above procedure and substituting the appropriate substituted thieno[2,3-b]pyridine-5,6-dicarboxylic acid yields the compounds illustrated below.

| | | |
|---|---|---|
| R9 | R10 | mp °C. |
| CH3 | H | 176–180 |
| H | Br | 228.5–231 |
| H | Cl | 230–300 (slow dec) |
| H | H | |
| H | — | |
| H | I | |
| H | F | |
| H | CN | |
| H | SCH3 | |
| H | N(CH3)2 | |
| H | NO2 | |
| H | CHO | |
| H | CH2Cl | |
| H | CH3 | |
| CH3 | H | |
| Cl | H | |
| Cl | Cl | |
| CH3 | CH3 | |
| C6H5 | H | |
| H | SO2N(CH3)2 | |
| —(CH2)3— | | |
| —(CH2)4— | | |
| —(CH)4— | | |
| H | C6H5 | |
| H | OC6H5 | |
| CF3 | H | |

| | | |
|---|---|---|
| R9 | R10 | mp °C. |
| CH3 | H | 207–208 |
| H | Br | 176–178 |
| H | Cl | 156–158 |
| H | H | |
| H | I | |
| H | F | |
| H | CN | |
| H | SCH3 | |
| H | OCH3 | |
| H | N(CH3)2 | |
| H | NO2 | |
| H | CHO | |
| H | CH2Cl | |
| H | CH3 | |
| Cl | H | |
| Cl | Cl | |
| CH3 | CH3 | |
| C6H5 | H | |
| H | SO2N(CH3)2 | |
| —(CH2)3— | | |
| —(CH2)4— | | |
| —(CH)4— | | |
| H | C6H5 | |
| H | OC6H5 | |
| CF3 | H | |

EXAMPLE 54

Preparation of 6-[(1-carbamoyl-1,2-dimethylpropyl)carbamoyl]-thieno[2,3-b]pyridine-5-carboxylic acid

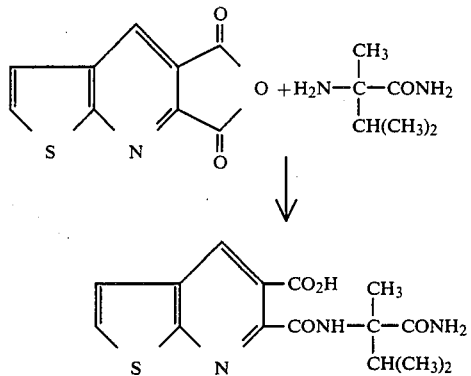

2-Amino-2,3-dimethylbutyramide (9.84 g, 0.076 mol) is added to a stirred suspension of thieno[2,3-b]pyridine-5,6-dicarboxylic acid anhydride (14.8 g, 0.072 mol) in THF under an inert atmosphere of N2 at room temperature. The dark solution is stirred at room temperature overnight and the resulting solid filtered off, washed with THF and air dried to give 17.35 g (72%) of 6-[(1-carbamoyl-1,2-dimethylpropyl)carbamoyl]thieno[2,3-b]pyridine-5-carboxylic acid.

Utilizing the above procedure and substituting the appropriate substituted thieno[2,3-b]pyridine-5,6-dicarboxylic acid anhydride yields the compounds illustrated below.

EXAMPLE 55

Preparation of 6-(4-isopropyl-4-methyl-5-oxo-2-imidazolin-2-yl)thieno[2,3-b]pyridine-5-carboxylic acid

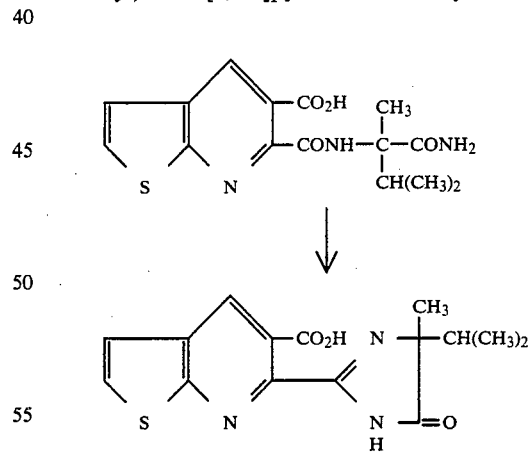

6-[(1-Carbamoyl-1,2-dimethylpropyl)carbamoyl]-thieno[2,3-b]pyridine-5-carboxylic acid (17.35 g, 0.052 mol) is added to water (225 mL) containing sodium hydroxide (10.35 g, 0.26 mol). The resulting basic solution is heated at 80° C. for two hours and 45 minutes, cooled in an ice-water bath and acidified with 6N H2SO4. The product 6-(4-isopropyl-4-methyl-5-oxo-2-imidazolin-2-yl)thieno[2,3-b]pyridine-5-carboxylic acid is filtered off, washed with water and air dried yielding 1.54 g, 70.3%, mp 221°–223° C.

EXAMPLE 56

Preparation of 2-isopropyl-2-methyl-5H-Imidazo[1',2':1,2]pyrrolo[3,4-b]thieno[3,2-e]pyridine-3(2H),5-dione

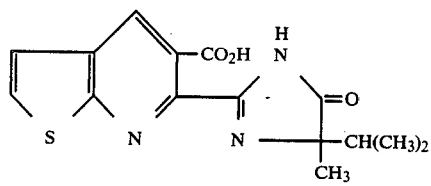

↓ DCC

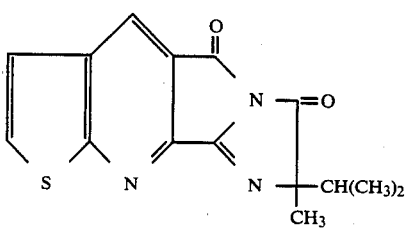

Dicyclohexylcarbodiimide (1.07 g, 0.005 mol) in methylene chloride (20 mL) is added dropwise to a stirred methylene chloride (30 mL) suspension of 6-(4-isopropyl-4-methyl-5-oxo-2-imidazolin-2-yl)thieno[2,3-b]-5-carboxylic acid (1.5 g, 0.0047 mol) under an $N_2$ atmosphere. After stirring the reaction mixture for 16 hours, it was clarified by filtration, concentrated to dryness and the resulting material purified by column chromatography on silica gel eluting with acetonitrile/methylene chloride (½). The solid product was crystallized from toluene to give the pure 3,5-dione as white crystals mp 214.5°–216.5° C.

EXAMPLE 57

Preparation of 2-propynyl 6-(4-isopropyl-4-methyl-5-oxo-2-imidazolin-2-yl)thieno[2,3-b]pyridine-5-carboxylate

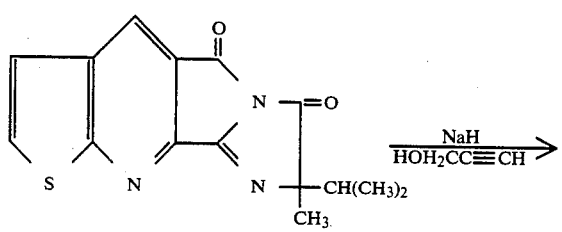

Sodium hydride (2.4 g, 60%, 0.126 mol) is added to the 3,5-dione (0.9 g, 0.003 mol) in propargyl alcohol (25 mL) at 10° C. under an inert $N_2$ atmosphere. The reaction mixture is stirred at room temperature for 60 hours and then neutralized with a saturated ammonium chloride solution. The resulting mixture is concentrated on a rotary evaporator, diluted with water and extracted with ethyl acetate. The organic layer is separated, dried over anhydrous $MgSO_4$ and concentrated to dryness.

Purification of the product by column chromatography on silica gel with methylene chloride/acetonitrile (85/15) yields 2-propynyl 6-(4-isopropyl-4-methyl-5-oxo-2-imidazolin-2-yl)pyridine-5-carboxylate, which after crystallization from toluene has a mp 188°–189.5° C.

Utilizing the procedures of Examples 49, 55, 56 and 57 and substituting the appropriate thieno or furo[3,2-b]pyridine or thieno or furo[2,3-b]pyridine compounds, yields the compounds illustrated below.

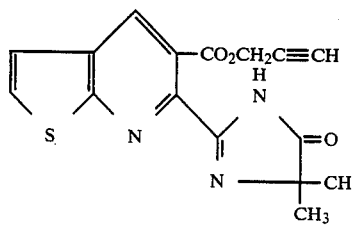

| B | $R_9$ | $R_{10}$ | R | mp °C. |
|---|---|---|---|---|
| S | H | H | $CH_3$ | 215–217 |
| S | H | H | H | 220–223.5 (dec) |
| S | H | H | $-CH_2C\equiv CH$ | 188–189.5 |
| S | H | H | $-CH_2-\underset{O}{\text{furyl}}$ | 140–142 |
| S | H | H | $-CH_2\underset{|}{C}=CH_2$, $CH_3$ | 108–110 |
| S | $CH_3$ | H | H | 225.5–227.5 |
| S | H | Br | H | 274–276 |
| S | H | Cl | H | 266–267 |
| O | H | H | H | 237–244 |
| S | H | $NO_2$ | $-CH_3$ | 201–202.5° C. |
| S | H | $NO_2$ | H | 260 (dec) |
| S | Cl | H | H | 268 (dec) |
| S | H | $CH_3$ | H | 255–257 |
| S | $-(CH_2)_4-$ | | H | 234–237 |
| O | H | Cl | H | 239–240 |
| O | H | H | $CH_3$ | 134–137 |
| O | H | Br | H | 239–245 |
| O | $CH_3$ | H | H | 174–177 |
| O | $C_2H_5$ | H | H | 170–172 |
| O | $C_6H_5$ | H | H | 244–245 |
| O | H | Cl | $CH_3$ | 137–141 |
| O | H | H | $-CH_2-\underset{O}{\text{furyl}}$ | 137–141 |
| O | H | H | $CH_2C\equiv CH$ | 150–156 |

| B | $R_{10}$ | $R_9$ | R | mp °C. |
|---|---|---|---|---|
| S | H | H | H | 242–244 |
| S | H | Cl | H | 238–239 |

-continued

| | | | | |
|---|---|---|---|---|
| S | H | Br | H | 226–227 |
| S | H | H | —CH₂—[furan] | 156–157 |
| O | H | H | H | 214–223 |
| S | Cl | H | H | 266–267 |

EXAMPLE 58

Preparation of methyl 5-(4-isopropyl-4-methyl-5-oxo-2-imidazolidinyl)-furo[3,2-b]pyridine-6-carboxylate

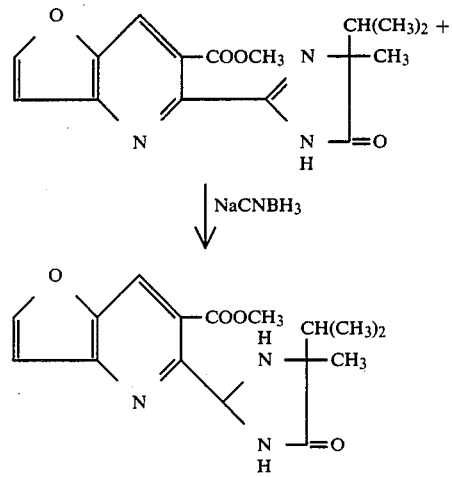

A solution of 22.1 mmol of methyl 5-(4-isopropyl-4-methyl-5-oxo-2-imidazolin-2-yl)furo[3,2-b]pyridine-6-carboxylate in methanol is cooled to 0° C. and a few drops of methyl orange indicator added. The solution is stirred and treated with 22.1 mmol of concentrated hydrochloric acid. The solution is then treated with 22.1 mmol of sodium cyanoborohydride, and the pH maintained at ~3 by the additon of 2N methanolic HCl, stirred overnight, cooled to 0° C. and the pH of the solution adjusted to about 0 with HCl to decompose residual NaCNBH₃. The pH is thereafter adjusted to 5–6 with 5N NaOH. The methanol is removed in vacuo and water added to dissolve inorganic salts. The mixture is extracted with CH₂Cl₂ and the extracts dried and concentrated to give the title compound.

Utilizing the above procedure with the appropriately substituted methyl 2-(2-imidazolin-2-yl)furo[3,2-b]pyridine-6-carboxylate yields the corresponding 2-(2-imidazolidinyl)furo[3,2-b]pyridine-6-carboxylate. Similarly, reaction of the appropriately substituted methyl 2-(2-imidazolin-2-yl)thieno[3,2-b]pyridine-6-carboxylate yields the corresponding methyl 2-(2-imidazolinyl)-thieno[3,2-b]pyridine-6-carboxylate. The reaction products are illustrated below:

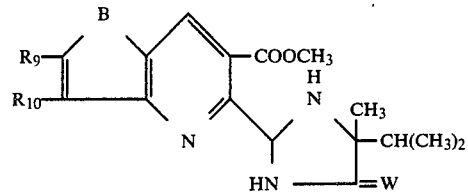

Similarly, using the above procedure with the appropriately substituted methyl 2-(2-imidazolin-2-yl)dihydrofuro- or dihydrothieno[3,2-b]pyridine-6-carboxylate yields the corresponding substituted methyl 2-(2-imidazolidinyl)dihydrofuro- or dihydrothieno[3,2-b]pyridine-6-carboxylate. The reaction products are illustrated below:

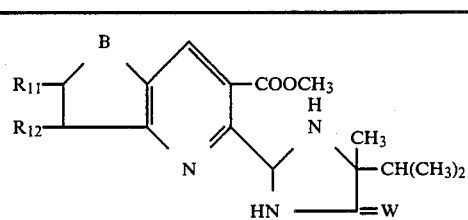

| B | W | R₉ | R₁₀ | mp °C. |
|---|---|---|---|---|
| O | O | H | H | |
| S | S | H | H | |
| S | O | H | H | |
| O | S | H | H | |
| O | O | H | Cl | |
| S | S | H | Cl | |
| S | O | H | Cl | |
| O | S | H | Cl | |
| O | O | CH₃ | H | |
| S | S | CH₃ | H | |
| S | O | CH₃ | H | |
| O | S | CH₃ | H | |
| O | O | H | CH₃ | |
| S | S | H | CH₃ | |
| S | O | H | CH₃ | |
| O | S | H | CH₃ | |
| O | O | C₂H₅ | H | |
| S | S | C₂H₅ | H | |
| S | O | C₂H₅ | H | |
| O | S | C₂H₅ | H | |
| O | O | H | C₂H₅ | |
| S | S | H | C₂H₅ | |
| S | O | H | C₂H₅ | |
| O | S | H | C₂H₅ | |
| O | O | CH₃ | CH₃ | |
| S | S | CH₃ | CH₃ | |
| S | O | CH₃ | CH₃ | |
| O | S | CH₃ | CH₃ | |
| O | O | H | Br | |
| S | S | H | Br | |
| S | O | H | Br | |
| O | S | H | Br | |

EXAMPLE 59

Preparation of cis- and trans-methyl 6-(4-isopropyl-4-methyl-5-oxo-2-imidazolidinyl)-thieno[2,3-b]pyridine-5-carboxylates

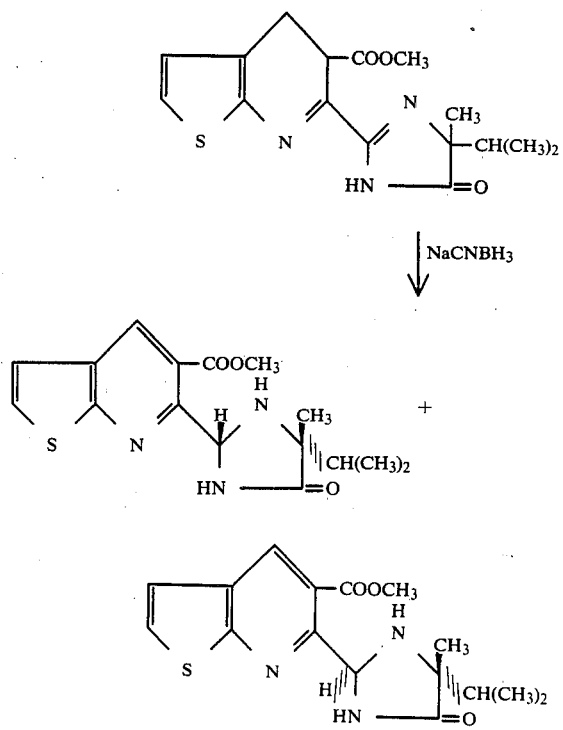

Using essentially the same procedure as described in Example 58 but substituting methyl 6-(4-isopropyl-4-methyl-5-oxo-2-imidazolin-2-yl)thieno[2,3-b]pyridine-5-carboxylate for methyl 5-(4-isopropyl-4-methyl-5-oxo)-2-imidazolin-2-yl)furo[3,2-b]pyridine-6-carboxylate yields the two products cis-methyl 6-(4-isopropyl-4-methyl-5-oxo-2-imidazolidinyl)thieno[3,2-b]pyridine-5-carboxylate mp 185°–186° C. and trans-methyl 6-(4-isopropyl-4-methyl-5-oxo-2-imidazolidinyl)thieno[2,3-b]pyridine-5-carboxylate mp 145°–148° C.

Utilizing the above procedure with the appropriately substituted methyl thieno-,dihydrothieno-, furo- or dihydrofuro[2,3-b]pyridine-5-carboxylate yields the reaction products illustrated below.

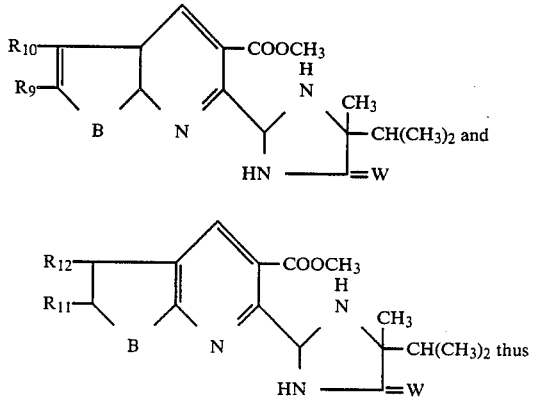

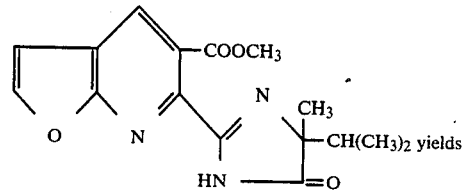

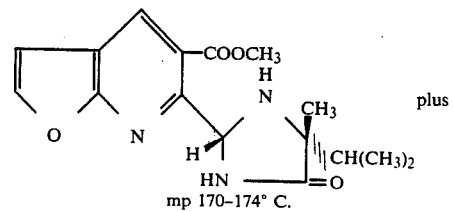

mp 170–174° C.

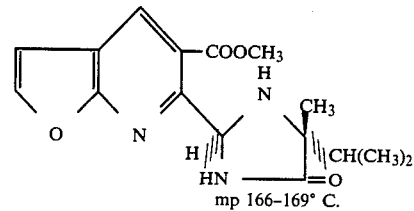

mp 166–169° C.

EXAMPLE 60

Preparation of trans-6-(4-isopropyl-4-methyl-5-oxo-2-imidazolidinyl)-thieno[2,3-b]pyridine-5-carboxylic acid

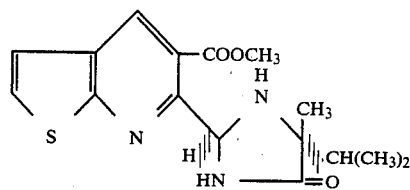

 NaOH

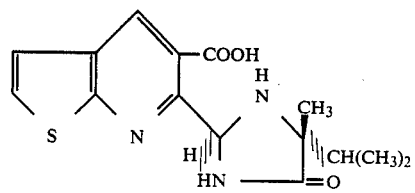

Using essentially the same conditions as those described in Example 32 but substituting trans-methyl 6-(4-isopropyl-4-methyl-5-oxo-2-imidazolidinyl)- thieno[2,3-b]pyridine-5-carboxylate for cis-methyl 6-(allyloxy)-2-(4-isopropyl-4-methyl-5-oxo-2-imidazolidinyl)nicotinate gives the product trans-6-(4-isopropyl-4-methyl-5-oxo-2-imidazolidinyl)thieno[2,3-b]pyridine-5-carboxylic acid, mp 225°–226° C. as a sesquehydrate.

Similarly the furano analog yields the corresponding imidazolidinones below.

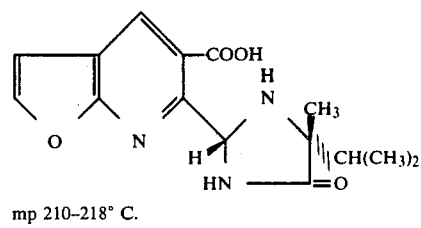

mp 210–218° C.

and

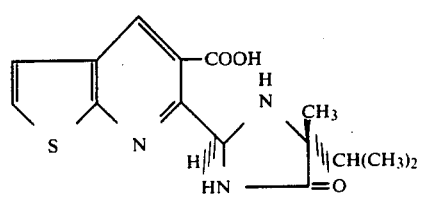

mp 176–178° C.

EXAMPLE 61

Preparation of diethyl 5-acetyl-1,6-dihydro-6-oxo-2,3-pyridinedicarboxylate

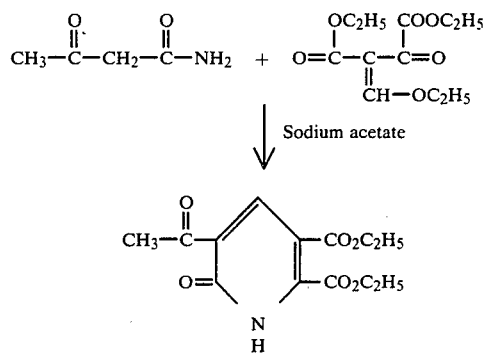

Sodium acetate (30 g, 0.37 mol) is added to a stirred mixture of diethyl(ethoxymethylene)oxalacetate (87 g, 0.36 mol) and acetoacetamide (36 g, 0.36 mol) in absolute ethanol (300 mL). After stirring the reaction mixture for 30 minutes, the ethanol is distilled off under reduced pressure, the residue acidified to pH 2 with dilute aqueous hydrochloric acid and the resulting solid filtered off. Crystallization from an ethanol-water mixture affords diethyl 5-acetyl-1,6-dihydro-6-oxo-2,3-pyridinedicarboxylate as crystals mp 200°–209° C.

EXAMPLE 62

Preparation of diethyl 5-(bromoacetyl)-1,6-dihydro-6-oxo-2,3-pyridinedicarboxylate

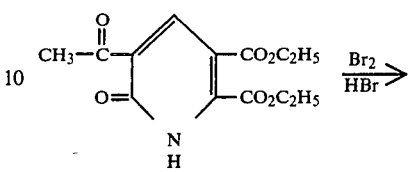

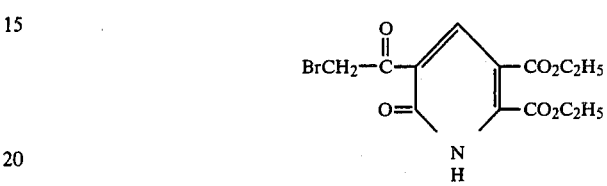

Bromine (8.0 g, 0.050 mol) in 48% HBr is added dropwise to a stirred solution of diethyl-5-acetyl-1,6-dihydro-6-oxo-2,3-pyridinedicarboxylate (14.05 g, 0.05 mol) in 48% HBr (200 mL). Upon completion of this bromine addition the reaction mixture is poured onto ice (200 g) and the mixture is stirred until the ice has melted. Th crude product is collected by filtration and crystallized twice from an ethyl acetate-hexane mixture (½) affording diethyl 5-(bromoacetyl)-1,6-dihydro-6-oxo-2,3-pyridinedicarboxylate with mp 141°–142° C.

EXAMPLE 63

Preparation of diethyl 5-(2-bromo-1-hydroxyethyl)-1,6-dihydro-6-oxo-2,3-pyridinedicarboxylate and diethyl 2,3-dihydro-3-hydroxy-furo[2,3-b]pyridine-5,6-dicarboxylate

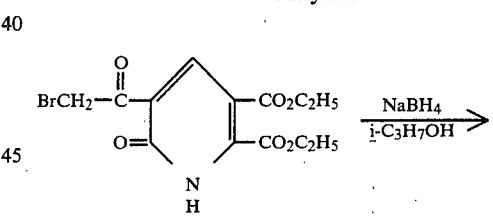

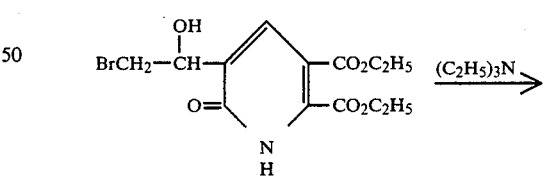

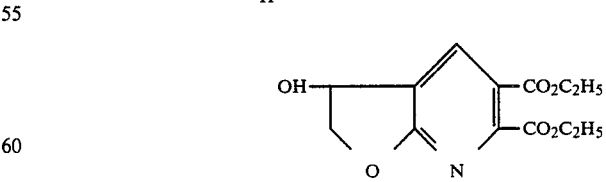

Sodium borohydride (2.54 g, 0.066 mol) is added in portions over a 30 minute period to a stirred suspension of diethyl 5-(bromoacetyl)-1,6-dihydro-6-oxo-2,3-pyridinedicarboxylate (57.2 g, 0.159 mol) at 10°–20° C. Upon completion of the sodium borohydride addition, the reaction mixture is stirred while attaining room temperature. Ice (100 g) is added and the mixture stirred until the ice has melted. The mixture is then concentrated in vacuo and the residue crystallized twice from an ethyl acetate-hexane mixture to give pure diethyl 5-(2-bromo-1-hydroxyethyl)-1,6-dihydro-6-oxo-2,3-pyridinedicarboxylate mp 134°–138° C.

Stirring this compound with triethylamine (1.0 mL/g of solid) in methylene chloride for one hour, followed by washing the organic solution with dilute hydrochloric acid, water, brine and drying over anhydrous MgSO4 yields the crude furo[2,3-b]pyridine as an oil upon removing the solvent in vacuo. Crystallization from a cyclohexane-toluene mixture affords pure diethyl 2,3-dihydro-3-hydroxy-furo[2,3-b]pyridine-5,6-dicarboxylate mp 73°–77° C.

EXAMPLE 64

Preparation of diethyl furo[2,3-b]pyridine-5,6-dicarboxylate

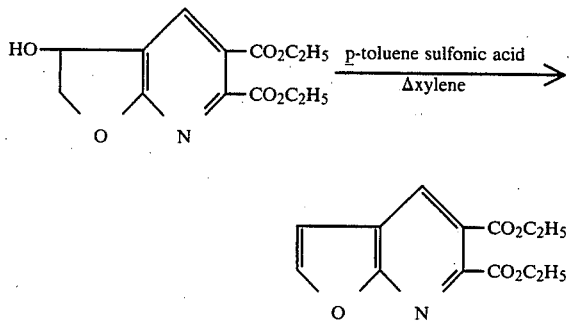

A xylene solution of the hydroxy-furo compound obtained in Example 61, (3.7 g) containing para-toluene sulfonic acid (0.01 g) is heated at reflux for two hours. The solution is cooled and the xylene solution decanted off. The residue is extracted with ether and the extracts combined with the xylene. Distillation of the solvents gives a yellow solid which is crystallized from a cyclohexane-toluene mixture to give pure diethyl furo[2,3-b]pyridine-5,6-dicarboxylate mp 66°–77° C.

EXAMPLE 65

Preparation of furo[2,3-b]pyridine-5,6-dicarboxylic acid

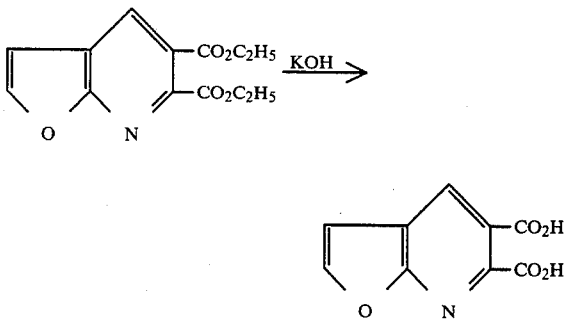

Potassium hydroxide (5.60 g, 85%, 0.087 mol) in water (5 mL) is added to a stirred suspension of diethyl furo[2,3-b]pyridine-5,6-dicarboxylate (9.3 g, 0.035 mol) in absolute ethanol (100 mL). The reaction mixture is heated at 60° C. for one hour, then cooled and anhydrous acetone added. The precipitate is filtered off, dried, suspended in dry acetone and treated with hydrogen chloride to adjust to a pH of 2. Crystallization of the isolated solids from an ethyl acetate-acetone mixture affords furo[2,3-b]pyridine-5,6-dicarboxylic acid mp 189°–192° C.

EXAMPLE 66

Preparation of furo[2,3-b]pyridine-5,6-dicarboxylic anhydride

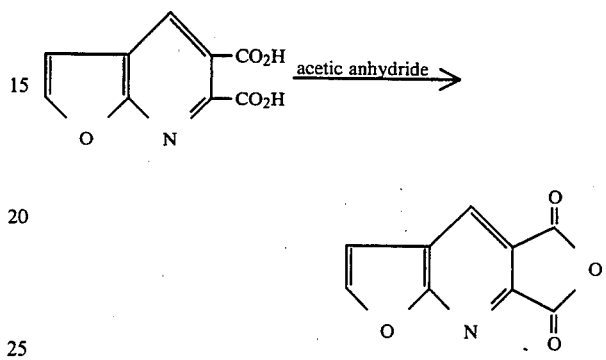

Furo[2,3-b]pyridine-5,6-dicarboxylic acid (6.7 g, 0.032 mol) is heated at 60° C. for 30 minutes in acetic anhydride (150 mL). The reaction mixture is cooled to room temperature and concentrated in vacuo and the residue triturated with cyclohexane-ether (5:1), filtered off and dried to give 5.35 g furo[2,3-b]pyridine-5,6-dicarboxylic acid anhydride.

EXAMPLE 67

Preparation of 6-[(1-carbamoyl-1,2-dimethylpropyl)carbamoyl]-furo[2,3-b]pyridine-5-carboxylic acid

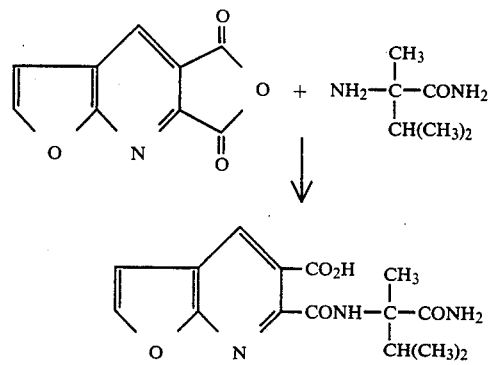

2-Amino-2,3-dimethylbutyramide (2.1 g, 0.016 mol) is added to a stirred suspension of furo[2,3-b]pyridine-5,6-dicarboxylic acid anhydride (3.0 g, 0.016 mol) in tetrahydrofuran (7.5 mL) and the mixture allowed to stir at room temperature for 16 hours. The reaction mixture is then stirred at 60° C. for one hour, cooled to room temperature, ether added, and the solid filtered off and dried to give 5 g of 6-[(1-carbamoyl-1,2-dimethylpropyl)carbamoyl]furo[2,3-b]pyridine-5-carboxylic acid mp 192°–196° C. (dec).

EXAMPLE 68

Preparation of 6-(4-isopropyl-4-methyl-5-oxo-2-imidazolin-2-yl)furo[2,3-b]pyridine-5-carboxylic acid

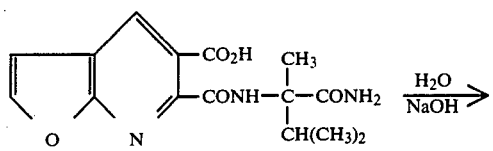

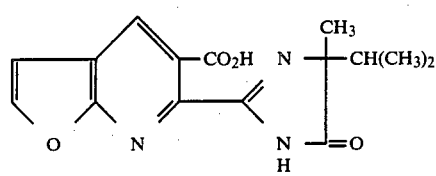

A solution containing 6-[(1-carbamoyl-1,2-dimethylpropyl)carbamoyl]furo[2,3-b]pyridine-5-carboxylic acid (3.8 g, 0.012 mol) in aqueous sodium hydroxide 2.4 g, 0.06 mol) in water (40 mL) is stirred at 65° C. for three hours. The reaction mixture is then heated at 75° C. for one hour, allowed to cool, poured into ice, acidified to pH 2-3 and the resulting solid filtered off and dried. Crystallization from an acetone-methanol mixture affords pure 6-(4-isopropyl-4-methyl-5-oxo-2-imidazolin-2-yl)furo[2,3-b]pyridine-5-carboxylic acid mp 237°-244° C.

EXAMPLE 69

Preparation of 2,3-dihydro-6-(4-isopropyl-4-methyl-5-oxo-2-imidazolin-2-yl)furo[2,3-b]pyridine-5-carboxylic acid

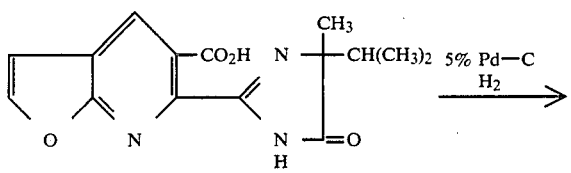

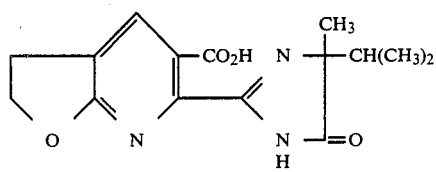

A solution of 6-(4-isopropyl-4-methyl-5-oxo-2-imidazolin-2-yl)furo[2,3-b]pyridine-5-carboxylic acid (1.7 g 0.056 mol) and 1.0 g (0.0072 mol) potassium carbonate in 200 mL 9:1 ethanol:water is added to 100 mg 5% palladium on carbon catalyst in a 500 mL pressure bottle. The bottle is fitted to a Parr hydrogenation apparatus, pressurized to 30 psi, with hydrogen, then shaken at room temperature for 10 hours. The catalyst is removed by filtration through a sintered glass funnel, and the filtrate concentrated in vacuo to 10 mL. Acidification of the residue to pH 2 gives a white precipitate which is removed by filtration, washed with water and air dried to give 1.0 g (63%) of 2,3-dihydro-6-(4-isopropyl-4-methyl-5-oxo-2-imidazolin-2-yl)furo[2,3-b]pyridine-5-carboxylic acid as an off-white solid, mp 189°-192° C.

EXAMPLE 70

Preparation of 4-mercaptoacetyl butyronitrile

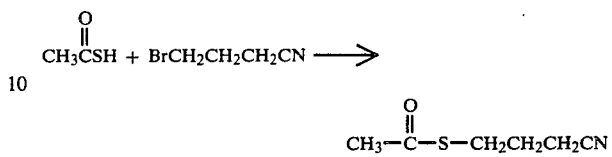

Thiolacetic acid (49 mL, 0.69 mol) is added to potassium carbonate (93.4 g, 0.68 mol) dissolved in water (150 mL). Ethanol (260 mL) is added and then 4-bromobutyronitrile is added at 15° to 28° C. and the reaction mixture stirred at room temperature for 16 hours. The resulting inorganic solids are filtered off and the filtrate extracted with toluene. The organic layer is separated, dried over anhydrous Na$_2$SO$_4$ and concentrated to give the desired 4-mercaptoacetyl butyronitrile as a yellow oil.

EXAMPLE 71

Preparation of dihydrothiophenimine hydrochloride

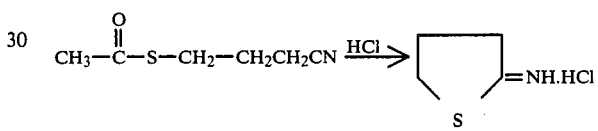

Hydrogen chloride is introduced to a cooled solution of the nitrile in methanol (220 mL) for one hour and the mixture then stirred at room temperature for 16 hours. The resulting product is filtered off, washed with ether and dried to give 55.38 g of dihydrothiophenimine hydrochloride, mp 189°-195° C.

EXAMPLE 72

Preparation of dimethyl [(tetrahydro-2-thienylidene)amino]fumarate (and maleate)acid

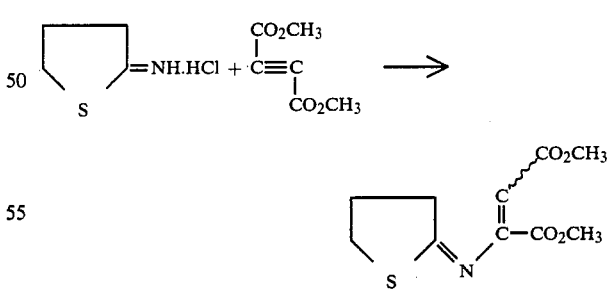

Dimethylacetylenedicarboxylate (0.45 mL, 0.037 mol) is added to a stirred solution of dihydrothiophenimine hydrochloride (0.5 g, 0.0036 mol) in methanol (60 mL) containing sodium acetate (0.3 g, 0.0036 mol) under an inert N$_2$ atmosphere at −15° C. After stirring for 16 hours at room temperature, the solvent is removed on a rotary evaporator and the resulting mixture separated by column chromatography on silica gel eluting with a methylene chloride-acetonitrile mixture

EXAMPLE 73

Preparation of dimethyl 2,3-dihydrothieno[2,3-b]pyridine-5,6-dicarboxylate

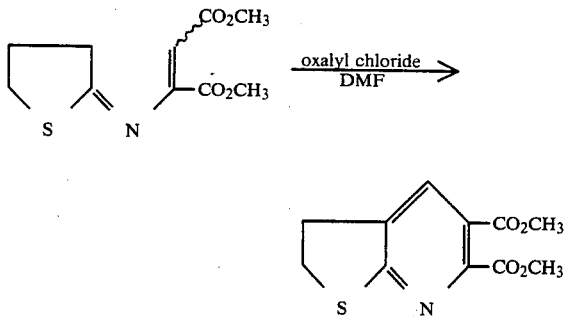

A Vilsmeier reagent is prepared by adding oxalyl chloride (0.25 mL, 0.0028 mol) to a stirred solution of DMF (0.22 mL, 0.0028 mol) in 1,2-dichloroethane (50 mL) at room temperature in an inert $N_2$ atmosphere. A 1,2-dichloroethane (50 mL) solution of dimethyl [(tetrahydro-2-thienylidine)amino]fumarate (and maleate) (0.0028 mol) is added to the Vilsmeier reagent and the reaction mixture heated at reflux for four hours. The reaction mixture is quenched with water, made basic with sodium bicarbonate and the organic layer separated and dried over anhydrous $Na_2SO_4$.

The solvent is removed in vacuo and the residue purified by column chromatographed on silica gel, eluting with a methylene chloride-acetonitrile mixture (19:1). Crystallization from toluene-hexane affords dimethyl 2,3-dihydrothieno[2,3-b]pyridine-5,6-dicarboxylate as a white solid with mp 102°-103.5° C.

EXAMPLE 74

Postemergence herbicidal evaluation of test compounds

The postemergence herbicidal activity of the compounds of the present invention is demonstrated by the following tests, wherein a variety of monocotyledonous and dicotyledonous plants are treated with test compounds dispersed in aqueous acetone mixtures. In the tests, seedling plants are grown in jiffy flats for about two weeks. The test compounds are dispersed in 50/50 acetone/water mixtures containing 0.5% TWEEN® 20, a polyoxyethylene sorbitan monolaurate surfactant of Atlas Chemical Industries, in sufficient quantities to provide the equivalent of about 0.16 kg to 2.0 kg per hectare of active compound when applied to the plants through a spray nozzle operating at 40 psig for a predetermined time. After spraying, the plants are placed on greenhouse benches and are cared for in the usual manner, commensurate with conventional greenhouse practices. From four to five weeks after treatment, the seedling plants, are examined and rated according to the rating system provided below. The data obtained are recorded in Table V below.

| Rating System | | % Difference in Growth from the Check |
|---|---|---|
| 0 | No Effect | 0 |
| 1 | Possible effect | 1–10 |
| 2 | Slight effect | 11–25 |
| 3 | Moderate effect | 26–40 |
| 5 | Definite injury | 41–60 |
| 6 | Herbicidal effect | 61–75 |
| 7 | Good herbicidal effect | 76–90 |
| 8 | Approaching complete kill | 91–99 |
| 9 | Complete kill | 100 |
| 4 | Abnormal growth, that is, a definite physiological malformation but with an over-all effect less than a 5 on the rating scale. | |

In most cases the data are for a single test, but in several instances, they are average values obtained from more than one test.

| Plant Species Used | |
|---|---|
| Barnyardgrass | (Echinochloa crusgalli) |
| Green foxtail | (Setaria viridis) |
| Purple Nutsedge | (Cyperus rotundus L.) |
| Wild Oats | (Avena fatua) |
| Quackgrass | (Agropyron repens) |
| Field Bindweed | (Convolvulus arvensis L.) |
| Morningglory | (Ipomoea purpurea) |
| Velvetleaf | (Abutilon theophrasti) |
| Barley | (Hordeum vulgare) |
| Corn | (Zea mays) |
| Soybean | (Glycine max) |
| Sunflower | (Helianthus annus) |
| Wheat | (Triticum aestivum) |
| Large Crabgrass | (Digitaria sanguinalis, L.) |
| Lolium | (Lolium, SPP.) |
| Mustard | (Brassica kaber, L.C.) |
| Sugarbeets | (Beta vulgaris, L.) |

TABLE V

POST-EMERGENCE TESTS - RATES IN KG/HA

| Compound | RATE | BARNY ARDGR | LARGE CRAB | GREEN FOX | P NUT SEDGE | WILD OATS | LOLIU M PER | QUACK GRASS | FLD B INDWD | MRNGL RY SP | WILD MUSTD | VELVET TLEAF | S BAR LY LA | SUGAR BEETS | CORN FIELD |
|---|---|---|---|---|---|---|---|---|---|---|---|---|---|---|---|
| Isomeric mixture of 6-(4-isopropyl-4-methyl-5-oxo-2-imidazolidinyl)-m-toluic acid, methylester and 2-(4-isopropyl-4-methyl-5-oxo-2-imidazolidinyl)-p-toluic acid, methylester | 2.000 | 3.0 | 2.0 | 3.5 | 0.0 | 7.0 | 0.0 | 0.0 | 9.0 | 0.0 | 9.0 | 7.5 | 1.0 | 8.0 | 0.0 |
| | 1.000 | 2.0 | 0.0 | 0.5 | 0.0 | 2.5 | 0.0 | 0.0 | 0.0 | 0.0 | 9.0 | 7.0 | 0.5 | 7.0 | 0.0 |
| | .500 | 1.5 | 0.0 | 0.0 | 0.0 | 2.0 | 0.0 | 0.0 | 0.0 | 0.0 | 8.5 | 5.5 | 0.0 | 8.0 | 0.0 |
| | .250 | 1.0 | 0.0 | 0.0 | 0.0 | 1.0 | 0.0 | 0.0 | 0.0 | 0.0 | 6.0 | 4.0 | 0.0 | 6.0 | 0.0 |
| | .125 | 0.5 | 0.0 | 0.0 | 0.0 | 0.5 | 0.0 | 0.0 | 0.0 | 0.0 | 3.5 | 1.0 | 0.0 | 2.0 | 0.0 |
| | .063 | 0.0 | 0.0 | 0.0 | 0.0 | 0.0 | 0.0 | 0.0 | 0.0 | 0.0 | 1.5 | 1.0 | 0.0 | 0.0 | 0.0 |
| cis-Methyl 2-(4-isopropyl-4-methyl-5-oxo-2-imadazolindinyl)nicotinate | 8.000 | 9.0 | 9.0 | 9.0 | 9.0 | 9.0 | | | 9.0 | 9.0 | 9.0 | 9.0 | | | 9.0 |
| | 1.000 | 9.0 | | | 5.5 | 9.0 | | 8.0 | 9.0 | 9.0 | | 9.0 | | 9.0 | 9.0 |
| | .500 | 8.5 | | | 3.5 | 9.0 | | 7.5 | 9.0 | 8.0 | | 9.0 | | 9.0 | 9.0 |
| | .250 | 8.0 | | | 4.5 | 9.0 | | 7.0 | 8.0 | 8.5 | | 9.0 | | 9.0 | 6.0 |
| | .125 | 2.5 | | | 2.5 | 8.5 | | 6.5 | 7.5 | 5.5 | | 8.0 | | 9.0 | 6.0 |
| | .063 | 2.0 | | | 1.5 | 7.5 | | 4.5 | 5.0 | 8.0 | | 7.5 | | 9.0 | 5.0 |
| | .032 | 0.5 | | | 0.5 | 2.5 | | 1.0 | 7.0 | 5.0 | | 4.5 | | 9.0 | 4.0 |
| cis-Benzyl 2-(4-isopropyl-4-methyl-5-oxo-2-imidazolidinyl)nicotinate | 1.000 | 9.0 | 8.5 | 9.0 | 7.0 | 9.0 | | 7.0 | 9.0 | 9.0 | 9.0 | 9.0 | 9.0 | 9.0 | 8.0 |
| | .750 | 9.0 | 9.0 | 9.0 | | 9.0 | 9.0 | | | 9.0 | | 9.0 | | 9.0 | 9.0 |
| | .500 | 8.0 | 8.0 | 8.5 | 4.0 | 9.0 | 9.0 | 6.5 | 9.0 | 9.0 | 9.0 | 9.0 | 8.0 | 9.0 | 8.3 |
| | .250 | 5.3 | 5.0 | 8.0 | 2.0 | 8.0 | 9.0 | 6.0 | 8.0 | 8.3 | 9.0 | 8.7 | 7.0 | 9.0 | 5.8 |
| | .125 | 2.7 | 0.5 | 8.0 | 1.0 | 5.0 | 3.0 | 5.5 | 8.5 | 8.3 | 9.0 | 8.3 | 6.0 | 9.0 | 4.0 |
| | .063 | 0.7 | 0.0 | 6.5 | 0.0 | 5.0 | 0.0 | 3.0 | 7.5 | 8.0 | 9.0 | 7.7 | 4.0 | 8.5 | 0.5 |
| | .032 | 0.0 | 0.0 | 3.0 | 0.0 | 4.0 | | 1.0 | 4.5 | 6.0 | | 4.0 | 3.0 | 7.5 | 0.7 |
| cis-2-(4-Isopropyl-4-methyl-5-oxo-2-imidazolidinyl)-nicotinic acid | 1.000 | 9.0 | | | 9.0 | 9.0 | | 9.0 | 9.0 | 9.0 | | 9.0 | | 9.0 | 9.0 |
| | .500 | 9.0 | | | 9.0 | 9.0 | | 8.5 | 9.0 | 9.0 | | 9.0 | | 9.0 | 9.0 |
| | .250 | 9.0 | | | 8.0 | 9.0 | | 7.5 | 8.5 | 9.0 | | 8.5 | | 9.0 | 9.0 |
| | .125 | 6.5 | | | 4.0* | 9.0 | | 6.0 | 8.5 | 9.0 | | 5.0 | | 9.0 | 6.5 |
| | .063 | 5.0 | | | 4.0* | 8.0 | | 4.0 | 7.0 | 7.5 | | 0.0 | | 9.0 | 9.0 |
| | .032 | 2.0 | | | 0.0 | 6.0 | | 4.5 | 8.5 | 7.6 | 8.5 | 8.0 | | 9.0 | 2.6 |
| cis and trans 5-Ethyl-2-(4-isopropyl-4-methyl-5-oxo-2-imidazolidinyl)-nicotinic acid | 1.000 | 8.5 | 6.2 | 8.7 | 6.0 | 5.5 | 9.0 | 4.5 | | 9.0 | 9.0 | 8.0 | | 9.0 | 3.4 |
| | .750 | 7.0 | 7.0 | 9.0 | 9.0 | 4.0 | 9.0 | | | 9.0 | 8.5 | 8.0 | | | 1.8 |
| | .500 | 7.0 | 5.3 | 8.0 | 4.5 | 3.5 | 0.0 | 4.0 | 8.5 | 6.3 | | 6.6 | | 9.0 | 0.7 |
| | .375 | | | | | | | | | | | | | | 0.8 |
| | .250 | 6.3 | 2.5 | 6.8 | 4.0 | 1.0 | 3.0 | 2.5 | 7.5 | 4.9 | 8.0 | 5.4 | | 9.0 | 0.8 |
| | .125 | 3.8 | 0.7 | 4.2 | 3.0 | 0.0 | 0.0 | 1.0 | 7.5 | 2.8 | 5.5 | 4.6 | | 9.0 | 0.5 |
| | .063 | 1.5 | 0.3 | 2.7 | 2.0 | 0.0 | 0.0 | 0.0 | 6.5 | 1.4 | 8.0 | 2.6 | | 9.0 | 0.5 |
| | .032 | 0.7 | 0.5 | 0.8 | 0.0 | 0.0 | | 0.0 | 4.0 | 0.3 | 0.0 | 0.8 | | 9.0 | 0.7 |
| cis-Methyl 5-ethyl-2-(4-isopropyl-4-methyl-5-oxo-2-imadazolidinyl)-nicotinate | 1.000 | 7.0 | | | 4.0 | 0.0 | | 0.0 | 9.0 | 8.0 | | 4.0 | | 9.0 | 0.0 |
| | .500 | 4.0 | | | 3.0 | 0.0 | | 0.0 | 7.0 | 7.0 | | 3.0 | | 8.0 | 0.5 |
| | .250 | 2.0 | | | 2.0 | 0.0 | | 0.0 | 7.0 | 6.0 | | 2.0 | | 7.0 | 0.0 |
| | .125 | 0.0 | | | 0.0 | 0.0 | | | 6.0 | 4.0 | | 2.0 | | 3.0 | 0.0 |
| | .063 | 0.0 | | | 0.0 | 0.0 | | | 4.0 | 3.0 | | 0.0 | | 2.0 | 0.0 |
| | .032 | 0.0 | | | 0.0 | 0.0 | | 0.0 | 0.0 | 1.0 | | 0.0 | | 1.0 | 0.0 |
| trans-Furfuryl 2-(4-isopropyl-4-methyl-5-oxo-2-imidazolidinyl)nicotinate | 1.000 | 9.0 | | | 9.0 | 9.0 | | 0.0 | 9.0 | 9.0 | | 9.0 | | 9.0 | 9.0 |
| | .500 | 8.0 | | | 9.0 | 9.0 | | 8.0 | 9.0 | 9.0 | | 9.0 | | 9.0 | 9.0 |
| | .250 | 8.0 | | | 9.0 | 9.0 | | 8.0 | 7.0 | 7.0 | | 9.0 | | 9.0 | 9.0 |
| | .125 | 8.0 | | | 8.0 | 9.0 | | 7.0 | 6.0 | 7.0 | | 9.0 | | 9.0 | 9.0 |
| | .063 | 4.0 | | | 2.0 | 7.0 | | 4.0 | 0.0 | 7.0 | | 7.0 | | 9.0 | 6.0 |
| | .032 | 2.0 | | | 0.0 | 0.0 | | 6.0 | 0.0 | 3.0 | | 9.0 | | 9.0 | 9.0 |
| cis-Furfuryl 2-(4-isopropyl-4-methyl-5-oxo-2-imidazolidinyl)nicotinate | 1.000 | 9.0 | | | 9.0 | 9.0 | | 9.0 | 9.0 | 9.0 | | 9.0 | | 9.0 | 9.0 |
| | .500 | 9.0 | | | 7.0 | 9.0 | | 7.0 | 9.0 | 9.0 | | 9.0 | | 9.0 | 9.0 |
| | .250 | 8.0 | | | 7.0 | 9.0 | | 7.0 | 9.0 | 9.0 | | 8.0 | | 9.0 | 9.0 |

TABLE V-continued

POST-EMERGENCE TESTS - RATES IN KG/HA

| Compound | RATE | BARNY ARDGR | LARGE CRAB | GREEN FOX | P NUT SEDGE | WILD OATS | LOLIU M PER | QUACK GRASS | FLD B INDWD | MRNGL RY SP | WILD MUSTD | VELVET TLEAF | S BAR LY | LY LA | SUGAR BEETS | CORN FIELD |
|---|---|---|---|---|---|---|---|---|---|---|---|---|---|---|---|---|
| trans-2-Propynyl 2-(4-isopropyl-4-methyl-5-oxo-2-imidazolidinyl)-nicotinate | .125 | 6.0 | | | 2.0 | 7.0 | | 6.0 | 8.0 | 9.0 | | 8.0 | | | 9.0 | 4.0 |
| | .063 | 2.0 | | | 0.0 | 4.0 | | 4.0 | 7.0 | 8.0 | | 3.0 | | | 9.0 | 2.0 |
| | .032 | 0.0 | | | 0.0 | 2.0 | | 2.0 | 7.0 | 8.0 | | 2.0 | | | 4.0 | 2.0 |
| | 1.000 | 9.0 | | | 9.0 | 9.0 | | 9.0 | 9.0 | 9.0 | | 9.0 | | | 9.0 | 9.0 |
| | .500 | 9.0 | | | 9.0 | 9.0 | | 9.0 | 9.0 | 9.0 | | 9.0 | | | 9.0 | 9.0 |
| | .250 | 8.0 | | | 7.0 | 9.0 | | 7.0 | 9.0 | 9.0 | | 8.0 | | | 9.0 | 9.0 |
| | .125 | 6.0 | | | 7.0 | 9.0 | | 7.0 | 9.0 | 9.0 | | 8.0 | | | 9.0 | 4.0 |
| | .063 | 2.0 | | | 2.0 | 7.0 | | 6.0 | 8.0 | 8.0 | | 3.0 | | | 9.0 | 4.0 |
| | .032 | 0.0 | | | 0.0 | 4.0 | | 4.0 | 7.0 | 8.0 | | 3.0 | | | 9.0 | 2.0 |
| cis-2-Propynyl 2-(4-isopropyl-4-methyl-5-oxo-2-imidazolidinyl)-nicotinate | 1.000 | 9.0 | | | 9.0 | 9.0 | | 9.0 | 9.0 | 9.0 | | 2.0 | | | 4.0 | 2.0 |
| | .500 | 9.0 | | | 9.0 | 9.0 | | 9.0 | 9.0 | 9.0 | | 9.0 | | | 9.0 | 9.0 |
| | .250 | 8.0 | | | 7.0 | 9.0 | | 7.0 | 9.0 | 9.0 | | 9.0 | | | 9.0 | 9.0 |
| | .125 | 6.0 | | | 7.0 | 7.0 | | 6.0 | 8.0 | 9.0 | | 8.0 | | | 9.0 | 9.0 |
| | .063 | 0.0 | | | 2.0 | 4.0 | | 4.0 | 7.0 | 8.0 | | 8.0 | | | 9.0 | 4.0 |
| | .032 | 0.0 | | | 0.0 | 2.0 | | 2.0 | 4.0 | 8.0 | | 3.0 | | | 4.0 | 2.0 |
| trans-Methyl 5-ethyl-2-(4-isopropyl-4-methyl-5-oxo-2-imidazolidinyl)-nicotinate | 1.000 | 6.0 | | | 2.0 | 2.0 | | 2.0 | 9.0 | 8.0 | | 2.0 | | | 4.0 | 2.0 |
| | .500 | 2.0 | | | 0.0 | 0.0 | | 0.0 | 9.0 | 7.0 | | 7.0 | | | 8.0 | 6.0 |
| | .250 | 0.0 | | | 0.0 | 0.0 | | 0.0 | 6.0 | 4.0 | | 3.0 | | | 7.0 | 0.0 |
| | .125 | 0.0 | | | 0.0 | 0.0 | | 0.0 | 4.0 | 3.0 | | 3.0 | | | 4.0 | 0.0 |
| | .063 | 0.0 | | | 0.0 | 0.0 | | 0.0 | 2.0 | 0.0 | | 0.0 | | | 3.0 | 0.0 |
| | .032 | 0.0 | | | 0.0 | 0.0 | | 0.0 | 0.0 | 0.0 | | 0.0 | | | 2.0 | 0.0 |
| trans-Allyl 2-(4-isopropyl-4-methyl-5-oxo-2-imidazolidinyl)nicotinate | 1.000 | 9.0 | | | 2.0 | 0.0 | | 0.0 | 9.0 | 9.0 | | 0.0 | | | 2.0 | 6.0 |
| | .500 | 8.0 | | | 0.0 | 9.0 | | 9.0 | 9.0 | 9.0 | | 0.0 | | | 2.0 | 4.0 |
| | .250 | 5.0 | | | 0.0 | 9.0 | | 6.0 | 9.0 | 9.0 | | 7.0 | | | 9.0 | 4.0 |
| | .125 | 2.0 | | | 0.0 | 9.0 | | 5.0 | 8.0 | 8.0 | | 3.0 | | | 9.0 | 1.0 |
| | .063 | 0.0 | | | 0.0 | 7.0 | | 1.0 | 8.0 | 7.0 | | 3.0 | | | 7.0 | 1.0 |
| | .032 | 0.0 | | | 0.0 | 4.0 | | 1.0 | 7.0 | 7.0 | | 3.0 | | | 3.0 | 1.0 |
| cis-Allyl 2-(4-isopropyl-4-methyl-5-oxo-2-imidazolidinyl)nicotinate | 1.000 | 9.0 | | | 0.0 | 3.0 | | 0.0 | 0.0 | 4.0 | | 0.0 | | | 2.0 | 0.0 |
| | .500 | 9.0 | | | 6.0 | 9.0 | | 8.0 | 9.0 | 9.0 | | 9.0 | | | 9.0 | 9.0 |
| | .250 | 9.0 | | | 8.0 | 9.0 | | 8.0 | 9.0 | 9.0 | | 9.0 | | | 9.0 | 9.0 |
| | .125 | 8.0 | | | 7.0 | 9.0 | | 7.0 | 9.0 | 9.0 | | 9.0 | | | 9.0 | 9.0 |
| | .063 | 6.0 | | | 4.0 | 7.0 | | 7.0 | 8.0 | 8.0 | | 9.0 | | | 9.0 | 6.0 |
| | .032 | 2.0 | | | 1.0 | 6.0 | | 4.0 | 7.0 | 9.0 | | 9.0 | | | 7.0 | 5.0 |
| trans-Methyl 2-(4-isopropyl-4-methyl-5-oxo-2-imidazolidinyl)-nicotinate | 1.000 | 9.0 | | | 0.0 | 3.0 | | 2.0 | 7.0 | 7.0 | | 9.0 | | | 9.0 | 2.0 |
| | .500 | 7.0 | | | 3.0 | 9.0 | | 6.0 | 9.0 | 9.0 | | 9.0 | | | 9.0 | 7.0 |
| | .250 | 5.0 | | | 2.0 | 9.0 | | 4.0 | 9.0 | 8.0 | | 7.0 | | | 9.0 | 7.0 |
| | .125 | 5.0 | | | 0.0 | 9.0 | | 4.0 | 9.0 | 8.0 | | 8.0 | | | 7.0 | 7.0 |
| | .063 | 0.0 | | | 0.0 | 8.0 | | 2.0 | 9.0 | 8.0 | | 6.0 | | | 7.0 | 2.0 |
| | .032 | 0.0 | | | 0.0 | 6.0 | | 2.0 | 7.0 | 7.0 | | 2.0 | | | 2.0 | 1.0 |
| cis-Methyl 2-(4-isopropyl-4-methyl-5-oxo-2-imidazolidinyl)-6-methoxynicotinate | 1.000 | 6.5 | 7.0 | 8.0 | 6.0 | 7.0 | | 6.5 | 7.5 | 9.0 | 7.0 | 5.5 | 0.0 | | 8.0 | 1.0 |
| | .500 | 3.5 | 4.0 | 7.0 | 4.0 | 7.0 | | 5.5 | 7.5 | 9.0 | 9.0 | 5.5 | 1.5 | | 6.5 | 1.0 |
| | .250 | 5.0 | 4.0 | 6.0 | 4.0 | 5.5 | | 4.0 | 7.0 | 9.0 | 5.0 | 5.5 | 1.0 | | 5.5 | 2.0 |
| | .125 | 1.5 | 3.0 | 4.0 | 1.0 | 3.5 | | 1.0 | 6.5 | 7.0 | 4.0 | 4.5 | 0.0 | | 3.0 | 0.5 |
| | .063 | 0.0 | 0.0 | 3.0 | 0.0 | 2.0 | | 1.0 | 0.0 | 6.0 | 4.0 | 3.0 | 0.0 | | 1.0 | 0.5 |
| | .032 | 0.0 | 0.0 | | 0.0 | 1.0 | | 0.5 | 0.0 | 6.0 | 3.0 | 3.0 | 2.0 | | 0.5 | 0.5 |
| trans-Methyl 2-(4-isopropyl-4-methyl-5-oxo-2-imidazolidinyl)-6-methoxynicotinate | 1.000 | 7.5 | 4.0 | 7.0 | 6.0 | 6.5 | | 6.5 | 6.5 | 8.0 | 9.0 | 3.0 | 1.0 | | 5.0 | 1.0 |
| | .500 | 6.7 | 5.0 | 7.0 | 4.0 | 6.0 | | 4.7 | 6.0 | 8.5 | 9.0 | 3.0 | 1.0 | | 7.0 | 0.5 |
| | .250 | 5.0 | 1.0 | 5.5 | 0.0 | 5.0 | | 3.7 | 5.3 | 8.0 | 8.0 | 1.3 | 1.0 | | 3.0 | 1.0 |
| | .125 | 1.0 | 1.0 | 2.5 | 0.0 | 2.0 | | 0.7 | 3.3 | 7.5 | 5.0 | 0.7 | 0.0 | | 2.0 | 0.5 |
| | .063 | 0.0 | 0.0 | 2.0 | 0.0 | 1.0 | | 0.0 | 0.0 | 6.0 | 4.0 | 0.0 | 0.0 | | 0.0 | 1.0 |
| | .032 | 0.0 | 0.0 | 0.0 | 0.0 | 0.0 | | 0.0 | 0.0 | 4.0 | 2.0 | 0.0 | 0.0 | | 0.0 | 1.0 |

TABLE V-continued

POST-EMERGENCE TESTS - RATES IN KG/HA

| Compound | RATE | BARNY ARDGR | LARGE CRAB | GREEN FOX | P NUT SEDGE | WILD OATS | LOLIU M PER | QUACK GRASS | FLD B INDWD | MRNGL RY SP | WILD MUSTD | VELVET TLEAF | S BAR LY LA | SUGAR BEETS | CORN FIELD |
|---|---|---|---|---|---|---|---|---|---|---|---|---|---|---|---|
| cis-Methyl 6-chloro-2-(4-isopropyl-4-methyl-5-oxo-2-imidazolidinyl)-nicotinate | 1.000 | 6.0 | 6.0 | 7.0 | 2.0 | 8.0 | | 7.5 | 3.5 | 8.5 | 9.0 | 3.5 | | 9.0 | 1.5 |
| | .500 | 4.0 | 2.0 | 2.0 | 0.0 | 8.0 | | 6.5 | 3.5 | 7.5 | 8.0 | 2.0 | | 9.0 | 1.0 |
| | .250 | 1.0 | 0.0 | 1.0 | 0.0 | 7.0 | | 6.5 | 2.0 | 7.0 | 6.0 | 2.0 | | 8.0 | 1.0 |
| | .125 | 1.0 | 0.0 | 0.0 | 0.0 | 4.0 | | 5.5 | 1.5 | 5.5 | 2.0 | 0.0 | | 6.0 | 0.5 |
| | .063 | 1.0 | 0.0 | 0.0 | 0.0 | 3.0 | | 2.0 | 0.0 | 4.5 | 0.0 | 0.0 | | 6.0 | 0.5 |
| | .032 | 0.5 | 0.0 | 0.0 | 0.0 | 1.0 | | 0.0 | 0.0 | 2.0 | 0.0 | 0.0 | | 4.0 | 0.5 |
| trans-Methyl 6-chloro-2-(4-isopropyl-4-methyl-5-oxo-2-imidazolidinyl)-nicotinate | 1.000 | 7.0 | | | 0.0 | 8.0 | | 8.0 | 3.0 | 9.0 | | 2.0 | | 9.0 | 1.0 |
| | .500 | 2.0 | | | 0.0 | 8.0 | | 6.0 | 1.0 | 7.0 | | 1.0 | | 9.0 | 1.0 |
| | .250 | 1.0 | | | 0.0 | 7.0 | | 6.0 | 0.0 | 7.0 | | 0.0 | | 9.0 | 1.0 |
| | .125 | 0.0 | | | 0.0 | 2.0 | | 4.0 | 0.0 | 7.0 | | 0.0 | | 7.0 | 1.0 |
| | .063 | 0.0 | | | 0.0 | 2.0 | | 0.0 | 0.0 | 6.0 | | 0.0 | | 4.0 | 1.0 |
| | .032 | 0.0 | | | 0.0 | 0.0 | | 0.0 | 0.0 | 4.0 | | 0.0 | | 2.0 | 2.0 |
| trans-Benzyl 5-ethyl-2-(4-isopropyl-4-methyl-5-oxo-2-imidazolidinyl)-nicotinate | 1.000 | 8.0 | | | 0.0 | 0.0 | | 0.0 | 8.0 | 3.0 | | 4.0 | | 9.0 | 2.0 |
| | .500 | 7.0 | | | 0.0 | 0.0 | | 0.0 | 7.0 | 1.0 | | 2.0 | | 9.0 | 2.0 |
| | .250 | 3.0 | | | 0.0 | 0.0 | | 0.0 | 6.0 | 0.0 | | 2.0 | | 9.0 | 2.0 |
| | .125 | 1.0 | | | 0.0 | 0.0 | | 0.0 | 5.0 | 0.0 | | 1.0 | | 4.0 | 2.0 |
| | .063 | 0.0 | | | 0.0 | 0.0 | | 0.0 | 3.0 | 0.0 | | 0.0 | | 1.0 | 2.0 |
| | .032 | 0.0 | | | 0.0 | 0.0 | | 0.0 | 2.0 | 0.0 | | 0.0 | | 0.0 | 2.0 |
| cis-Benzyl 5-ethyl-2-(4-isopropyl-4-methyl-5-oxo-2-imidazolidinyl)-nicotinate | 1.000 | 9.0 | | | 0.0 | 0.0 | | 0.0 | 9.0 | 6.0 | | 7.0 | | 9.0 | 2.0 |
| | .500 | 4.0 | | | 0.0 | 0.0 | | 0.0 | 9.0 | 4.0 | | 7.0 | | 9.0 | 2.0 |
| | .250 | 3.0 | | | 0.0 | 0.0 | | 0.0 | 7.0 | 4.0 | | 3.0 | | 9.0 | 2.0 |
| | .125 | 1.0 | | | 0.0 | 0.0 | | 0.0 | 6.0 | 2.0 | | 1.0 | | 3.0 | 2.0 |
| | .063 | 1.0 | | | 0.0 | 0.0 | | 0.0 | 5.0 | 1.0 | | 1.0 | | 3.0 | 1.0 |
| | .032 | 0.0 | | | 0.0 | 0.0 | | 0.0 | 2.0 | 0.0 | | 0.0 | | 2.0 | 2.0 |
| cis-Methyl 2-(4-isopropyl-4-methyl-5-oxo-2-imidazolidinyl)-5-methylnicotinate | 1.000 | 8.0 | | | 6.0 | 9.0 | | 8.0 | 9.0 | 9.0 | | 8.0 | | 9.0 | 2.0 |
| | .500 | 4.0 | | | 4.0 | 8.0 | | 2.0 | 9.0 | 9.0 | | 8.0 | | 9.0 | 2.0 |
| | .250 | 1.0 | | | 0.0 | 8.0 | | 1.0 | 8.0 | 8.0 | | 7.0 | | 9.0 | 2.0 |
| | .125 | 0.0 | | | 0.0 | 7.0 | | 0.0 | 4.0 | 7.0 | | 3.0 | | 9.0 | 1.0 |
| | .063 | 0.0 | | | 0.0 | 3.0 | | 0.0 | 2.0 | 2.0 | | 2.0 | | 3.0 | 2.0 |
| | .032 | 0.0 | | | 0.0 | 0.0 | | 0.0 | 0.0 | 0.0 | | 0.0 | | 0.0 | 2.0 |
| trans-Methyl 2-(4-isopropyl-4-methyl-5-oxo-2-imidazolidinyl)-5-methylnicotinate | 1.000 | 7.0 | 7.0 | 8.0 | 3.0 | 8.0 | | 3.0 | 7.5 | 8.0 | 7.0 | 7.5 | | 9.0 | 2.5 |
| | .500 | 3.0 | 4.0 | 5.0 | 1.0 | 7.0 | | 1.5 | 7.5 | 7.5 | 7.0 | 7.0 | | 9.0 | 2.0 |
| | .250 | 1.0 | 0.0 | 3.0 | 0.0 | 4.0 | | 0.5 | 6.0 | 4.5 | 3.0 | 2.0 | | 9.0 | 0.5 |
| | .125 | 1.0 | 0.0 | 3.0 | 0.0 | 2.0 | | 0.0 | 5.5 | 2.5 | | 1.0 | | 6.0 | 0.5 |
| | .063 | 0.0 | 0.0 | 0.0 | 0.0 | 0.0 | | 0.0 | 2.0 | 0.0 | 0.0 | 0.0 | | 4.0 | 0.5 |
| | .032 | 0.0 | 0.0 | 0.0 | 0.0 | 0.0 | | 0.0 | 1.0 | 0.0 | 0.0 | 0.0 | | 0.0 | 0.5 |
| cis-2-(4-Isopropyl-4-methyl-5-oxo-2-imidazolidinyl)-5-methylnicotinic acid | 1.000 | 9.0 | 9.0 | 9.0 | 8.5 | 9.0 | 9.0 | 7.0 | 9.0 | 9.0 | 9.0 | 9.0 | | 9.0 | 5.8 |
| | .750 | 9.0 | 9.0 | 9.0 | 8.0 | 9.0 | 9.0 | | | 9.0 | 9.0 | 9.0 | | | 7.2 |
| | .500 | 9.0 | 9.0 | 9.0 | 8.5 | 9.0 | 9.0 | 2.0 | 9.0 | 9.0 | 9.0 | 9.0 | | 9.0 | 4.3* |
| | .375 | | | | | | | | | | | | | | 4.3* |
| | .250 | 9.0 | 7.0 | 9.0 | 8.0 | 9.0 | 9.0 | 4.0 | 9.0 | 8.5 | 9.0 | 9.0 | | 9.0 | 4.4* |
| | .125 | 7.5 | 6.0 | 9.0 | 7.5 | 9.0 | 9.0 | 0.0 | 9.0 | 7.0 | 9.0 | 9.0 | | 9.0 | 4.0 |
| | .063 | 5.5 | 3.0 | 7.0 | 4.5 | 7.5 | 7.0 | 0.0 | 8.0 | 6.5 | 7.0 | 6.0 | | 9.0 | 1.5 |
| | .032 | 2.0 | | | 1.0 | 2.0 | | 0.0 | 2.0 | 0.0 | | 4.0 | | 9.0 | 1.0 |
| cis-(R)—(—)-Methyl 2-(4-isopropyl-4-methyl-5-oxo-2-imidazolidinyl)nicotinate | 1.000 | 9.0 | | 9.0 | 7.0 | 9.0 | | 9.0 | 9.0 | 9.0 | 9.0 | 9.0 | | 9.0 | 9.0 |
| | .500 | 9.0 | | 9.0 | 8.0 | 9.0 | | 9.0 | 9.0 | 9.0 | 9.0 | 9.0 | | 9.0 | 9.0 |
| | .250 | 9.0 | | 7.0 | 7.0 | 7.5 | | 9.0 | 9.0 | 9.0 | 7.0 | 9.0 | | 9.0 | 9.0 |
| | .125 | 8.0 | | | 5.0 | 9.0 | | 7.0 | 9.0 | 9.0 | | 9.0 | | 9.0 | 8.0 |
| | .063 | 7.0 | | | 2.0 | 8.0 | | 6.0 | 8.0 | 9.0 | | 8.0 | | 9.0 | 6.0 |
| | .032 | 2.0 | | | 0.0 | 4.0 | | 4.0 | 8.0 | 8.0 | | 8.0 | | 9.0 | 5.0 |

TABLE V-continued

POST-EMERGENCE TESTS - RATES IN KG/HA

| Compound | RATE | BARNY ARDGR | LARGE CRAB | GREEN FOX | P NUT SEDGE | WILD OATS | LOLIU M PER | QUACK GRASS | FLD B INDWD | MRNGL RY SP | WILD MUSTD | VELVET TLEAF | S BAR LY LA | SUGAR BEETS | CORN FIELD |
|---|---|---|---|---|---|---|---|---|---|---|---|---|---|---|---|
| trans-(R)—(—)-Methyl 2-(4-isopropyl-4-methyl-5-oxo-2-imidazolidinyl)-nicotinate | 1.000 | 9.0 | | | 8.0 | 9.0 | | 8.0 | 9.0 | 9.0 | | 9.0 | | 9.0 | 9.0 |
| | .500 | 9.0 | | | 7.0 | 9.0 | | 8.0 | 8.0 | 9.0 | | 9.0 | | 9.0 | 8.0 |
| | .250 | 6.0 | | | 5.0 | 8.0 | | 8.0 | 8.0 | 9.0 | | 9.0 | | 9.0 | 8.0 |
| | .125 | 2.0 | | | 4.0 | 7.0 | | 7.0 | 7.0 | 9.0 | | 8.0 | | 9.0 | 7.0 |
| | .063 | 0.0 | | | 2.0 | 5.0 | | 7.0 | 7.0 | 8.0 | | 7.0 | | 9.0 | 5.0 |
| | .032 | 0.0 | | | 0.0 | 2.0 | | 2.0 | 2.0 | 8.0 | | 7.0 | | 2.0 | 2.0 |
| cis-(R)—(+)-2-(4-Isopropyl-4-methyl-5-oxo-2-imidazolidinyl)-nicotinate acid | 1.000 | 9.0 | | | 9.0 | 9.0 | | 9.0 | 9.0 | 9.0 | | 9.0 | | 9.0 | 9.0 |
| | .500 | 9.0 | | | 9.0 | 9.0 | | 9.0 | 9.0 | 8.0 | | 9.0 | | 9.0 | 9.0 |
| | .250 | 9.0 | | | 9.0 | 9.0 | | 9.0 | 9.0 | 9.0 | | 9.0 | | 9.0 | 9.0 |
| | .125 | 9.0 | | | 8.0 | 9.0 | | 9.0 | 9.0 | 9.0 | | 9.0 | | 9.0 | 9.0 |
| | .063 | 8.0 | | | 7.0 | 8.0 | | 9.0 | 9.0 | 9.0 | | 8.0 | | 9.0 | 9.0 |
| | .032 | 7.0 | | | 4.0 | 8.0 | | 8.0 | 9.0 | 9.0 | | 7.0 | | 9.0 | 9.0 |
| cis-Methyl 2-(4-isopropyl-4-methyl-5-oxo-2-imidazolidinyl)-6-methylnicotinate | 1.000 | 8.0 | | | 6.0 | 9.0 | | 8.0 | 9.0 | 8.0 | | 8.0 | | 9.0 | 9.0 |
| | .500 | 8.0 | | | 3.0 | 9.0 | | 7.0 | 9.0 | 9.0 | | 7.0 | | 9.0 | 0.0 |
| | .250 | 7.0 | | | 3.0 | 8.0 | | 2.0 | 9.0 | 9.0 | | 7.0 | | 9.0 | 0.0 |
| | .125 | 3.0 | | | 0.0 | 6.0 | | 0.0 | 8.0 | 8.0 | | 7.0 | | 9.0 | 0.0 |
| | .063 | 0.0 | | | 0.0 | 0.0 | | 0.0 | 9.0 | 6.0 | | 6.0 | | 7.0 | 0.0 |
| | .032 | 0.0 | | | 0.0 | 0.0 | | 0.0 | 4.0 | 4.0 | | 6.0 | | 5.0 | 0.0 |
| trans-Methyl 2-(4-isopropyl-4-methyl-5-oxo-2-imidazolidinyl)-6-methylnicotinate | 1.000 | 8.0 | | | 4.0 | 9.0 | | 7.0 | 7.0 | 2.0 | | 4.0 | | 2.0 | 0.0 |
| | .500 | 7.0 | | | 2.0 | 9.0 | | 7.0 | 7.0 | 9.0 | | 6.0 | | 9.0 | 0.0 |
| | .250 | 4.0 | | | 1.0 | 7.0 | | 2.0 | 7.0 | 9.0 | | 4.0 | | 9.0 | 0.0 |
| | .125 | 2.0 | | | 0.0 | 2.0 | | 0.0 | 7.0 | 9.0 | | 3.0 | | 7.0 | 0.0 |
| | .063 | 0.0 | | | 0.0 | 0.0 | | 0.0 | 4.0 | 8.0 | | 0.0 | | 4.0 | 0.0 |
| | .032 | 0.0 | | | 0.0 | 0.0 | | 0.0 | 0.0 | 7.0 | | 0.0 | | 0.0 | 0.0 |
| cis-2-(4-Isopropyl-4-methyl-5-oxo-2-imidazolidinyl)-6-methyl-nicotinic acid | 1.000 | 9.0 | | | 8.0 | 9.0 | | 9.0 | 9.0 | 9.0 | | 9.0 | | 9.0 | 0.0 |
| | .500 | 9.0 | | | 8.0 | 9.0 | | 9.0 | 9.0 | 9.0 | | 9.0 | | 9.0 | 0.0 |
| | .250 | 8.0 | | | 7.0 | 8.0 | | 8.0 | 9.0 | 9.0 | | 8.0 | | 9.0 | 7.0 |
| | .125 | 7.0 | | | 7.0 | 8.0 | | 7.0 | 9.0 | 8.0 | | 8.0 | | 9.0 | 6.0 |
| | .063 | 4.0 | | | 6.0 | 8.0 | | 8.0 | 9.0 | 7.0 | | 2.0 | | 9.0 | 5.0 |
| | .032 | 0.0 | | | 0.0 | 3.0 | | 4.0 | 7.0 | 5.0 | | 2.0 | | 9.0 | 2.0 |
| trans-Methyl 6-(allyloxy)-2-(4-isopropyl-4-methyl-5-oxo-2-imidazolidinyl)-nicotinate | 1.000 | 0.0 | | | 0.0 | 9.0 | | 9.0 | 0.0 | 0.0 | | 0.0 | | 9.0 | 0.0 |
| | .500 | 0.0 | | | 0.0 | 9.0 | | 9.0 | 0.0 | 0.0 | | 0.0 | | 6.0 | 0.0 |
| | .250 | 0.0 | | | 0.0 | 0.0 | | 8.0 | 0.0 | 0.0 | | 0.0 | | 3.0 | 7.0 |
| | .125 | 0.0 | | | 0.0 | 0.0 | | 7.0 | 0.0 | 0.0 | | 0.0 | | 2.0 | 6.0 |
| | .063 | 0.0 | | | 0.0 | 0.0 | | 0.0 | 0.0 | 0.0 | | 0.0 | | 1.0 | 5.0 |
| | .032 | 0.0 | | | 0.0 | 0.0 | | 2.0 | 0.0 | 0.0 | | 0.0 | | 0.0 | 2.0 |
| cis-Methyl 6-(allyloxy)-2-(4-isopropyl-4-methyl-5-oxo-2-imidazolidinyl)-nicotinate | 1.000 | 0.0 | | | 0.0 | 0.0 | | 0.0 | 0.0 | 0.0 | | 0.0 | | 0.0 | 0.0 |
| | .500 | 0.0 | | | 0.0 | 0.0 | | 0.0 | 0.0 | 0.0 | | 0.0 | | 0.0 | 0.0 |
| | .250 | 0.0 | | | 0.0 | 0.0 | | 0.0 | 0.0 | 0.0 | | 0.0 | | 0.0 | 0.0 |
| | .125 | 0.0 | | | 0.0 | 0.0 | | 0.0 | 0.0 | 0.0 | | 0.0 | | 0.0 | 0.0 |
| | .063 | 0.0 | | | 0.0 | 0.0 | | 0.0 | 0.0 | 0.0 | | 0.0 | | 0.0 | 0.0 |
| | .032 | 0.0 | | | 0.0 | 0.0 | | 0.0 | 0.0 | 0.0 | | 0.0 | | 0.0 | 0.0 |
| cis-Methyl 2-(3-acetyl-4-isopropyl-4-methyl-5-oxo-2-imidazolidinyl)-nicotinate | | | | | | | | | | | | | | | |
| cis-6-Chloro-2-(4-isopropyl-4-methyl-5-oxo-2-imidazolidinyl)-nicotinic acid | 1.000 | 5.0 | | | 8.0 | 9.0 | | 9.0 | 8.0 | 9.0 | | 8.0 | | 9.0 | 8.0 |
| | .500 | 4.0 | | | 7.0 | 9.0 | | 9.0 | 7.0 | 8.0 | | 6.0 | | 9.0 | 8.0 |
| | .250 | 3.0 | | | 8.0 | 9.0 | | 9.0 | 6.0 | 7.0 | | 7.0 | | 9.0 | 6.0 |
| | .125 | 1.0 | | | 3.0 | 9.0 | | 9.0 | 2.0 | 6.0 | | 4.0 | | 9.0 | 3.0 |

TABLE V-continued

POST-EMERGENCE TESTS - RATES IN KG/HA

| Compound | RATE | BARNY ARDGR | LARGE CRAB | GREEN FOX | P NUT SEDGE | WILD OATS | LOLIU M PER | QUACK GRASS | FLD B INDWD | MRNGL RY SP | WILD MUSTD | VELVET TLEAF | S BAR LY LA | SUGAR BEETS | CORN FIELD |
|---|---|---|---|---|---|---|---|---|---|---|---|---|---|---|---|
| cis-2-(4-Isopropyl-4-methyl-5-oxo-2-imidazolidinyl)-6-methoxy-nicotinic acid | .063 | 1.0 | | | 3.0 | 8.0 | | 8.0 | 1.0 | 5.0 | | 3.0 | | 9.0 | 2.0 |
| | .032 | 0.0 | | | 1.0 | 3.0 | | 2.0 | 0.0 | 2.0 | | 0.0 | | 8.0 | 2.0 |
| | 1.000 | 4.0 | | | 8.0 | 9.0 | | 9.0 | 9.0 | 9.0 | | 8.0 | | 9.0 | 6.0 |
| | .500 | 2.0 | | | 8.0 | 7.0 | | 9.0 | 9.0 | 8.0 | | 4.0 | | 9.0 | 3.0 |
| | .250 | 1.0 | | | 9.0 | 6.0 | | 9.0 | 8.0 | 8.0 | | 2.0 | | 9.0 | 3.0 |
| | .125 | 0.0 | | | 7.0 | 3.0 | | 5.0 | 4.0 | 7.0 | | 2.0 | | 6.0 | 2.0 |
| | .063 | 0.0 | | | 7.0 | 2.0 | | 5.0 | 2.0 | 7.0 | | 0.0 | | 9.0 | 2.0 |
| | .032 | 0.0 | | | 2.0 | 1.0 | | 0.0 | 0.0 | 2.0 | | 0.0 | | 6.0 | 1.0 |
| cis-Methyl 2-(4-isopropyl-4-methyl-5-oxo-2-imidazolidinyl)nicotinate hydrochloride | | | | | | | | | | | | | | | |
| trans-o-(4-Isopropyl-4-methyl-5-oxo-2-imidazolidinyl)benzoic acid | 1.000 | 6.0 | | 4.0 | 8.0 | 5.0 | | 9.0 | 9.0 | 8.0 | 9.0 | 8.0 | 3.0 | 9.0 | 5.0 |
| | .500 | 4.0 | | 4.0 | 7.0 | 3.0 | | 0.0 | 9.0 | 8.0 | 9.0 | 8.0 | 2.0 | 9.0 | 3.0 |
| | .250 | 3.0 | | 0.0 | 5.0 | 2.0 | | 4.0 | 8.0 | 8.0 | 9.0 | 7.0 | 2.0 | 9.0 | 2.0 |
| | .125 | 2.0 | | 0.0 | 3.0 | 0.0 | | | 7.0 | 8.0 | 9.0 | 5.0 | 1.0 | 9.0 | 1.0 |
| | .063 | 0.0 | | 0.0 | 2.0 | 0.0 | | | 7.0 | 6.0 | 9.0 | 2.0 | 1.0 | 9.0 | 1.0 |
| | .032 | 0.0 | | 0.0 | 1.0 | 0.0 | | | 3.0 | 3.0 | 9.0 | 2.0 | 1.0 | 9.0 | 0.0 |
| 2-Propynyl o-(5-isopropyl-5-methyl-4-oxo-2-imidazolindinyl)benzoate | 2.000 | 2.0 | 0.0 | 3.0 | 9.0 | 3.0 | | 0.0 | | 9.0 | | 0.0 | 1.0 | | 0.0 |
| | 1.000 | 2.0 | 0.0 | 3.0 | 7.0 | 4.0 | | 0.0 | 7.0 | 9.0 | | 7.0 | 0.0 | | 7.0 |
| | .500 | 0.0 | 0.0 | 1.5 | 6.5 | 0.5 | | | 7.0 | 7.5 | | 7.5 | 0.0 | | 6.5 |
| | .250 | 0.0 | 0.0 | 0.5 5.5 | 0.0 | 0.0 | | 3.0 | 6.5 | 7.5 | | 6.5 | 0.0 | 5.0 | 5.0 |
| | .125 | 0.0 | 0.0 | 0.0 | 2.5 | 0.0 | | | 2.0 | 5.5 | | 0.0 | | | 1.0 |
| | .063 | 0.0 | 0.0 | 0.0 | 1.0 | 0.0 | | | 0.0 | 4.5 | 4.0 | 1.5 | 0.0 | | 0.0 |
| | .032 | | 0.0 | 0.0 | 0.0 | 0.0 | | | 0.0 | 3.0 | | 0.5 | 0.0 | | 0.0 |
| | .016 | | 0.0 | 0.0 | 0.0 | 0.0 | | | 0.0 | 0.0 | | 1.0 | 0.0 | | 0.0 |
| trans-Methyl 2-(4-isopropyl-4-methyl-5-thioxo-2-imidazolidinyl)nicotinate | 1.000 | 7.0 | | | 8.0 | 9.0 | | 8.0 | 9.0 | 9.0 | | 9.0 | | 9.0 | 9.0 |
| | .500 | 6.0 | | | 8.0 | 9.0 | | 8.0 | 8.0 | 9.0 | | 9.0 | | 9.0 | 9.0 |
| | .250 | 4.0 | | | 7.0 | 9.0 | | 2.0 | 8.0 | 9.0 | | 9.0 | | 9.0 | 9.0 |
| | .125 | 1.0 | | | 2.0 | 8.0 | | 1.0 | 6.0 | 8.0 | | 8.0 | | 8.0 | 9.0 |
| | .063 | 1.0 | | | 1.0 | 4.0 | | 0.0 | 4.0 | 7.0 | | 7.0 | | 6.0 | 8.0 |
| | .032 | 0.0 | | | 0.0 | 1.0 | | 0.0 | 0.0 | 2.0 | | 7.0 | | 4.0 | 8.0 |
| cis-Methyl 2-(4-isopropyl-4-methyl-5-thioxo-2-imidazolidinyl)nicotinate | 1.000 | 9.0 | | | 8.0 | 9.0 | | 8.0 | 9.0 | 9.0 | | 9.0 | | 9.0 | 9.0 |
| | .500 | 9.0 | | | 7.0 | 9.0 | | 8.0 | 8.0 | 9.0 | | 9.0 | | 9.0 | 9.0 |
| | .250 | 7.0 | | | 6.0 | 9.0 | | 4.0 | 8.0 | 9.0 | | 9.0 | | 8.0 | 8.0 |
| | .125 | 3.0 | | | 4.0 | 6.0 | | 2.0 | 8.0 | 8.0 | | 9.0 | | 7.0 | 8.0 |
| | .063 | 1.0 | | | 2.0 | 5.0 | | 1.0 | 7.0 | 6.0 | | 8.0 | | 7.0 | 8.0 |
| | .032 | 0.0 | | | 0.0 | 3.0 | | 0.0 | 4.0 | 2.0 | | 7.0 | | 8.0 | 7.0 |
| cis-2-(4-Isopropyl-4-methyl-5-thioxo-2-imidazolidinyl)-nicotinic acid | | | | | | | | | | | | | | | |
| Propyl o-(5-isopropyl-5-methyl-4-oxo-2-imidazolindinyl)benzoate | | | | | | | | | | | | | | | |

EXAMPLE 75

Preemergence herbicidal evaluation of test compounds

The preemergence herbicidal activity of the compounds of the present invention is exemplified by the following tests in which the seeds of a variety of monocotyledonous and dicotyledonous plants are separately mixed with potting soil and planted on top of approximately one inch of soil in separate pint cups. After planting, the cups are sprayed with the selected aqueous acetone solution containing test compound in sufficient quantity to provide the equivalent of about 0.016 to 2.0 kg per hectare of test compound per cup. The treated cups are then placed on greenhouse benches, watered and cared for in accordance with conventional greenhouse procedures. From four to five weeks after treatment, the tests are terminated and each cup is examined and rated according to the rating system set forth above. The herbicidal proficiency of the active ingredients of the present invention is evident from the test results which are recorded in Table VI below. Where more than one test is involved for a given compound, the data are averaged.

TABLE VI

POST-EMERGENCE TESTS - RATES IN KG/HA

| Compound | RATE | BARNY ARDGR | GREEN FOX | P NUT SEDGE | WILD OATS | QUACK GRASS | FLD B INDWD | MRNGL RY SP | VELVET LEAF | S BAR LY LA | CORN FIELD | RICE, NATO | S WHE AT ER | SOYBE AN WI | SUNFL R XXX |
|---|---|---|---|---|---|---|---|---|---|---|---|---|---|---|---|
| Isomeric mixture of 6-(4-isopropyl-4-methyl-5-oxo-2-imidazolidinyl)-m-toluic acid, methylester and 2-(4-isopropyl-4-methyl-5-oxo-2-imidazolidinyl)-p-toluic acid, methylester | 2.000 | 7.5 | 9.0 | 8.0 | 9.0 | 7.5 | 9.0 | 8.0 | 8.0 | 1.0 | 1.5 | 6.0 | | 9.0 | 4.0 |
| | 1.000 | 7.0 | 7.5 | 6.0 | 8.5 | 2.0 | 9.0 | 9.0 | 7.0 | 0.0 | 0.0 | 1.0 | | 8.0 | 2.0 |
| | .500 | 4.5 | 7.0 | 6.0 | 8.0 | 0.0 | 9.0 | 8.0 | 6.0 | 0.0 | 0.0 | 0.0 | | 7.0 | 2.0 |
| | .250 | 3.5 | 3.0 | 0.0 | 7.0 | 0.0 | 9.0 | 7.0 | 4.5 | 0.0 | 0.0 | 0.0 | | 6.0 | 0.0 |
| | .125 | 3.5 | 1.5 | 0.0 | 5.0 | 0.0 | 7.5 | 3.0 | 3.0 | 0.0 | 0.0 | 0.0 | | 5.0 | 0.0 |
| | .063 | 2.0 | 0.5 | 0.0 | 2.5 | 0.0 | 4.0 | 0.0 | 1.5 | 0.0 | 0.0 | 0.0 | | 4.0 | 0.0 |
| cis-Methyl 2-(4-isopropyl-4-methyl-5-oxo-2-imadazolindinyl)nicotinate | .500 | 7.5 | | 6.5 | 9.0 | 9.0 | 9.0 | 9.0 | 9.0 | | 8.5 | 8.0 | 8.5 | 8.5 | 9.0 |
| | .250 | 7.5 | 6.5 | 9.0 | 7.5 | 9.0 | 9.0 | 9.0 | | 7.5 | 7.0 | 8.0 | 7.5 | 7.0 | |
| | .125 | 4.5 | | 4.0 | 8.5 | 7.0 | 9.0 | 9.0 | 8.5 | | 7.0 | 6.5 | 7.5 | 7.0 | 5.0 |
| | .063 | 1.5 | | 3.0 | 7.5 | 7.0 | 8.5 | 8.0 | 7.5 | | 5.0 | 4.5 | 6.5 | 6.0 | 3.5 |
| | .032 | 0.5 | | 3.0 | 7.5 | 6.0 | 7.0 | 7.0 | 7.5 | | 3.0 | 4.0 | 6.5 | 4.0 | 2.0 |
| | .016 | 0.0 | | 0.5 | 4.0 | 2.0 | 4.0 | 4.5 | 5.0 | | 2.0 | 2.0 | 4.5 | 3.5 | 2.0 |
| cis-Benzyl 2-(4-isopropyl-4-methyl-5-oxo-2-imidazolidinyl)nicotinate | 1.000 | 9.0 | 9.0 | | 9.0 | 7.0 | 9.0 | 8.0 | 9.0 | 9.0 | 9.0 | 9.0 | 8.0 | 6.0 | 6.5 |
| | .500 | 8.0 | 9.0 | | 6.0 | 8.0 | 9.0 | 5.0 | 9.0 | 9.0 | 7.0 | 9.0 | 8.0 | 6.0 | 5.0 |
| | .250 | 7.0 | 8.0 | | 6.0 | 6.0 | 7.0 | 3.5 | 9.0 | 8.0 | 5.5 | 8.0 | 7.0 | 6.0 | 3.5 |
| | .125 | 5.0 | 7.0 | | 0.0 | 6.0 | 7.0 | 1.5 | 9.0 | 5.0 | 4.0 | 7.0 | 6.0 | 5.0 | 2.5 |
| cis-2-(4-Isopropyl-4-methyl-5-oxo-2-imidazolidinyl)-nicotinic acid | .500 | 9.0 | | 9.0 | 9.0 | 9.0 | 9.0 | 9.0 | 9.0 | | 9.0 | 9.0 | 9.0 | 7.0 | 9.0 |
| | .250 | 6.0 | | 9.0 | 6.0 | 9.0 | 9.0 | 8.0 | 8.0 | | 9.0 | 9.0 | 9.0 | 6.0 | 4.0 |
| | .125 | 0.0 | | 3.0 | 6.0 | 8.0 | 9.0 | 2.0 | 3.0 | | 8.0 | 8.0 | 9.0 | 1.0 | 2.0 |
| | .063 | 0.0 | | 1.0 | 2.0 | 6.0 | 9.0 | 0.0 | 4.0 | | 6.0 | 8.0 | 9.0 | 0.0 | 1.0 |
| | .032 | 0.0 | | 0.0 | 0.0 | 2.0 | 8.0 | 0.0 | 0.0 | | 3.0 | 4.0 | 7.0 | 0.0 | 1.0 |
| cis and trans 5-Ethyl-2-(4-isopropyl-4-methyl-5-oxo-2-imidazolidinyl)-nicotinic acid | 1.000 | 9.0 | 8.0 | | 9.0 | 9.0 | 9.0 | 8.0 | 9.0 | | 8.0 | 9.0 | | | 9.0 |
| | .500 | 8.5 | 8.0 | 9.0 | 9.0 | 8.5 | 9.0 | 5.0 | 9.0 | 9.0 | 6.0 | 9.0 | 5.0 | 1.0 | 9.0 |
| | .250 | 5.0 | 7.0 | 9.0 | 6.0 | 7.0 | 9.0 | 3.5 | 9.0 | 9.0 | 3.5 | 9.0 | 3.0 | 1.0 | 7.5 |
| | .125 | 4.5 | 4.0 | 8.0 | 0.0 | 6.0 | 9.0 | 1.5 | 8.0 | 8.0 | 2.0 | 6.0 | 0.0 | 1.0 | 7.0 |
| | .063 | 0.5 | 2.0 | 4.0 | 0.0 | 2.0 | 9.0 | 1.0 | 4.5 | 5.0 | 1.5 | 4.0 | 0.0 | 0.0 | 3.0 |
| | .032 | 0.0 | 0.0 | 2.0 | 0.0 | 1.0 | 9.0 | 0.0 | 1.0 | | 1.0 | 1.0 | 0.0 | 0.0 | 2.5 |
| | .016 | 0.0 | 0.0 | 0.0 | 0.0 | 0.0 | | 0.0 | 0.0 | | 1.0 | 1.0 | 0.0 | 0.0 | 0.0 |
| cis-Methyl 5-ethyl-2-(4-Isopropyl-4-methyl-5-oxo-2-imadazolidinyl)-nicotinate | .500 | 8.0 | | 6.0 | 6.0 | 9.0 | 9.0 | 2.0 | 8.0 | | 2.0 | 9.0 | 2.0 | 0.0 | 7.0 |
| | .250 | 7.0 | | 3.0 | 4.0 | 9.0 | 9.0 | 0.0 | 8.0 | | 2.0 | 8.0 | 1.0 | 0.0 | 7.0 |
| | .125 | 1.0 | | 0.0 | 0.0 | 6.0 | 9.0 | 0.0 | 3.0 | | 0.0 | 2.0 | 1.0 | 0.0 | 1.0 |
| | .063 | 0.0 | | 0.0 | 0.0 | 2.0 | 9.0 | 0.0 | 6.0 | | 0.0 | 1.0 | 0.0 | 0.0 | 0.0 |
| | .032 | 0.0 | | 0.0 | 0.0 | 0.0 | 8.0 | 0.0 | 2.0 | | 0.0 | 1.0 | 0.0 | 0.0 | 0.0 |
| | .016 | 0.0 | | 0.0 | 0.0 | 0.0 | 2.0 | 0.0 | 1.0 | | 0.0 | 0.0 | 0.0 | 0.0 | 0.0 |
| trans-Furfuryl 2-(4-isopropyl-4-methyl-5-oxo-2-imidazolidinyl)nicotinate | .500 | 8.0 | | 8.0 | 9.0 | 8.0 | 9.0 | 8.0 | 8.0 | | 0.0 | 9.0 | 2.0 | 0.0 | 7.0 |
| | .250 | 6.0 | | 3.0 | 7.0 | 8.0 | 9.0 | 5.0 | 8.0 | | 2.0 | 8.0 | 1.0 | 0.0 | 7.0 |
| | .125 | 2.0 | | 2.0 | 7.0 | 8.0 | 9.0 | 0.0 | 6.0 | | 0.0 | 2.0 | 1.0 | 0.0 | 1.0 |
| | .063 | 0.0 | | 2.0 | 3.0 | 6.0 | 8.0 | 2.0 | 3.0 | | 0.0 | 1.0 | 1.0 | 0.0 | 0.0 |
| | .032 | 0.0 | | 2.0 | 2.0 | 0.0 | 6.0 | 0.0 | 1.0 | | 4.0 | 3.0 | 7.0 | 0.0 | 0.0 |
| | .016 | 0.0 | | 2.0 | 0.0 | 0.0 | 4.0 | 0.0 | 0.0 | | 4.0 | 2.0 | 5.0 | 0.0 | 0.0 |
| cis-Furfuryl 2-(4-iso-propyl-4-methyl-5-oxo-2-imidazolidinyl)nicotinate | .500 | 8.0 | | 9.0 | 9.0 | 8.0 | 9.0 | 9.0 | 9.0 | | 9.0 | 9.0 | 9.0 | 7.0 | 9.0 |
| | .250 | 8.0 | | 9.0 | 9.0 | 8.0 | 9.0 | 9.0 | 9.0 | | 9.0 | 9.0 | 8.0 | 6.0 | 7.0 |
| | .125 | 2.0 | | 7.0 | 7.0 | 8.0 | 8.0 | 8.0 | 8.0 | | 9.0 | 8.0 | 9.0 | 4.0 | 3.0 |
| | .063 | 0.0 | | 4.0 | 4.0 | 7.0 | 8.0 | 7.0 | 5.0 | | 2.0 | 4.0 | 8.0 | 2.0 | 0.0 |
| | .032 | 0.0 | | 2.0 | 1.0 | 6.0 | 8.0 | 5.0 | 3.0 | | 3.0 | 3.0 | 7.0 | 1.0 | 0.0 |
| | .016 | 0.0 | | 1.0 | 1.0 | 1.0 | 8.0 | 0.0 | 1.0 | | 2.0 | 2.0 | 4.0 | 1.0 | 0.0 |
| trans-2-Propynyl 2-(4-isopropyl-4-methyl-5-oxo-2-imidazolidinyl)- | .500 | 7.0 | | 4.0 | 9.0 | 8.0 | 9.0 | 8.0 | 9.0 | | 9.0 | 9.0 | 9.0 | 6.0 | 8.0 |
| | .250 | 7.0 | | 3.0 | 7.0 | 8.0 | 9.0 | 8.0 | 9.0 | | 9.0 | 9.0 | 9.0 | 5.0 | 4.0 |
| | .125 | 2.0 | | 2.0 | 7.0 | 8.0 | 9.0 | 6.0 | 6.0 | | 8.0 | 7.0 | 8.0 | 2.0 | 4.0 |

TABLE VI-continued

POST-EMERGENCE TESTS - RATES IN KG/HA

| Compound | RATE | BARNY ARDGR | GREEN FOX | P NUT SEDGE | WILD OATS | QUACK GRASS | FLD B INDWD | MRNGL RY SP | VELVET LEAF | S BAR LY LA | CORN FIELD | RICE, NATO | S WHE AT ER | SOYBE AN WI | SUNFL R XXX |
|---|---|---|---|---|---|---|---|---|---|---|---|---|---|---|---|
| nicotinate | .063 | 1.0 | | 2.0 | 2.0 | 6.0 | 9.0 | 2.0 | 3.0 | | 6.0 | 3.0 | 7.0 | 0.0 | 3.0 |
| | .032 | 0.0 | | 1.0 | 0.0 | 0.0 | 2.0 | 0.0 | 1.0 | | 3.0 | 3.0 | 7.0 | 0.0 | 1.0 |
| | .016 | 0.0 | | 0.0 | 0.0 | 0.0 | 0.0 | 0.0 | 0.0 | | 2.0 | 2.0 | 5.0 | 0.0 | 1.0 |
| cis-2-Propynyl 2-(4- | .500 | 2.0 | | 0.0 | 9.0 | 9.0 | 9.0 | 8.0 | 0.0 | | 9.0 | 9.0 | 9.0 | 7.0 | 9.0 |
| isopropyl-4-methyl-5- | .250 | | | 4.0 | 9.0 | 8.0 | 9.0 | 8.0 | 9.0 | | 9.0 | 9.0 | 9.0 | 6.0 | 7.0 |
| oxo-2-imidazolidinyl)- | .125 | 1.0 | | 4.0 | 6.0 | 8.0 | 9.0 | 7.0 | 6.0 | | 7.0 | 7.0 | 8.0 | 3.0 | 4.0 |
| nicotinate | .063 | 0.0 | | 2.0 | 2.0 | 7.0 | 8.0 | 3.0 | 2.0 | | 4.0 | 7.0 | 8.0 | 1.0 | 1.0 |
| | .032 | 0.0 | | 0.0 | 0.0 | 4.0 | 8.0 | 2.0 | 2.0 | | 2.0 | 7.0 | 7.0 | 0.0 | 0.0 |
| trans-Methyl 5-ethyl-2- | .500 | 8.0 | | 7.0 | 0.0 | 2.0 | 9.0 | 7.0 | 9.0 | | 0.0 | 9.0 | 0.0 | 0.0 | 0.0 |
| (4-isopropyl-4-methyl-5- | .250 | 4.0 | | 5.0 | 0.0 | 0.0 | 9.0 | 7.0 | 7.0 | | 0.0 | 8.0 | 0.0 | 3.0 | 5.0 |
| oxo-2-imidazolidinyl)- | .125 | 2.0 | | 4.0 | 0.0 | 0.0 | 2.0 | 0.0 | 6.0 | | 0.0 | 6.0 | 0.0 | 2.0 | 3.0 |
| nicotinate | .063 | 0.0 | | 2.0 | 0.0 | 0.0 | 0.0 | 0.0 | 2.0 | | 0.0 | 2.0 | 0.0 | 2.0 | 3.0 |
| | .032 | 0.0 | | 0.0 | 0.0 | 0.0 | 0.0 | 0.0 | 0.0 | | 0.0 | 0.0 | 0.0 | 2.0 | 0.0 |
| | .016 | 0.0 | | 0.0 | 0.0 | 0.0 | 0.0 | 0.0 | 0.0 | | 0.0 | 0.0 | 0.0 | 0.0 | 0.0 |
| trans-Allyl 2-(4-iso- | .500 | 9.0 | | 2.0 | 9.0 | 8.0 | 9.0 | 9.0 | 9.0 | | 9.0 | 9.0 | 9.0 | 8.0 | 6.0 |
| propyl-4-methyl-5-oxo- | .250 | 9.0 | | 9.0 | 9.0 | 7.0 | 9.0 | 9.0 | 9.0 | | 9.0 | 9.0 | 9.0 | 8.0 | 5.0 |
| 2-imidazolidinyl)- | .125 | 4.0 | | 2.0 | 8.0 | 7.0 | 9.0 | 8.0 | 8.0 | | 8.0 | 6.0 | 9.0 | 8.0 | 3.0 |
| nicotinate | .063 | 2.0 | | 1.0 | 5.0 | 7.0 | 9.0 | 8.0 | 7.0 | | 7.0 | 4.0 | 9.0 | 7.0 | 2.0 |
| | .032 | 1.0 | | 0.0 | 6.0 | 4.0 | 4.0 | 0.0 | 7.0 | | 2.0 | 3.0 | 8.0 | 4.0 | 1.0 |
| | .016 | 0.0 | | 0.0 | 4.0 | 3.0 | 2.0 | 4.0 | 3.0 | | 2.0 | 3.0 | 8.0 | 3.0 | 0.0 |
| cis-Allyl 2-(4-isopropyl- | .500 | 9.0 | | 9.0 | 9.0 | 9.0 | 9.0 | 9.0 | 9.0 | | 1.0 | 2.0 | 8.0 | 2.0 | 9.0 |
| 4-methyl-5-oxo-2-imidazo- | .250 | 8.0 | | 8.0 | 9.0 | 9.0 | 9.0 | 9.0 | 9.0 | | 9.0 | 9.0 | 9.0 | 8.0 | 9.0 |
| lidinyl)nicotinate | .125 | 5.0 | | 2.0 | 7.0 | 7.0 | 9.0 | 9.0 | 9.0 | | 8.0 | 9.0 | 9.0 | 8.0 | 8.0 |
| | .063 | 2.0 | | 0.0 | 7.0 | 7.0 | 8.0 | 9.0 | 8.0 | | 7.0 | 6.0 | 9.0 | 7.0 | 6.0 |
| | .032 | 0.0 | | 0.0 | 7.0 | 7.0 | 9.0 | 8.0 | 8.0 | | 4.0 | 3.0 | 9.0 | 6.0 | 1.0 |
| | .016 | 0.0 | | 0.0 | 4.0 | 6.0 | 9.0 | 8.0 | 4.0 | | 2.0 | 2.0 | 7.0 | 4.0 | 0.0 |
| trans-Methyl 2-(4-iso- | .500 | 7.0 | | 4.0 | 0.0 | 2.0 | 9.0 | 9.0 | 9.0 | | 2.0 | 2.0 | 9.0 | 3.0 | 9.0 |
| propyl-4-methyl-5-oxo- | .250 | 5.0 | | 3.0 | 9.0 | 8.0 | 9.0 | 9.0 | 9.0 | | 8.0 | 6.0 | 9.0 | 8.0 | 9.0 |
| 2-imidazolidinyl)- | .125 | 0.0 | | 1.0 | 8.0 | 7.0 | 9.0 | 9.0 | 7.0 | | 7.0 | 4.0 | 8.0 | 7.0 | 4.0 |
| nicotinate | .063 | 0.0 | | 0.0 | 7.0 | 6.0 | 8.0 | 8.0 | 7.0 | | 7.0 | 4.0 | 8.0 | 7.0 | 1.0 |
| | .032 | 0.0 | | 0.0 | 2.0 | 4.0 | 2.0 | 6.0 | 7.0 | | 2.0 | 2.0 | 7.0 | 6.0 | 0.0 |
| | .016 | 0.0 | | 0.0 | 1.0 | 2.0 | 4.0 | 2.0 | 3.0 | | 2.0 | 2.0 | 6.0 | 4.0 | 0.0 |
| cis-Methyl 2-(4-isopropyl- | 1.000 | 9.0 | 9.0 | 0.0 | 0.0 | 8.0 | 9.0 | 8.0 | 8.0 | 8.0 | 2.0 | 0.0 | 4.0 | | 0.0 |
| 4-methyl-5-oxo-2-imidazo- | .500 | 8.5 | 8.0 | 6.0 | 9.0 | 7.5 | 8.5 | 8.0 | 7.5 | 7.5 | 8.0 | 8.0 | 8.0 | 5.0 | 2.5 |
| lidinyl)-6-methoxynico- | .250 | 8.5 | 8.0 | 5.0 | 8.5 | 7.5 | 8.5 | 8.0 | 7.0 | 7.0 | 7.0 | 8.0 | 7.5 | 6.5 | 0.3 |
| tinate | .125 | 8.0 | 9.0 | 5.0 | 8.5 | 5.0 | 9.0 | 9.0 | 6.0 | 4.5 | 5.0 | 7.0 | 6.5 | 5.0 | 0.3 |
| | .063 | 6.0 | 6.0 | 5.0 | 7.5 | 4.5 | 8.0 | 9.0 | 6.0 | 4.0 | 2.5 | 5.5 | 5.5 | 4.5 | 0.0 |
| | .032 | 5.0 | 4.0 | 0.0 | 7.0 | 2.5 | 3.0 | 8.0 | 3.5 | 1.5 | 1.0 | 3.5 | 2.5 | 2.0 | 0.0 |
| | .016 | 0.0 | | 0.0 | 5.0 | 0.0 | 0.0 | | 2.0 | | 1.0 | 1.5 | 0.0 | 1.0 | 0.0 |
| trans-Methyl 2-(4-iso- | 1.000 | 8.0 | 9.0 | | 2.0 | 0.0 | 9.0 | | 0.0 | | 2.0 | 2.0 | 0.0 | 2.0 | 0.0 |
| propyl-4-methyl-5-oxo- | .500 | 8.3 | 8.5 | 3.0 | 9.0 | 8.0 | 9.0 | 8.5 | 7.0 | 8.0 | 6.0 | 6.0 | 8.0 | 9.0 | 4.0 |
| 2-imidazolidinyl)-6- | .250 | 8.0 | 8.0 | 1.0 | 8.5 | 7.7 | 7.7 | 7.0 | 7.3 | 8.0 | 3.0 | 6.0 | 7.0 | 7.0 | 1.7 |
| methoxynicotinate | .125 | 6.7 | 6.5 | 0.0 | 8.5 | 7.3 | 7.0 | 5.0 | 6.0 | 8.0 | 2.5 | 4.0 | 3.0 | 6.0 | 0.7 |
| | .063 | 2.3 | 3.5 | 0.0 | 7.5 | 5.7 | 4.3 | 3.5 | 4.0 | 5.0 | 2.0 | 3.0 | 2.0 | 3.0 | 0.7 |
| | .032 | 1.3 | 1.0 | 0.0 | 6.0 | 2.7 | 1.3 | 2.0 | 3.0 | 2.0 | 1.5 | 3.0 | 0.0 | 2.0 | 0.3 |
| | .016 | 0.0 | | | 1.5 | 1.3 | 0.0 | 2.0 | 1.0 | | 2.0 | 3.0 | 0.0 | 0.0 | 0.3 |
| | | | | | 0.0 | 0.0 | 0.0 | 0.0 | 0.5 | | 5.0 | 2.0 | 0.0 | 0.0 | 0.0 |
| cis-Methyl 6-chloro-2- | 1.000 | 9.0 | 9.0 | 7.0 | 9.0 | 9.0 | 9.0 | 8.5 | 8.0 | | 4.0 | 7.0 | 8.0 | 7.0 | 9.0 |
| (4-isopropyl-4-methyl-5- | .500 | 8.0 | 8.0 | 7.0 | 9.0 | 8.0 | 9.0 | 8.5 | 8.0 | | 4.0 | 7.0 | 7.0 | 7.0 | 8.5 |
| oxo-2-imidazolidinyl)- | .250 | 7.5 | 8.0 | | 9.0 | 7.0 | 6.5 | 8.0 | | | 3.0 | | | | 8.5 |

TABLE VI-continued

POST-EMERGENCE TESTS - RATES IN KG/HA

| Compound | RATE | BARNY ARDGR | GREEN FOX | P NUT SEDGE | WILD OATS | QUACK GRASS | FLD B INDWD | MRNGL RY SP | VELVET LEAF | S BAR LY LA | CORN FIELD | RICE, NATO | S WHE AT ER | SOYBE AN WI | SUNFL R XXX |
|---|---|---|---|---|---|---|---|---|---|---|---|---|---|---|---|
| nicotinate | .125 | 7.0 | 7.0 | 6.0 | 9.0 | 6.5 | 5.0 | 6.5 | 6.0 | | 2.5 | 5.0 | 7.0 | 3.0 | 6.5 |
| | .063 | 3.0 | 2.0 | 5.0 | 7.0 | 5.0 | 3.5 | 5.5 | 3.0 | | 2.0 | 3.0 | 5.0 | 2.0 | 1.5 |
| | .032 | 1.0 | 0.0 | 2.0 | 7.0 | 3.5 | 1.0 | 5.0 | 1.0 | | 1.5 | 3.0 | 0.0 | 2.0 | 1.0 |
| | .016 | 0.0 | | 2.0 | 5.0 | 4.0 | 0.0 | 5.0 | 0.0 | | 1.0 | 3.0 | 3.0 | 2.0 | 0.0 |
| trans-Methyl 6-chloro-2-(4-isopropyl-4-methyl-5-oxo-2-imidazolidinyl)-nicotinate | .500 | 8.0 | | 7.0 | 9.0 | 8.0 | 9.0 | 9.0 | 7.0 | | 3.0 | 7.0 | 8.0 | 7.0 | 9.5 |
| | .250 | 8.0 | | 7.0 | 9.0 | 8.0 | 7.0 | 9.0 | 7.0 | | 2.0 | 5.0 | 6.0 | 4.0 | 8.0 |
| | .125 | 7.0 | | 4.0 | 7.0 | 7.0 | 7.0 | 8.0 | 7.0 | | 2.0 | 3.0 | 5.0 | 3.0 | 3.0 |
| | .063 | 2.0 | | 2.0 | 7.0 | 7.0 | 4.0 | 7.0 | 3.0 | | 2.0 | 3.0 | 4.0 | 2.0 | 0.0 |
| | .032 | 0.0 | | 0.0 | 6.0 | 6.0 | 0.0 | 7.0 | 1.0 | | 1.0 | 3.0 | 0.0 | 2.0 | 0.0 |
| | .016 | 0.0 | | 0.0 | 4.0 | 2.0 | 0.0 | 5.0 | 0.0 | | 1.0 | 2.0 | 0.0 | 1.0 | 0.0 |
| trans-Benzyl 5-ethyl-2-(4-isopropyl-4-methyl-5-oxo-2-imidazolidinyl)-nicotinate | .500 | 9.0 | | 9.0 | 6.0 | 9.0 | 8.0 | 6.0 | 7.0 | | 1.0 | 2.0 | 0.0 | 1.0 | 7.5 |
| | .250 | 3.0 | | 5.0 | 6.0 | 3.0 | 6.0 | 2.0 | 4.0 | | 6.0 | 9.0 | 3.0 | 2.0 | 4.0 |
| | .125 | 0.0 | | 3.0 | 3.0 | 1.0 | 6.0 | 0.0 | 4.0 | | 5.0 | 3.0 | 3.0 | 1.0 | 2.0 |
| | .063 | 0.0 | | 1.0 | 0.0 | 0.0 | 2.0 | 0.0 | 2.0 | | 3.0 | 2.0 | 2.0 | 1.0 | 2.0 |
| | .032 | 0.0 | | 0.0 | 0.0 | 0.0 | 0.0 | 0.0 | 1.0 | | 3.0 | 0.0 | 1.0 | 1.0 | 0.0 |
| | .016 | 0.0 | | 0.0 | 0.0 | 0.0 | 0.0 | 0.0 | 0.0 | | 2.0 | 0.0 | 0.0 | 0.0 | 0.0 |
| cis-Benzyl 5-ethyl-2-(4-isopropyl-4-methyl-5-oxo-2-imidazolidinyl)-nicotinate | .500 | 8.0 | | 9.0 | 7.0 | 8.0 | 8.0 | 3.0 | 9.0 | | 2.0 | 8.0 | 7.0 | 3.0 | 8.4 |
| | .250 | 7.0 | | 6.0 | 2.0 | 3.0 | 6.0 | 0.0 | 5.0 | | 6.0 | 6.0 | 3.0 | 0.0 | 4.0 |
| | .125 | 2.0 | | 3.0 | 1.0 | 1.0 | 6.0 | 0.0 | 3.0 | | 2.0 | 2.0 | 2.0 | 0.0 | 6.0 |
| | .063 | 0.0 | | 1.0 | 0.0 | 0.0 | 6.0 | 0.0 | 2.0 | | 3.0 | 0.0 | 2.0 | 0.0 | 2.0 |
| | .032 | 0.0 | | 1.0 | 0.0 | 0.0 | 0.0 | 0.0 | 2.0 | | 2.0 | 0.0 | 2.0 | 0.0 | 2.0 |
| | .016 | 0.0 | | 0.0 | 0.0 | 0.0 | 0.0 | 0.0 | 0.0 | | 2.0 | 0.0 | 2.0 | 0.0 | 2.0 |
| cis-Methyl 2-(4-isopropyl-4-methyl-5-oxo-2-imidazolidinyl)-5-methylnicotinate | .500 | 6.0 | | 9.0 | 9.0 | 8.0 | 9.0 | 9.0 | 9.0 | | 4.0 | 7.0 | 7.0 | 6.0 | 7.0 |
| | .250 | 7.0 | | 9.0 | 9.0 | 4.0 | 9.0 | 9.0 | 9.0 | | 3.0 | 7.0 | 7.0 | 3.0 | 6.0 |
| | .125 | 4.0 | | 7.0 | 6.0 | 8.0 | 6.0 | 8.0 | 9.0 | | 2.0 | 4.0 | 3.0 | 3.0 | 5.0 |
| | .063 | 0.0 | | 2.0 | 6.0 | 0.0 | 6.0 | 0.0 | 7.0 | | 1.0 | 4.0 | 1.0 | 0.0 | 2.0 |
| | .032 | 0.0 | | 2.0 | 3.0 | 0.0 | 6.0 | 2.0 | 6.0 | | 1.0 | 3.0 | 0.0 | 0.0 | 2.0 |
| | .016 | 0.0 | | 0.0 | 0.0 | 0.0 | 2.0 | 0.0 | 4.0 | | 0.0 | 1.0 | 0.0 | 0.0 | 1.0 |
| trans-Methyl 2-(4-isopropyl-4-methyl-5-oxo-2-imidazolidinyl)-5-methylnicotinate | 1.000 | 8.0 | | 9.0 | | 8.0 | 9.0 | 7.0 | 9.0 | | 3.0 | | 3.0 | 3.0 | 7.0 |
| | .500 | 7.0 | | 7.0 | 9.0 | 7.5 | 5.5 | 6.5 | 8.0 | | 3.5 | 8.0 | 0.0 | 0.0 | 5.5 |
| | .250 | 6.5 | 9.0 | 7.0 | 8.0 | 5.0 | 5.5 | 5.5 | 7.0 | | 2.0 | 8.0 | 0.0 | 3.0 | 3.5 |
| | .125 | 1.5 | 8.0 | 4.0 | 3.0 | 2.0 | 4.0 | 3.0 | 6.0 | | 1.5 | 6.0 | 0.0 | 1.0 | 2.5 |
| | .063 | 0.0 | 8.0 | 1.0 | 0.0 | 0.0 | 1.5 | 0.0 | 2.0 | | 1.5 | 3.0 | 0.0 | 1.0 | 2.0 |
| | .032 | 0.0 | 6.0 | 0.0 | 0.0 | 0.0 | 0.0 | 0.0 | 2.0 | | 1.5 | 2.0 | 0.0 | 1.0 | 1.0 |
| | .016 | 9.0 | 0.0 | 0.0 | 9.0 | 9.0 | 9.0 | 9.0 | 9.0 | | 0.0 | 9.0 | 9.0 | 1.0 | 1.0 |
| cis-2-(4-Isopropyl-4-methyl-5-oxo-2-imidazolidinyl)-5-methylnicotinic acid | .500 | | | | | | | | | | | | | | |
| | .375 | | | | | | | | | | | | | | |
| | .250 | 8.0 | | 9.0 | 9.0 | 8.0 | 9.0 | 8.0 | 9.0 | | 5.5 | 9.0 | 8.0 | 6.0 | 9.0 |
| | .125 | 2.0 | | 9.0 | 8.0 | 6.0 | 9.0 | 7.0 | 8.0 | | 5.0 | 9.0 | 6.0 | 4.0 | 9.0 |
| | .063 | 0.0 | | 7.0 | 3.0 | 4.0 | 9.0 | 7.0 | 7.0 | | 5.0 | 8.0 | 0.0 | 2.0 | 9.0 |
| | .032 | 0.0 | | 4.0 | 0.0 | 0.0 | 9.0 | 0.0 | 6.0 | | 2.0 | 7.0 | 0.0 | 2.0 | 6.0 |
| | .016 | 0.0 | | 0.0 | 0.0 | 0.0 | 9.0 | 0.0 | 2.0 | | 9.0 | 3.0 | 0.0 | 2.0 | 2.0 |
| cis-(R)—(—)-Methyl 2-(4-isopropyl-4-methyl-5-oxo-2-imidazolidinyl)nicotinate | .500 | 9.0 | | 8.0 | 9.0 | 9.0 | 9.0 | 9.0 | 9.0 | | 9.0 | 8.0 | 9.0 | 9.0 | 9.0 |
| | .250 | 9.0 | | 7.0 | 9.0 | 9.0 | 9.0 | 9.0 | 9.0 | | 9.0 | 8.0 | 9.0 | 9.0 | 8.0 |
| | .125 | 8.0 | | 7.0 | 8.0 | 8.0 | 9.0 | 9.0 | 9.0 | | 9.0 | 5.0 | 8.0 | 7.0 | 5.0 |
| | .063 | 7.0 | | 8.0 | 7.0 | 7.0 | 8.0 | 8.0 | 9.0 | | 7.0 | 4.0 | 7.0 | 7.0 | 4.0 |
| | .032 | 2.0 | | 4.0 | 4.0 | 6.0 | 5.0 | 7.0 | 9.0 | | 3.0 | 3.0 | 6.0 | 5.0 | 2.0 |
| | .016 | 0.0 | | 9.0 | 4.0 | 9.0 | 0.0 | 9.0 | 9.0 | | 2.0 | 2.0 | 4.0 | 2.0 | 0.0 |
| trans-(R)—(—)-Methyl 2-(4-isopropyl-4-methyl-5-oxo-2-imidazolidinyl)- | .500 | 8.0 | | 9.0 | 9.0 | 9.0 | 9.0 | 9.0 | 9.0 | | 9.0 | 7.0 | 9.0 | 8.0 | 8.0 |
| | .250 | 9.0 | | 9.0 | 9.0 | 8.0 | 9.0 | 9.0 | 9.0 | | 9.0 | 7.0 | 8.0 | 8.0 | 8.0 |
| | .125 | 0.0 | | 6.0 | 9.0 | 7.0 | 9.0 | 9.0 | 9.0 | | 8.0 | 6.0 | 7.0 | 7.0 | 3.0 |

TABLE VI-continued

POST-EMERGENCE TESTS - RATES IN KG/HA

| Compound | RATE | BARNY ARDGR | GREEN FOX | P NUT SEDGE | WILD OATS | QUACK GRASS | FLD B INDWD | MRNGL RY SP | VELVET LEAF | S BAR LY LA | CORN FIELD | RICE, NATO | S WHE AT ER | SOYBE AN WI | SUNFL R XXX |
|---|---|---|---|---|---|---|---|---|---|---|---|---|---|---|---|
| nicotinate | .063 | 0.0 | | 3.0 | 8.0 | 6.0 | 9.0 | 9.0 | 8.0 | | 6.0 | 4.0 | 7.0 | 6.0 | 2.0 |
| | .032 | 0.0 | | 0.0 | 2.0 | 4.0 | 9.0 | 8.0 | 6.0 | | 2.0 | 3.0 | 4.0 | 4.0 | 2.0 |
| | .016 | 0.0 | | 0.0 | 2.0 | 0.0 | 8.0 | 7.0 | 4.0 | | 2.0 | 3.0 | 3.0 | 2.0 | 2.0 |
| cis-(R)—(+)-2-(4-Iso- | .500 | 9.0 | | 9.0 | 9.0 | 9.0 | 9.0 | 9.0 | 9.0 | | 9.0 | 9.0 | 9.0 | 8.0 | 9.0 |
| propyl-4-methyl-5-oxo- | .250 | 9.0 | | 9.0 | 9.0 | 9.0 | 9.0 | 9.0 | 9.0 | | 9.0 | 9.0 | 9.0 | 8.0 | 8.0 |
| 2-imidazolidinyl)- | .125 | 3.0 | | 9.0 | 9.0 | 9.0 | 9.0 | 8.0 | 9.0 | | 9.0 | 6.0 | 9.0 | 5.0 | 8.0 |
| nicotinate acid | .063 | 4.0 | | 9.0 | 7.0 | 8.0 | 7.0 | 8.0 | 9.0 | | 8.0 | 6.0 | 8.0 | 5.0 | 7.0 |
| | .032 | 0.0 | | 8.0 | 0.0 | 2.0 | 6.0 | 8.0 | 6.0 | | 4.0 | 3.0 | 7.0 | 5.0 | 7.0 |
| | .016 | 0.0 | | 2.0 | 0.0 | 0.0 | 4.0 | 4.0 | 4.0 | | 3.0 | 3.0 | 4.0 | 2.0 | 2.0 |
| cis-Methyl 2-(4-iso- | .500 | 9.0 | | 8.0 | 9.0 | 8.0 | 9.0 | 9.0 | 9.0 | | 5.0 | 8.0 | 8.0 | 2.0 | 7.0 |
| propyl-4-methyl-5-oxo-2- | .250 | 9.0 | | 7.0 | 9.0 | 7.0 | 8.0 | 9.0 | 8.0 | | 4.0 | 8.0 | 7.0 | 7.0 | 6.0 |
| imidazolidinyl)-6-methyl- | .125 | 4.0 | | 6.0 | 9.0 | 2.0 | 8.0 | 8.0 | 6.0 | | 2.0 | 5.0 | 2.0 | 6.0 | 2.0 |
| nicotinate | .063 | 1.0 | | 2.0 | 8.0 | 0.0 | 4.0 | 4.0 | 6.0 | | 2.0 | 4.0 | 2.0 | 3.0 | 2.0 |
| | .032 | 0.0 | | 0.0 | 6.0 | 0.0 | 2.0 | 2.0 | 2.0 | | 2.0 | 3.0 | 0.0 | 2.0 | 1.0 |
| | .016 | 0.0 | | 0.0 | 2.0 | 0.0 | 0.0 | 0.0 | 0.0 | | 1.0 | 3.0 | 1.0 | 1.0 | 1.0 |
| trans-Methyl 2-(4-iso- | .500 | 7.0 | | 8.0 | 9.0 | 9.0 | 9.0 | 8.0 | 8.0 | | 1.0 | 7.0 | 8.0 | 6.0 | 6.0 |
| propyl-4-methyl-5-oxo- | .250 | 6.0 | | 7.0 | 9.0 | 2.0 | 9.0 | 8.0 | 9.0 | | 3.0 | 6.0 | 7.0 | 5.0 | 3.0 |
| 2-imidazolidinyl)-6- | .125 | 2.0 | | 2.0 | 8.0 | 2.0 | 9.0 | 6.0 | 3.0 | | 2.0 | 4.0 | 3.0 | 5.0 | 2.0 |
| methylnicotinate | .063 | 0.0 | | 1.0 | 6.0 | 2.0 | 3.0 | 2.0 | 1.0 | | 2.0 | 3.0 | 2.0 | 2.0 | 2.0 |
| | .032 | 0.0 | | 0.0 | 2.0 | 0.0 | 1.0 | 0.0 | 0.0 | | 2.0 | 3.0 | 1.0 | 0.0 | 1.0 |
| | .016 | 0.0 | | 0.0 | 0.0 | 0.0 | 0.0 | 0.0 | 0.0 | | 1.0 | 2.0 | 1.0 | 0.0 | 0.0 |
| cis-2-(4-Isopropyl-4- | .500 | 0.0 | | 9.0 | 9.0 | 9.0 | 9.0 | 8.0 | 8.0 | | 9.0 | 6.0 | 9.0 | 6.0 | 9.0 |
| methyl-5-oxo-2-imidazo- | .250 | 4.0 | | 9.0 | 9.0 | 2.0 | 9.0 | 8.0 | 9.0 | | 9.0 | | 9.0 | 6.0 | 9.0 |
| lidinyl)-6-methyl- | .125 | 0.0 | | 9.0 | 9.0 | 9.0 | 9.0 | 6.0 | 3.0 | | 6.0 | 7.0 | 8.0 | 6.0 | 8.0 |
| nicotinic acid | .063 | 2.0 | | 9.0 | 8.0 | 9.0 | 9.0 | | 8.0 | | 6.0 | 7.0 | 9.0 | 5.0 | 6.0 |
| | .032 | 0.0 | | 9.0 | 3.0 | 1.0 | 9.0 | 4.0 | 4.0 | | 3.0 | 4.0 | 9.0 | 3.0 | 2.0 |
| | .016 | 0.0 | | 8.0 | 0.0 | 0.0 | 4.0 | 0.0 | 1.0 | | 4.0 | 3.0 | 2.0 | 2.0 | 0.0 |
| trans-Methyl 6-(allyloxy)- | .500 | 6.0 | | 6.0 | 4.0 | 0.0 | 2.0 | 0.0 | 6.0 | | 0.0 | 3.0 | 2.0 | 0.0 | 0.0 |
| 2-(4-isopropyl-4-methyl-5- | .250 | 3.0 | | 0.0 | 2.0 | 5.0 | 0.0 | 2.0 | 0.0 | | 2.0 | 2.0 | 1.0 | 0.0 | 0.0 |
| oxo-2-imidazolidinyl)- | .125 | 0.0 | | 0.0 | 0.0 | 1.0 | 0.0 | 1.0 | 0.0 | | 2.0 | 1.0 | 0.0 | 0.0 | 0.0 |
| nicotinate | .063 | 0.0 | | 0.0 | 0.0 | 0.0 | 0.0 | 0.0 | 0.0 | | 1.0 | 0.0 | 0.0 | 0.0 | 0.0 |
| | .032 | 0.0 | | 0.0 | 0.0 | 0.0 | 0.0 | 0.0 | 0.0 | | 0.0 | 0.0 | 0.0 | 0.0 | 0.0 |
| | .016 | 0.0 | | 0.0 | 0.0 | 0.0 | 0.0 | 0.0 | 0.0 | | 0.0 | 0.0 | 0.0 | 0.0 | 0.0 |
| cis-Methyl 6-(allyloxy)- | .500 | 2.0 | | 7.0 | 4.0 | 0.0 | 8.0 | 6.0 | 6.0 | | 2.0 | 2.0 | 7.0 | 6.0 | 0.0 |
| 2-(4-isopropyl-4-methyl-5- | .250 | 1.0 | | 0.0 | 1.0 | 3.0 | 4.0 | 3.0 | 4.0 | | 2.0 | 1.0 | 3.0 | 3.0 | 0.0 |
| oxo-2-imidazolidinyl)- | .125 | 0.0 | | 0.0 | 0.0 | 2.0 | 2.0 | 6.0 | 0.0 | | 1.0 | 0.0 | 2.0 | 0.0 | 0.0 |
| nicotinate | .063 | 0.0 | | 0.0 | 0.0 | 1.0 | 2.0 | 3.0 | 0.0 | | 1.0 | 0.0 | 0.0 | 0.0 | 0.0 |
| | .032 | 0.0 | | 0.0 | 0.0 | 0.0 | 0.0 | 0.0 | 0.0 | | 0.0 | 0.0 | 0.0 | 0.0 | 0.0 |
| | .016 | 0.0 | | 0.0 | 0.0 | 0.0 | 0.0 | 0.0 | 0.0 | | 0.0 | 0.0 | 0.0 | 0.0 | 0.0 |
| cis-Methyl 2-(3-acetyl-4- | .500 | 2.0 | | 2.0 | 4.0 | 3.0 | 8.0 | 8.0 | 8.0 | | 1.0 | 3.0 | 7.0 | 6.0 | |
| isopropyl-4-methyl-5-oxo- | .250 | 0.0 | | 1.0 | 2.0 | 2.0 | 4.0 | 7.0 | 6.0 | | 1.0 | 2.0 | 3.0 | 3.0 | |
| 2-imidazolidinyl)- | .125 | 0.0 | | 0.0 | 1.0 | 1.0 | 2.0 | 6.0 | 0.0 | | 1.0 | 1.0 | 2.0 | 0.0 | |
| nicotinate | .063 | 0.0 | | 0.0 | 0.0 | 0.0 | 2.0 | 3.0 | 0.0 | | 1.0 | 0.0 | 0.0 | 0.0 | |
| cis-6-Chloro-2-(4-iso- | .500 | 9.0 | | 9.0 | 9.0 | 9.0 | 9.0 | 9.0 | 8.0 | | 9.0 | 8.0 | 9.0 | 6.0 | 9.0 |
| propyl-4-methyl-5-oxo- | .250 | 8.0 | | 8.0 | 9.0 | 9.0 | 9.0 | 8.0 | 8.0 | | 9.0 | 6.0 | 9.0 | 3.0 | 9.0 |
| 2-imidazolidinyl)- | .125 | 2.0 | | 8.0 | 9.0 | 9.0 | 9.0 | 8.0 | 7.0 | | 7.0 | 6.0 | 9.0 | 3.0 | 9.0 |
| nicotinic acid | .063 | 2.0 | | 7.0 | 9.0 | 8.0 | 9.0 | 6.0 | 4.0 | | 3.0 | 4.0 | 8.0 | 2.0 | 8.0 |
| | .032 | 0.0 | | 5.0 | 9.0 | 8.0 | 2.0 | 3.0 | 2.0 | | 2.0 | 3.0 | 6.0 | 1.0 | 7.0 |
| | .016 | 0.0 | | 9.0 | 9.0 | 9.0 | 9.0 | 2.0 | 8.0 | | 2.0 | 2.0 | 9.0 | 8.0 | 7.0 |
| cis-2-(4-Isopropyl-4- | .500 | 9.0 | | 9.0 | 9.0 | 9.0 | 9.0 | 9.0 | 8.0 | | 9.0 | 9.0 | 9.0 | 8.0 | 9.0 |

TABLE VI-continued
POST-EMERGENCE TESTS - RATES IN KG/HA

| Compound | RATE | BARNY ARDGR | GREEN FOX | P NUT SEDGE | WILD OATS | QUACK GRASS | FLD B INDWD | MRNGL RY SP | VELVET LEAF | S BAR LY LA | CORN FIELD | RICE, NATO | S WHE AT ER | SOYBE AN WI | SUNFL R XXX |
|---|---|---|---|---|---|---|---|---|---|---|---|---|---|---|---|
| methyl-5-oxo-2-imidazo- | .250 | 9.0 | | 9.0 | 9.0 | 9.0 | 9.0 | 9.0 | 8.0 | | 9.0 | 9.0 | 9.0 | 7.0 | 9.0 |
| lidinyl)-6-methoxy- | .125 | 7.0 | | 9.0 | 9.0 | 9.0 | 9.0 | 8.0 | 6.0 | | 8.0 | 8.0 | 7.0 | 7.0 | 8.0 |
| nicotinic acid | .063 | 3.0 | | 8.0 | 9.0 | 9.0 | 6.0 | 7.0 | 6.0 | | 5.0 | 6.0 | 7.0 | 3.0 | 7.0 |
| | .032 | 0.0 | | 8.0 | 8.0 | 9.0 | 3.0 | 5.0 | 4.0 | | 3.0 | 4.0 | 4.0 | 2.0 | 7.0 |
| | .016 | 0.0 | | 4.0 | 6.0 | 7.0 | 0.0 | 2.0 | 2.0 | | 3.0 | 3.0 | 2.0 | 2.0 | 2.0 |
| cis-Methyl 2-(4-isopropyl- | .500 | 9.0 | | 7.0 | 9.0 | 8.0 | 9.0 | 9.0 | 9.0 | | 9.0 | 6.0 | 9.0 | | |
| 4-methyl-5-oxo-2-imidazo- | .250 | 9.0 | | 6.0 | 9.0 | 9.0 | 9.0 | 9.0 | 9.0 | | 9.0 | 6.0 | 8.0 | | |
| lidinyl)nicotinate hydro- | .125 | 6.0 | | 4.0 | 9.0 | 9.0 | 9.0 | 8.0 | 9.0 | | 7.0 | 6.0 | 8.0 | | |
| chloride | .063 | 3.0 | | 4.0 | 8.0 | 8.0 | 7.0 | 8.0 | 9.0 | | 6.0 | 4.0 | 8.0 | | |
| | .032 | 1.0 | | 3.0 | 7.0 | 7.0 | 4.0 | 7.0 | 7.0 | | 3.0 | 3.0 | 7.0 | | |
| | .016 | 0.0 | | 0.0 | 3.0 | 3.0 | 0.0 | 4.0 | 7.0 | | 2.0 | 3.0 | 7.0 | | |
| trans-o-(4-Isopropyl-4- | 2.000 | 9.0 | 9.0 | 9.0 | 8.0 | 9.0 | 9.0 | 8.0 | 9.0 | 8.0 | 9.0 | | 9.0 | 8.0 | 8.0 |
| methyl-5-oxo-2-imidazo- | 1.000 | 9.0 | 9.0 | 9.0 | 7.0 | 9.0 | 9.0 | 8.0 | 9.0 | 7.0 | 9.0 | | 8.0 | 8.0 | 8.0 |
| lidinyl)benzoic acid | .500 | 9.0 | 7.0 | 9.0 | 5.0 | 9.0 | 9.0 | 8.0 | 8.0 | 3.0 | 9.0 | | 7.0 | 7.0 | 7.0 |
| | .250 | 5.0 | 6.0 | 9.0 | 3.0 | 9.0 | 8.0 | 7.0 | 8.0 | 2.0 | 8.0 | | 7.0 | 7.0 | 7.0 |
| | .125 | 0.0 | 4.0 | 9.0 | 0.0 | 9.0 | 3.0 | 3.0 | 8.0 | 1.0 | 8.0 | | 3.0 | 5.0 | 3.0 |
| | .063 | 0.0 | 3.0 | 5.0 | 0.0 | 9.0 | 3.0 | 3.0 | 2.0 | 0.0 | 3.0 | | 3.0 | 5.0 | 3.0 |
| trans-Methyl 2-(4-iso- | .500 | 8.0 | | 8.0 | 9.0 | | 9.0 | 9.0 | 9.0 | | 9.0 | 7.0 | 9.0 | | |
| propyl-4-methyl-5-thioxo- | .250 | 8.0 | | 7.0 | 9.0 | | 9.0 | 9.0 | 9.0 | | 8.0 | 7.0 | 8.0 | | |
| 2-imidazolidinyl)nicotinate | .125 | 6.0 | | 5.0 | 8.0 | | 9.0 | 8.0 | 8.0 | | 4.0 | 5.0 | 7.0 | | |
| | .063 | 4.0 | | 2.0 | 2.0 | | 8.0 | 7.0 | 5.0 | | 3.0 | 3.0 | 7.0 | | |
| | .032 | 2.0 | | 0.0 | 0.0 | | 3.0 | 4.0 | 2.0 | | 2.0 | 1.0 | 3.0 | | |
| | .016 | 0.0 | | 0.0 | 0.0 | | 0.0 | 0.0 | 0.0 | | 2.0 | 0.0 | 2.0 | | |
| cis-Methyl 2-(4-isopropyl- | .500 | 9.0 | | 8.0 | 9.0 | 9.0 | 9.0 | 9.0 | 9.0 | | 9.0 | 7.0 | 9.0 | | |
| 4-methyl-5-thioxo-2-imidaz- | .250 | 8.0 | | 8.0 | 8.0 | 9.0 | 9.0 | 9.0 | 9.0 | | 9.0 | 8.0 | 9.0 | | |
| olidinyl)nicotinate | .125 | 6.0 | | 6.0 | 8.0 | 8.0 | 9.0 | 9.0 | 9.0 | | 8.0 | 6.0 | 9.0 | | |
| | .063 | 2.0 | | 2.0 | 6.0 | 8.0 | 6.0 | 8.0 | 8.0 | | 7.0 | 4.0 | 8.0 | | |
| | .032 | 0.0 | | 0.0 | 2.0 | | 4.0 | 7.0 | 7.0 | | 3.0 | 3.0 | 6.0 | | |
| | .016 | 0.0 | | 0.0 | 0.0 | | 0.0 | 4.0 | 3.0 | | 7.0 | 2.0 | 3.0 | | |
| cis-2-(4-Isopropyl-4-methyl- | .500 | 9.0 | | 9.0 | 9.0 | 2.0 | 9.0 | 2.0 | 9.0 | | 9.0 | 2.0 | 2.0 | | |
| 5-thioxo-2-imidazolidinyl)- | .250 | 8.0 | | 9.0 | 9.0 | 9.0 | 8.0 | 8.0 | 9.0 | | 9.0 | 9.0 | 9.0 | | |
| nicotinic acid | .125 | 3.0 | | 8.0 | 9.0 | 9.0 | 7.0 | 7.0 | 7.0 | | 9.0 | 7.0 | 9.0 | | |
| | .063 | 1.0 | | 6.0 | 6.0 | 9.0 | 7.0 | 7.0 | 7.0 | | 7.0 | 6.0 | 9.0 | | |
| | .032 | 0.0 | | 2.0 | 3.0 | 3.0 | 2.0 | 4.0 | 4.0 | | 5.0 | 5.0 | 8.0 | | |
| | .016 | 0.0 | | 0.0 | 1.0 | 1.0 | 2.0 | 1.0 | 3.0 | | 2.0 | 4.0 | 6.0 | | |
| Propyl o-(5-isopropyl-5- | 4.000 | 0.0 | 9.0 | 0.0 | 0.0 | 0.0 | 0.0 | 0.0 | 0.0 | | 2.0 | 4.0 | 3.0 | | |
| methyl-4-oxo-2-imidazo- | 1.000 | 7.0 | 9.0 | 8.0 | 8.0 | 9.0 | 9.0 | 9.0 | 0.0 | | 5.0 | | | | |
| lindinyl)]benzoate | .500 | 2.0 | 9.0 | | 8.0 | 8.0 | 9.0 | 0.0 | 0.0 | | 2.0 | | | | |
| | .250 | 0.0 | 7.0 | | 7.0 | 8.0 | 9.0 | 9.0 | 0.0 | | 1.0 | | | | |
| 2-Propynyl o-(5-isopropyl- | 2.000 | 9.0 | 5.0 | 9.0 | 9.0 | | 9.0 | 8.0 | 9.0 | 7.0 | 0.0 | | 8.0 | | |
| 5-methyl-4-oxo-2-imidazo- | 1.000 | 9.0 | 8.0 | 9.0 | 9.0 | | 9.0 | 8.0 | 8.5 | 5.0 | 9.0 | | 8.0 | | |
| lindinyl)]benzoate | .500 | 8.0 | 8.0 | 9.0 | 7.5 | | 9.0 | 8.0 | 8.0 | 2.0 | 7.5 | | 8.0 | | |
| | .250 | 8.0 | 7.5 | 9.0 | 6.5 | | 8.0 | 8.0 | 7.5 | 0.0 | 3.5 | | 7.0 | | |
| | .125 | 7.0 | 6.5 | 9.0 | 3.0 | | 8.0 | 7.5 | 6.5 | 0.0 | 1.0 | | 3.0 | | |
| | .063 | 6.0 | 5.5 | 6.0 | 0.5 | | 7.0 | 7.0 | 5.5 | 0.0 | 0.5 | | 3.0 | | |
| | .032 | | 0.0 | 5.0 | 0.0 | | 5.0 | 5.0 | 0.0 | | 0.5 | | 0.0 | | |
| cis-2-(4-Isopropyl-4- | .500 | 9.0 | | 9.0 | 9.0 | 9.0 | 9.0 | 8.0 | 8.0 | | 0.0 | 9.0 | 8.0 | | |
| methyl-5-oxo-2-imidazo- | .250 | 7.0 | | 9.0 | 8.0 | 9.0 | 9.0 | 8.0 | 8.0 | | 0.0 | 7.0 | 8.0 | | |
| lidinyl)]-3-quinoline- | .125 | 5.0 | | 9.0 | 8.0 | 9.0 | 8.0 | 7.0 | 7.0 | | 9.0 | 7.0 | 7.0 | | |
| carboxylic acid | .063 | 2.0 | | 8.0 | 3.0 | 9.0 | 7.0 | 4.0 | 3.0 | | 9.0 | 4.0 | 5.0 | | |
| | .032 | 1.0 | | 7.0 | 1.0 | 8.0 | 4.0 | 0.0 | 2.0 | | 2.0 | 2.0 | 1.0 | | |
| | .016 | 0.0 | | 3.0 | 0.0 | 2.0 | 1.0 | 0.0 | 1.0 | | 2.0 | 2.0 | 0.0 | | |

What is claimed is:
1. A compound having the structure:

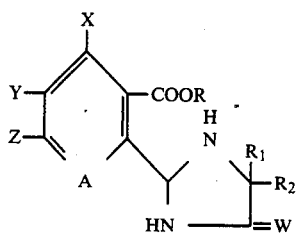

wherein

R is hydrogen;
  $C_1-C_{12}$ alkyl optionally substituted with one of the following groups: $C_1-C_4$ alkoxy, halogen, hydroxyl, $C_3-C_6$ cycloalkyl, benzyloxy, furyl, phenyl, halophenyl, $C_1-C_4$ alkylphenyl, $C_1-C_4$ alkoxyphenyl, nitrophenyl, carboxyl, $C_1-C_3$ alkoxycarbonyl, cyano or tri($C_1-C_3$)alkylammonium;
  $C_3-C_{12}$ alkenyl optionally substituted with one of the following groups: $C_1-C_3$ alkoxy, phenyl, halogen, or $C_1-C_3$ alkoxycarbonyl or with two $C_1-C_4$ alkoxy groups or two halogen atoms;
  $C_3-C_6$ cycloalkyl optionally substituted with one or two $C_1-C_3$ alkyl groups;
  $C_3-C_{10}$ alkynyl or,
  a cation of alkali metals or organic-ammonium;
$R_1$ and $R_2$ each represents $C_1-C_3$ alkyl or cyclopropyl, with the proviso that the sum of the number of carbon atoms in $R_1$ and $R_2$ is 2 to 5; and when $R_1$ and $R_2$ are taken together with the carbon to which they are attached, they may form a $C_3-C_6$ cycloalkyl ring optionally substituted with methyl;
A is nitrogen or $-CR_3$;
W is oxygen or sulfur;
X is hydrogen, halogen or methyl;
Y and Z are each hydrogen, halogen, $C_1-C_6$ alkyl, $C_1-C_4$ hydroxyalkyl, $C_1-C_6$ alkoxy, $C_1-C_4$ alkylthio, phenoxy, $C_1-C_4$ haloalkyl, $OCF_2CHF_2$, $OCF_3$, $OCHF_2$, nitro, cyano, $NR_4R_5$, $C_3-C_8$ straight or branched alkenyloxy optionally substituted with one to three halogens, $C_3-C_8$ straight or branched alkynyloxy optionally substituted with one to three halogens, or phenyl optionally substituted with one $C_1-C_4$ alkyl, $C_1-C_4$ alkoxy or halogen;
$R_3$ is hydrogen, halogen, $C_1-C_4$ alkyl, $C_1-C_4$ alkoxy, $CF_3$, $NO_2$, $OCF_3$, $OCHF_2$ or $OCF_2CHF_2$;
$R_4$ is hydrogen or $C_1-C_4$ alkyl;
$R_5$ is $C_1-C_4$ alkyl; and, when taken together, Y and Z may form a ring in which YZ is represented by
  (1) the structure: $-(CH_2)_n-$, where n is an integer of 2, 3 and 4, provided that when A is $-CR_3$, then X is hydrogen; or
  (2) by the structure:

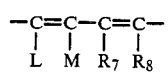

where, when A is $CR_3$, L, M, $R_7$ and $R_8$ each represent hydrogen, halogen, $C_1-C_4$ alkyl or $C_1-C_3$ alkoxy, and X is hydrogen; and when A is nitrogen, L, M, $R_7$ and $R_8$ each represent hydrogen, halogen, $C_1-C_4$ alkyl, $C_1-C_4$ alkoxy, $C_1-C_4$ alkylthio, $C_1-C_4$ alkylsulfonyl, $C_1-C_4$ haloalkyl, $NO_2$, CN, phenyl, phenoxy, amino, $C_1-C_4$ alkylamino, dialkyl($C_1-C_4$)amino, $OCF_3$, $OCHF_2$, $OCF_2CHF_2$, chlorophenyl, methylphenyl, $C_3-C_8$ straight or branched alkenyloxy optionally substituted with one to three halogens, $C_3-C_8$ straight or branched alkynyloxy optionally substituted with one to three halogens, or phenoxy substituted with one Cl, $CF_3$, $NO_2$ or $CH_3$ group, with the proviso that only one of L, M, $R_7$ or $R_8$, may represent a substituent other than hydrogen, halogen, $C_1-C_4$ alkyl or $C_1-C_4$ alkoxy; or
(3) by the structures:

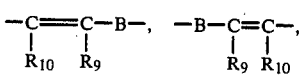

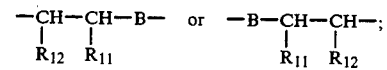

where B is oxygen or sulfur; $R_9$ and $R_{10}$ each represent hydrogen, halogen, phenyl, or $C_1-C_4$ alkyl; $R_{11}$ and $R_{12}$ each represent hydrogen, $C_1-C_4$ alkyl and phenyl;
and when $R_1$ and $R_2$ are not the same, the optical or cis- or trans-isomer thereof or except when R is a salt-forming cation, the acid addition salts thereof.

2. A compound according to claim 1 having the structure:

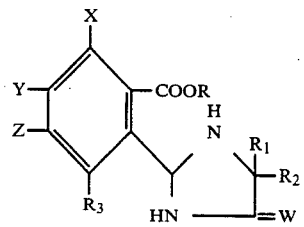

wherein R, $R_1$, $R_2$, $R_3$, X and W are as defined in claim 1 above; Y and Z each, independently, represent hydrogen, halogen, $C_1-C_6$ alkyl, $C_1-C_6$ alkoxy, $C_1-C_4$ alkylthio, phenoxy, nitro, $C_1-C_4$ haloalkyl, $OCF_2CHF_2$, $OCF_3$, $OCHF_2$, CN, $NR_4R_5$, $C_3-C_8$ straight or branched alkenyloxy optionally substituted with one to three halogens, $C_3-C_8$ straight or branched alkynyloxy optionally substituted with one to three halogens, or phenyl optionally substituted with one $C_1-C_4$ alkyl, $C_1-C_4$ alkoxy or halogen; $R_4$ is hydrogen or $C_1-C_4$ alkyl; $R_5$ is $C_1-C_4$ alkyl; and when taken together, Y and Z may form a ring in which YZ are represented by the structure: $-(CH_2)_n-$, where n is an integer of 2, 3 or 4 and X is hydrogen, or by the structure:

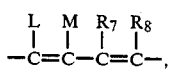

where L, M, $R_7$ and $R_8$ each represent hydrogen, $C_1-C_4$ alkyl and $C_1-C_3$ alkoxy; and when $R_1$ and $R_2$ are not the same, the optical or cis- or trans-isomers thereof or except when R is a salt-forming cation, the acid addition salts thereof.

3. A compound according to claim 1, having the structure:

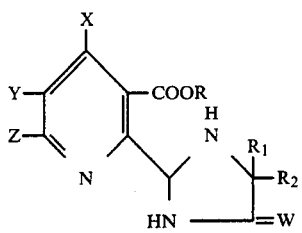

wherein R, $R_1$, $R_2$, W and X are as defined in claim 1 above; Y and Z each, independently, represent hydrogen, halogen, $C_1$-$C_6$ alkyl, $C_1$-$C_6$ alkoxy, CN, $NO_2$, $OCF_3$, $OCHF_2$, $OCF_2CHF_2$, phenoxy, $C_1$-$C_4$ haloalkyl, $C_1$-$C_4$ alkylthio, $C_1$-$C_4$ hydroxyalkyl, $NR_4R_5$, $C_3$-$C_8$ straight or branched alkenyloxy optionally substituted with one to three halogens, $C_3$-$C_8$ straight or branched alkynyloxy optionally substituted with one to three halogens, or phenyl optionally substituted with one $C_1$-$C_4$ alkyl, $C_1$-$C_4$ alkoxy or halogen; $R_4$ is hydrogen or $C_1$-$C_4$ alkyl; $R_5$ is $C_1$-$C_4$ alkyl; and when taken together Y and Z may form a ring in which YZ are represented by the structure: —$(CH_2)_n$—, where n is an integer of 2, 3 or 4; and when $R_1$ and $R_2$ are not the same, the optical and cis- or trans-isomers thereof or except when R is a salt-forming cation, the acid addition salts thereof.

4. A compound according to claim 1, having the structure:

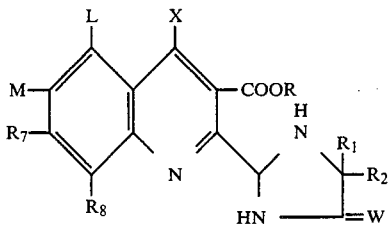

wherein R, $R_1$, $R_2$, W and X, are as defined above in claim 1 and L, M, $R_7$ and $R_8$ represent hydrogen, halogen, $C_1$-$C_4$ alkyl, $C_1$-$C_4$ alkoxy, $C_1$-$C_4$ alkylthio, $C_1$-$C_4$ alkylsulfonyl, $C_1$-$C_4$ haloalkyl, $NO_2$, CN, phenyl, phenoxy, amino, $OCF_3$, $OCHF_2$, $OCF_2CHF_2$, $C_1$-$C_4$ alkylamino, dialkyl($C_1$-$C_4$)amino, chlorophenyl, methylphenyl, $C_3$-$C_8$ straight or branched alkenyloxy optionally substituted with one to three halogens, $C_3$-$C_8$ straight or branched alkynyloxy optionally substituted with one to three halogens, or phenoxy substituted with one Cl, $CF_3$, $NO_2$ or $CH_3$ group, with the proviso that only one of L, M, $R_7$ or $R_8$, may represent a substituent other than hydrogen, halogen, $C_1$-$C_4$ alkyl or $C_1$-$C_4$ alkoxy; or phenyl; and when $R_1$ and $R_2$ are not the same, the optical and cis- or trans-isomers thereof or except when R is a salt-forming cation, the acid addition salts thereof.

5. A compound according to claim 1, having a structure:

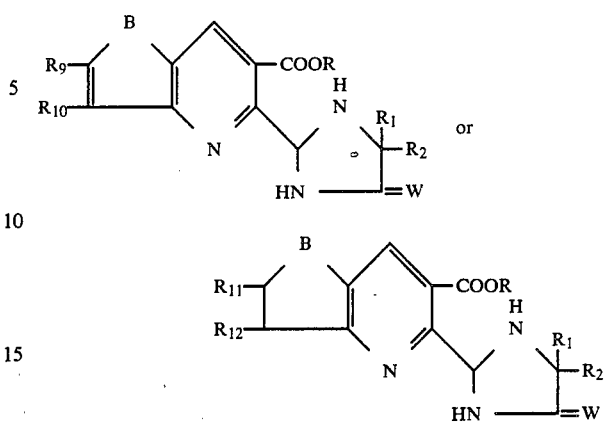

wherein R, $R_1$, $R_2$, W and B, are as defined above in claim 1; $R_9$ and $R_{10}$ each represent hydrogen, halogen, $C_1$-$C_4$ alkyl or phenyl; and $R_{11}$ and $R_{12}$ each represent hydrogen, $C_1$-$C_4$ alkyl or phenyl; and when $R_1$ and $R_2$ are not the same, the optical or cis- or trans-isomers thereof or except when R is a salt-forming cation, the acid addition salts thereof.

6. A compound according to claim 1, having a structure:

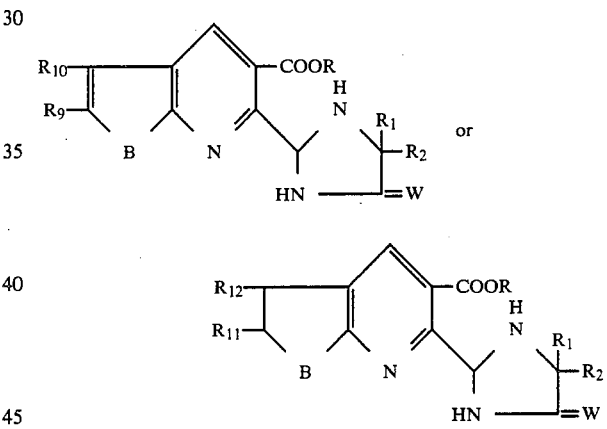

wherein R, $R_1$, $R_2$, W and B, are as defined above in claim 1, $R_9$ and $R_{10}$ each represent hydrogen, halogen, $C_1$-$C_4$ alkyl or phenyl; $R_{11}$ and $R_{12}$ each represent hydrogen, $C_1$-$C_4$ alkenyl or phenyl; and when $R_1$ and $R_2$ are not the same, the optical isomers thereof and except when R is a salt-forming cation, the acid addition salts thereof.

7. A compound according to claim 2, o-(4-isopropyl-4-methyl-5-oxo-2-imidazolidinyl)benzoic acid and the cis-, trans- or optical isomers thereof.

8. A compound according to claim 2, the regio isomeric mixture of methyl 6-(4-isopropyl-4-methyl-5-oxo-2-imidazolidinyl)-m-toluate and methyl 2-(4-isopropyl-4-methyl-5-oxo-2-imidazolidinyl)-p-toluate and the cis-, trans- or optical isomers thereof.

9. A compound according to claim 3, 2-(4-isopropyl-4-methyl-5-oxo-2-imidazolidinyl)-5-methylnicotinic acid or the cis-, trans- or optical isomers thereof.

10. A compound according to claim 3, 5-ethyl-2-(4-isopropyl-4-methyl-5-oxo-2-imidazolidinyl)nicotinic acid or the cis-, trans- or optical isomers thereof.

11. A compound according to claim 3, benzyl 2-(4-isopropyl-4-methyl-5-oxo-2-imidazolidinyl)nicotinate or the cis-, trans- or optical isomers thereof.

12. A compound according to claim 3, methyl 2-(4-isopropyl-4-methyl-5-oxo-2-imidazolidinyl)-6-methoxynicotinate or the cis-, trans- or optical isomers thereof.

13. A compound according to claim 3, 2-(4-isopropyl-4-methyl-5-oxo-2-imidazolidinyl)nicotinic acid or the cis-, trans- or optical isomers thereof.

14. A compound according to claim 4, 2-(4-isopropyl-4-methyl-5-oxo-2-imidazolidinyl)-3-quinolinecarboxylic acid or the cis-, trans- or optical isomers thereof.

15. A compound according to claim 3, 2-(4-isopropyl-4-methyl-5-oxo-2-imidazolinyl)-5-methylnicotinic acid and the cis-, trans- or optical isomers thereof.

16. A method for the control of undesirable monocotyledonous and dicotyledonous plant species comprising: applying to the foliage of said plants or to soil containing seeds or other propagating organs thereof, a herbicidally effective amount of a compound having the structure:

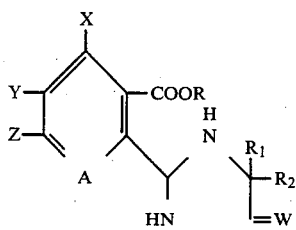

wherein
R is hydrogen;
  $C_1-C_{12}$ alkyl optionally substituted with one of the following groups: $C_1-C_4$ alkoxy, halogen, hydroxyl, $C_3-C_6$ cycloalkyl, benzyloxy, furyl, phenyl, halophenyl, $C_1-C_4$ alkylphenyl, $C_1-C_4$ alkoxyphenyl, nitrophenyl, carboxyl, $C_1-C_3$ alkoxycarbonyl, cyano or tri($C_1-C_3$)alkylammonium;
  $C_3-C_{12}$ alkenyl optionally substituted with one of the following groups: $C_1-C_3$ alkoxy, phenyl, halogen, or $C_1-C_3$ alkoxycarbonyl or with two $C_1-C_4$ alkoxy groups or two halogen atoms;
  $C_3-C_6$ cycloalkyl optionally substituted with one or two $C_1-C_3$ alkyl groups;
  $C_3-C_{10}$ alkynyl or,
  a cation of alkali metals or organic-ammonium;
$R_1$ and $R_2$ each represent $C_1-C_3$ alkyl or cyclopropyl, with the proviso that the sum of the number of carbon atoms in $R_1$ and $R_2$ is 2 to 5; and when $R_1$ and $R_2$ are taken together with the carbon to which they are attached, they may form a $C_3-C_6$ cycloalkyl ring optionally substituted with methyl;
A is nitrogen or —$CR_3$;
W is oxygen or sulfur;
X is hydrogen, halogen or methyl;
Y and Z are each hydrogen, halogen, $C_1-C_6$ alkyl, $C_1-C_4$ hydroxyalkyl, $C_1-C_6$ alkoxy, $C_1-C_4$ alkylthio, phenoxy, $C_1-C_4$ haloalkyl, $OCF_2CHF_2$, $OCF_3$, $OCHF_2$, nitro, cyano, $NR_4R_5$, $C_3-C_8$ straight or branched alkenyloxy optionally substituted with one to three halogens, $C_3-C_8$ straight or branched alkynyloxy optionally substituted with one to three halogens, or phenyl optionally substituted with one $C_1-C_4$ alkyl, $C_1-C_4$ alkoxy or halogen;

$R_3$ is hydrogen, halogen, $C_1-C_4$ alkyl, $C_1-C_4$ alkoxy, $CF_3$, $NO_2$, $OCF_3$, $OCHF_2$ or $OCF_2CHF_2$;
$R_5$ is hydrogen or $C_1-C_4$ alkyl;
$R_5$ is $C_1-C_4$ alkyl;
And, when taken together, Y and Z may form a ring in which YZ is represented by
  (1) the structure: —$(CH_2)_n$—, where n is an integer of 2, 3 and 4, provided that when A is —$CR_3$, then X is hydrogen; or
  (2) by the structure:

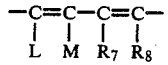

where, when A is $CR_3$, L, M, $R_7$ and $R_8$ each represent hydrogen, halogen, $C_1-C_4$ alkyl or $C_1-C_3$ alkoxy, or X is hydrogen; and when A is nitrogen, L, M, $R_7$ and $R_8$ each represent hydrogen, halogen, $C_1-C_4$ alkyl, $C_1-C_4$ alkoxy, $C_1-C_4$ alkylthio, $C_1-C_4$ alkylsulfonyl, $C_1-C_4$ haloalkyl, $NO_2$, CN, phenyl, phenoxy, amino, $OCF_3$, $OCHF_2$, $OCF_2CHF_2$, $C_1-C_4$ alkylamino, dialkyl($C_1-C_4$)amino, chlorophenoxy, methylphenyl, $C_3-C_8$ straight or branched alkenyloxy optionally substituted with one to three halogens, $C_3-C_8$ straight or branched alkynyloxy optionally substituted with one to three halogens, or phenoxy substituted with one Cl, $CF_3$, $NO_2$ or $CH_3$ group, with the proviso that only one of L, M, $R_7$ or $R_8$, may represent a substituent other than hydrogen, halogen, $C_1-C_4$ alkyl or $C_1-C_4$ alkoxy; or
  (3) by the structures:

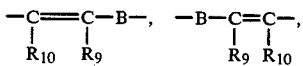

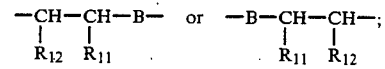

where B is oxygen or sulfur; $R_9$ and $R_{10}$ each represent hydrogen, halogen, phenyl, or $C_1-C_4$ alkyl; $R_{11}$ and $R_{12}$ each represent hydrogen, $C_1-C_4$ alkyl and phenyl;
and when $R_1$ and $R_2$ are not the same, the optical or cis- or trans-isomer thereof or except when R is a salt-forming cation, the acid addition salts thereof.

17. A method according to claim 16 wherein said compound has the structure:

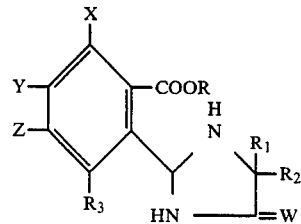

wherein R, $R_1$, $R_2$, $R_3$, X and W are as defined in claim 16 above; Y and Z each, independently, represent hydrogen, halogen, $C_1-C_6$ alkyl, $C_1-C_6$ alkoxy, $C_1-C_4$ alkylthio, phenoxy, nitro, $C_1-C_4$ haloalkyl, $OCF_2CHF_2$, OCF₃, OCHF₂, CN, NR₄R₅, C₃-C₈ straight or branched alkenyloxy optionally substituted with one to three halogens, C₃-C₈ straight or branched alkynyloxy optionally substituted with one to three halogens, or phenyl optionally substituted with one $C_1$-$C_4$ alkyl, $C_1$-$C_4$ alkoxy or halogen; R₄ is hydrogen or $C_1$-$C_4$ alkyl; R₅ is $C_1$-$C_4$ alkyl; and when taken together, Y and Z may form a ring in which YZ are represented by the structure: —(CH₂)ₙ—, where n is an integer of 2, 3 or 4 and X is hydrogen, or by the structure:

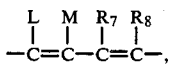

where L, M, R₇ and R₈ each represent hydrogen, halogen, $C_1$-$C_4$ alkyl and $C_1$-$C_3$ alkoxy; and when R₁ and R₂ are not the same, the optical or cis- or trans-isomers thereof or except when R is a salt-forming cation, the acid addition salts thereof.

18. A method according to claim 16, wherein said compound has the structure:

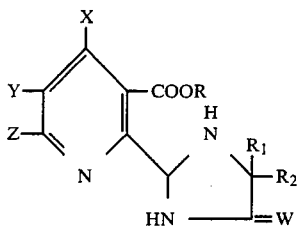

wherein R, R₁, R₂, W and X are as defined in claim 16 above; Y and Z each, independently, represent hydrogen, halogen, $C_1$-$C_6$ alkyl, $C_1$-$C_6$ alkoxy, CN, NO₂, OCF₃, OCHF₂, OCF₂CHF₂, phenoxy, $C_1$-$C_4$ haloalkyl, $C_1$-$C_4$ alkylthio, $C_1$-$C_4$ hydroxyalkyl, NR₄R₅, C₃-C₈ straight or branched alkenyloxy optionally substituted with one to three halogens, C₃-C₈ straight or branched alkynyloxy optionally substituted with one to three halogens, or phenyl optionally substituted with one $C_1$-$C_4$ alkyl, $C_1$-$C_4$ alkoxy or halogen; R₄ is hydrogen or $C_1$-$C_4$ alkyl; R₅ is $C_1$-$C_4$ alkyl; and when taken together Y and Z may form a ring in which YZ are represented by the structure: —(CH₂)ₙ—, where n is an integer of 2, 3 or 4; and when R₁ and R₂ are not the same, the optical and cis- or trans-isomers thereof or except when R is a salt-forming cation, the acid addition salts thereof.

19. A method according to claim 16, wherein said compound has the structure:

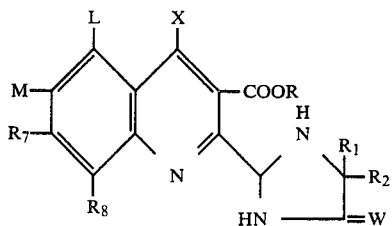

wherein R, R₁, R₂, W and X, are as defined above in claim 16 and L, M, R₇ and R₈ represent hydrogen, halogen, $C_1$-$C_4$ alkyl, $C_1$-$C_4$ alkoxy, $C_1$-$C_4$ alkylthio, $C_1$-$C_4$ alkylsulfonyl, $C_1$-$C_4$ haloalkyl, NO₂, CN, phenyl, phenoxy, amino, OCF₃, OCHF₂, OCF₂CHF₂, $C_1$-$C_4$ alkylamino, dialkyl($C_1$-$C_4$)amino, chlorophenyl, methylphenyl, or phenoxy substituted with one Cl, CF₃, NO₂ or CH₃ group, with the proviso that only one of L, M, R₇ or R₈, may represent a substituent other than hydrogen, halogen, $C_1$-$C_4$ alkyl or $C_1$-$C_4$ alkoxy; or phenyl; and when R₁ and R₂ are not the same, the optical and cis- or trans-isomers thereof or except when R is a salt-forming cation, the acid addition salts thereof.

20. A method according to claim 16, wherein the compound has a structure:

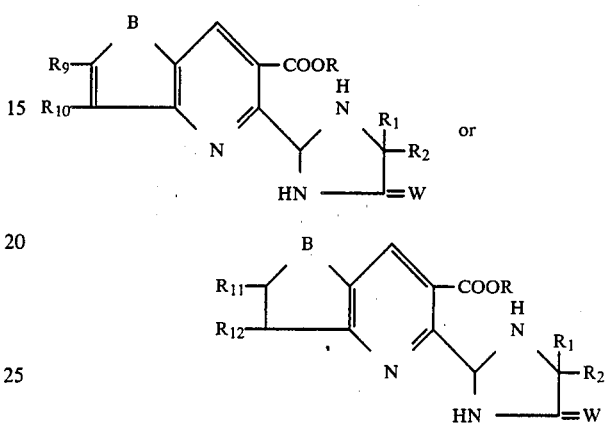

wherein R, R₁, R₂, W and B, are as defined above in claim 16; R₉ and R₁₀ each represent hydrogen, halogen, $C_1$-$C_4$ alkyl or phenyl; and R₁₁ and R₁₂ each represent hydrogen, $C_1$-$C_4$ alkyl or phenyl; and when R₁ and R₂ are not the same, the optical or cis- or trans-isomers thereof or except when R is a salt-forming cation, the acid addition salts thereof.

21. A method according to claim 16, wherein the compound has a structure:

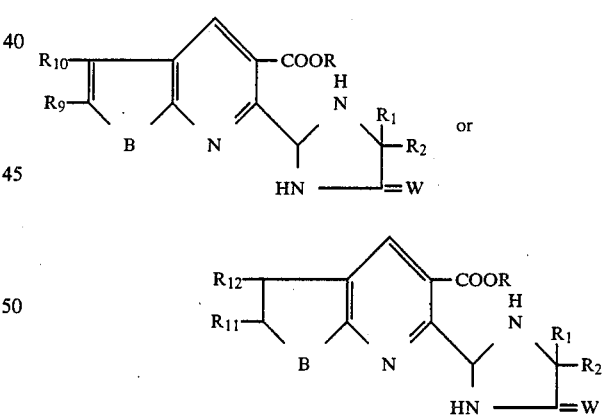

wherein R, R₁, R₂, W and B, are as defined above in claim 16; R₉ and R₁₀ each represent hydrogen, halogen, $C_1$-$C_4$ alkyl or phenyl; R₁₁ and R₁₂ each represent hydrogen, $C_1$-$C_4$ alkyl or phenyl; and when R₁ and R₂ are not the same, the optical isomers thereof or except when R is a salt-forming cation, the acid addition salts thereof.

22. A method for the selective control of undesirable monocotyledonous and dicotyledonous plant species in the presence of graminaceous crops, leguminous crops or sunflowers, comprising: applying to the locus in which the crops are planted or growing, an effective amount of a compound having the structure:

$$\begin{array}{c} X \\ \| \\ Y \diagdown \diagup \diagdown \diagup COOR \\ Z \diagup \diagdown \diagup \diagdown \diagup H \\ | \quad \quad N-CR_1R_2 \\ A \\ HN \underline{\quad\quad} = W \end{array}$$

wherein
R is hydrogen;
$C_1$-$C_{12}$ alkyl optionally substituted with one of the following groups: $C_1$-$C_4$ alkoxy, halogen, hydroxyl, $C_3$-$C_6$ cycloalkyl, benzyloxy, furyl, phenyl, halophenyl, $C_1$-$C_4$ alkylphenyl, $C_1$-$C_4$ alkoxyphenyl, nitrophenyl, carboxyl, $C_1$-$C_3$ alkoxycarbonyl, cyano or tri($C_1$-$C_3$)alkylammonium;
$C_3$-$C_{12}$ alkenyl optionally substituted with one of the following groups: $C_1$-$C_3$ alkoxy, phenyl, halogen, or $C_1$-$C_3$ alkoxycarbonyl or with two $C_1$-$C_4$ alkoxy groups or two halogen atoms;
$C_3$-$C_6$ cycloalkyl optionally substituted with one or two $C_1$-$C_3$ alkyl groups;
$C_3$-$C_{10}$ alkynyl or,
a cation of alkali metals or organicammonium;
$R_1$ and $R_2$ each represent $C_1$-$C_3$ alkyl or cyclopropyl, with the proviso that the sum of the number of carbon atoms in $R_1$ and $R_2$ is 2 to 5; and when $R_1$ and $R_2$ are taken together with the carbon to which they are attached, they may form a $C_3$-$C_6$ cycloalkyl ring optionally substituted with methyl;
A is nitrogen or —$CR_3$;
W is oxygen or sulfur;
X is hydrogen, halogen or methyl;
Y and Z are each hydrogen, halogen, $C_1$-$C_6$ alkyl, $C_1$-$C_4$ hydroxyalkyl, $C_1$-$C_6$ alkoxy, $C_1$-$C_4$ alkylthio, phenoxy, $C_1$-$C_4$ haloalkyl, $OCF_2CHF_2$, $OCF_3$, $OCHF_2$, nitro, cyano, $NR_4R_5$, $C_3$-$C_8$ straight or branched alkenyloxy optionally substituted with one to three halogens, $C_3$-$C_8$ straight or branched alkynyloxy optionally substituted with one to three halogens, or phenyl optionally substituted with one $C_1$-$C_4$ alkyl, $C_1$-$C_4$ alkoxy or halogen;
$R_3$ is hydrogen, halogen, $C_1$-$C_4$ alkyl, $C_1$-$C_4$ alkoxy, $CF_3$, $NO_2$, $OCF_3$, $OCHF_2$ or $OCF_2CHF_2$;
$R_4$ is hydrogen or $C_1$-$C_4$ alkyl;
$R_5$ is $C_1$-$C_4$ alkyl;
and, when taken together, Y and Z may form a ring in which YZ is represented by
(1) the structure: —$(CH_2)_n$—, where n is an integer of 2, 3 or 4, provided that when A is —$CR_3$, then X is hydrogen; or
(2) by the structure:

$$\begin{array}{c} -C=C-C=C- \\ | \quad | \quad | \quad | \\ L \quad M \quad R_7 \quad R_8 \end{array}$$

where, when A is $CR_3$, L, M, $R_7$ and $R_8$ each represent hydrogen, halogen, $C_1$-$C_4$ alkyl and $C_1$-$C_3$ alkoxy, and X is hydrogen; and when A is nitrogen, L, M, $R_7$ and $R_8$ each represent hydrogen, halogen, $C_1$-$C_4$ alkyl, $C_1$-$C_4$ alkoxy, $C_1$-$C_4$ alkyltho, $C_1$-$C_4$ alkylsulfonyl, $C_1$-$C_4$ haloalkyl, $NO_2$, CN, phenyl, phenoxy, amino, $OCF_3$, $OCHF_2$, $OCF_2CHF_2$, $C_1$-$C_4$ alkylamino, dialkyl($C_1$-$C_4$)amino, chlorophenyl, methylphenyl, $C_3$-$C_8$ straight or branched alkenyloxy optionally substituted with one to three halogens, $C_3$-$C_8$ straight or branched alkynyloxy optionally substituted with one to three halogens, or phenoxy substituted with one Cl, $CF_3$, $NO_2$ or $CH_3$ group, with the proviso that only one of L, M, $R_7$ or $R_8$, may represent a substituent other than hydrogen, halogen, $C_1$-$C_4$ alkyl or $C_1$-$C_4$ alkoxy; or
(3) by the structures:

$$\begin{array}{cc} -C=C-B-, & -B-C=C-, \\ | \quad | & | \quad | \\ R_{10} \quad R_9 & R_9 \quad R_{10} \end{array}$$

$$\begin{array}{cc} -CH-CH-B- \quad \text{or} & -B-CH-CH-; \\ | \quad | & | \quad | \\ R_{12} \quad R_{11} & R_{11} \quad R_{12} \end{array}$$

where B is oxygen or sulfur; $R_9$ and $R_{10}$ each represent hydrogen, halogen, phenyl, or $C_1$-$C_4$ alkyl; $R_{11}$ and $R_{12}$ each represent hydrogen, $C_1$-$C_4$ alkyl or phenyl;
and when $R_1$ and $R_2$ are not the same, the optical or cis- or trans-isomers thereof or except when R is a salt-forming cation, the acid addition salts thereof.

23. A method according to claim 22, wherein said compound is applied at the rate of from about 0.063 to 4.0 kg/ha.

24. A method according to claim 22, wherein said compound is applied to the locus in which the crops are planted or growing at a rate of from 0.063 to 4.0 kg/ha.

25. A method for regulating the growth of graminaceous crops, leguminous crops or sunflowers, comprising: applying to the foliage of the crops or to the soil in which there have been planted, a plant growth regulating amount of a compound having the structure:

$$\begin{array}{c} X \\ \| \\ Y \diagdown \diagup \diagdown \diagup COOR \\ Z \diagup \diagdown \diagup \diagdown \diagup H \\ | \quad \quad N-CR_1R_2 \\ A \\ HN \underline{\quad\quad} = W \end{array}$$

wherein
R is hydrogen;
$C_1$-$C_{12}$ alkyl optionally substituted with one of the following groups: $C_1$-$C_4$ alkoxy, halogen, hydroxyl, $C_3$-$C_6$ cycloalkyl, benzoyloxy, furyl, phenyl, halophenyl, $C_1$-$C_4$ alkylphenyl, $C_1$-$C_4$ alkoxyphenyl, nitrophenyl, carboxyl, $C_1$-$C_3$ alkoxycarbonyl, cyano or tri($C_1$-$C_3$)alkylammonium;
$C_3$-$C_{12}$ alkenyl optionally substituted with one of the following groups: $C_1$-$C_3$ alkoxy, phenyl, halogen, or $C_1$-$C_3$ alkoxycarbonyl or with two $C_1$-$C_4$ alkoxy groups or two halogen atoms;
$C_3$-$C_6$ cycloalkyl optionally substituted with one or two $C_1$-$C_3$ alkyl groups;
$C_3$-$C_{10}$ alkynyl or, a cation of alkali metals and organicammonium;

$R_1$ and $R_2$ each represent $C_1$-$C_3$ alkyl or cyclopropyl, with the proviso that the sum of the number of carbon atoms in $R_1$ and $R_2$ is 2 to 5; and when $R_1$ and $R_2$ are taken together with the carbon to which they are attached, they may form a $C_3$-$C_6$ cycloalkyl ring optionally substituted with methyl;

A is nitrogen or —$CR_3$;

W is oxygen or sulfur;

X is hdyrogen, halogen or methyl;

Y and Z are each hydrogen, halogen, $C_1$-$C_6$ alkyl, $C_1$-$C_4$ hydroxyalkyl, $C_1$-$C_6$ alkoxy, $C_1$-$C_4$ alkylthio, phenoxy, $C_1$-$C_4$ haloalkyl, $OCF_2CHF_2$, $OCF_3$, $OCHF_2$, nitro, cyano, $NR_4R_5$, $C_3$-$C_8$ straight or branched alkenyloxy optionally substituted with one to three halogens, $C_3$-$C_8$ straight or branched alkynyloxy optionally substituted with one to three halogens, or phenyl optionally substituted with one $C_1$-$C_4$ alkyl, $C_1$-$C_4$ alkoxy or halogen;

$R_3$ is hydrogen, halogen, $C_1$-$C_4$ alkyl, $C_1$-$C_4$ alkoxy, $CF_3$, $NO_2$, $OCF_3$, $OCHF_2$ or $OCF_2CHF_2$;

$R_4$ is hydrogen or $C_1$-$C_4$ alkyl;

$R_5$ is $C_1$-$C_4$ alkyl;

and, when taken together, Y and Z may form a ring in which YZ is represented by (1) the structure: —$(CH_2)_n$—, where n is an integer of 2, 3 or 4, provided that when A is —$CR_3$, then X is hydrogen; or (2) by the structure:

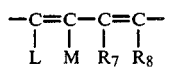

where, when A is $CR_3$, L, M, $R_7$ and $R_8$ each represent hydrogen, halogen, $C_1$-$C_4$ alkyl and $C_1$-$C_3$ alkoxy, and X is hydrogen; and when A is nitrogen, L, M, $R_7$ and $R_8$ each represent hydrogen, halogen, $C_1$-$C_4$ alkyl, $C_1$-$C_4$ alkoxy, $C_1$-$C_4$ alkylthio, $C_1$-$C_4$ alkylsulfonyl, $C_1$-$C_4$ haloalkyl, $NO_2$, CN, phenyl, phenoxy, amino, $OCF_3$, $OCHF_2$, $OCF_2CHF_2$, $C_1$-$C_4$ alkylamino, dialkyl($C_1$-$C_4$)amino, chlorophenyl, methylphenyl, $C_3$-$C_8$ straight or branched alkenyloxy optionally substituted with one to three halogens, $C_3$-$C_8$ straight or branched alkynyloxy optionally substituted with one to three halogens, or phenoxy substituted with one Cl, $CF_3$, $NO_2$ or $CH_3$ group, with the proviso that only one of L, M, $R_7$ or $R_8$, may represent a substituent other than hydrogen, halogen, $C_1$-$C_4$ alkyl or $C_1$-$C_4$ alkoxy; or (3) by the structures:

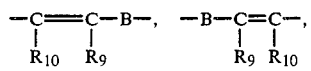

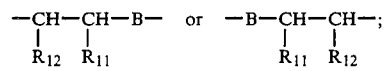

where B is oxygen or sulfur; $R_9$ and $R_{10}$ each represent hydrogen, halogen, phenyl, or $C_1$-$C_4$ alkyl; $R_{11}$ and $R_{12}$ each represent hydrogen, $C_1$-$C_4$ alkyl or phenyl.

26. A herbicidal composition comprising an inert diluent and a herbicidally effective amount of a compound having the structure:

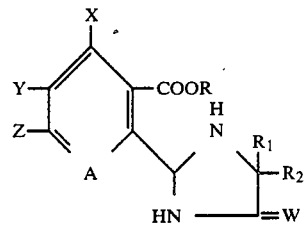

wherein

R is hydrogen;

$C_1$-$C_{12}$ alkyl optionally substituted with one of the following groups: $C_1$-$C_4$ alkoxy, halogen, hydroxyl, $C_3$-$C_6$ cycloalkyl, benzyloxy, furyl, phenyl, halophenyl, $C_1$-$C_4$ alkylphenyl, $C_1$-$C_4$ alkoxyphenyl, nitrophenyl, carboxyl, $C_1$-$C_3$ alkoxycarbonyl, cyano or tri($C_1$-$C_3$)alkylammonium;

$C_3$-$C_{12}$ alkenyl optionally substituted with one of the following groups: $C_1$-$C_3$ alkoxy, phenyl, halogen, or $C_1$-$C_3$ alkoxycarbonyl or with two $C_1$-$C_4$ alkoxy groups or two halogen atoms;

$C_3$-$C_6$ cycloalkyl optionally substituted with one or two $C_1$-$C_3$ alkyl groups;

$C_3$-$C_{10}$ alkynyl or, a cation of alkali metals and organic-ammonium;

$R_1$ and $R_2$ each represent $C_1$-$C_3$ alkyl or cyclopropyl, with the proviso that the sum of the number of carbon atoms in $R_1$ and $R_2$ is 2 to 5; and when $R_1$ and $R_2$ are taken together with the carbon to which they are attached, they may form a $C_3$-$C_6$ cycloalkyl ring optionally substituted with methyl;

A is nitrogen or —$CR_3$;

W is oxygen or sulfur;

X is hydrogen, halogen or methyl;

Y and Z are each hydrogen, halogen, $C_1$-$C_6$ alkyl, $C_1$-$C_4$ hydroxyalkyl, $C_1$-$C_6$ alkoxy, $C_1$-$C_4$ alkylthio, phenoxy, $C_1$-$C_4$ haloalkyl, $OCF_2CHF_2$, $OCF_3$, $OCHF_2$, nitro, cyano, $NR_4R_5$, $C_3$-$C_8$ straight or branched alkenyloxy optionally substituted with one to three halogens, $C_3$-$C_8$ straight or branched alkynyloxy optionally substituted with one to three halogens, or phenyl optionally substituted with one $C_1$-$C_4$ alkyl, $C_1$-$C_4$ alkoxy or halogen;

$R_3$ is hydrogen, halogen, $C_1$-$C_4$ alkyl, $C_1$-$C_4$ alkoxy, $CF_3$, $NO_2$, $OCF_3$, $OCHF_2$ or $OCF_2CHF_2$;

$R_4$ is hydrogen or $C_1$-$C_4$ alkyl;

$R_5$ is $C_1$-$C_4$ alkyl;

and, when taken together, Y and Z may form a ring in which YZ is represented by (1) the structure: —$(CH_2)_n$—, where n is an integer of 2, 3 or 4, provided that when A is —$CR_3$, then X is hydrogen; or (2) by the structure:

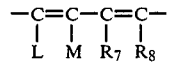

where, when A is $CR_3$, L, M, $R_7$ and $R_8$ each represent hydrogen, halogen, $C_1$-$C_4$ alkyl or $C_1$-$C_3$ alkoxy, and X is hydrogen; and when A is nitrogen, L, M, R$_7$ and R$_8$ each represent hydrogen, halogen, C$_1$-C$_4$ alkyl, C$_1$-C$_4$ alkoxy, C$_1$-C$_4$ alkylthio, C$_1$-C$_4$ alkylsulfonyl, C$_1$-C$_4$ haloalkyl, NO$_2$, CN, phenyl, phenoxy, amino, OCF$_3$, OCHF$_2$, OCF$_2$CHF$_2$, C$_1$-C$_4$ alkylamino, dialkyl(C$_1$-C$_4$)amino, chlorophenyl, methylphenyl, C$_3$-C$_8$ straight or branched alkenyloxy optionally substituted with one to three halogens, C$_3$-C$_8$ straight or branched alkynyloxy optionally substituted with one to three halogens, or phenoxy substituted with one Cl, CF$_3$, NO$_2$ or CH$_3$ group, with the proviso that only one of L, M, R$_7$ or R$_8$, may represent a substituent other than hydrogen, halogen, C$_1$-C$_4$ alkyl or C$_1$-C$_4$ alkoxy; or (3) by the structures:

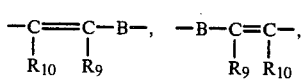

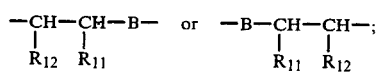

where B is oxygen or sulfur; R$_9$ and R$_{10}$ each represent hydrogen, halogen, phenyl, or C$_1$-C$_4$ alkyl; R$_{11}$ and R$_{12}$ each represent hydrogen, C$_1$-C$_4$ alkyl or phenyl;

and when R$_1$ and R$_2$ are not the same, the optical or cis- or trans-isomers thereof or except when R is a salt-forming cation, the acid addition salts thereof.

27. A process for the production of the compound of the formula

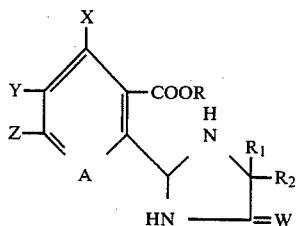

wherein

R may be hydrogen, but preferably is
  C$_1$-C$_{12}$ alkyl optionally substituted with one of the following groups: C$_1$-C$_4$ alkoxy, halogen, hydroxyl, C$_3$-C$_6$ cycloalkyl, benzyloxy, furyl, phenyl, halophenyl, C$_1$-C$_4$ alkylphenyl, C$_1$-C$_4$ alkoxyphenyl, nitrophenyl, carboxyl, C$_1$-C$_3$ alkoxycarbonyl, cyano or tri(C$_1$-C$_3$)alkylammonium;
  C$_3$-C$_{12}$ alkenyl optionally substituted with one of the following groups: C$_1$-C$_3$ alkoxy, phenyl, halogen, or C$_1$-C$_3$ alkoxycarbonyl or with two C$_1$-C$_4$ alkoxy groups or two halogen atoms;
  C$_3$-C$_6$ cycloalkyl optionally substituted with one or two C$_1$-C$_3$ alkyl groups; or
  C$_3$-C$_{10}$ alkynyl;

R$_1$ and R$_2$ each represent C$_1$-C$_3$ alkyl or cyclopropyl, with the proviso that the sum of the number of carbon atoms in R$_1$ and R$_2$ is 2 to 5; and when R$_1$ and R$_2$ are taken together with the carbon to which they are attached, they may form a C$_3$-C$_6$ cycloalkyl ring optionally substituted with methyl;

A is nitrogen of —CR$_3$;
W is oxygen or sulfur;
X is hydrogen, halogen or methyl;
Y and Z are each hydrogen, halogen, C$_1$-C$_6$ alkyl, C$_1$-C$_4$ hydroxyalkyl, C$_1$-C$_6$ alkoxy, C$_1$-C$_4$ alkylthio, phenoxy, C$_1$-C$_4$ haloalkyl, OCF$_2$CHF$_2$, OCF$_3$, OCHF$_2$, nitro, cyano, NR$_4$R$_5$, C$_3$-C$_8$ straight or branched alkenyloxy optionally substituted with one to three halogens, C$_3$-C$_8$ straight or branched alkynyloxy optionally substituted with one to three halogens, or phenyl optionally substituted with one C$_1$-C$_4$ alkyl, C$_1$-C$_4$ alkoxy or halogen;
R$_3$ is hydrogen, chlorine, bromine, iodine, C$_1$-C$_4$ alkyl, C$_1$-C$_4$ alkoxy, CF$_3$, NO$_2$, OCF$_3$, OCHF$_2$ or OCF$_2$CHF$_2$;
R$_4$ is hydrogen or C$_1$-C$_4$ alkyl;
R$_5$ is C$_1$-C$_4$ alkyl;
and, when taken together, Y and Z may form a ring in which YZ is represented by
  (1) the structure: —(CH$_2$)$_n$—, where n is an integer of 2, 3 or 4, provided that when A is —CR$_3$, then X is hydrogen; or
  (2) by the structures:

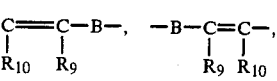

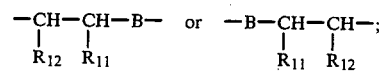

where B is oxygen or sulfur; R$_9$ and R$_{10}$ each represent hydrogen, halogen, phenyl, or C$_1$-C$_4$ alkyl; R$_{11}$ and R$_{12}$ each represent hydrogen, C$_1$-C$_4$ alkyl or phenyl;

and when R$_1$ and R$_2$ are not the same, the optical or cis- or trans-isomers thereof characterized by reducing a compound of the formula

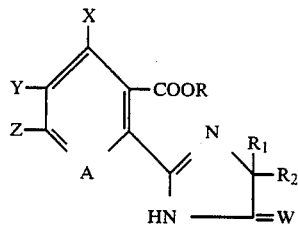

28. A process according to claim 27 wherein the reducing agent is NaCNBH$_3$ and the reaction is

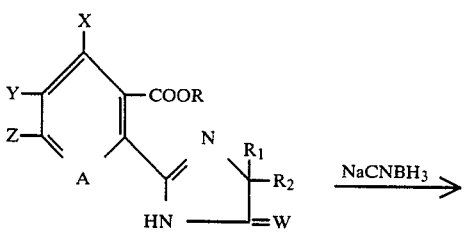

-continued

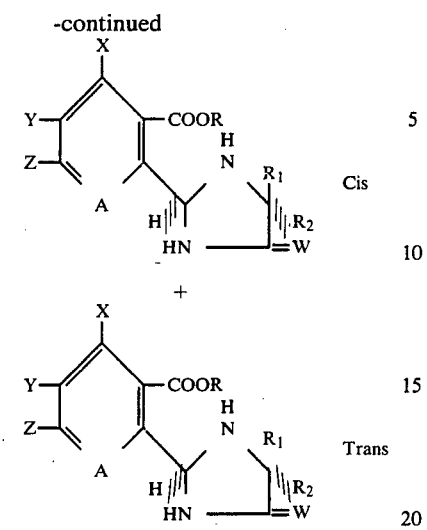

wherein A, R, $R_1$, $R_2$, W, X, Y and Z are as described in said claim 27.

29. A process for the production of a compound of the formula:

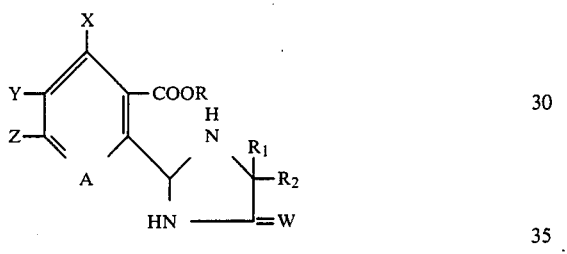

wherein

R is preferably methyl but may be $C_1$-$C_{12}$ alkyl optionally substituted with one of the following groups: $C_1$-$C_4$ alkoxy, halogen, hydroxyl, $C_3$-$C_6$ cycloalkyl, benzyloxy, furyl, phenyl, halophenyl, $C_1$-$C_4$ alkylphenyl, $C_1$-$C_4$ alkoxyphenyl, nitrophenyl, carboxyl, $C_1$-$C_3$ alkoxycarbonyl, cyano or tri($C_1$-$C_3$)alkylammonium;

$C_3$-$C_{12}$ alkenyl optionally substituted with one of the following groups: $C_1$-$C_3$ alkoxy, phenyl, halogen, or $C_1$-$C_3$ alkoxycarbonyl or with two $C_1$-$C_4$ alkoxy groups or two halogen atoms;

$C_3$-$C_6$ cycloalkyl optionally substituted with one or two $C_1$-$C_3$ alkyl groups; or $C_3$-$C_{10}$ alkynyl;

$R_1$ and $R_2$ each represent $C_1$-$C_3$ alkyl or cyclopropyl, with the proviso that the sum of the number of carbon atoms in $R_1$ and $R_2$ is 2 to 5; and when $R_1$ and $R_2$ are taken together with the carbon to which they are attached, they may form a $C_3$-$C_6$ cycloalkyl ring optionally substituted with methyl;

A is nitrogen or —$CR_3$;

W is oxygen or sulfur;

X is hydrogen, halogen or methyl;

Y and Z are each hydrogen, halogen, $C_1$-$C_6$ alkyl, $C_1$-$C_4$ hydroxyalkyl, $C_1$-$C_6$ alkoxy, $C_1$-$C_4$ alkylthio, phenoxy, $C_1$-$C_4$ haloalkyl, $OCF_2CHF_2$, $OCF_3$, $OCHF_2$, nitro, cyano, $NR_4R_5$, $C_3$-$C_8$ straight or branched alkenyloxy optionally substituted with one to three halogens, $C_3$-$C_8$ straight or branched alkynyloxy optionally substituted with one to three halogens, or phenyl optionally substituted with one $C_1$-$C_4$ alkyl, $C_1$-$C_4$ alkoxy or halogen;

$R_3$ is hydrogen, halogen, $C_1$-$C_4$ alkyl, $C_1$-$C_4$ alkoxy, $CF_3$, $NO_2$, $OCF_3$, $OCHF_2$ or $OCF_2CHF_2$;

$R_4$ is hydrogen or $C_1$-$C_4$ alkyl;

$R_5$ is $C_1$-$C_4$ alkyl;

and, when taken together, Y and Z may form a ring in which YZ is represented by (1) the structure: —($CH_2$)$_n$—, where n is an integer of 2, 3 or 4, provided that when A is —$CR_3$, then X is hydrogen; or (2) by the structure:

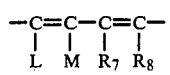

where, when A is $CR_3$, L, M, $R_7$ and $R_8$ each represent hydrogen, halogen, $C_1$-$C_4$ alkyl or $C_1$-$C_3$ alkoxy, and X is hydrogen; and when A is nitrogen, L, M, $R_7$ and $R_8$ each represent hydrogen, halogen, $C_1$-$C_4$ alkyl, $C_1$-$C_4$ alkoxy, $C_1$-$C_4$ alkylthio, $C_1$-$C_4$ alkylsulfonyl, $C_1$-$C_4$ haloalkyl, $NO_2$, CN, phenyl, phenoxy, amino, $C_1$-$C_4$ alkylamino, dialkyl($C_1$-$C_4$)amino, $OCF_3$, $OCHF_2$, $OCF_2CHF_2$, chlorophenyl, methylphenyl, $C_3$-$C_8$ straight or branched alkenyloxy optionally substituted with one to three halogens, $C_3$-$C_8$ straight or branched alkynyloxy optionally substituted with one to three halogens, or phenoxy substituted with one Cl, $CF_3$, $NO_2$ or $CH_3$ group, with the proviso that only one of L, M, $R_7$ or $R_8$, may represent a substituent other than hydrogen, halogen, $C_1$-$C_4$ alkyl or $C_1$-$C_4$ alkoxy; or (3) by the structures:

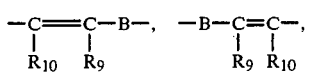

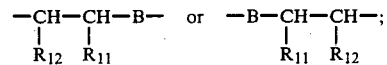

where B is oxygen or sulfur; $R_9$ and $R_{10}$ each represent hydrogen, halogen, phenyl, or $C_1$-$C_4$ alkyl; $R_{11}$ and $R_{12}$ each represent hydrogen, $C_1$-$C_4$ alkyl or phenyl;

and when $R_1$ and $R_2$ are not the same, the optical or cis- or trans-isomers thereof characterized by reacting a compound of the formula

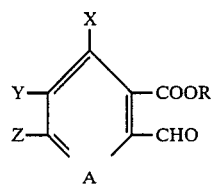

with a compound of the formula

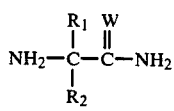

where R, A, $R_1$, $R_2$, W, X, Y and Z are as defined, above, with the provisos that (1) when A is $-CR_3$, W is S; and (2) when taken together, Y and Z may form a ring in which YZ are represented by (a) the structure: $-(CH_2)_n-$, where n is an integer of 2, 3 or 4, in which instance $R_3$ and X are each hydrogen; or (b)

$$-\overset{L}{C}=\overset{M}{C}-\overset{R_7}{C}=\overset{R_8}{C}-,$$

where L, M, $R_7$ and $R_8$ each represent hydrogen, halogen, $C_1$-$C_4$ alkyl or $C_1$-$C_4$ alkoxy and $R_3$ and X are each hydrogen characterized by reacting the compounds in the presence of a strong organic acid.

30. A process according to claim 29 wherein the organic acid is p-toluenesulfonic acid.

31. A process according to claim 29 wherein the organic acid is p-toluenesulfonic acid followed by further treatment of the resulting product with trifluoroacetic acid.

* * * * *

UNITED STATES PATENT OFFICE
CERTIFICATE OF CORRECTION

Patent No. 4,608,079         Dated August 26, 1986

Inventor(s)   Marinus Los

It is certified that error appears in the above-identified patent and that said Letters Patent are hereby corrected as shown below:

In the title, both on the cover page of the patent and in Column 1, "Imidazolidienthiones" should read -- Imidazolidinethiones --

In Columns 143-152 the heading for Table VI should read -- Pre-emergence Tests - Rates in KG/HA --

Claim 16, first structure should read as follows:

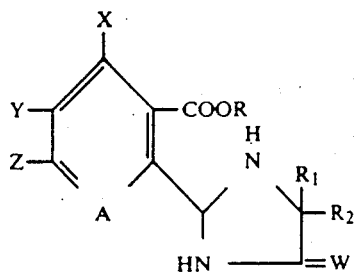

Signed and Sealed this

Twenty-seventh Day of January, 1987

Attest:

DONALD J. QUIGG

Attesting Officer      Commissioner of Patents and Trademarks

UNITED STATES PATENT OFFICE
CERTIFICATE OF CORRECTION

Patent No. 4,608,079     Dated August 26, 1986

Inventor(s) Marinus Los

It is certified that error appears in the above-identified patent and that said Letters Patent are hereby corrected as shown below:

In the title, both on the cover page of the patent and in Column 1, "Imidazolidienthiones" should read -- Imidazolidinethiones --

In Columns 143-152 the heading for Table VI should read -- Pre-emergence Tests - Rates in KG/HA --

Claim 16, first structure should read as follows:

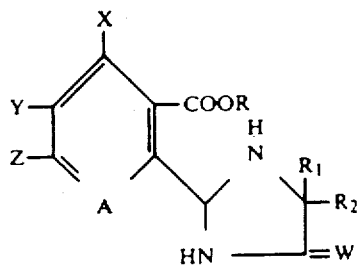

Signed and Sealed this

Twenty-seventh Day of January, 1987

Attest:

DONALD J. QUIGG

Attesting Officer     Commissioner of Patents and Trademarks